US007842856B2

(12) United States Patent
Tranel et al.

(10) Patent No.: US 7,842,856 B2
(45) Date of Patent: *Nov. 30, 2010

(54) HERBICIDE RESISTANCE GENE, COMPOSITIONS AND METHODS

(75) Inventors: Patrick Tranel, Ogden, IL (US); Aaron Hager, Saint Joseph, IL (US); William Patzoldt, Raleigh, NC (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 412 days.

This patent is subject to a terminal disclaimer.

(21) Appl. No.: 12/040,857

(22) Filed: Feb. 29, 2008

(65) Prior Publication Data

US 2010/0100988 A1   Apr. 22, 2010

Related U.S. Application Data

(63) Continuation-in-part of application No. 11/466,662, filed on Aug. 23, 2006, now Pat. No. 7,671,254.

(60) Provisional application No. 60/807,780, filed on Jul. 19, 2006, provisional application No. 60/711,204, filed on Aug. 25, 2005.

(51) Int. Cl.
C12N 5/09 (2010.01)
C12N 15/82 (2006.01)

(52) U.S. Cl. ............... 800/300; 800/306; 800/312; 800/314; 800/315; 800/317.2; 800/317.3; 800/317.4; 800/320; 800/322; 435/430; 435/468; 435/470

(58) Field of Classification Search .............. None
See application file for complete search history.

(56) References Cited

U.S. PATENT DOCUMENTS

| | | | |
|---|---|---|---|
| 4,746,352 A | 5/1988 | Wenger et al. | |
| 5,183,492 A | 2/1993 | Suchy et al. | |
| 5,290,696 A | 3/1994 | Parker et al. | |
| 5,405,829 A | 4/1995 | Hatfiel et al. | |
| 5,451,513 A | 9/1995 | Maliga et al. | |
| 5,545,817 A | 8/1996 | McBride et al. | |
| 5,545,818 A | 8/1996 | McBride et al. | |
| 5,565,350 A | 10/1996 | Kmiec | |
| 5,731,181 A | 3/1998 | Kmiec | |
| 5,877,462 A | 3/1999 | Chenais | |
| 5,939,602 A | 8/1999 | Volrath et al. | |
| 6,282,837 B1 | 9/2001 | Ward et al. | |
| 6,696,294 B1 | 2/2004 | Konzak | |
| 6,808,904 B2 | 10/2004 | Ward et al. | |
| 6,870,075 B1 | 3/2005 | Beetham et al. | |
| 7,034,208 B1 | 4/2005 | Smith | |
| 2005/0044597 A1 | 2/2005 | Konzak | |
| 2005/0177899 A1 | 8/2005 | Beetham et al. | |
| 2007/0028318 A1 | 2/2007 | Livore et al. | |
| 2007/0033670 A1 | 2/2007 | Konzak et al. | |

FOREIGN PATENT DOCUMENTS

| | | |
|---|---|---|
| WO | WO 9310100 A1 | 5/1993 |
| WO | WO 9408999 A1 | 4/1994 |
| WO | WO 9516783 A1 | 6/1995 |
| WO | WO 9732977 A1 | 9/1997 |
| WO | WO 0183459 A2 | 11/2001 |

OTHER PUBLICATIONS

Moore et al., Abstracts of the Weed Science Society of America (1993) 33:9.
*Arabidopsis* Genome Initiative. (2000). Analysis of the genome sequence of the flowering plant *Arabidopsis thaliana*. Nature 408:796-815.
Bartlett et al. In: Edelmann et al. (Eds.) Methods in Chloroplast Molecular Biology, Elsevier, pp. 1081-1091, 1982.
Beale et al. 1990. Tetrapyrrole Metabolism in Photosynthetic Organisms in Biosynthesis of Heme and Chlorophylls (ed. by H.A. Dailey). McGraw-Hill, New York. pp. 287-391.
Camadro et al. 1982. A new Assay for Protoporphyrinogen Oxidase—Evidence for a Total Deficiency in that Activity in a Heme-Less Mutant of *Saccharomyces cerevisiae*. Biochem. Biophys. Res. Comm. 106: 724-730.
Chabregas et al. 2001. Dual Targeting Properties of the N-terminal Signal Sequence of *Araidopsis thaliana* THI1 Protein to Mitochondria and Chloroplasts. Plant Mol. Biol. 46:639-650.
Che et al. 1993. Localization of Target-Site of the Protoporphyrinogen Oxidase-Inhibiting Herbicide, S-23142, in *Spinacia oleracea* L. Z. Naturforsch. 48c: 350-355.
Che et al. 2000. Molecular Characterization and Subcellular Localization of Protoporphyrinogen Oxidase in Spinach Chloroplasts. Plant Physiol. 124:59-70.
Choi K. W. et al. 1998. Generation of Resistance to the Diphenyl Ether Hericde, Oxyfluorfen, via Expression of the *Bacillus subtilis* Protoporphyrinogen Oxidase Gene in Transgenic Tobacco Plants. Biosci. Biotech. Biochem. 62:558-560.
Chow, K. S. et al. 1997. A Single Precursor Protein for Ferrochelatase-I From *Arabidopsis* is Imported in Vitro Into Both Chloroplasts and Mitochondria. A J. Biol. Chem. 272:27565-27571.
Comai et al. 1985. Expression in Plants of a Mutant aroA gene from *Salmonella typhimurium* Confers Tolerance to Glyphosate Nature 317:741-744.

(Continued)

*Primary Examiner*—Eileen B O Hara
(74) *Attorney, Agent, or Firm*—Greenlee Sullivan P.C.

(57) ABSTRACT

The present disclosure provides methods, recombinant DNA molecules, recombinant host cells containing the DNA molecules, and transgenic and genetically engineered plant cells, plant tissue, seeds and plants which contain and express an herbicide resistant protoporphyrinogen oxidase such that they germinate from seed and grow in the presence of an amount of herbicide where the parent plant does not. Such plants are especially appropriate for use in agriculture or horticulture where herbicides are used to kill undesirable plants which might contaminate or compete with the transgenic plant of interest.

13 Claims, 11 Drawing Sheets

OTHER PUBLICATIONS

Comai et al. 1988. Chloroplast Transport of a Ribulose Biophosphate Carboxylase Small Subunit-5-Enolpyruvyl 3-Phosphoshikimate Synthase Chimeric Protein Requires Part of the Mature Small Subunit in Addition to the Transit Peptide. J. Biol. Chem. 263: 15104-15109.

Cox et al. 1983. Excited State Interactions of Protoporphyrin IX and Related Porphyrins with Molecular Oxygen in Solutions and Organized Assemblies, in Porphyrin Photosensitization (ed. by D. Kessel and T.J. Dougherty). Plenum Press, New York, NY.

Dailey et al. 1994. Expression of a Cloned Protoporphyrinogen Oxidase. J. Biol. Chem. 269: 813-815.

Dayan, et al. 1997. Phytotoxicity of Protoporphyrinogen Oxidase Inhibitors: Phenomenology, Mode of Action and Mechanisms of Resistance, in Herbicide Activity: Toxicology, Biochemistry and Molecular Biology (ed. by R.M. Roe, J.D. Burton and R.J. Kuhr) IOS Press, Amsterdam, Netherlands. pp. 11-36.

Duke, S. O. et al. 1997. Mechanisms of Resistance to Protoporphyrinogen Oxidase-Inhibiting Herbicides in Weed and Crop Resistance to Herbicides (ed. by R. De Prado, J. Jorrín, and L. García-Torres). Kluwer Academic Publishers. Netherlands. pp. 155-160.

Duke et al. 1991. Protoporphyrinogen Oxidase-Inhibiting Herbicides. Weed Sci. 39: 465-473.

Emanuelsson, et al. 2000. Predicting Subcellular Localization of Proteins Based on their N-terminal Amino Acid Sequence. J. Mol. Biol. 300:1005-1016.

1994. Efficiency of the Tetracycline-Dependent Gene Expression System: Complete Suppression and Efficient Induction of the ro IB Phenotype in Transgenic Plants. Mol. Gen. Genetics 243:32-38, Roder at al.

Gordon-Kamm et al. 1990. Transformation of Maize Cells and Regeneration of Fertile Transgenic Plants. Plant Cell 2:603-618.

Ha et al. 2004. The Plastidic Arabidopsis Protoporphyrinogen IX Oxidase Gene, With or Without the Transit Sequence, Confers Resistance to the Diphenyl Ether Herbicide in Rice. Plant Cell Environ. 27: 79- 88.

Harley and Reynolds. 1987. Analysis of E. coli Promoter Sequences. Nucleic Acids Res. 15:2343-2361.

1991. Regulation of a Modified CaMV 35S Promoter by the Tn10-Encoded Tet Repressor in Transgenic Tobacco. Mol. Gen. Genetics 227:229-237, Gatz et al.

Hinchee et al. 1988. Production of Transgenic Soybean Plants Using Agrobacterium-Mediated DNA Transfer. Bio/Technology 6:915-922.

Horikoshi, M. and T. Hirooka. 1999. Selection of Tobacco Cell Lines Resistant to Photobleaching Hericides. Pestic. Sci. 24:13-16.

Horikoshi, M., K. et al. Jan. 5, 1999. Nicotiana tabacum Protoporphyrinogen Oxidase PX-2 mRNA. GenBank Accession No. AF044129.

Jackson and Moore, in Plant Organelles, Reid, ed., pp. 1-12, 1979.

Jacobs and Jacobs. 1982. Assay for Enzymatic Protoporphyrinogen Oxidation, a Late Step in Heme Synthesis. Enyzme 28: 206-219.

Jacobs, J. M. and N. J. Jacobs. 1984. Protoporphyrinogen Oxidation, an Enzymatic Step in Heme and Chlorophyll Synthesis: Partial Characterization of the Reaction in Plant Organelles and Comparison with Mammalian and Bacterial Systems. Arch. Biochem. Biophys. 229:312-319.

Jacobs, J. M. and N. J. Jacobs. 1993. Porphyrin Accumulation and Export by Isolated Barley (Hordeum vulgare) Plastids. Plant Physiol. 101:1181-1187.

Johnson, D. J., et al. Apr. 15, 2005. Solanum tuberosum, Cultivar Binje, mRNA for Ferrochelatase. GenBank assession AJ005802.

Johnson, D. J., et al. Feb. 9, 1999. Solanum tuberosum (Cultivar Bintje) Cholorplastid Protoporphyrinogen IX Oxidase. GenBank accession AJ225107.

Johnson, D.J., et al. Apr. 10, 2000. Solanum tuberosum (Cultivar Bintje) Mitochondrial Protoporphyrinogen IX Oxidase. GenBank accession AJ225108.

Jung et al. 2004. Dual Targeting of Myxococcus xanthus Protoporphyrinogen Oxidase into Choloroplasts and Mitochondria and High Level Oxyfluorfen Resistance. Plant Cell Environ. 27, 1436-1446.

Kashi, Y. and King, D. G. 2006. Simple Sequence Repeats as Advantageous Mutators in Evolution. Trends Genetics 22: 253-259.

Kataoka et al. 1990. Isolation and Partial Characterization of Mutant Chlamydomonas reinhardtii Resistant to Herbicide S-23142. J. Pesticide Sci. 15: 449-451.

Koch et al. 2004. Crystal Structure of Protoporphyrinogen IX Oxidase: A Key Enzyme in Haem and Chlorophyll Biosynthesis. EMBO 23:1720-1728.

Koehler and Ho. 1990. Hormonal Regulation, Processing, and Secretion of Cysteine Proteinases in Barley Aleurone Layers. Plant Cell 2: 769-783.

Lee, H. J. and S. O. Duke. 1994. Protoporphyrinogen IX-Oxidizing Activities Involved in the Mode of Action of Peroxidizing Herbicides. J. Agric. Food Chem. 42:2610-2618.

Lee, H. J. et al. 1993. Cellular Localization of Protoporphyrinogen—Oxidizing Activities of Etiolated Barley (Hordeum vulgare L.) Leaves. Plant Physiol. 102:881-889.

Lee, H. J. et al. 2000. Transgenic Rice Plants Expressing a Bacillus subtilis Protoporphyrinogen Oxidase Gene are Resistant to Diphenyl Ether Herbicide Oxyfluorfen. Plant Cell Physiol. 41:743-749.

Lee, Y., Jung, S., and Back, K. (2004) Expression of Human Protoporphyrinogen Oxidase in Transgenic Rice Induces Both a Photodynamic Response and Oxyfluorfen Resistance. Pestic. Biochem. Physiol. 80, 65-74.

Lermontova, I. and B. Grimm. 2000. Overexpression of Plastidic Protoporphyrinogen IX Oxidase Leads to Resistance to the Diphehyl-Ether Herbicide Acifluorfen. Plant Physiol. 122:75-83.

Lermontova, I. et al. 1997. Cloning and Characterization of a Plastidal and a Mitochondrial Isoform of Tobacco Protoporphyrinogen IX Oxidase. PNAS 94:8895-8900.

Li et al. 2004. Physiological basis for Resistance to Diphenyl Ether Herbicides in Common Waterhemp (Amaranthus rudis) Weed Sci. 52: 333-338.

Li, X. and D. Nicholl. 2005. Development of PPO Inhibitor-Resistant Cultures and Crops. Pest Manag. Sci. 61:277-285.

Li et al. 2003. Development of Protoporphyrinogen Oxidase as an Efficient Selection Marker for Agrobacterium tumefaciens-Mediated Transformation of Maize. Plant Physiol. 133:736-747.

Lyga et al. 1994. Synthesis Mechanism of Action, and QSAR of Herbicidal 3-Substituted-2-aryl-4,5,6,7-tetrahydroindazoles. Pesticide Sci. 42:29-36.

Martz, E. 2002. Protein Explorer: Easy Yet Powerful Macromolecular Visualization. Trends Biochem. Sci. 27: 107-109.

Matringe et al. 1989. Protoporphyrinogen Oxidase as a Molecular Target for Diphenyl Ether Hericides. Biochem. J. 260: 231-235.

Matringe et al. 1989. Protoporphyrinogen Oxidase Inhibition by Three Peroxidizing Herbicides: Oxidation, LS 82-556 and M&B 39279. FEBS Lett. 245: 35-38.

Matringe, M. et al. 1992. Localization Within Chloroplasts of Protoporphyrinogen Oxidase, The Target Enzyme for Diphenylether-Like Herbicides. J. Biol. Chem. 267:4646-4651.

McBride et al. 1994. Controlled Expression of Plastid Transgenes in Plants Based on a Nuclear DNA-encoded and Plastid-Targeted T7 RNA Polymerase. Proc. Natl. Acad. Sci. USA 91: 7301-7305.

Nandihalli et al. 1992. Quantitative Structure—Activity Relationships of Protoporphyrinogen Oxidase-inhibiting Diphenyl Ether Herbicides. Pesticide Biochem. Physiol. 43: 193-211.

Narita, S. et al. 1996. Molecular Cloning and Characterization of a cDNA that Encodes Protoporphyrinogen Oxidase of Arabidopsis thaliana. Gene 182:169-175.

Oshio et al. 1993. Isolation and Characterization of a Chlamydomonas reinhardtii Mutant Resistant to Photobleaching Herbicides. Z. Naturforsch. 48c: 339-344.

Papenbrock, J. and B. Grimm. 2001. Regulatory Network of Tetrapyrrole Biosynthesis—Studies of Intracellular Signalling Involved in Metabolic and Developmental Control of Plastids. Planta 213:667-681.

Patzold et al. 2002. Variable Herbicide Responses Among Illinois Waterhemp (Amaranthus rudis and A. tuberculatus) Populations. Crop Prot. 21:707-712.

Patzoldt et al. 2005. A Waterhemp (Amaranthus tuberculatus) Biotype with Multiple Resistance Across Three Herbicide Sites of Action. Weed Sci. 53:30-36.

Patzoldt et al. 2001. A Common Ragweed Population Resistant to Cloransulam-Methyl. Weed Sci. 49: 485-490.

Patzoldt et al. 2006. A Codon Deletion Confers Resistance to Herbicides Inhibiting Protoporphyrinogen Oxidase. PNAS. 103:12329-12334.

Patzoldt, W.L., et al. Aug. 18, 2006. *Amaranthus tuberculatus* Biotype Herbicide-Susceptible WC Plastid Protoporphyrinogen Oxidase (PPX!) mRNA; Nuclear Gene for Plastid Product. NCBI GenBank accession DQ386112.

Patzoldt, W.L., et al. Aug. 18, 2006. *Amaranthus tuberculatus* Biotype Herbicide-Susceptible WC Plastid Protoporphyrinogen Oxidase (PPX1) mRNA; Nuclear Gene for Plastid Product. NCBI GenBank accession DQ386113.

Patzoldt, W.L., et al. Aug. 18, 2006. *Amaranthus tuberculatus* Biotype Herbicide-Susceptible WC Plastid Protoporphyrinogen Oxidase (PPX1) mRNA; Nuclear Gene for Plastid Product. NCBI GenBank accession DQ386114.

Patzoldt, W.L., et al. Aug. 18, 2006. *Amaranthus tuberculatus* Biotype Herbicide-Susceptible WC Plastid Protoporphyrinogen Oxidase (PPX1) mRNA; Nuclear Gene for Plastid Product. NCBI GenBank accession DQ386115.

Patzoldt, W.L., et al. Aug. 18, 2006. *Amaranthus tuberculatus* Biotype Herbicide-Susceptible WC Plastid Protoporphyrinogen Oxidase (PPX1) mRNA; Nuclear Gene for Plastid Product. NCBI GenBank accession DQ386116.

Patzoldt, W.L., et al. Aug. 18, 2006. *Amaranthus tuberculatus* Biotype Herbicide-Susceptible WC Plastid Protoporphyrinogen Oxidase (PPX1) mRNA; Nuclear Gene for Plastid Product. NCBI GenBank accession DQ386117.

Patzoldt, W.L., et al. Aug. 18, 2006. *Amaranthus tuberculatus* Biotype Herbicide-Susceptible WC Plastid Protoporphyrinogen Oxidase (PPX1) mRNA; Nuclear Gene for Plastid Product. NCBI GenBank accession DQ386118.

Patzoldt, W.L., et al. Aug. 18, 2006 *Amaranthus tuberculatus* Biotype Herbicide-Susceptible WC Plastid Protoporphyrinogen Oxidase (PPX1) mRNA; Nuclear Gene for Plastid Product. NCBI GenBank accession DQ394875.

Patzoldt, W.L., et al. Aug. 18, 2006. *Amaranthus tuberculatus* Biotype Herbicide-Susceptible WC Plastid Protoporphyrinogen Oxidase (PPX!) mRNA; Nuclear Gene for Plastid Product. NCBI GenBank accession DQ394876.

Pornprom, T. et al. 1994. Characterization of Oxyfluorfen Tolerance in Selected Soybean Cell Line. Pestic. Biochem. Physiol. 50:107-114.

Prado et al. 1979. ATP Requirement for Mg Chelatase in Developing Chloroplasts. Plant Physiol. 65: 956-960.

Retzlaff, K. and P. Böger. 1996. An Endoplasmic Reticulum Plant Enzyme Has Protoporphyrinogen IX Oxidase Activity. Pest. Biochem. Physiol. 54:105-114.

Roberts, et al. 1979. A General Method for Maximizing the Expression of a Cloned Gene. Proc. Natl. Acad. Sci. USA 76:760-764.

Rogers et al. 1985. Aleurain: A Barley Thiol Protease Closely Related to Mammalian Cathepsin H. Proc. Natl. Acad. Sci. USA 82: 6512-6516.

Sasarman, A. et al. 1993. Nucleotide Sequence of the *HemG* gene Involved in the Protoporphyrinogen Oxidase Activity of *Escherichia coli* K12. Can. J. Microbiol. 39:1155-1161.

Sasarman, A. et al. 1979. Mapping of a New *Hem* Gene in *Escherichia coli* K12. J. Gen. Microbiol. 113: 297-303.

Sato et al. 1994. Chapter 7—Characterization of a Mutant of *Chlamydomonas reinhardtii* Resistant to Protoporphyrinogen Oxidase Inhibitors. In ACS Symposium on Porphyric Pesticides, S. Duke, ed. ACS Press: Washington, DC.

Seefeldt, S. S. et al. 1995. Log-Logistic Analysis of Herbicide Dose-Response Relationships. Weed Technol. 9:218-227.

Sherman et al. 1991. Physiological Basis for Differential Sensitivities of Plant Species to Protoporphyrinogen Oxidase-Inhibiting Herbicides. Plant Physiol. 97:280-287.

Shibata et al. 1992. Isolation and Characterization of a *Chlamydomonas reinhardtii* Mutant Resistant to an Experimental Herbicide S-23142, Which Inhibits Chlorophyll Synthesis. In Research in Photosynthesis, vol. III, N. Murata, ed. Kluwer:Netherlands. pp. 567-570.

Shinshi et al. 1990. Structure of a Tobacco Endochitinase Gene: Evidence that Different Chitinase Genes can Arise by Transposition of Sequences Encoding a Cystein-Rich Domain. Plant Molec. Biol. 14: 357-368.

Shoup, D. E. and Al-Khatib, K. 2005. Fate of Acifluorfen and Lactofen in Common Waterhemp (*Amaranthus rudis*) Resistant to Protoporphyrinogen Oxidase-Inhibiting Herbicides. Weed Sci. 53: 284-289.

Shoup, D. E. et al. 2003. Common Waterhemp (*Amaranthus rudis*) Resistance to Protoporphyrinogen Oxidase-Inhibiting Herbicides. Weed Sci. 51:145-150.

Smith, A. G. et al. 1993. Investigation of the Subcellular Location of the Tetrapyrrole-Biosynthesis Enzyme Coproporphyrinogen Oxidase in Higher Plants. Biochem J. 292:503-508.

Stalker et al. 1988. Purification and Properties of a Nitrilase Specific For The Herbicide Bromoxynil and Corresponding Nucleotide Sequence Analysis Of The bxn Gene. J. Biol. Chem. 263:6310-6314.

Stalker et al. 1988. Herbicide Resistance in Transgenic Plants Expressing a Bacterial Detoxification Gene. Science. 242:419-423.

Staub et al. (1992) Long Regions of Homologous DNA Are Incorporated into the Tobacco Plastid Genome by Transformation. Plant Cell 4, 39-45.

Staub et al. 1993. Accumulation of D1 Polypeptide in Tobacco Plastids is Regulated Via the Untranslated Region of the *psbA* mRNA EMBO J. 12: 601-606.

Stone, B. F. 1968. A Formula For Determining Degree of Dominance In Cases of Monofactorial Inheritance of Resistance to Chemicals. Bull. W.H.O. 38:325-326.

Suggs, S.V. et al. 1981. Use of Synthetic Oligodeoxyribonucleotides for the Isolation of Specific Cloned DNA Sequences. ICB-UCLA Symp. Dev. Biol. Using Purified Genes, D.D. Brown (ed.), Academic Press, New York, 23:683-693.

Svab et al. 1990. Stable Transformation of Plastids in Higher Plants. Proc. Natl. Acad. Sci. USA 87: 8526-8530.

Svab et al. 1993. High-Frequency Plastid Transformation in Tobacco by Selection for a Chimeric aadA Gene. Proc. Natl. Acad. Sc. USA 90: 913-917.

Thompson et al. 1994. Clustal W: Improving the Sensitivity of Progressive Multiple Sequence Alignment Through Sequence Weighting, Position-Specific Gap Penalties and Weight Matrix Choice Nucleic Acids Res. 22: 4673-4690.

Unger et al. 1989. Isolation of a cDNA Encoding Mitochondrial Citrate Synthase from *Arabidopsis thaliana*. Plant Molec. Biol. 13: 411-418.

van den Broeck et al. 1985. Targeting of a Foreign Protein to Chloroplasts by Fusion to the Transit Peptide From the Small Subunit of Ribulose 1, 5-Bisphosphate Carboxylase. Nature 313: 358-363.

Wasmann et al. 1986. The Importance of the Transit Peptide and the Transported Protein for Protein Import into Chloroplasts. Mol. Gen. Genet. 205: 446-453.

Watanabe, N. et al. 1998. Molecular Characterization of Photomixotrophic Tobacco Cells Resistant to Protoporphyrinogen Oxidase-Inhibiting Herbicides. Plant Physiol. 118:751-758.

Watanabe, N. et al. 2001. Dual Targeting of Spinach Protoporphyrinogen Oxidase II to Mitochondria and Chloroplasts by Alternative Use of Two In-Frame Initiation Codons. J. Biol. Chem. 276:20474-20481.

Written Opinion of the International Searching Authority for PCT/US06/32453.

Xu et al. 1992. The Genes Required for Heme Synthesis in *Salmonella typhimurium* Include Those Encoding Alternative Functions For Aerobic and Anaerobic Coproporphyrinogen Oxidation. J. Bacteriol. 174: 3953-3963.

Yanase and Andoh. 1989. Porphyrin Synthesis Involvement in Diphenyl Ether-Like Mode of Action of TNPP-Ethyl, A Novel Phenylpyrazole Herbicide. Pesticide Biochem. Physiol. 35: 70-80.

Yang, H. et al. 1996. Proc. Natl. Acad. Sci USA 93:2459-2463.

Beetham et al. (1999) A Tool for Functional Plant Genomics: Chimeric RNA/DNA Oligonucleotides Cause in vivo Gene-Specific Mutations. PNAS 96:8774-8778.

Dong et al. (2006) Oligonucleotide-Directed Gene Repair in Wheat Using a Transient Plasmid Gene Repair Assay System. Plant Cell Rep. 25:457-465.

Kochevenko et al (2003) Chimeric RNA/DNA Oligonucleotide-based Site-Specific Modification of the Tobacco Acetolactate Synthase Gene. Plant Phys. 132: 174-184.

Liu et al. (2001) In vivo Gene Repair of Point and Frameshift Mutations Directed by Chimeric RNA/DNA Oligonucleotides and Modified Single-Stranded Oligonucleotides. Nucleic Acids Research 29(20):4238-4250.

Okuzaki et al. (2004) Chimeric RNA/DNA Oligonucleotide-Directed Gene Targeting in Rice. Plant Cell Rep. 22:509-512.

Zhu et al (1999) Targeted Manipulation of Maize Genes in vivo Using Chimeric RNA/DNA Oligonucleotides. PNAS 96:8768-8773.

Zhu et al (2000) Engineering Herbicide-Resistant Maize Using Chimeric RNA/DNA Oligonucleotides. Nature Biotechnol. 18:555-558.

```
              1
S-WT          MVIQSITHLS PNLALPSPLS VSTKNYPVAV MGNISEREEP TSAKRVAVVG AGVSGLAAAY
S-BioAC       MVIQSITHLS PNLALPSPLS VSTKNYPVAV MGNISEREEP TSAKRVAVVG AGVSGLAAAY
R-BioAC       MVIQSITHLS PNLALPSPLS VSTKNYPVAV MGNISEREEP TSAKRVAVVG AGVSGLAAAY
R-BioCC       MVIQSITHLS PNLALPSPLS VSTKNYPVAV MGNISEREEP TSAKRVAVVG AGVSGLAAAY

61                *
S-WT          KLKSHGLSVT LFEADSRAGG KLKTVKKDGF IWDEGANTMT ESEAEVSSLI DDLGLREKQQ
S-BioAC       KLKSHGLSVT LFEADSRAGG KLKTVKKDGF IWDEGANTMT ESEAEVSSLI DDLGLREKQQ
R-BioAC       KLKSHGLSVT LFEADSRAGG KLKTVKKDGF IWDEGANTMT ESEAEVSSLI DDLGLREKQQ
R-BioCC       KLKSHGLSVT LFEANSRAGG KLKTVKKDGF IWDEGANTMT ESEAEVSSLI DDLGLREKQQ

121               *
S-WT          LPISQNKRYI ARDGLPVLLF SNPAALLTSN ILSAKSKLQI MLEPFLWRKH NATELSDEHV
S-BioAC       LPISQNKRYI ARAGLPVLLF SNPAALLTSN ILSAKSKLQI MLEPFLWRKH NATELSDEHV
R-BioAC       LPISQNKRYI ARDGLPVLLF SNPAALLTSN ILSAKSKLQI MLEPFLWRKH NATELSDEHV
R-BioCC       LPISQNKRYI ARDGLPVLLF SNPAALLTSN ILSAKSKLQI MLEPFLWRKH NATELSDEHV

181                                  *         *
S-WT          QESVGEFFER HFGKEFVDYV IDPFVAGTC▓ GDPQSLSMHH TFPEVWNIEK RFGSVFAGLI
S-BioAC       QESVGEFFER HFGKEFVDYV IDPFVAGTC▓ GDPQSLSMHH TFPEVWNIEK RFGSVFAGLI
R-BioAC       QESVGEFFER HFGKEFVDYV IDPFVAGTC▓ GDPQSLSMHH TFPEVWNIEK RFGSVFAGLI
R-BioCC       QESVGEFFER HFGKEFVDYV IDPFVAGTC▓ GDPQSLSMYH TFPEVWNIEK RFGSVFAGLI

241
S-WT          QSTLLSKKEK GGENASIKKP RVRGSFSFQG GMQTLVDTMC KQLGEDELKL QCEVLSLSYN
S-BioAC       QSTLLSKKEK GGENASIKKP RVRGSFSFQG GMQTLVDTMC KQLGEDELKL QCEVLSLSYN
R-BioAC       QSTLLSKKEK GGENASIKKP RVRGSFSFQG GMQTLVDTMC KQLGEDELKL QCEVLSLSYN
R-BioCC       QSTLLSKKEK GGENASIKKP RVRGSFSFQG GMQTLVDTMC KQLGEDELKL QCEVLSLSYN

301
S-WT          QKGIPSLGNW SVSSMSNNTS EDQSYDAVVV TAPIRNVKEM KIMKFGNPFS LDFIPEVTYV
S-BioAC       QKGIPSLGNW SVSSMSNNTS EDQSYDAVVV TAPIRNVKEM KIMKFGNPFS LDFIPEVTYV
R-BioAC       QKGIPSLGNW SVSSMSNNTS EDQSYDAVVV TAPIRNVKEM KIMKFGNPFS LDFIPEVTYV
R-BioCC       QKGIPSLGNW SVSSMSNNTS EDQSYDAVVV TAPIRNVKEM KIMKFGNPFS LDFIPEVTYV

361
S-WT          PLSVMITAFK KDKVKRPLEG FGVLIPSKEQ HNGLKTLGTL FSSMMFPDRA PSDMCLFTTF
S-BioAC       PLSVMITAFK KDKVKRPLEG FGVLIPSKEQ HNGLKTLGTL FSSMMFPDRA PSDMCLFTTF
R-BioAC       PLSVMITAFK KDKVKRPLEG FGVLIPSKEQ HNGLKTLGTL FSSMMFPDRA PSDMCLFTTF
R-BioCC       PLSVMITAFK KDKVKRPLEG FGVLIPSKEQ HNGLKTLGTL FSSMMFPDRA PSDMCLFTTF

421                                                            *
S-WT          VGGSRNRKLA NASTDELKQI VSSDLQQLLG TEDEPSFVNH LFWSNAFPLY GHNYDSVLRA
S-BioAC       VGGSRNRKLA NASTDELKQI VSSDLQQLLG TEDEPSFVNH LFWSNAFPLY GHNYDSVLRA
R-BioAC       VGGSRNRKLA NASTDELKQI VSSDLQQLLG TEDEPSFVNH LFWSNAFPLY GHNYDCVLRA
R-BioCC       VGGSRNRKLA NASTDELKQI VSSDLQQLLG TEDEPSFVNH LFWSNAFPLY GHNYDSVLRA

481
S-WT          IDKMEKDLPG FFYAGNHKGG LSVGKAMASG CKAAELVISY LDSHIYVKMD EKTA
S-BioAC       IDKMEKDLPG FFYAGNHKGG LSVGKAMASG CKAAELVISY LDSHIYVKMD EKTA
R-BioAC       IDKMEKDLPG FFYAGNHKGG LSVGKAMASG CKAAELVISY LDSHIYVKMD EKTA
R-BioCC       IDKMEKDLPG FFYAGNHKGG LSVGKAMASG CKAAELVISY LDSHIYVKMD EKTA
```

Figure 7

| | Reference Sequence SEQ ID NO:15 | SEQ ID NO:21 | Additional Sensitive PPX2L Isolate | SEQ ID NO:27 | "pBAD" Sensitive | SEQ ID NO:46 | Synthetic (Sensitive) | Synthetic (Resistant) | Additional Synthetic (Resistant) |
|---|---|---|---|---|---|---|---|---|---|
| Difference | | A to C @ 66 | | | | | A to C @ 66 | A to C @ 66 | A to C @ 66 |
| AA Change | | none | | | | | none* | none* | none* |
| Difference | | | | | | | G to A @111 | G to A @111 | G to A @111 |
| AA Change | | | | | | | none* | none* | none* |
| Difference | | | | A to C @398 | | | | | |
| AA Change | | | | D to A | | | | | |
| Difference | | | | C to T @ 603 | | | C to T @ 603 | C to T @ 603 | C to T @ 603 |
| AA Change | | | | none | | | none* | none* | none* |
| Difference | | | | | G to A @ 641 | G to A @ 641 | | | |
| AA Change | | | | | Q to R | Q to R | | | |
| Difference | | | | T to C @711 | | | | | |
| AA Change | | | | none | | | | | |
| Difference | | | | T to C @919 | | | | | |
| AA Change | | | | none | | | | | |
| Difference | | | | | A to G @ 1016 | | | | |
| AA Change | | | | | E to G | | | | |
| Difference | | | | | | | | C to T @ 1272 | C to T @ 1272 |
| AA Change | | | | | | | | none | none |
| Difference | | | | | | | C to G @ 1427 | C to G @ 1427 | C to G @ 1427 |
| AA Change | | | | | | | S to C* | S to C* | S to C* |
| Difference | | | | | | | | T to C @ 1461 | T to C @ 1461 |
| AA Change | | | | | | | | none | none |
| Difference | | | | | | | | | A to G at 1571 |
| AA Change | | | | | | | | | H to R** |
| Difference | | | T to C @ 1578 | T to C @ 1578 | T to C @ 1578 | T to C @ 1578 | T to C @ 1578 | T to C @ 1578 | T to C @ 1578 |
| AA Change | | | none | none | none | none | none | none | none |

* synthesized clone was made to match Resistant allele at these spots

Figure 10A

| Reference Sequence SEQ ID NO:13 | SEQ ID NO:25 | SEQ ID NO:21 | Additional Isolate | "pBAD" Resistant Additional Isolate | SEQ ID NO:45 | Additional Isolate | Additional Isolate |
|---|---|---|---|---|---|---|---|
| Difference | A to C @ 66 | A to C @ 66 | A to C @ 66 | | A to C @ 66 | A to C @ 66 | A to C @ 66 |
| AA Change | none | none | none | | none | none | none |
| Difference | G to A @ 111 | | | | | G to A @ 111 | G to A @ 111 |
| AA Change | none | | | | | none | none |
| Difference | | G to A @ 223 | | | | | |
| AA Change | | D to N | | | | | |
| Difference | C to T @ 603 | C to T @ 603 | | C to T @ 603 | C to T @ 603 | C to T @ 603 | C to T @ 603 |
| AA Change | none | none | | none | none | none | none |
| Difference | | | | C to T @ 652 | | | |
| AA Change | | | | H to Y | | | |
| Difference | | | | | | C to T @ 1269 | |
| AA Change | | | | | | None | |
| Difference | C to G @ 1424 | | | C to G @ 1424 | | C to G @ 1424 | C to G @ 1424 |
| AA Change | S to C | | | S to C | | S to C | S to C |
| Difference | | | | | | T to C @ 1458 | |
| AA Change | | | | | | None | |
| Difference | T to C @ 1575 | T to C @ 1575 | | T to C @ 1575 | T to C @ 1575 | T to C @ 1575 | A to G at 1568 |
| AA Change | none | none | | none | none | none | H to R** |
| Difference | | | | | | | T to C @ 1575 |
| AA Change | | | | | | | none |

NB the deletion that causes tolerance is a deletion base 628-630 in the wild-type, a glycine codon.

** not all clones carried this mutation, nor did the parent CDS only clone; it was caused by cloning or E. coli

Figure 10B

SEQUENCE LISTING

<160> NUMBER OF SEQ ID NOS: 83

<210> SEQ ID NO 1
<211> LENGTH: 22
<212> TYPE: DNA
<213> ORGANISM: Artificial
<220> FEATURE:
<223> OTHER INFORMATION: Synthetic: oligonucleotide useful as primer.

<400> SEQUENCE: 1
gagagagtgc gagagagatg ag                                              22

<210> SEQ ID NO 2
<211> LENGTH: 23
<212> TYPE: DNA
<213> ORGANISM: Artificial
<220> FEATURE:
<223> OTHER INFORMATION: Synthetic: oligonucleotide useful as primer

<400> SEQUENCE: 2
caagatgctg gagccctatt gac                                             23

<210> SEQ ID NO 3
<211> LENGTH: 22
<212> TYPE: DNA
<213> ORGANISM: Artificial
<220> FEATURE:
<223> OTHER INFORMATION: Synthetic: oligonucleotide useful as primer

<400> SEQUENCE: 3
gccatcgcca ttgtcagttt ac                                              22

<210> SEQ ID NO 4
<211> LENGTH: 24
<212> TYPE: DNA
<213> ORGANISM: Artificial
<220> FEATURE:
<223> OTHER INFORMATION: Synthetic: oligonucleotide useful as primer

<400> SEQUENCE: 4
gaattacgcg gtcttctcat ccat                                            24

<210> SEQ ID NO 5
<211> LENGTH: 25
<212> TYPE: DNA
<213> ORGANISM: Artificial
<220> FEATURE:
<223> OTHER INFORMATION: Synthetic: oligonucleotide useful as primer

```
<400> SEQUENCE: 5
gacaaaattg gattcagaat ttagc                                          25

<210> SEQ ID NO 6
<211> LENGTH: 24
<212> TYPE: DNA
<213> ORGANISM: Artificial
<220> FEATURE:
<223> OTHER INFORMATION: Synthetic:  oligonucleotide useful as primer

<400> SEQUENCE: 6
gaattacgcg gtcttctcat ccat                                           24

<210> SEQ ID NO 7
<211> LENGTH: 21
<212> TYPE: DNA
<213> ORGANISM: Artificial
<220> FEATURE:
<223> OTHER INFORMATION: Synthetic:  oligonucleotide useful as primer

<400> SEQUENCE: 7
tgataagtcg ctcaatggag a                                              21

<210> SEQ ID NO 8
<211> LENGTH: 21
<212> TYPE: DNA
<213> ORGANISM: Artificial
<220> FEATURE:
<223> OTHER INFORMATION: Synthetic:  oligonucleotide useful as primer

<400> SEQUENCE: 8
agatttgtag cacctccaat g                                              21

<210> SEQ ID NO 9
<211> LENGTH: 21
<212> TYPE: DNA
<213> ORGANISM: Artificial
<220> FEATURE:
<223> OTHER INFORMATION: Synthetic:  oligonucleotide useful as primer

<400> SEQUENCE: 9
aagagacctc ttgagggctt c                                              21

<210> SEQ ID NO 10
<211> LENGTH: 24
<212> TYPE: DNA
<213> ORGANISM: Artificial
<220> FEATURE:
<223> OTHER INFORMATION: Synthetic:  oligonucleotifde useful as primer

<400> SEQUENCE: 10
gaattacgcg gtcttctcat ccat                                           24

<210> SEQ ID NO 11
<211> LENGTH: 30
<212> TYPE: DNA
<213> ORGANISM: Artificial
<220> FEATURE:
<223> OTHER INFORMATION: Synthetic:   oligonucleotide useful as primer

<400> SEQUENCE: 11
caggaataag taatgggcaa catttctgag                                     30

<210> SEQ ID NO 12
<211> LENGTH: 24
```

<210> TYPE: DNA
<213> ORGANISM: Artificial
<220> FEATURE:
<223> OTHER INFORMATION: Synthetic: oligonucleotide useful as primer

<400> SEQUENCE: 12

```
gaagaattac gcggtcttct catc                                              24
```

<210> SEQ ID NO 13
<211> LENGTH: 1602
<212> TYPE: DNA
<213> ORGANISM: Amaranthus tuberculatus

<400> SEQUENCE: 13

```
atggtaattc aatccattac ccacctttca ccaaaccttg cattgccatc gccattgtca       60
gtttcaacca agaactaccc agtagctgta atgggcaaca tttctgagcg ggaagaaccc      120
acttctgcta aaagggttgc tgttgttggt gctggagtta gtggacttgc tgctgcatat      180
aagctaaaat cccatggttt gagtgtgaca ttgtttgaag ctgattctag agctggaggc      240
aaacttaaaa ctgttaaaaa agatggtttt atttgggatg aggggcaaa tactatgaca       300
gaaagtgagg cagaggtctc gagtttgatc gatgatcttg ggcttcgtga aagcaacag       360
ttgccaattt cacaaaataa aagatacata gctagagacg tcttcctgt gctactacct       420
tcaaatcccg ctgcactact cacgagcaat atcctttcag caaaatcaaa gctgcaaatt      480
atgttggaac catttctctg gagaaaaacac aatgctactg aactttctga tgagcatgtt     540
caggaaagcg ttggtgaatt ttttgagcga catttttggga aagagtttgt tgattatgtt     600
atcgacccctt tgttgcggg tacatgtgga gatcctcaat cgctttccat gcaccataca     660
tttccagaag tatggaatat tgaaaaaagg tttggctctg tgtttgctgg actaattcaa      720
tcaacattgt tatctaagaa ggaaaagggt ggagaaaatg cttctattaa gaagcctcgt      780
gtacgtggtt cattttcatt tcaaggtgga atgcagacac ttgttgacac aatgtgcaaa      840
cagcttggtg aagatgaact caaactccag tgtgaggtgc tgtccttgtc atataaccag      900
aaggggatcc cctcattagg gaattggtca gtctcttcta tgtcaaataa taccagtgaa      960
gatcaatctt atgatgctgt ggttgtcact gctccaattc gcaatgtcaa agaaatgaag     1020
attatgaaat ttgaaaatcc attttcactt gactttattc cagaggtgac gtacgtaccc     1080
ctttccgtta tgattactgc attcaaaaag ataaagtga agagacctct tgagggcttc     1140
ggagttctta tccctctaa agagcaacat aatggactga agactcttgg tactttattt     1200
tcctccatga tgtttcctga tcgtgctcca tctgacatgt gtctctttac tacatttgtc     1260
ggaggaagca gaaatagaaa acttgcaaac gcttcaacgg atgaattgaa gcaaatagtt     1320
tcttctgacc ttcagcagct gttgggcact gaggacgaac cttcatttgt caatcatctc     1380
ttttggagca acgcattccc attgtatgga cacaattacg attctgtttt gagagccata     1440
gacaagatgg aaaaggatct tcctggattt ttttatgcag gtaaccataa gggtggactt     1500
tcagtgggaa aagcgatggc ctccggatgc aaggctgcgg aacttgtaat atcctatctg     1560
gactctcata tatatgtgaa gatggatgag aagaccgcgt aa                        1602
```

<210> SEQ ID NO 14
<211> LENGTH: 533
<212> TYPE: PRT
<213> ORGANISM: Amaranthus tuberculatus

<400> SEQUENCE: 14

-continued

```
Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Pro Thr Ser Ala Lys Arg Val Ala Val
        35              40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
            115                 120                 125

Tyr Ile Ala Arg Asp Gly Leu Pro Val Leu Leu Pro Ser Asn Pro Ala
        130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Asp Pro Gln Ser Leu Ser Met His His Thr Phe Pro Glu Val
    210                 215                 220

Trp Asn Ile Glu Lys Arg Phe Gly Ser Val Phe Ala Gly Leu Ile Gln
225                 230                 235                 240

Ser Thr Leu Leu Ser Lys Lys Glu Lys Gly Gly Glu Asn Ala Ser Ile
                245                 250                 255

Lys Lys Pro Arg Val Arg Gly Ser Phe Ser Phe Gln Gly Gly Met Gln
            260                 265                 270

Thr Leu Val Asp Thr Met Cys Lys Gln Leu Gly Glu Asp Glu Leu Lys
        275                 280                 285

Leu Gln Cys Glu Val Leu Ser Leu Ser Tyr Asn Gln Lys Gly Ile Pro
    290                 295                 300

Ser Leu Gly Asn Trp Ser Val Ser Ser Met Ser Asn Thr Ser Glu
305                 310                 315                 320

Asp Gln Ser Tyr Asp Ala Val Val Val Thr Ala Pro Ile Arg Asn Val
            325                 330                 335

Lys Glu Met Lys Ile Met Lys Phe Gly Asn Pro Phe Ser Leu Asp Phe
        340                 345                 350

Ile Pro Glu Val Thr Tyr Val Pro Leu Ser Val Met Ile Thr Ala Phe
    355                 360                 365

Lys Lys Asp Lys Val Lys Arg Pro Leu Glu Gly Phe Gly Val Leu Ile
        370                 375                 380

Pro Ser Lys Glu Gln His Asn Gly Leu Lys Thr Leu Gly Thr Leu Phe
385                 390                 395                 400

Ser Ser Met Met Phe Pro Asp Arg Ala Pro Ser Asp Met Cys Leu Phe
                405                 410                 415

Thr Thr Phe Val Gly Gly Ser Arg Asn Arg Lys Leu Ala Asn Ala Ser
```

```
                    420              425              430
Thr Asp Glu Leu Lys Gln Ile Val Ser Ser Asp Leu Gln Gln Leu Leu
            435                  440                  445

Gly Thr Glu Asp Glu Pro Ser Phe Val Asn His Leu Phe Trp Ser Asn
        450                  455                  460

Ala Phe Pro Leu Tyr Gly His Asn Tyr Asp Ser Val Leu Arg Ala Ile
465                  470                  475                  480

Asp Lys Met Glu Lys Asp Leu Pro Gly Phe Phe Tyr Ala Gly Asn His
                485                  490                  495

Lys Gly Gly Leu Ser Val Gly Lys Ala Met Ala Ser Gly Cys Lys Ala
            500                  505                  510

Ala Glu Leu Val Ile Ser Tyr Leu Asp Ser His Ile Tyr Val Lys Met
        515                  520                  525

Asp Glu Lys Thr Ala
        530

<210> SEQ ID NO 15
<211> LENGTH: 1605
<212> TYPE: DNA
<213> ORGANISM: Amaranthus tuberculatus

<400> SEQUENCE: 15
atggtaattc aatccattac ccacctttca ccaaaccttg cattgccatc gccattgtca      60
gtttcaacca agaactaccc agtagctgta atgggcaaca tttctgagcg ggaagaaccc     120
acttctgcta aagggttgc tgttgttggt gctggagtta gtggacttgc tgctgcatat     180
aagctaaaat cccatggttt gagtgtgaca ttgtttgaag ctgattctag agctggaggc     240
aaacttaaaa ctgttaaaaa agatggtttt atttgggatg aggggggaaa tactatgaca     300
gaaagtgagg cagaggtctc gagtttgatc gatgatcttg gcttcgtga aagcaacag      360 ttgccaattt cacaaaataa aagatacata gctagagacg tcttcctgt gctactacct     420 tcaaatcccg ctgcactact cacgagcaat atccctttcag caaaatcaaa gctgcaaatt     480
atgttggaac catttctctg gagaaaacac aatgctactg aactttctga tgagcatgtt     540
caggaaagcg ttggtgaatt ttttgagcga cattttggga agagtttgt tgattatgtt     600 atcgacccct tgttgcgggt acatgtggt ggagatcctc aatcgctttc catgcaccat     660
acatttccag aagtatggaa tattgaaaaa ggtttggct ctgtgtttgc tggactaatt     720
caatcaacat tgttatctaa gaaggaaaag ggtggagaaa atgcttctat taagaagcct     780
cgtgtacgtg gttcattttc atttcaaggt ggaatgcaga cacttgttga cacaatgtgc     840
aaacagcttg gtgaagatga actcaaactc cagtgtgagg tgctgtcctt gtcatataac     900
cagaagggga tcccctcatt agggaattgg tcagtctctt ctatgtcaaa aataccagt     960 gaagatcaat cttatgatgc tgtggttgtc actgctccaa ttcgcaatgt caaagaaatg    1020
aagattatga atttggaaa tccattttca cttgactta ttccagaggt gacgtacgta    1080
cccctttccg ttatgattac tgcattcaaa aaggataaag tgaagagacc tcttgagggc    1140
ttcggagttc ttatcccctc taagagcaa cataatggac tgaagactct tggtacttta    1200
ttttcctcca tgatgtttcc tgatcgtgct ccatctgaca tgtgtctctt tactacatt    1260 gtcggaggaa gcagaaatag aaaacttgca aacgcttcaa cggatgaatt gaagcaaata    1320
gtttcttctg accttcagca gctgttgggc actgaggacg aaccttcatt tgtcaatcat    1380
ctcttttgga gcaacgcatt cccattgtat ggacacaatt acgattctgt tttgagagcc    1440
```

```
atagacaaga tggaaaagga tcttcctgga ttttttatg caggtaacca taagggtgga    1500
ctttcagtgg gaaaagcgat ggcctccgga tgcaaggctg cggaacttgt aatatcctat    1560
ctggactctc atatatatgt gaagatggat gagaagaccg cgtaa                    1605
```

<210> SEQ ID NO 16
<211> LENGTH: 534
<212> TYPE: PRT
<213> ORGANISM: Amaranthus tuberculatus

<400> SEQUENCE: 16

```
Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Gly Asp Pro Gln Ser Leu Ser Met His His Thr Phe Pro Glu
    210                 215                 220

Val Trp Asn Ile Glu Lys Arg Phe Gly Ser Val Phe Ala Gly Leu Ile
225                 230                 235                 240

Gln Ser Thr Leu Leu Ser Lys Lys Glu Lys Gly Gly Glu Asn Ala Ser
                245                 250                 255

Ile Lys Lys Pro Arg Val Arg Gly Ser Phe Ser Phe Gln Gly Gly Met
            260                 265                 270

Gln Thr Leu Val Asp Thr Met Cys Lys Gln Leu Gly Glu Asp Glu Leu
        275                 280                 285

Lys Leu Gln Cys Glu Val Leu Ser Leu Ser Tyr Asn Gln Lys Gly Ile
    290                 295                 300

Pro Ser Leu Gly Asn Trp Ser Val Ser Ser Met Ser Asn Asn Thr Ser
305                 310                 315                 320

Glu Asp Gln Ser Tyr Asp Ala Val Val Thr Ala Pro Ile Arg Asn
                325                 330                 335

Val Lys Glu Met Lys Ile Met Lys Phe Gly Asn Pro Phe Ser Leu Asp
            340                 345                 350
```

```
Phe Ile Pro Glu Val Thr Tyr Val Pro Leu Ser Val Met Ile Thr Ala
        355                 360                 365
Phe Lys Lys Asp Lys Val Lys Arg Pro Leu Glu Gly Phe Gly Val Leu
        370                 375                 380
Ile Pro Ser Lys Glu Gln His Asn Gly Leu Lys Thr Leu Gly Thr Leu
385                 390                 395                 400
Phe Ser Ser Met Met Phe Pro Asp Arg Ala Pro Ser Asp Met Cys Leu
                405                 410                 415
Phe Thr Thr Phe Val Gly Gly Ser Arg Asn Arg Lys Leu Ala Asn Ala
                420                 425                 430
Ser Thr Asp Glu Leu Lys Gln Ile Val Ser Ser Asp Leu Gln Gln Leu
        435                 440                 445
Leu Gly Thr Glu Asp Glu Pro Ser Phe Val Asn His Leu Phe Trp Ser
    450                 455                 460
Asn Ala Phe Pro Leu Tyr Gly His Asn Tyr Asp Ser Val Leu Arg Ala
465                 470                 475                 480
Ile Asp Lys Met Glu Lys Asp Leu Pro Gly Phe Phe Tyr Ala Gly Asn
                485                 490                 495
His Lys Gly Gly Leu Ser Val Gly Lys Ala Met Ala Ser Gly Cys Lys
                500                 505                 510
Ala Ala Glu Leu Val Ile Ser Tyr Leu Asp Ser His Ile Tyr Val Lys
        515                 520                 525
Met Asp Glu Lys Thr Ala
        530

<210> SEQ ID NO 17
<211> LENGTH: 1653
<212> TYPE: DNA
<213> ORGANISM: Amaranthus tuberculatus

<400> SEQUENCE: 17
atgagtgcga tggcgttatc gagcagcatt ctacaatgtc cgccgcactc cgacatctcg      60
ttccgctttt ttgctcatac acgaacccaa ccccccatct tcttcggaag accacgaaaa     120
ttatcatata tccattgttc cacaagctca agctcaactg ccaattacca gaacaccatt     180
acgagccaag gagaaggaga taaagtatta gattgtgtaa ttgttggagc tggtatcagt     240
ggactttgca ttgctcaggc tctttctacc aaacacattc aatccaatct caatttcatt     300
gtcactgaag ctaaacatcg tgttggaggt aatatcacta ccatggagtc cgatggctat     360
atctgggaag agggtcctaa tagtttccaa ccctccgatc ctgtgcttac tatggcggtt     420
gacagtggat tgaaagacga tttggtcttg gagatcccta atgcccctcg tttcgtgctc     480
tggaatggta aattaaggcc tgttccttcc aaacctacgg accttccctt ttttgatctc     540
atgagctttc ctggtaagat tagggctggt cttggtgcac ttggtcttcg tcctcctcct     600
ccttcttatg aggaatctgt tgaagaattt gtgcgccgta atctcggcga tgaggtcttc     660
gaacgcttga tcgaaccctt tgttctggt gtctatgctg gtgatcctgc aaagttgagt     720
atgaaagctg catttggaaa ggtctggacc ttagagcaaa agggtggtag tatcatagcc     780
ggtacactca aaactattca ggaaaggaaa ataatcctc acccccctcg agaccccgc      840
cttcctaaac ctaagggcca gactgttgga tcctttagga aagggctcat tatgttacct     900
accgccattg ctgctaggct tggcagtaaa gtcaaactat cgtggacact ttctaatatt     960
gataagtcgc tcaatggaga atacaatctc acttatcaaa cacccgatgg accggtttct    1020
```

-continued

```
gttaggacca aagcggttgt catgaccgtc ccttcgtaca ttgcaagtag cttgcttcgt      1080
ccgctctcag atgttgctgc agattctctt tctaaatttt actatccacc agtcgcagca      1140
gtgtcccttt cttatcccaa agaagcaatt agaccagaat gcttgatcga tggtgaacta      1200
aaaggattcg ggcaattgca tccccgcagc cagggtgtgg aaaccttggg aacaatttat      1260
agttcatctc ttttccctgg tcgagcaccc cccggtagga ccttgatctt gagctacatt      1320
ggaggtgcta caaatcttgg catattacaa aagagtgaag atgaacttgc ggagacagtt      1380
gataaggatc tcagaaaaat tctgataaat ccaaatgcga aaggcagccg tgttctggga      1440
gtgagagtat ggccaaaagc aatcccccaa tttttagttg gtcactttga tgtgctagat      1500
gctgcaaaag ctggtttggc aaatgctggg caaaaggggt tgtttcttgg tggtaattat      1560
gtatcaggtg ttgccttggg gaggtgtata gagggtgctt atgactctgc ttctgaggta      1620
gtggatttcc tctcacagta caaagataag tag                                   1653
```

<210> SEQ ID NO 18
<211> LENGTH: 550
<212> TYPE: PRT
<213> ORGANISM: Amaranthus tuberculatus

<400> SEQUENCE: 18

```
Met Ser Ala Met Ala Leu Ser Ser Ile Leu Gln Cys Pro Pro His
1               5                   10                  15

Ser Asp Ile Ser Phe Arg Phe Ala His Thr Arg Thr Gln Pro Pro
            20                  25                  30

Ile Phe Phe Gly Arg Pro Arg Lys Leu Ser Tyr Ile His Cys Ser Thr
            35                  40                  45

Ser Ser Ser Ser Thr Ala Asn Tyr Gln Asn Thr Ile Thr Ser Gln Gly
    50                  55                  60

Glu Gly Asp Lys Val Leu Asp Cys Val Ile Val Gly Ala Gly Ile Ser
65                  70                  75                  80

Gly Leu Cys Ile Ala Gln Ala Leu Ser Thr Lys His Ile Gln Ser Asn
                85                  90                  95

Leu Asn Phe Ile Val Thr Glu Ala Lys His Arg Val Gly Gly Asn Ile
            100                 105                 110

Thr Thr Met Glu Ser Asp Gly Tyr Ile Trp Glu Glu Gly Pro Asn Ser
        115                 120                 125

Phe Gln Pro Ser Asp Pro Val Leu Thr Met Ala Val Asp Ser Gly Leu
    130                 135                 140

Lys Asp Asp Leu Val Leu Gly Asp Pro Asn Ala Pro Arg Phe Val Leu
145                 150                 155                 160

Trp Asn Gly Lys Leu Arg Pro Val Pro Ser Lys Pro Thr Asp Leu Pro
                165                 170                 175

Phe Phe Asp Leu Met Ser Phe Pro Gly Lys Ile Arg Ala Gly Leu Gly
            180                 185                 190

Ala Leu Gly Leu Arg Pro Pro Pro Ser Tyr Glu Glu Ser Val Glu
        195                 200                 205

Glu Phe Val Arg Arg Asn Leu Gly Asp Glu Val Phe Glu Arg Leu Ile
    210                 215                 220

Glu Pro Phe Cys Ser Gly Val Tyr Ala Gly Asp Pro Ala Lys Leu Ser
225                 230                 235                 240

Met Lys Ala Ala Phe Gly Lys Val Trp Thr Leu Glu Gln Lys Gly Gly
                245                 250                 255

Ser Ile Ile Ala Gly Thr Leu Lys Thr Ile Gln Glu Arg Lys Asn Asn
```

|     |     |     |     | 260 |     |     |     |     | 265 |     |     |     |     | 270 |     |
| --- | --- | --- | --- | --- | --- | --- | --- | --- | --- | --- | --- | --- | --- | --- | --- |
| Pro | Pro | Pro | Pro | Arg | Asp | Pro | Arg | Leu | Pro | Lys | Pro | Lys | Gly | Gln | Thr |
|     |     |     | 275 |     |     |     |     | 280 |     |     |     |     | 285 |     |     |

Val Gly Ser Phe Arg Lys Gly Leu Ile Met Leu Pro Thr Ala Ile Ala
    290                 295                 300

Ala Arg Leu Gly Ser Lys Val Lys Leu Ser Trp Thr Leu Ser Asn Ile
305                 310                 315                 320

Asp Lys Ser Leu Asn Gly Glu Tyr Asn Leu Thr Tyr Gln Thr Pro Asp
                325                 330                 335

Gly Pro Val Ser Val Arg Thr Lys Ala Val Val Met Thr Val Pro Ser
            340                 345                 350

Tyr Ile Ala Ser Ser Leu Leu Arg Pro Leu Ser Asp Val Ala Ala Asp
                355                 360                 365

Ser Leu Ser Lys Phe Tyr Tyr Pro Pro Val Ala Ala Val Ser Leu Ser
    370                 375                 380

Tyr Pro Lys Glu Ala Ile Arg Pro Glu Cys Leu Ile Asp Gly Glu Leu
385                 390                 395                 400

Lys Gly Phe Gly Gln Leu His Pro Arg Ser Gln Gly Val Glu Thr Leu
                405                 410                 415

Gly Thr Ile Tyr Ser Ser Ser Leu Phe Pro Gly Arg Ala Pro Pro Gly
            420                 425                 430

Arg Thr Leu Ile Leu Ser Tyr Ile Gly Gly Ala Thr Asn Leu Gly Ile
                435                 440                 445

Leu Gln Lys Ser Glu Asp Glu Leu Ala Glu Thr Val Asp Lys Asp Leu
    450                 455                 460

Arg Lys Ile Leu Ile Asn Pro Asn Ala Lys Gly Ser Arg Val Leu Gly
465                 470                 475                 480

Val Arg Val Trp Pro Lys Ala Ile Pro Gln Phe Leu Val Gly His Phe
                485                 490                 495

Asp Val Leu Asp Ala Ala Lys Ala Gly Leu Ala Asn Ala Gly Gln Lys
            500                 505                 510

Gly Leu Phe Leu Gly Gly Asn Tyr Val Ser Gly Val Ala Leu Gly Arg
    515                 520                 525

Cys Ile Glu Gly Ala Tyr Asp Ser Ala Ser Glu Val Val Asp Phe Leu
530                 535                 540

Ser Gln Tyr Lys Asp Lys
545                 550

<210> SEQ ID NO 19
<211> LENGTH: 1518
<212> TYPE: DNA
<213> ORGANISM: Amaranthus tuberculatus

<400> SEQUENCE: 19

| atgggcaaca tttctgagcg ggatgaaccc acttctgcta aaagggttgc tgttgttggt | 60 |
| gctggagtta gtggacttgc tgctgcatat aagctaaaat cccatggttt gaatgtgaca | 120 |
| ttgtttgaag ctgattctag agctggaggc aaacttaaaa ctgttaaaaa agatggtttt | 180 |
| atttgggatg agggggcaaa tactatgaca gaaagtgagg cagaagtctc gagtttgatc | 240 |
| gatgatcttg gcttcgtga aagcaacag ttgccaattt cacaaaataa agatacata | 300 |
| gctagagatg gtcttcctgt gctactacct tcaaatcccg ctgcactgct cacgagcaat | 360 |
| atcctttcag caaaatcaaa gctgcaaatt atgttggaac cattttttctg agaaaacac | 420 |
| aatgctactg agctttctga tgagcatgtt caggaaagcg ttggtgaatt ttttgagcga | 480 |

-continued

```
catttttggga aagagtttgt tgattatgtt attgaccctt ttgttgcggg tacatgtggt      540
ggagatcctc aatcgctttc tatgcaccat acatttccag aagtatggaa tattgaaaaa      600
aggtttggct ctgtgtttgc tggactaatt caatcaacat tgttatctaa gaaggaaaag      660
ggtggaggag gaaatgcttc tatcaagaag cctcgtgtac gtggttcatt ttcattccat      720
ggtggaatgc agacacttgt tgacacaata tgcaaacagc ttggtgaaga tgaactcaaa      780
ctccagtgtg aggtgctgtc cttgtcatac aaccagaagg ggatcccttc attagggaat      840
tggtcagtct cttctatgtc aaataatacc agtgaagatc aatcttatga tgctgtggtt      900
gtcactgctc caattcgcaa tgtcaaagaa atgaagatta tgaaattcgg aaatccattt      960
tcacttgact ttattccaga ggtgagttac gtaccctct ctgttatgat tactgcattc     1020
aagaaggata aagtgaagag accactcgag ggctttggag ttcttatccc ctctaaagag     1080
caacataatg gactgaagac tcttggtact ttatttcct ccatgatgtt tcccgatcgt     1140
gctccatctg acatgtgtct ctttactaca tttgtcggag gaagcagaaa tagaaaactt     1200
gcaaacgctt caacggatga attgaagcaa atagtttctt ctgaccttca gcagctgttg     1260
ggcactgagg acgaaccttc atttgtcaat catctctttt ggagcaacgc attcccgttg     1320
tatggacaca attacgattc tgttttgaga gccatagaca agatggaaaa ggatcttcct     1380 ggatttttt atgcaggtaa ccataagggt ggactttcag tgggaaaagc gatggcctcc     1440
ggatgcaagg ctgcggaact tgtaatatcc tatctggact ctcatatata tgtgaagatg     1500
gatgagaaga ccgcgtaa                                                   1518
```

<210> SEQ ID NO 20
<211> LENGTH: 505
<212> TYPE: PRT
<213> ORGANISM: Amaranthus tuberculatus

<400> SEQUENCE: 20

```
Met Gly Asn Ile Ser Glu Arg Asp Glu Pro Thr Ser Ala Lys Arg Val
1               5                   10                  15

Ala Val Val Gly Ala Gly Val Ser Gly Leu Ala Ala Ala Tyr Lys Leu
            20                  25                  30

Lys Ser His Gly Leu Asn Val Thr Leu Phe Glu Ala Asp Ser Arg Ala
        35                  40                  45

Gly Gly Lys Leu Lys Thr Val Lys Lys Asp Gly Phe Ile Trp Asp Glu
    50                  55                  60

Gly Ala Asn Thr Met Thr Glu Ser Glu Ala Glu Val Ser Ser Leu Ile
65                  70                  75                  80

Asp Asp Leu Gly Leu Arg Glu Lys Gln Gln Leu Pro Ile Ser Gln Asn
                85                  90                  95

Lys Arg Tyr Ile Ala Arg Asp Gly Leu Pro Val Leu Leu Pro Ser Asn
            100                 105                 110

Pro Ala Ala Leu Leu Thr Ser Asn Ile Leu Ser Ala Lys Ser Lys Leu
        115                 120                 125

Gln Ile Met Leu Glu Pro Phe Phe Trp Arg Lys His Asn Ala Thr Glu
    130                 135                 140

Leu Ser Asp Glu His Val Gln Glu Ser Val Gly Glu Phe Phe Glu Arg
145                 150                 155                 160

His Phe Gly Lys Glu Phe Val Asp Tyr Val Ile Asp Pro Phe Val Ala
                165                 170                 175

Gly Thr Cys Gly Gly Asp Pro Gln Ser Leu Ser Met His His Thr Phe
```

```
                180             185              190
Pro Glu Val Trp Asn Ile Glu Lys Arg Phe Gly Ser Val Phe Ala Gly
            195                 200                 205
Leu Ile Gln Ser Thr Leu Leu Ser Lys Lys Glu Lys Gly Gly Gly Gly
            210                 215                 220
Asn Ala Ser Ile Lys Lys Pro Arg Val Arg Gly Ser Phe Ser Phe His
225                 230                 235                 240
Gly Gly Met Gln Thr Leu Val Asp Thr Ile Cys Lys Gln Leu Gly Glu
                245                 250                 255
Asp Glu Leu Lys Leu Gln Cys Glu Val Leu Ser Leu Ser Tyr Asn Gln
            260                 265                 270
Lys Gly Ile Pro Ser Leu Gly Asn Trp Ser Val Ser Ser Met Ser Asn
            275                 280                 285
Asn Thr Ser Glu Asp Gln Ser Tyr Asp Ala Val Val Thr Ala Pro
290                 295                 300
Ile Arg Asn Val Lys Glu Met Lys Ile Met Lys Phe Gly Asn Pro Phe
305                 310                 315                 320
Ser Leu Asp Phe Ile Pro Glu Val Ser Tyr Val Pro Leu Ser Val Met
                325                 330                 335
Ile Thr Ala Phe Lys Lys Asp Lys Val Lys Arg Pro Leu Glu Gly Phe
                340                 345                 350
Gly Val Leu Ile Pro Ser Lys Glu Gln His Asn Gly Leu Lys Thr Leu
            355                 360                 365
Gly Thr Leu Phe Ser Ser Met Met Phe Pro Asp Arg Ala Pro Ser Asp
            370                 375                 380
Met Cys Leu Phe Thr Thr Phe Val Gly Gly Ser Arg Asn Arg Lys Leu
385                 390                 395                 400
Ala Asn Ala Ser Thr Asp Glu Leu Lys Gln Ile Val Ser Ser Asp Leu
                405                 410                 415
Gln Gln Leu Leu Gly Thr Glu Asp Pro Ser Phe Val Asn His Leu
            420                 425                 430
Phe Trp Ser Asn Ala Phe Pro Leu Tyr Gly His Asn Tyr Asp Ser Val
            435                 440                 445
Leu Arg Ala Ile Asp Lys Met Glu Lys Asp Leu Pro Gly Phe Phe Tyr
450                 455                 460
Ala Gly Asn His Lys Gly Gly Leu Ser Val Gly Lys Ala Met Ala Ser
465                 470                 475                 480
Gly Cys Lys Ala Ala Glu Leu Val Ile Ser Tyr Leu Asp Ser His Ile
                485                 490                 495
Tyr Val Lys Met Asp Glu Lys Thr Ala
                500                 505

<210> SEQ ID NO 21
<211> LENGTH: 1605
<212> TYPE: DNA
<213> ORGANISM: Amaranthus tuberculatus

<400> SEQUENCE: 21
atggtaattc aatccattac ccacctttca ccaaaccttg cattgccatc gccattgtca    60
gtttcaacca agaactaccc agtagctgta atgggcaaca tttctgagcg ggaagaaccc   120
acttctgcta aagggttgc tgttgttggt gctggagtta gtggacttgc tgctgcatat    180
aagctaaaat cccatggttt gagtgtgaca ttgtttgaag ctgattctag agctggaggc   240
aaacttaaaa ctgttaaaaa agatggtttt atttgggatg agggggcaaa tactatgaca   300
```

```
gaaagtgagg cagaggtctc gagtttgatc gatgatcttg ggcttcgtga gaagcaacag    360
ttgccaattt cacaaaataa aagatacata gctagagacg tcttcctgt gctactacct    420 tcaaatcccg ctgcactact cacgagcaat atcctttcag caaaatcaaa gctgcaaatt    480
atgttggaac catttctctg gagaaaacac aatgctactg aactttctga tgagcatgtt    540
caggaaagcg ttggtgaatt ttttgagcga cattttggga agagtttgt tgattatgtt    600 atcgacccttt ttgttgcggg tacatgtggt ggagatcctc aatcgctttc catgcaccat    660
acatttccag aagtatggaa tattgaaaaa aggtttggct ctgtgtttgc tggactaatt    720
caatcaacat tgttatctaa aaggaaaag ggtggagaaa atgcttctat taagaagcct    780
cgtgtacgtg gttcattttc atttcaaggt ggaatgcaga cacttgttga cacaatgtgc    840
aaacagcttg gtgaagatga actcaaactc cagtgtgagg tgctgtcctt gtcatataac    900
cagaagggga tcccctcatt agggaattgg tcagtctctt ctatgtcaaa taataccagt    960
gaagatcaat cttatgatgc tgtggttgtc actgctccaa ttcgcaatgt caaagaaatg   1020
aagattatga aatttggaaa tccattttca cttgacttta ttccagaggt gacgtacgta   1080 ccccttttccg ttatgattac tgcattcaaa aaggataaag tgaagagacc tcttgagggc   1140
ttcggagttc ttatcccctc taaagagcaa cataatggac tgaagactct tggtacttta   1200
ttttcctcca tgatgtttcc tgatcgtgct ccatctgaca tgtgtctctt tactacattt   1260
gtcggaggaa gcagaaatag aaaacttgca aacgcttcaa cggatgaatt gaagcaaata   1320
gtttcttctg accttcagca gctgttgggc actgaggacg aaccttcatt tgtcaatcat   1380 ctctttttgga gcaacgcatt cccattgtat ggacacaatt acgattctgt tttgagagcc   1440
atagacaaga tggaaaagga tcttcctgga ttttttttatg caggtaacca taagggtgga   1500
ctttcagtgg gaaaagcgat ggcctccgga tgcaaggctg cggaacttgt aatatcctat   1560
ctggactctc atatatacgt gaagatggat gagaagaccg cgtaa                   1605
```

<210> SEQ ID NO 22
<211> LENGTH: 534
<212> TYPE: PRT
<213> ORGANISM: Amaranthus tuberculatus

<400> SEQUENCE: 22

```
Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
    130                 135                 140
```

```
Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
            165                 170                 175

Asp Glu His Val Gln Glu Ser Val Gly Glu Phe Phe Glu Arg His Phe
        180                 185                 190

Gly Lys Glu Phe Val Asp Tyr Val Ile Asp Pro Phe Val Ala Gly Thr
    195                 200                 205

Cys Gly Gly Asp Pro Gln Ser Leu Ser Met His His Thr Phe Pro Glu
210                 215                 220

Val Trp Asn Ile Glu Lys Arg Phe Gly Ser Val Phe Ala Gly Leu Ile
225                 230                 235                 240

Gln Ser Thr Leu Leu Ser Lys Lys Glu Lys Gly Gly Glu Asn Ala Ser
                245                 250                 255

Ile Lys Lys Pro Arg Val Arg Gly Ser Phe Ser Phe Gln Gly Gly Met
            260                 265                 270

Gln Thr Leu Val Asp Thr Met Cys Lys Gln Leu Gly Glu Asp Glu Leu
        275                 280                 285

Lys Leu Gln Cys Glu Val Leu Ser Leu Ser Tyr Asn Gln Lys Gly Ile
    290                 295                 300

Pro Ser Leu Gly Asn Trp Ser Val Ser Ser Met Ser Asn Asn Thr Ser
305                 310                 315                 320

Glu Asp Gln Ser Tyr Asp Ala Val Val Val Thr Ala Pro Ile Arg Asn
                325                 330                 335

Val Lys Glu Met Lys Ile Met Lys Phe Gly Asn Pro Phe Ser Leu Asp
            340                 345                 350

Phe Ile Pro Glu Val Thr Tyr Val Pro Leu Ser Val Met Ile Thr Ala
        355                 360                 365

Phe Lys Lys Asp Lys Val Lys Arg Pro Leu Glu Gly Phe Gly Val Leu
    370                 375                 380

Ile Pro Ser Lys Glu Gln His Asn Gly Leu Lys Thr Leu Gly Thr Leu
385                 390                 395                 400

Phe Ser Ser Met Met Phe Pro Asp Arg Ala Pro Ser Asp Met Cys Leu
                405                 410                 415

Phe Thr Thr Phe Val Gly Gly Ser Arg Asn Arg Lys Leu Ala Asn Ala
            420                 425                 430

Ser Thr Asp Glu Leu Lys Gln Ile Val Ser Ser Asp Leu Gln Gln Leu
        435                 440                 445

Leu Gly Thr Glu Asp Glu Pro Ser Phe Val Asn His Leu Phe Trp Ser
    450                 455                 460

Asn Ala Phe Pro Leu Tyr Gly His Asn Tyr Asp Ser Val Leu Arg Ala
465                 470                 475                 480

Ile Asp Lys Met Glu Lys Asp Leu Pro Gly Phe Phe Tyr Ala Gly Asn
                485                 490                 495

His Lys Gly Gly Leu Ser Val Gly Lys Ala Met Ala Ser Gly Cys Lys
            500                 505                 510

Ala Ala Glu Leu Val Ile Ser Tyr Leu Asp Ser His Ile Tyr Val Lys
        515                 520                 525

Met Asp Glu Lys Thr Ala
    530

<210> SEQ ID NO 23
<211> LENGTH: 1659
```

```
<212> TYPE: DNA
<213> ORGANISM: Amaranthus tuberculatus

<400> SEQUENCE: 23
atgagtgcga tggcgttatc gagcagcatt ctacaatgtc cgccgcactc cgacatctcg     60
ttccgctttt ttgctcatac acgaaccca tccccatct tcttcggaag aacacgaaaa      120
ttatcatata tccattgttc cacaagctca agctcaactg ccaattacca gaacacgatt    180
acgagccaag gagaaggaga taaagtatta gattgtgtaa ttgttggagc tggtatcagt    240
ggactttgca ttgctcaggc tctttctacc aaacacattc aatccaatct caatttcatt    300
gtcactgaag ctaaacatcg tgttggaggt aatatcacta ccatggagtc cgatggctat    360
atctgggaag agggtcctaa tagtttccaa ccctccgatc ctgtgcttac tatggcggtt    420
gacagtggat tgaaagacga tttagtcttg ggagatccta atgcccctcg tttcgtgctc    480
tggaatggta aattaaggcc tgttccttcc aaacctacgg accttccctt ttttgatctc    540
atgagctttc ctggtaagat tagggctggt cttggtgcac ttggtcttcg tcctcctcct    600
cctcctcctt cttatgagga atctgttgaa gaatttgtgc gccgtaatct cggcgatgag    660
gtcttcgaac gcttgatcga acccttttgt tctggtgtct atgctggtga tcctgcaaag    720
ttgagtatga agctgcatt tggaaaggtc tggaccttag agcaaaaggg tggtagtatc    780
atagccggta cactcaaaac tattcaggaa aggaaaaata tcctccacc ccctcgagac     840
ccccgccttc ctaaacctaa gggccagact gttggatcct ttaggaaagg gctcattatg    900
ttacctaccg ccattgctgc taggcttggc agtaaagtca aactatcgtg gacactttct    960
aatattgata gtcgctcaa tggagaatac aatctcactt atcaaacacc cgatggaccg   1020
gtttctgtta ggaccaaagc ggttgtcatg accgtccctt cgtacattgc aagtagcttg   1080
cttcgtccgc tctcagatgt tgctgcagat tctctttcta aattttacta tccaccagtc   1140
gcagcagtgt ccctttctta tcccaaagaa gcaattagac cagaatgctt gattgatgga   1200
gaactaaaag gattcgggca attgcatccc cgcagccagg gtgtggaaac cttgggaaca   1260
atttatagtt catctctttt ccctggtcga gcaccacccg gtaggacctt gatcttgagc   1320
tacattggag gtgctacaaa tcttggcata ttacaaaga gtgaagatga actcgcggag    1380
acagttgata aggatctcag aaaaattctg ataaatccaa atgcgaaagg cagccgtgtt   1440
ctgggagtga gagtatggcc aaaggcaatc ccccaatttt tagttggtca ctttgatgtg   1500
ctagatgctg caaaagctgg tttggcaaat gctgggctaa aggggttgtt tcttggtggt   1560
aattatgtat caggtgttgc cttggggagg tgtatagagg gtgcttatga ctctgcttct   1620
gaggtagtgg atttcctctc acagtacaaa gataagtag                          1659

<210> SEQ ID NO 24
<211> LENGTH: 552
<212> TYPE: PRT
<213> ORGANISM: Amaranthus tuberculatus

<400> SEQUENCE: 24

Met Ser Ala Met Ala Leu Ser Ser Ser Ile Leu Gln Cys Pro Pro His
1               5                   10                  15

Ser Asp Ile Ser Phe Arg Phe Phe Ala His Thr Arg Thr Pro Ser Pro
                20                  25                  30

Ile Phe Phe Gly Arg Thr Arg Lys Leu Ser Tyr Ile His Cys Ser Thr
            35                  40                  45

Ser Ser Ser Ser Thr Ala Asn Tyr Gln Asn Thr Ile Thr Ser Gln Gly
```

-continued

```
             50                  55                  60
Glu Gly Asp Lys Val Leu Asp Cys Val Ile Val Gly Ala Gly Ile Ser
 65                  70                  75                  80

Gly Leu Cys Ile Ala Gln Ala Leu Ser Thr Lys His Ile Gln Ser Asn
                 85                  90                  95

Leu Asn Phe Ile Val Thr Glu Ala Lys His Arg Val Gly Gly Asn Ile
            100                 105                 110

Thr Thr Met Glu Ser Asp Gly Tyr Ile Trp Glu Gly Pro Asn Ser
            115                 120                 125

Phe Gln Pro Ser Asp Pro Val Leu Thr Met Ala Val Asp Ser Gly Leu
        130                 135                 140

Lys Asp Leu Val Leu Gly Asp Pro Asn Ala Pro Arg Phe Val Leu
145                 150                 155                 160

Trp Asn Gly Lys Leu Arg Pro Val Pro Ser Lys Pro Thr Asp Leu Pro
                165                 170                 175

Phe Phe Asp Leu Met Ser Phe Pro Gly Lys Ile Arg Ala Gly Leu Gly
            180                 185                 190

Ala Leu Gly Leu Arg Pro Pro Pro Pro Ser Tyr Glu Glu Ser
        195                 200                 205

Val Glu Glu Phe Val Arg Arg Asn Leu Gly Asp Glu Val Phe Glu Arg
210                 215                 220

Leu Ile Glu Pro Phe Cys Ser Gly Val Tyr Ala Gly Asp Pro Ala Lys
225                 230                 235                 240

Leu Ser Met Lys Ala Ala Phe Gly Lys Val Trp Thr Leu Glu Gln Lys
                245                 250                 255

Gly Gly Ser Ile Ile Ala Gly Thr Leu Lys Thr Ile Gln Glu Arg Lys
            260                 265                 270

Asn Asn Pro Pro Pro Arg Asp Pro Arg Leu Pro Lys Pro Lys Gly
        275                 280                 285

Gln Thr Val Gly Ser Phe Arg Lys Gly Leu Ile Met Leu Pro Thr Ala
        290                 295                 300

Ile Ala Ala Arg Leu Gly Ser Lys Val Lys Leu Ser Trp Thr Leu Ser
305                 310                 315                 320

Asn Ile Asp Lys Ser Leu Asn Gly Glu Tyr Asn Leu Thr Tyr Gln Thr
                325                 330                 335

Pro Asp Gly Pro Val Ser Val Arg Thr Lys Ala Val Val Met Thr Val
            340                 345                 350

Pro Ser Tyr Ile Ala Ser Ser Leu Leu Arg Pro Leu Ser Asp Val Ala
        355                 360                 365

Ala Asp Ser Leu Ser Lys Phe Tyr Tyr Pro Pro Val Ala Ala Val Ser
        370                 375                 380

Leu Ser Tyr Pro Lys Glu Ala Ile Arg Pro Glu Cys Leu Ile Asp Gly
385                 390                 395                 400

Glu Leu Lys Gly Phe Gly Gln Leu His Pro Arg Ser Gln Gly Val Glu
                405                 410                 415

Thr Leu Gly Thr Ile Tyr Ser Ser Leu Phe Pro Gly Arg Ala Pro
            420                 425                 430

Pro Gly Arg Thr Leu Ile Leu Ser Tyr Ile Gly Gly Ala Thr Asn Leu
        435                 440                 445

Gly Ile Leu Gln Lys Ser Glu Asp Glu Leu Ala Glu Thr Val Asp Lys
        450                 455                 460

Asp Leu Arg Lys Ile Leu Ile Asn Pro Asn Ala Lys Gly Ser Arg Val
465                 470                 475                 480
```

Leu Gly Val Arg Val Trp Pro Lys Ala Ile Pro Gln Phe Leu Val Gly
            485                 490                 495

His Phe Asp Val Leu Asp Ala Ala Lys Ala Gly Leu Ala Asn Ala Gly
                500                 505                 510

Leu Lys Gly Leu Phe Leu Gly Gly Asn Tyr Val Ser Gly Val Ala Leu
        515                 520                 525

Gly Arg Cys Ile Glu Gly Ala Tyr Asp Ser Ala Ser Glu Val Val Asp
    530                 535                 540

Phe Leu Ser Gln Tyr Lys Asp Lys
545                 550

<210> SEQ ID NO 25
<211> LENGTH: 1602
<212> TYPE: DNA
<213> ORGANISM: Amaranthus tuberculatus

<400> SEQUENCE: 25

| | |
|---|---|
| atggtaattc aatccattac ccacctttca ccaaaccttg cattgccatc gccattgtca | 60 |
| gtttccacca agaactaccc agtagctgta atgggcaaca tttctgagcg agaagaaccc | 120 |
| acttctgcta aagggttgc tgttgttggt gctggagtta gtggacttgc tgctgcatat | 180 |
| aagctaaaat cccatggttt gagtgtgaca ttgtttgaag ctgattctag agctggaggc | 240 |
| aaacttaaaa ctgttaaaaa gatggttttt atttgggatg agggggcaaa tactatgaca | 300 |
| gaaagtgagg cagaggtctc gagtttgatc gatgatcttg gcttcgtga aagcaacag | 360 |
| ttgccaattt cacaaaataa agatacata gctagagacg tcttcctgt gctactacct | 420 |
| tcaaatcccg ctgcactact cacgagcaat atcctttcag caaatcaaa gctgcaaatt | 480 |
| atgttggaac catttctctg gagaaaacac aatgctactg aactttctga tgagcatgtt | 540 |
| caggaaagcg ttggtgaatt ttttgagcga catttgggga aagagtttgt tgattatgtt | 600 |
| attgacccct tgttgcggg tacatgtgga gatcctcaat cgctttccat gcaccataca | 660 |
| tttccagaag tatggaatat tgaaaaaagg tttggctctg tgtttgctgg actaattcaa | 720 |
| tcaacattgt tatctaagaa ggaaaagggt ggagaaaatg cttctattaa gaagcctcgt | 780 |
| gtacgtggtt cattttcatt tcaaggtgga atgcagacac ttgttgacac aatgtgcaaa | 840 |
| cagcttggtg aagatgaact caaactccag tgtgaggtgc tgtccttgtc atataaccag | 900 |
| aaggggatcc cctcattagg gaattggtca gtctcttcta tgtcaaataa taccagtgaa | 960 |
| gatcaatctt atgatgctgt ggttgtcact gctccaattc gcaatgtcaa agaaatgaag | 1020 |
| attatgaaat ttggaaatcc attttcactt gactttattc cagaggtgac gtacgtaccc | 1080 |
| ctttccgtta tgattactgc attcaaaaag gataaagtga agagacctct tgagggcttc | 1140 |
| ggagttctta tccctctaa agagcaacat aatggactga agactcttgg tactttattt | 1200 |
| tcctccatga tgtttcctga tcgtgctcca tctgacatgt gtctctttac tacatttgtc | 1260 |
| ggaggaagca gaaatagaaa acttgcaaac gcttcaacgg atgaattgaa gcaaatagtt | 1320 |
| tcttctgacc ttcagcagct gttgggcact gaggacgaac cttcatttgt caatcatctc | 1380 |
| ttttggagca acgcattccc attgtatgga cacaattacg attgtgtttt gagagccata | 1440 |
| gacaagatgg aaaaggatct tcctggattt tttatgcag gtaaccataa gggtggactt | 1500 |
| tcagtgggaa aagcgatggc ctccggatgc aaggctgcgg aacttgtaat atcctatctg | 1560 |
| gactctcata tatacgtgaa gatggatgag aagaccgcgt aa | 1602 |

<210> SEQ ID NO 26
<211> LENGTH: 533
<212> TYPE: PRT
<213> ORGANISM: Amaranthus tuberculatus

<400> SEQUENCE: 26

```
Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Pro Thr Ser Ala Lys Arg Val Ala Val
        35                  40                  45

Val Gly Ala Gly Val Ser Gly Leu Ala Ala Ala Tyr Lys Leu Lys Ser
50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Glu Arg His Phe
            180                 185                 190

Gly Lys Glu Phe Val Asp Tyr Val Ile Asp Pro Phe Ala Gly Thr
        195                 200                 205

Cys Gly Asp Pro Gln Ser Leu Ser Met His His Thr Phe Pro Glu Val
    210                 215                 220

Trp Asn Ile Glu Lys Arg Phe Gly Ser Val Phe Ala Gly Leu Ile Gln
225                 230                 235                 240

Ser Thr Leu Leu Ser Lys Lys Glu Lys Gly Gly Glu Asn Ala Ser Ile
                245                 250                 255

Lys Lys Pro Arg Val Arg Gly Ser Phe Ser Phe Gln Gly Gly Met Gln
            260                 265                 270

Thr Leu Val Asp Thr Met Cys Lys Gln Leu Gly Glu Asp Glu Leu Lys
        275                 280                 285

Leu Gln Cys Glu Val Leu Ser Leu Ser Tyr Asn Gln Lys Gly Ile Pro
290                 295                 300

Ser Leu Gly Asn Trp Ser Val Ser Ser Met Ser Asn Asn Thr Ser Glu
305                 310                 315                 320

Asp Gln Ser Tyr Asp Ala Val Val Val Thr Ala Pro Ile Arg Asn Val
                325                 330                 335

Lys Glu Met Lys Ile Met Lys Phe Gly Asn Pro Phe Ser Leu Asp Phe
            340                 345                 350

Ile Pro Glu Val Thr Tyr Val Pro Leu Ser Val Met Ile Thr Ala Phe
        355                 360                 365

Lys Lys Asp Lys Val Lys Arg Pro Leu Glu Gly Phe Gly Val Leu Ile
370                 375                 380
```

```
Pro Ser Lys Glu Gln His Asn Gly Leu Lys Thr Leu Gly Thr Leu Phe
385                 390                 395                 400

Ser Ser Met Met Phe Pro Asp Arg Ala Pro Ser Asp Met Cys Leu Phe
            405                 410                 415

Thr Thr Phe Val Gly Gly Ser Arg Asn Arg Lys Leu Ala Asn Ala Ser
        420                 425                 430

Thr Asp Glu Leu Lys Gln Ile Val Ser Ser Asp Leu Gln Gln Leu Leu
    435                 440                 445

Gly Thr Glu Asp Glu Pro Ser Phe Val Asn His Leu Phe Trp Ser Asn
450                 455                 460

Ala Phe Pro Leu Tyr Gly His Asn Tyr Asp Cys Val Leu Arg Ala Ile
465                 470                 475                 480

Asp Lys Met Glu Lys Asp Leu Pro Gly Phe Phe Tyr Ala Gly Asn His
            485                 490                 495

Lys Gly Gly Leu Ser Val Gly Lys Ala Met Ala Ser Gly Cys Lys Ala
        500                 505                 510

Ala Glu Leu Val Ile Ser Tyr Leu Asp Ser His Ile Tyr Val Lys Met
    515                 520                 525

Asp Glu Lys Thr Ala
    530

<210> SEQ ID NO 27
<211> LENGTH: 1605
<212> TYPE: DNA
<213> ORGANISM: Amaranthus tuberculatus

<400> SEQUENCE: 27
atggtaattc aatccattac ccacctttca ccaaaccttg cattgccatc gccattgtca      60
gtttcaacca agaactaccc agtagctgta atgggcaaca tttctgagcg ggaagaaccc     120
acttctgcta aaagggttgc tgttgttggt gctggagtta gtggacttgc tgctgcatat     180
aagctaaaat cccatggttt gagtgtgaca ttgtttgaag ctgattctag agctggaggc     240
aaacttaaaa ctgttaaaaa agatggtttt atttgggatg aggggcaaa tactatgaca      300
gaaagtgagg cagaggtctc gagtttgatc gatgatcttg ggcttcgtga aagcaacag      360
ttgccaattt cacaaaataa agatacata gctagagccg tcttcctgt gctactacct      420
tcaaatcccg ctgcactact cacgagcaat atcctttcag caaaatcaaa gctgcaaatt     480
atgttggaac catttctctg agaaaaacac aatgctactg aactttctga tgagcatgtt     540
caggaaagcg ttggtgaatt ttttgagcga cattttggga aagagtttgt tgattatgtt     600
attgacccct tgttgcggg tacatgtggt ggagatcctc aatcgctttc catgcaccat     660
acatttccag aagtatggaa tattgaaaaa aggtttggct ctgtgtttgc cggactaatt     720
caatcaacat tgttatctaa gaaggaaaag ggtggagaaa atgcttctat taagaagcct     780
cgtgtacgtg ttcatttc atttcaaggt ggaatgcaga cacttgttga cacaatgtgc      840
aaacagcttg gtgaagatga actcaaactc cagtgtgagg tgctgtcctt gtcatataac     900
cagaaggga tcccctcact agggaattgg tcagtctctt ctatgtcaaa taataccagt     960
gaagatcaat cttatgatgc tgtggttgtc actgctccaa ttcgcaatgt caaagaaatg    1020
aagattatga aatttggaaa tccatttca cttgacttta ttccagaggt gacgtacgta    1080
cccctttccg ttatgattac tgcattcaaa aaggataaag tgaagagacc tcttgagggc    1140
ttcggagttc ttatcccctc taagagcaa cataatggac tgaagactct ggtactttta    1200
ttttcctcca tgatgtttcc tgatcgtgct ccatctgaca tgtgtctctt tactacattt    1260
```

```
gtcggaggaa gcagaaatag aaaacttgca aacgcttcaa cggatgaatt gaagcaaata    1320
gtttcttctg accttcagca gctgttgggc actgaggacg aaccttcatt tgtcaatcat    1380
ctctttggga gcaacgcatt cccattgtat ggacacaatt acgattctgt tttgagagcc    1440
atagacaaga tggaaaagga tcttcctgga ttttttatg caggtaacca taagggtgga     1500
ctttcagtgg gaaaagcgat ggcctccgga tgcaaggctg cggaacttgt aatatcctat    1560
ctggactctc atatatacgt gaagatggat gagaagaccg cgtaa                    1605
```

<210> SEQ ID NO 28
<211> LENGTH: 534
<212> TYPE: PRT
<213> ORGANISM: Amaranthus tuberculatus

<400> SEQUENCE: 28

```
Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Ala Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Gly Asp Pro Gln Ser Leu Ser Met His His Thr Phe Pro Glu
    210                 215                 220

Val Trp Asn Ile Glu Lys Arg Phe Gly Ser Val Phe Ala Gly Leu Ile
225                 230                 235                 240

Gln Ser Thr Leu Leu Ser Lys Lys Glu Lys Gly Gly Glu Asn Ala Ser
                245                 250                 255

Ile Lys Lys Pro Arg Val Arg Gly Ser Phe Ser Phe Gln Gly Gly Met
            260                 265                 270

Gln Thr Leu Val Asp Thr Met Cys Lys Gln Leu Gly Glu Asp Glu Leu
        275                 280                 285

Lys Leu Gln Cys Glu Val Leu Ser Leu Ser Tyr Asn Gln Lys Gly Ile
    290                 295                 300

Pro Ser Leu Gly Asn Trp Ser Val Ser Ser Met Ser Asn Asn Thr Ser
```

```
305                 310                 315                 320
Glu Asp Gln Ser Tyr Asp Ala Val Val Thr Ala Pro Ile Arg Asn
                325                 330                 335
Val Lys Glu Met Lys Ile Met Lys Phe Gly Asn Pro Phe Ser Leu Asp
            340                 345                 350
Phe Ile Pro Glu Val Thr Tyr Val Pro Leu Ser Val Met Ile Thr Ala
            355                 360                 365
Phe Lys Lys Asp Lys Val Lys Arg Pro Leu Glu Gly Phe Gly Val Leu
            370                 375                 380
Ile Pro Ser Lys Glu Gln His Asn Gly Leu Lys Thr Leu Gly Thr Leu
385                 390                 395                 400
Phe Ser Ser Met Met Phe Pro Asp Arg Ala Pro Ser Asp Met Cys Leu
            405                 410                 415
Phe Thr Thr Phe Val Gly Gly Ser Arg Asn Arg Lys Leu Ala Asn Ala
            420                 425                 430
Ser Thr Asp Glu Leu Lys Gln Ile Val Ser Ser Asp Leu Gln Gln Leu
            435                 440                 445
Leu Gly Thr Glu Asp Glu Pro Ser Phe Val Asn His Leu Phe Trp Ser
450                 455                 460
Asn Ala Phe Pro Leu Tyr Gly His Asn Tyr Asp Ser Val Leu Arg Ala
465                 470                 475                 480
Ile Asp Lys Met Glu Lys Asp Leu Pro Gly Phe Phe Tyr Ala Gly Asn
                485                 490                 495
His Lys Gly Gly Leu Ser Val Gly Lys Ala Met Ala Ser Gly Cys Lys
            500                 505                 510
Ala Ala Glu Leu Val Ile Ser Tyr Leu Asp Ser His Ile Tyr Val Lys
            515                 520                 525
Met Asp Glu Lys Thr Ala
            530

<210> SEQ ID NO 29
<211> LENGTH: 1602
<212> TYPE: DNA
<213> ORGANISM: Amaranthus tuberculatus

<400> SEQUENCE: 29
atggtaattc aatccattac ccacctttca ccaaaccttg cattgccatc gccattgtca      60
gtttccacca agaactaccc agtagctgta atgggcaaca tttctgagcg ggaagaaccc     120
acttctgcta aagggttgc tgttgttggt gctggagtta gtggacttgc tgctgcatat      180
aagctaaaat cccatggttt gagtgtgaca ttgtttgaag ctaattctag agctggaggc     240
aaacttaaaa ctgttaaaaa agatggtttt atttgggatg aggggcaaa tactatgaca     300 gaaagtgagg cagaggtctc gagtttgatc gatgatcttg gcttcgtga agcaacag      360 ttgccaattt cacaaaataa agatacata gctagagacg tcttcctgt gctactacct     420 tcaaatcccg ctgcactact cacgagcaat atcctttcag caaaatcaaa gctgcaaatt     480
atgttggaac catttctctg gagaaaacac aatgctactg aactttctga tgagcatgtt     540
caggaaagcg ttggtgaatt ttttgagcga cattttggga agagtttgt tgattatgtt     600 attgacccctt tgttgcggg tacatgtgga atcctcaat cgctttccat gtaccataca     660
tttccagaag tatggaatat tgaaaaaagg tttggctctg tgtttgctgg actaattcaa     720
tcaacattgt tatctaagaa ggaaaagggt ggagaaaatg cttctattaa gaagcctcgt     780
gtacgtggtt catttcatt tcaaggtgga atgcagacac ttgttgacac aatgtgcaaa     840
```

-continued

```
cagcttggtg aagatgaact caaactccag tgtgaggtgc tgtccttgtc atataaccag    900
aaggggatcc cctcattagg gaattggtca gtctcttcta tgtcaaataa taccagtgaa    960
gatcaatctt atgatgctgt ggttgtcact gctccaattc gcaatgtcaa agaaatgaag   1020
attatgaaat ttggaaatcc attttcactt gactttattc cagaggtgac gtacgtaccc   1080
ctttccgtta tgattactgc attcaaaaag gataaagtga agagacctct tgagggcttc   1140
ggagttctta tccccctctaa agagcaacat aatggactga agactcttgg tactttattt   1200
tcctccatga tgtttcctga tcgtgctcca tctgacatgt gtctctttac tacatttgtc   1260
ggaggaagca gaaatagaaa acttgcaaac gcttcaacgg atgaattgaa gcaaatagtt   1320
tcttctgacc ttcagcagct gttgggcact gaggacgaac cttcatttgt caatcatctc   1380
ttttggagca acgcattccc attgtatgga cacaattacg attctgtttt gagagccata   1440
gacaagatgg aaaaggatct tcctggattt ttttatgcag gtaaccataa gggtggactt   1500
tcagtgggaa aagcgatggc ctccggatgc aaggctgcgg aacttgtaat atcctatctg   1560
gactctcata tatacgtgaa gatggatgag aagaccgcgt aa                      1602
```

<210> SEQ ID NO 30
<211> LENGTH: 533
<212> TYPE: PRT
<213> ORGANISM: Amaranthus tuberculatus

<400> SEQUENCE: 30

```
Met Val Ile Gln Ser Ile Thr His Leu Ser Pro Asn Leu Ala Leu Pro
1               5                  10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asn Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Asp Pro Gln Ser Leu Ser Met Tyr His Thr Phe Pro Glu Val
    210                 215                 220

Trp Asn Ile Glu Lys Arg Phe Gly Ser Val Phe Ala Gly Leu Ile Gln
225                 230                 235                 240
```

```
Ser Thr Leu Leu Ser Lys Lys Glu Lys Gly Gly Glu Asn Ala Ser Ile
            245                 250                 255

Lys Lys Pro Arg Val Arg Gly Ser Phe Ser Phe Gln Gly Met Gln
        260                 265                 270

Thr Leu Val Asp Thr Met Cys Lys Gln Leu Gly Glu Asp Glu Leu Lys
            275                 280                 285

Leu Gln Cys Glu Val Leu Ser Leu Ser Tyr Asn Gln Lys Gly Ile Pro
        290                 295                 300

Ser Leu Gly Asn Trp Ser Val Ser Ser Met Ser Asn Asn Thr Ser Glu
305                 310                 315                 320

Asp Gln Ser Tyr Asp Ala Val Val Thr Ala Pro Ile Arg Asn Val
            325                 330                 335

Lys Glu Met Lys Ile Met Lys Phe Gly Asn Pro Phe Ser Leu Asp Phe
            340                 345                 350

Ile Pro Glu Val Thr Tyr Val Pro Leu Ser Val Met Ile Thr Ala Phe
        355                 360                 365

Lys Lys Asp Lys Val Lys Arg Pro Leu Glu Gly Phe Gly Val Leu Ile
        370                 375                 380

Pro Ser Lys Glu Gln His Asn Gly Leu Lys Thr Leu Gly Thr Leu Phe
385                 390                 395                 400

Ser Ser Met Met Phe Pro Asp Arg Ala Pro Ser Asp Met Cys Leu Phe
            405                 410                 415

Thr Thr Phe Val Gly Gly Ser Arg Asn Arg Lys Leu Ala Asn Ala Ser
            420                 425                 430

Thr Asp Glu Leu Lys Gln Ile Val Ser Ser Asp Leu Gln Gln Leu Leu
        435                 440                 445

Gly Thr Glu Asp Glu Pro Ser Phe Val Asn His Leu Phe Trp Ser Asn
        450                 455                 460

Ala Phe Pro Leu Tyr Gly His Asn Tyr Asp Ser Val Leu Arg Ala Ile
465                 470                 475                 480

Asp Lys Met Glu Lys Asp Leu Pro Gly Phe Phe Tyr Ala Gly Asn His
            485                 490                 495

Lys Gly Gly Leu Ser Val Gly Lys Ala Met Ala Ser Gly Cys Lys Ala
        500                 505                 510

Ala Glu Leu Val Ile Ser Tyr Leu Asp Ser His Ile Tyr Val Lys Met
        515                 520                 525

Asp Glu Lys Thr Ala
        530

<210> SEQ ID NO 31
<211> LENGTH: 4797
<212> TYPE: DNA
<213> ORGANISM: Amaranthus tuberculatus

<400> SEQUENCE: 31
aagaattgaa ttggcagatt gagacaaaat tggattcaga atttagcaaa tttaaaccga      60
tcgtatggta attcaatcca ttacccacct ttcaccaaac cttgcattgc catcgccatt     120
gtcagtttca accaagaact acccagtagc tgtaatgggc aacatttctg agcgggaaga     180
acccagtaag tcaaccttcc ttcacatatc ttaaagcaat ccctttccaa ctacactttc     240
ttttgatgat tcacattcct gagttttttt tattgggat ttttagcttc tgctaaaagg      300
gttgctgttg ttggtgctgg agttaggtaa atttatgtt tcttttccag aaagattgta      360 aaatttgct ttgattgttc tgaattttga tgggttttg cataatgatt tgtatttggg        420
```

-continued

| | |
|---|---|
| atgggcaaat ttttcagtag atcatactac ttttaacttc tattttctgt ataatttat | 480 |
| tgatttccta aactgttttt gtggaattgt tctagtggac ttgctgctgc atataagcta | 540 |
| aaatcccatg gtttaagtgt gacattgttt gaagctgatt ctagagctgg aggcaaactt | 600 |
| aaaactgtta aaaagatgg ttttatttgg gatgagggg caaatactat ggtaatgttt | 660 |
| atcaacaatg ctggttttct gatttagaac caattacttg ctggattttg ggtcaattct | 720 |
| gtggttaaca tgtcactttc tgatatgctt gtagacagaa agtgaggcag aggtctcgag | 780 |
| tttgatcgat gatcttgggc ttcgtgagaa gcaacagttg gtaagttttc tgtctaagcc | 840 |
| cattcccttt gcttgctaga gtccgtagcg caaaaatacg gtaatagtca tgatcgtggt | 900 |
| aatgacatgg tgatgcggtg acaggagtca tgtgatcgtt attccaacta taggtcaaaa | 960 |
| acatgatatt ttccttgtga cgccccaaaa tgcagtattt ttacacctttt acattgcggg | 1020 |
| gaaaaatagg tttattatgt tgaaaacctt tacaaggcgg ctgatgcgat gcggccttgt | 1080 |
| ttttgcatta tgttcttgaa gcaacttatt atatctttga ttaatgtatc atcagcttaa | 1140 |
| aacagcctta ttgtacttct taatctagtt ttgacttttg aggttgcttt tacaagatct | 1200 |
| ttatatgatt ggttcttctg tcacagccaa tttcacaaaa taaaagatac atagctagag | 1260 |
| acggtcttcc tgtgctagta agtcctctgc atttacttttt gacctctatg aacttctaac | 1320 |
| actggatact aagttgtatt cgaggcaaat tctgtatttt ccaatctgct tattgacagt | 1380 |
| tgcttgcaaa ctttgcagct accttcaaat cccgctgcac tactcacgag caatatcctt | 1440 |
| tcagcaaaat caaggttat caatgctaaa atcatgtttg gtatttgatt acttagcttt | 1500 |
| tggtgtatgc aataatttgg tttctaaaac taagtgattg acggaaaagg agggacgaag | 1560 |
| gacatagaat tgcaatttttg tgttcttcat gtattttttac ttttagagta ggtaagtcac | 1620 |
| tttcggtccg tttggttaat ggtactagtt ggtggtaata ggaatgatttt gtagtgtaaa | 1680 |
| ttttcaagat atatatcatg tcattcccat ggtaatgaaa gtttgatcat aaaaaggttt | 1740 |
| tttgttcaca atttttccatt accacctaat accacatgtt taaatggtaa tgcattggaa | 1800 |
| tgagttttgt gaagaaaatg agtttgttga gaaagaataa gcatggtcat taaatttgtc | 1860 |
| aagagatatt cctatcaaaa ttacactagc tttccattat catttcacca tttagtaccg | 1920 |
| attaccaaat gggccgttta tagtttggga agagcatacg tttgtgtaaa acttttattt | 1980 |
| tgaagttgaa agaatttgtt gcaccttttg ttatgattag gttttgatgt ttttagctgc | 2040 |
| aataaatttg ttgatgaaaa agccactact ttttttctcag ctgcaaatta tgttggaacc | 2100 |
| atttctctgg agaaaacaca atgctactga actttctgat gagcatgttc aggaaaggca | 2160 |
| agtgccacat actattaagt gttagttgct gagaatatat ttgaatctaa gatgcacgaa | 2220 |
| gaccactggt gcccttgctc tatcaattct gatggaaagg attatcgctg aatttaccttt | 2280 |
| ctactaaaac atcgataaaa tacttcatta ttagcatcaa aagattccct ccatccttct | 2340 |
| ggttttgcta gacttgcctt atgaaggtgt tcaaggagta gtttgctacc cttcaagata | 2400 |
| gggtagtggt tgccgtctct cataattttca gtcactcgtt ttcctctcct aattcaagcc | 2460 |
| ataattttta tggttcctcc acacaacact tgctaaatttt gaaaagtagc aaagaggaag | 2520 |
| tgagcaaaat cagcaggagt aggactgatg agtaagagct tgattaagtg tagaggattt | 2580 |
| tcttttgtgt tgaatatgaa tgcatcatgc atgactgtag aattgacata atgatttgtc | 2640 |
| tgcagcgttg gtgaattttt tgagcgacat tttgggaaag aggtattgtt gccaattgcc | 2700 |
| atgctctatt cattccggtg aattaacaaa tgttgtgctt ctgcttacta ttgcttataa | 2760 |

```
ttattgtttg ttgcagtttg ttgattatgt tattgaccct tttgttgcgg gtacatgtgg    2820
tggagatcct caatcgcttt ccgtgagtta aatactgtgc ttgcttttt ttttcaacat    2880 tttctggagg ctgtaaataa attatactcc ttcctattct aatcaaatat cctatttccc    2940
cttttggcat attcaaattt agttaaatat tgtgtaaatt atttacacaa ttgccattaa    3000
attttcactt ttcccttact cactcttctc atgtgtccct tccccctttt cttaaaattg    3060
gtgcattatc aaataggaca tttgatttga ataggcggga gtttccaatt gtgcttccaa    3120
aggtagcttg tcacttttc tttttcttta aattttgtac catgccatgc attttgaacc    3180
tcaactcatt tcgccataaa ggaatattat gtttgagaag aacgaggata ctattatctt    3240
atagataaca tataggtttc attatcaatg attgtttgat tttcaactct tcttttcctt    3300
tcatgctcat attgatgtta tttctatttg ttatgaatta tgtccattgt gttaatgtct    3360
ttctttattg tagatgcacc atacatttcc agaagtatgg aatattgaaa aaggtatga    3420 accttaaagc tttaattttc ttcgaactta atgtttctta attgattctt ttggatcaat    3480
ttccataaga atggaaattt aaaaaaggt atgaacctta agatttctt cgaacttata    3540 tgttttgtaa ttcatgcttt tagatgttgc accatttat ctatgtgtct taagtttgtt    3600
gtaatcattt gtagaccaaa agaatgaatg gtctggtttg aaatggttca tcgtgcaaaa    3660
atgcgatttt gcttgtgatt gaggtaacat tcaaggtgat gtgtttgtcg tactgtcaaa    3720
tgtcttccta taccatatga tatatatata agcctaaaat gatatattgt atacctttag    3780
gatgtggata gcaggggttc agtacatatg aaaaatcctt gcaatttgat ctgtacgata    3840
caatgtgatt ttgccttttg cctttttgcct tttgttatat gatgatgatt ccatgtgaaa    3900
ttttgggatt tagaaaattc acttgtttaa gaacatttga atcaaacttt caccaatttc    3960
aaccacattt aattgcggca aagccgaact ttaaaagtca ctcccaatct ttgagatatc    4020
caaactccaa aacttctatt agctttcatg ttttcactaa gtaaagttgg tgcgactcct    4080
taccattttc tttattatgc atttcgttga tgtataatag tatagattgg tgctctcttc    4140
gctctccttc caacatgcat aacttctagt tcttgtcgtt ttctttcct ccctattttt    4200 atttgacttg tagctatttt tgttcactct tctcgcccaa tccaaaactt gtagctaaag    4260
aaacttgatt tcattgattt tgtaactgat atgcaattca tttttgtttg cttttagttg    4320
ttgattcaaa aacaataatg ctaaagccct aatcctaaca tgtcgggtta gctgttgaaa    4380
caatacttga aattgctata aaagggatt ttttcgggt acttcagttg ttgagattga    4440
tatggtcaag tataatttgt tttaacacaa tttgtaatga tttaatggct tagtttcata    4500
gctgtttgta ttaataaagg aaggaggact atccgaaatt gcaataggaa agagatttta    4560
gttcggtatt tggttgttta aattgatatg gccaagtaat gttcatttta cacaattggt    4620
aatgttttat tggctcaata gtgtttgtaa gtatgcgact caaatttaat caagtataac    4680
ttattgaaac ataataaat atccattagg tttggctctg tgtttgctgg actaattcaa    4740
tcaacattgt tatctaagaa ggaaagggt ggagaaaatg cttcataaga agcctcg        4797
```

<210> SEQ ID NO 32
<211> LENGTH: 230
<212> TYPE: PRT
<213> ORGANISM: Amaranthus tuberculatus

<400> SEQUENCE: 32

Met Val Ile Gln Ser Ile Thr His Leu Ser Pro Asn Leu Ala Leu Pro
1               5                   10                  15

```
Ser Pro Leu Ser Val Ser Thr Lys Asn Tyr Pro Val Ala Val Met Gly
        20                  25                  30

Asn Ile Ser Glu Arg Glu Pro Thr Ser Ala Lys Arg Val Ala Val
            35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                   70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
            115                 120                 125

Tyr Ile Ala Arg Asp Gly Leu Pro Val Leu Leu Pro Ser Asn Pro Ala
        130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
            195                 200                 205

Cys Gly Gly Asp Pro Gln Ser Leu Ser Met His His Thr Phe Pro Glu
        210                 215                 220

Val Trp Asn Ile Glu Lys
225                 230

<210> SEQ ID NO 33
<211> LENGTH: 4785
<212> TYPE: DNA
<213> ORGANISM: Amaranthus tuberculatus

<400> SEQUENCE: 33
aagaattgaa ttggcagatt gagacaaaat tggattcaga atttagcaaa tttaaaccga    60
tcgtatggta attcaatcca ttacccacct ttcaccaaac cttgcattgc catcgccatt   120
gtcagtttcc accaagaact acccagtagc tgtaatgggc aacatttctg agcgagaaga   180
acccagtaag tcaacctttc ttcacatatc ttaaagcaat ccctttcaa ctacactttc    240 ttttgatgat ttcacattct gagtttttt tattggggat ttttagcttc tgctaaaagg    300
gttgctgttg ttggtgctgg agttaggtaa attttatgtt tcttttccag aaagattgta   360 aaatttgct tgattgttc tgaattttga tgggttttg cataatgatt tgtatttggg      420
atgggcaaat ttttcagtag atcatactac ttttaacttc tatttctgt ataatttat    480 tgatttccta aattgttttt gtggaattgt tctagtggac ttgctgctgc atataagcta   540
aaatcccatg gtttgagtgt gacattgttt gaagctgatt ctagagctgg aggcaaactt   600
aaaactgtta aaaagatgg ttttatttgg gatgagggg caaatactat ggtaatgttt     660
atcaacaatg ctggttttct gatttagaac caattacttg ctggattttg gtcaattct    720 gtggttaaca tgtcactttc tgatatgctt gtagacagaa agtgaggcag aggtctcgag   780
tttgatcgat gatcttgggc ttcgtgagaa gcaacagttg gtaagttttc tgtctaagcc   840
cattcccttt gcttgctaga gtccgtagcg caaaaatacg gtaatagtca tgatcgtggt   900
```

```
aatgacatgg tgatgcggtg acaggagtca tgtgatcgtt attccaacta taggtcaaaa    960
acatgatatt ttccttgtga cgccccaaaa tgcggtattt ttacaccttt acattgcggg   1020
gaaaaatagg tttattatgt tgaaaacctt tacaaggcgg ctgatgcgat gcggccttgt   1080
ttttgcatta tgttctagaa gcaacttatt atatctttga ttaatgtatc atcagcttaa   1140
aacagcctta ttgtacttct taatctagtt ttgactttg aggttgcttt tacaagatct    1200
ttatatgatt ggttcttctg tcacagccaa tttcacaaaa taaagatac atagctagag    1260
acggtcttcc tgtgctagta agtcctctgc atttactttt gacctctatg aacttctaac   1320
actggatact aagttgtatt cgaggcaaat tctgtatttt ccaatctgct tattgacagt   1380
tgcttgcata ctttgcagct accttcaaat cccgctgcac tactcacgag caatatcctt   1440
tcagcaaaat caaggttat caatgctaaa atcatgtttg gtatttgatt acttagcttt    1500
tggtgtatgc aataatttgg tttctaaaac taagtgattg acggaaaagg agggacgaag   1560
gacatagaat tgcaattttg tgttcttcat gtattttac ttttagagta ggtaagtcac    1620
tttcggtccg tttggttaat ggtactagtt ggtggtaata ggaatgattt gtagtgtaaa   1680
ttttcaagat atatatcatg tcattcccat ggtaatgaaa gtttgatcat aaaaaggttt   1740
tttgttcaca attttccatt accacctaat accacatgtt taaatggtaa tgcattggaa   1800
tgagttttgt gaagaaaatg agtttgttga gaaagaataa gcatggtcat taaatttgtc   1860
aagagatatt cctatcaaaa ttacactagc tttccattat catttcacca tttagtaccg   1920
attaccaaat gggccgttta tagtttggga agagcatacg tttgtgtaaa acttttattt   1980
tgaagttgaa agaatttgtt gcacctttg ttatgattaa gttttgatgt ttttagctgc    2040
aataatttgt tgatgaaaaa gccactactt ttttctcagc tgcaaattat gttggaacca   2100
tttctctgga gaaacacaa tgctactgaa cttttctgatg agcatgttca ggaaaggcaa   2160
gtgccacata ctattaagtg ttagttgctg agaatatatt tgaatctaag atgcacgaag   2220
accactggtg cccttgctct atcaattctg atggaaagga ttatcgctga atttaccttc   2280
tactaaaaca tcgataaaat acttcattat tagcatcaaa agattccctc catccttctg   2340
gttttgctag acttgcctta tgaaggtgtt caaggagtag tttgctaccc ttcaagatag   2400
ggtagtggtt gccgtctctc ataatttcag tcactcgttt tcctctcccta attcaagcca   2460
taatttttat ggttcctcca cacaacactt gctaaatttg aaaagtagca aagaggaagt   2520
gagcaaaatc agcaggagta ggactgatga gtaagagctt gattaagtgt agaggatttt   2580
cttttgtgtt gaatatgaat gcatcatgca tgactgtaga attgacataa tgatttgtct   2640
gcagcgttgg tgaatttttt gagcgacatt ttgggaaaga ggtattgttg ccaattgcca   2700
tgctctattc attccggtga attaacaaat gttgtgcttc tgcttactat tgcttataat   2760
tattgtttgt tgcagtttgt tgattatgtt attgacccttt tgttgcggg tacatgtgga    2820
gatcctcaat cgctttccgt gagttaaata ctgtgcttgc ttttttttt caacatttc    2880
tggaggctgt aaataaatta tactccttcc tattctaatc aaatatccta tttcccttt    2940
tggcatattc aaatttagtt aaatattgtg taaattattt acacaattgc cattaaattt   3000
tcactttttcc cttactcttc tcatgtgtcc cttcccccttt tcttaaaat tggtgcatta   3060
tcaaatagga catttgattt gaataggcgg gagtttccaa ttgtgcttcc aaaggtagct   3120
tgtcactttt tcttttttctt taaatttgt accatgccat gcattttgaa cctcaactca   3180
tttcgccata aaggaatatt atgtttgaga agaacgagga tactattatc ttatagataa   3240
```

```
catataggtt tcattatcaa tgattgtttg attttcaact cttctttcc tttcatgctc      3300
atattgatgt tatttctatt tgttatgaat tatgtccatt gtgttaatgt ctttctttat      3360
tgtagatgca ccatacattt ccagaagtat ggaatattga aaaaaggtat gaaccttaaa      3420
gctttaattt tcttcgaact taatgtttct taattgattc ttttggatca atttccataa      3480
gaatggaaat ttaaaaaagg gtatgaacct taaagatttc ttcgaactta tatgttttgt      3540
aattcatgct tttagatgct gcaccatttt atctatgtgt cttaagtttg ttgtaatcat      3600
ttgtagacca aaagaatgaa tggtctggtt tgaaatggtt catcgtgcaa aaatgcgatt      3660
ttgcttgtga ttgaggtaac attcaaggtg gtgtgtttgt cgtactgtca aatgtcttcc      3720
tataccatgt gatatatata agcctaaaat gatatattgt acacctttag gatgtggata      3780
gcaggggttc agtacatatg aaaaatcctt gcaatttgat ctgtacgatc aatgtgattt      3840
tgccttttgc cttttgcctt ttgttatatg atgatgattc catgtgaaat tttgggattt      3900
agaaaattca cttgtttaag aacatttgaa tcaaactttc accaatttca accacattta      3960
attgcggcaa agccgaactt taaaagtcac tcccaatctt tgagatatcc aaactccaaa      4020
acttctatta gctttcatgt tttcactaag taaagttggt gcgactcctt accatttct      4080
ttattatgca tttcgttgat gtataatagt atagattggt gctctcttcg ctctccttcc      4140
aacatgcata acttctagtt cttgtcgttt tcttttcctc cctatttta tttgacttgt      4200
agctatttt gttcactctt ctcgcccaat ccatagctaa agaaacttga tttcattgat      4260
tttgtaactg atatgcaatt catttttgtt tgcttttagt tgttgattca aaaacaataa      4320
tgctaaagcc ctaatcctaa catgtcgggt tagctgttga aacaatactt gaaattgcta      4380
taaaaaggga ttttttttcgg gtacttcagt tgttgagatt gatatggtca agtataattt      4440
gttttaacac aatttgtaat gatttaatgg cttagtttca tagctgtttg tattaataaa      4500
ggaaggagga ctatctgaaa ttgcaatagg aaagagattt tagttcggta tttggttgtt      4560
taaattgata tggccaagta atgttcattt tacacaattg gtaatgtttt attggctcaa      4620
tagtgtttgt aagtatgcga ctcaaattta atcaagtata acttattgaa acataaataa      4680
atatccatta ggtttggctc tgtgtttgct ggactaattc aatcaacatt gttatctaag      4740
aaggaaaagg gtggagaaaa tgcttcataa gaagcctcgg acgtc                     4785
```

<210> SEQ ID NO 34
<211> LENGTH: 229
<212> TYPE: PRT
<213> ORGANISM: Amaranthus tuberculatus

<400> SEQUENCE: 34

Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp

```
                    100                 105                 110
Leu Gly Leu Arg Glu Lys Gln Gln Leu Pro Ile Ser Gln Asn Lys Arg
            115                 120                 125

Tyr Ile Ala Arg Asp Gly Leu Pro Val Leu Leu Pro Ser Asn Pro Ala
            130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
            195                 200                 205

Cys Gly Asp Pro Gln Ser Leu Ser Met His His Thr Phe Pro Glu Val
            210                 215                 220

Trp Asn Ile Glu Lys
225

<210> SEQ ID NO 35
<211> LENGTH: 1602
<212> TYPE: DNA
<213> ORGANISM: Amaranthus tuberculatus

<400> SEQUENCE: 35
atggtaattc aatccattac ccacctttca ccaaaccttg cattgccatc gccattgtca      60
gtttcaacca agaactaccc agtagctgta atgggcaaca tttctgagcg ggaagaaccc     120
acttctgcta aaagggttgc tgttgttggt gctggagtta gtggacttgc tgctgcatat     180
aagctaaaat cccatggttt gagtgtgaca ttgtttgaag ctgattctag agctggaggc     240
aaacttaaaa ctgttaaaaa agatggtttt atttgggatg aggggcaaa tactatgaca     300
gaaagtgagg cagaggtctc gagtttgatc gatgatcttg gcttcgtga agcaacag      360
ttgccaattt cacaaaataa agatacata gctagacg tcttcctgt gctactacct      420
tcaaatcccg ctgcactact cacgagcaat atcctttcag caaaatcaaa gctgcaaatt     480
atgttggaac catttctctg gagaaaacac aatgctactg aactttctga tgagcatgtt     540
caggaaagcg ttggtgaatt ttttgagcga catttgga aagagtttgt tgattatgtt     600
atcgacccttt tgttgcggg tacatgtgga atcctcaat cgctttccat gcaccataca     660
tttccagaag tatggaatat tgaaaaaagg tttggctctg tgtttgctgg actaattcaa     720
tcaacattgt tatctaagaa ggaaaagggt ggagaaaatg cttctattaa gaagcctcgt     780
gtacgtggtt catttttcatt tcaaggtgga atgcagacac ttgttgacac aatgtgcaaa     840
cagcttggtg aagatgaact caaactccag tgtgaggtgc tgtccttgtc atataaccag     900
aaggggatcc cctcattagg gaattggtca gtctcttcta tgtcaaataa taccagtgaa     960
gatcaatctt atgatgctgt ggttgtcact gctccaattc gcaatgtcaa agaaatgaag    1020
attatgaaat ttggaaatcc attttcactt gactttattc cagaggtgac gtacgtaccc    1080
ctttccgtta tgattactgc attcaaaaag gataaagtga agagacctct tgagggcttc    1140
ggagttctta tcccctctaa agagcaacat aatggactga agactcttgg tactttattt    1200
tcctccatga tgtttcctga tcgtgctcca tctgacatgt gtctctttac tacatttgtc    1260
ggaggaagca gaaatagaaa acttgcaaac gcttcaacgg atgaattgaa gcaaatagtt    1320
tcttctgacc ttcagcagct gttgggcact gaggacgaac cttcatttgt caatcatctc    1380
```

```
ttttggagca acgcattccc attgtatgga cacaattacg attctgtttt gagagccata    1440
gacaagatgg aaaaggatct tcctggattt ttttatgcag gtaaccataa gggtggactt    1500
tcagtgggaa aagcgatggc ctccggatgc aaggctgcgg aacttgtaat atcctatctg    1560
gactctcata tatatgtgaa gatggatgag aagaccgcgt aa                      1602

<210> SEQ ID NO 36
<211> LENGTH: 24
<212> TYPE: DNA
<213> ORGANISM: Artificial
<220> FEATURE:
<223> OTHER INFORMATION: Synthetic: oligonucleotide useful as primer

<400> SEQUENCE: 36
ggagcagtga caaccacagc atca                                            24

<210> SEQ ID NO 37
<211> LENGTH: 22
<212> TYPE: DNA
<213> ORGANISM: Artificial
<220> FEATURE:
<223> OTHER INFORMATION: Synthetic: oligonucleotide useful as primer

<400> SEQUENCE: 37
atcgatgatc ttgggcttcg tg                                              22

<210> SEQ ID NO 38
<211> LENGTH: 22
<212> TYPE: DNA
<213> ORGANISM: Artificial
<220> FEATURE:
<223> OTHER INFORMATION: Synthetic: oligonucleotide useful as primer

<400> SEQUENCE: 38
aatggtaagg agtcgcacca ac                                              22

<210> SEQ ID NO 39
<211> LENGTH: 20
<212> TYPE: DNA
<213> ORGANISM: Artificial
<220> FEATURE:
<223> OTHER INFORMATION: Synthetic: oligonucleotide useful as primer

<400> SEQUENCE: 39
cttcaaatcc cgctgcacta                                                 20

<210> SEQ ID NO 40
<211> LENGTH: 19
<212> TYPE: DNA
<213> ORGANISM: Artificial
<220> FEATURE:
<223> OTHER INFORMATION: Synthetic: oligonucleotide useful as primer

<400> SEQUENCE: 40
tacttctgga aatgtatgg                                                  19

<210> SEQ ID NO 41
<211> LENGTH: 22
<212> TYPE: DNA
<213> ORGANISM: Artificial
<220> FEATURE:
<223> OTHER INFORMATION: Synthetic: oligonucleotide useful as primer

<400> SEQUENCE: 41
```

```
gagaaaacac aatgctactg aa                                            22

<210> SEQ ID NO 42
<211> LENGTH: 20
<212> TYPE: DNA
<213> ORGANISM: Artificial
<220> FEATURE:
<223> OTHER INFORMATION: Synthetic:  oligonucleotide useful as primer

<400> SEQUENCE: 42
acagcctcca gaaaatgttg                                               20

<210> SEQ ID NO 43
<211> LENGTH: 66
<212> TYPE: DNA
<213> ORGANISM: Artificial
<220> FEATURE:
<223> OTHER INFORMATION: Synthetic:  partial coding sequence
      characteristic of herbicide sensitive PPX2L of Amaranthus
      tuberculatus

<400> SEQUENCE: 43
tttgttgatt atgttattga ccctttgtt gcgggtacat gtggtggaga tcctcaatcg    60
ccttcc                                                              66

<210> SEQ ID NO 44
<211> LENGTH: 63
<212> TYPE: DNA
<213> ORGANISM: Artificial
<220> FEATURE:
<223> OTHER INFORMATION: Synthetic:  partial coding sequence
      characteristic of herbicide resistant PPXL2 of Amaranthus
      tuberculatus

<400> SEQUENCE: 44
tttgttgatt atgttattga ccctttgtt gcgggtacat gtggagatcc tcaatcgcct    60
tcc                                                                 63

<210> SEQ ID NO 45
<211> LENGTH: 1602
<212> TYPE: DNA
<213> ORGANISM: Artificial
<220> FEATURE:
<223> OTHER INFORMATION: Synthetic construct:  chimeric, herbicide
      resistant PPX2L coding sequence
<220> FEATURE:
<221> NAME/KEY: CDS
<222> LOCATION: (1)..(1599)

<400> SEQUENCE: 45 atg gta att caa tcc att acc cac ctt tca cca aac ctt gca ttg cca    48
Met Val Ile Gln Ser Ile Thr His Leu Ser Pro Asn Leu Ala Leu Pro
1               5                   10                  15 tcg cca ttg tca gtt tca acc aag aac tac cca gta gct gta atg ggc    96
Ser Pro Leu Ser Val Ser Thr Lys Asn Tyr Pro Val Ala Val Met Gly
            20                  25                  30 aac att tct gag cgg gaa gaa ccc act tct gct aaa agg gtt gct gtt   144
Asn Ile Ser Glu Arg Glu Glu Pro Thr Ser Ala Lys Arg Val Ala Val
        35                  40                  45 gtt ggt gct gga gtt agt gga ctt gct gct gca tat aag cta aaa tcc   192
Val Gly Ala Gly Val Ser Gly Leu Ala Ala Ala Tyr Lys Leu Lys Ser
    50                  55                  60 cat ggt ttg agt gtg aca ttg ttt gaa gct gat tct aga gct gga ggc   240
His Gly Leu Ser Val Thr Leu Phe Glu Ala Asp Ser Arg Ala Gly Gly
65                  70                  75                  80
```

```
aaa ctt aaa act gtt aaa aaa gat ggt ttt att tgg gat gag ggg gca      288
Lys Leu Lys Thr Val Lys Lys Asp Gly Phe Ile Trp Asp Glu Gly Ala
                85                  90                  95 aat act atg aca gaa agt gag gca gag gtc tcg agt ttg atc gat gat      336
Asn Thr Met Thr Glu Ser Glu Ala Glu Val Ser Ser Leu Ile Asp Asp
            100                 105                 110 ctt ggg ctt cgt gag aag caa cag ttg cca att tca caa aat aaa aga      384
Leu Gly Leu Arg Glu Lys Gln Gln Leu Pro Ile Ser Gln Asn Lys Arg
        115                 120                 125 tac ata gct aga gac ggt ctt cct gtg cta cta cct tca aat ccc gct      432
Tyr Ile Ala Arg Asp Gly Leu Pro Val Leu Leu Pro Ser Asn Pro Ala
    130                 135                 140 gca cta ctc acg agc aat atc ctt tca gca aaa tca aag ctg caa att      480
Ala Leu Leu Thr Ser Asn Ile Leu Ser Ala Lys Ser Lys Leu Gln Ile
145                 150                 155                 160 atg ttg gaa cca ttt ctc tgg aga aaa cac aat gct act gaa ctt tct      528
Met Leu Glu Pro Phe Leu Trp Arg Lys His Asn Ala Thr Glu Leu Ser
                165                 170                 175 gat gag cat gtt cag gaa agc gtt ggt gaa ttt ttt gag cga cat ttt      576
Asp Glu His Val Gln Glu Ser Val Gly Glu Phe Phe Glu Arg His Phe
            180                 185                 190 ggg aaa gag ttt gtt gat tat gtt att gac cct ttt gtt gcg ggt aca      624
Gly Lys Glu Phe Val Asp Tyr Val Ile Asp Pro Phe Val Ala Gly Thr
        195                 200                 205 tgt gga gat cct caa tcg ctt tcc atg cac cat aca ttt cca gaa gta      672
Cys Gly Asp Pro Gln Ser Leu Ser Met His His Thr Phe Pro Glu Val
    210                 215                 220 tgg aat att gaa aaa agg ttt ggc tct gtg ttt gct gga cta att caa      720
Trp Asn Ile Glu Lys Arg Phe Gly Ser Val Phe Ala Gly Leu Ile Gln
225                 230                 235                 240 tca aca ttg tta tct aag aag gaa aag ggt gga gaa aat gct tct att      768
Ser Thr Leu Leu Ser Lys Lys Glu Lys Gly Gly Glu Asn Ala Ser Ile
                245                 250                 255 aag aag cct cgt gta cgt ggt tca ttt tca ttt caa ggt gga atg cag      816
Lys Lys Pro Arg Val Arg Gly Ser Phe Ser Phe Gln Gly Gly Met Gln
            260                 265                 270 aca ctt gtt gac aca atg tgc aaa cag ctt ggt gaa gat gaa ctc aaa      864
Thr Leu Val Asp Thr Met Cys Lys Gln Leu Gly Glu Asp Glu Leu Lys
        275                 280                 285 ctc cag tgt gag gtg ctg tcc ttg tca tat aac cag aag ggg atc ccc      912
Leu Gln Cys Glu Val Leu Ser Leu Ser Tyr Asn Gln Lys Gly Ile Pro
    290                 295                 300 tca tta ggg aat tgg tca gtc tct tct atg tca aat aat acc agt gaa      960
Ser Leu Gly Asn Trp Ser Val Ser Ser Met Ser Asn Asn Thr Ser Glu
305                 310                 315                 320 gat caa tct tat gat gct gtg gtt gtc act gct cca att cgc aat gtc     1008
Asp Gln Ser Tyr Asp Ala Val Val Val Thr Ala Pro Ile Arg Asn Val
                325                 330                 335 aaa gaa atg aag att atg aaa ttt gga aat cca ttt tca ctt gac ttt     1056
Lys Glu Met Lys Ile Met Lys Phe Gly Asn Pro Phe Ser Leu Asp Phe
            340                 345                 350 att cca gag gtg acg tac gta ccc ctt tcc gtt atg att act gca ttc     1104
Ile Pro Glu Val Thr Tyr Val Pro Leu Ser Val Met Ile Thr Ala Phe
        355                 360                 365 aaa aag gat aaa gtg aag aga cct ctt gag ggc ttc gga gtt ctt atc     1152
Lys Lys Asp Lys Val Lys Arg Pro Leu Glu Gly Phe Gly Val Leu Ile
    370                 375                 380 ccc tct aaa gag caa cat aat gga ctg aag act ctt ggt act tta ttt     1200
Pro Ser Lys Glu Gln His Asn Gly Leu Lys Thr Leu Gly Thr Leu Phe
```

```
                385                 390                 395                 400
tcc tcc atg atg ttt cct gat cgt gct cca tct gac atg tgt ctc ttt      1248
Ser Ser Met Met Phe Pro Asp Arg Ala Pro Ser Asp Met Cys Leu Phe
            405                 410                 415 act aca ttt gtc gga gga agc aga aat aga aaa ctt gca aac gct tca      1296
Thr Thr Phe Val Gly Gly Ser Arg Asn Arg Lys Leu Ala Asn Ala Ser
            420                 425                 430 acg gat gaa ttg aag caa ata gtt tct tct gac ctt cag cag ctg ttg      1344
Thr Asp Glu Leu Lys Gln Ile Val Ser Ser Asp Leu Gln Gln Leu Leu
            435                 440                 445 ggc act gag gac gaa cct tca ttt gtc aat cat ctc ttt tgg agc aac      1392
Gly Thr Glu Asp Glu Pro Ser Phe Val Asn His Leu Phe Trp Ser Asn
        450                 455                 460 gca ttc cca ttg tat gga cac aat tac gat tct gtt ttg aga gcc ata      1440
Ala Phe Pro Leu Tyr Gly His Asn Tyr Asp Ser Val Leu Arg Ala Ile
465                 470                 475                 480 gac aag atg gaa aag gat ctt cct gga ttt ttt tat gca ggt aac cat      1488
Asp Lys Met Glu Lys Asp Leu Pro Gly Phe Phe Tyr Ala Gly Asn His
            485                 490                 495 aag ggt gga ctt tca gtg gga aaa gcg atg gcc tcc gga tgc aag gct      1536
Lys Gly Gly Leu Ser Val Gly Lys Ala Met Ala Ser Gly Cys Lys Ala
            500                 505                 510 gcg gaa ctt gta ata tcc tat ctg gac tct cat ata tac gtg aag atg      1584
Ala Glu Leu Val Ile Ser Tyr Leu Asp Ser His Ile Tyr Val Lys Met
            515                 520                 525 gat gag aag acc gcg taa                                              1602
Asp Glu Lys Thr Ala
        530

<210> SEQ ID NO 46
<211> LENGTH: 533
<212> TYPE: PRT
<213> ORGANISM: Artificial
<220> FEATURE:
<223> OTHER INFORMATION: Synthetic Construct

<400> SEQUENCE: 46

Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
            85                  90                  95

Asn Thr Met Thr Glu Ser Glu Ala Glu Val Ser Ser Leu Ile Asp Asp
        100                 105                 110

Leu Gly Leu Arg Glu Lys Gln Gln Leu Pro Ile Ser Gln Asn Lys Arg
    115                 120                 125

Tyr Ile Ala Arg Asp Gly Leu Pro Val Leu Leu Pro Ser Asn Pro Ala
130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
```

```
                    165                 170                 175
Asp Glu His Val Gln Glu Ser Val Gly Glu Phe Phe Glu Arg His Phe
                180                 185                 190
Gly Lys Glu Phe Val Asp Tyr Val Ile Asp Pro Phe Val Ala Gly Thr
            195                 200                 205
Cys Gly Asp Pro Gln Ser Leu Ser Met His His Thr Phe Pro Glu Val
        210                 215                 220
Trp Asn Ile Glu Lys Arg Phe Gly Ser Val Phe Ala Gly Leu Ile Gln
225                 230                 235                 240
Ser Thr Leu Leu Ser Lys Lys Glu Lys Gly Gly Glu Asn Ala Ser Ile
                245                 250                 255
Lys Lys Pro Arg Val Arg Gly Ser Phe Ser Phe Gln Gly Gly Met Gln
            260                 265                 270
Thr Leu Val Asp Thr Met Cys Lys Gln Leu Gly Glu Asp Glu Leu Lys
        275                 280                 285
Leu Gln Cys Glu Val Leu Leu Ser Tyr Asn Gln Lys Gly Ile Pro
    290                 295                 300
Ser Leu Gly Asn Trp Ser Val Ser Ser Met Ser Asn Asn Thr Ser Glu
305                 310                 315                 320
Asp Gln Ser Tyr Asp Ala Val Val Val Thr Ala Pro Ile Arg Asn Val
                325                 330                 335
Lys Glu Met Lys Ile Met Lys Phe Gly Asn Pro Phe Ser Leu Asp Phe
            340                 345                 350
Ile Pro Glu Val Thr Tyr Val Pro Leu Ser Val Met Ile Thr Ala Phe
        355                 360                 365
Lys Lys Asp Lys Val Lys Arg Pro Leu Glu Gly Phe Gly Val Leu Ile
    370                 375                 380
Pro Ser Lys Glu Gln His Asn Gly Leu Lys Thr Leu Gly Thr Leu Phe
385                 390                 395                 400
Ser Ser Met Met Phe Pro Asp Arg Ala Pro Ser Asp Met Cys Leu Phe
                405                 410                 415
Thr Thr Phe Val Gly Gly Ser Arg Asn Arg Lys Leu Ala Asn Ala Ser
            420                 425                 430
Thr Asp Glu Leu Lys Gln Ile Val Ser Ser Asp Leu Gln Gln Leu Leu
        435                 440                 445
Gly Thr Glu Asp Glu Pro Ser Phe Val Asn His Leu Phe Trp Ser Asn
    450                 455                 460
Ala Phe Pro Leu Tyr Gly His Asn Tyr Asp Ser Val Leu Arg Ala Ile
465                 470                 475                 480
Asp Lys Met Glu Lys Asp Leu Pro Gly Phe Phe Tyr Ala Gly Asn His
                485                 490                 495
Lys Gly Gly Leu Ser Val Gly Lys Ala Met Ala Ser Gly Cys Lys Ala
            500                 505                 510
Ala Glu Leu Val Ile Ser Tyr Leu Asp Ser His Ile Tyr Val Lys Met
        515                 520                 525
Asp Glu Lys Thr Ala
    530

<210> SEQ ID NO 47
<211> LENGTH: 1605
<212> TYPE: DNA
<213> ORGANISM: Amaranthus tuberculatus
<220> FEATURE:
<221> NAME/KEY: CDS
<222> LOCATION: (1)..(1605)
```

<400> SEQUENCE: 47

```
atg gta att caa tcc att acc cac ctt tca cca aac ctt gca ttg cca        48
Met Val Ile Gln Ser Ile Thr His Leu Ser Pro Asn Leu Ala Leu Pro
1               5                   10                  15 tcg cca ttg tca gtt tca acc aag aac tac cca gta gct gta atg ggc        96
Ser Pro Leu Ser Val Ser Thr Lys Asn Tyr Pro Val Ala Val Met Gly
                20                  25                  30 aac att tct gag cgg gaa gaa ccc act tct gct aaa agg gtt gct gtt       144
Asn Ile Ser Glu Arg Glu Glu Pro Thr Ser Ala Lys Arg Val Ala Val
            35                  40                  45 gtt ggt gct gga gtt agt gga ctt gct gct gca tat aag cta aaa tcc       192
Val Gly Ala Gly Val Ser Gly Leu Ala Ala Ala Tyr Lys Leu Lys Ser
50                  55                  60 cat ggt ttg agt gtg aca ttg ttt gaa gct gat tct aga gct gga ggc       240
His Gly Leu Ser Val Thr Leu Phe Glu Ala Asp Ser Arg Ala Gly Gly
65                  70                  75                  80 aaa ctt aaa act gtt aaa aaa gat ggt ttt att tgg gat gag ggg gca       288
Lys Leu Lys Thr Val Lys Lys Asp Gly Phe Ile Trp Asp Glu Gly Ala
                85                  90                  95 aat act atg aca gaa agt gag gca gag gtc tcg agt ttg atc gat gat       336
Asn Thr Met Thr Glu Ser Glu Ala Glu Val Ser Ser Leu Ile Asp Asp
            100                 105                 110 ctt ggg ctt cgt gag aag caa cag ttg cca att tca caa aat aaa aga       384
Leu Gly Leu Arg Glu Lys Gln Gln Leu Pro Ile Ser Gln Asn Lys Arg
        115                 120                 125 tac ata gct aga gac ggt ctt cct gtg cta cta cct tca aat ccc gct       432
Tyr Ile Ala Arg Asp Gly Leu Pro Val Leu Leu Pro Ser Asn Pro Ala
    130                 135                 140 gca cta ctc acg agc aat atc ctt tca gca aaa tca aag ctg caa att       480
Ala Leu Leu Thr Ser Asn Ile Leu Ser Ala Lys Ser Lys Leu Gln Ile
145                 150                 155                 160 atg ttg gaa cca ttt ctc tgg aga aaa cac aat gct act gaa ctt tct       528
Met Leu Glu Pro Phe Leu Trp Arg Lys His Asn Ala Thr Glu Leu Ser
                165                 170                 175 gat gag cat gtt cag gaa agc gtt ggt gaa ttt ttt gag cga cat ttt       576
Asp Glu His Val Gln Glu Ser Val Gly Glu Phe Phe Glu Arg His Phe
            180                 185                 190 ggg aaa gag ttt gtt gat tat gtt atc gac cct ttt gtt gcg ggt aca       624
Gly Lys Glu Phe Val Asp Tyr Val Ile Asp Pro Phe Val Ala Gly Thr
        195                 200                 205 tgt ggt gga gat cct cga tcg ctt tcc atg cac cat aca ttt cca gaa       672
Cys Gly Gly Asp Pro Arg Ser Leu Ser Met His His Thr Phe Pro Glu
    210                 215                 220 gta tgg aat att gaa aaa agg ttt ggc tct gtg ttt gct gga cta att       720
Val Trp Asn Ile Glu Lys Arg Phe Gly Ser Val Phe Ala Gly Leu Ile
225                 230                 235                 240 caa tca aca ttg tta tct aag aag gaa aag ggt gga gaa aat gct tct       768
Gln Ser Thr Leu Leu Ser Lys Lys Glu Lys Gly Gly Glu Asn Ala Ser
                245                 250                 255 att aag aag cct cgt gta cgt ggt tca ttt tca ttt caa ggt gga atg       816
Ile Lys Lys Pro Arg Val Arg Gly Ser Phe Ser Phe Gln Gly Gly Met
            260                 265                 270 cag aca ctt gtt gac aca atg tgc aaa cag ctt ggt gaa gat gaa ctc       864
Gln Thr Leu Val Asp Thr Met Cys Lys Gln Leu Gly Glu Asp Glu Leu
        275                 280                 285 aaa ctc cag tgt gag gtg ctg tcc ttg tca tat aac cag aag ggg atc       912
Lys Leu Gln Cys Glu Val Leu Ser Leu Ser Tyr Asn Gln Lys Gly Ile
    290                 295                 300
```

```
ccc tca tta ggg aat tgg tca gtc tct tct atg tca aat aat acc agt      960
Pro Ser Leu Gly Asn Trp Ser Val Ser Ser Met Ser Asn Asn Thr Ser
305                 310                 315                 320 gaa gat caa tct tat gat gct gtg gtt gtc act gct cca att cgc aat     1008
Glu Asp Gln Ser Tyr Asp Ala Val Val Val Thr Ala Pro Ile Arg Asn
                325                 330                 335 gtc aaa gaa atg aag att atg aaa ttt gga aat cca ttt tca ctt gac     1056
Val Lys Glu Met Lys Ile Met Lys Phe Gly Asn Pro Phe Ser Leu Asp
        340                 345                 350 ttt att cca gag gtg acg tac gta ccc ctt tcc gtt atg att act gca     1104
Phe Ile Pro Glu Val Thr Tyr Val Pro Leu Ser Val Met Ile Thr Ala
355                 360                 365 ttc aaa aag gat aaa gtg aag aga cct ctt gag ggc ttc gga gtt ctt     1152
Phe Lys Lys Asp Lys Val Lys Arg Pro Leu Glu Gly Phe Gly Val Leu
    370                 375                 380 atc ccc tct aaa gag caa cat aat gga ctg aag act ctt ggt act tta     1200
Ile Pro Ser Lys Glu Gln His Asn Gly Leu Lys Thr Leu Gly Thr Leu
385                 390                 395                 400 ttt tcc tcc atg atg ttt cct gat cgt gct cca tct gac atg tgt ctc     1248
Phe Ser Ser Met Met Phe Pro Asp Arg Ala Pro Ser Asp Met Cys Leu
                405                 410                 415 ttt act aca ttt gtc gga gga agc aga aat aga aaa ctt gca aac gct     1296
Phe Thr Thr Phe Val Gly Gly Ser Arg Asn Arg Lys Leu Ala Asn Ala
        420                 425                 430 tca acg gat gaa ttg aag caa ata gtt tct tct gac ctt cag cag ctg     1344
Ser Thr Asp Glu Leu Lys Gln Ile Val Ser Ser Asp Leu Gln Gln Leu
435                 440                 445 ttg ggc act gag gac gaa cct tca ttt gtc aat cat ctc ttt tgg agc     1392
Leu Gly Thr Glu Asp Glu Pro Ser Phe Val Asn His Leu Phe Trp Ser
    450                 455                 460 aac gca ttc cca ttg tat gga cac aat tac gat tct gtt ttg aga gcc     1440
Asn Ala Phe Pro Leu Tyr Gly His Asn Tyr Asp Ser Val Leu Arg Ala
465                 470                 475                 480 ata gac aag atg gaa aag gat ctt cct gga ttt ttt tat gca ggt aac     1488
Ile Asp Lys Met Glu Lys Asp Leu Pro Gly Phe Phe Tyr Ala Gly Asn
                485                 490                 495 cat aag ggt gga ctt tca gtg gga aaa gcg atg gcc tcc gga tgc aag     1536
His Lys Gly Gly Leu Ser Val Gly Lys Ala Met Ala Ser Gly Cys Lys
        500                 505                 510 gct gcg gaa ctt gta ata tcc tat ctg gac tct cat ata tac gtg aag     1584
Ala Ala Glu Leu Val Ile Ser Tyr Leu Asp Ser His Ile Tyr Val Lys
515                 520                 525 atg gat gag aag acc gcg taa                                         1605
Met Asp Glu Lys Thr Ala
    530

<210> SEQ ID NO 48
<211> LENGTH: 534
<212> TYPE: PRT
<213> ORGANISM: Amaranthus tuberculatus

<400> SEQUENCE: 48

Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60
```

-continued

```
His Gly Leu Ser Val Thr Leu Phe Glu Ala Asp Ser Arg Ala Gly Gly
 65                  70                  75                  80

Lys Leu Lys Thr Val Lys Lys Asp Gly Phe Ile Trp Asp Glu Gly Ala
                 85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Gly Asp Pro Arg Ser Leu Ser Met His His Thr Phe Pro Glu
    210                 215                 220

Val Trp Asn Ile Glu Lys Arg Phe Gly Ser Val Phe Ala Gly Leu Ile
225                 230                 235                 240

Gln Ser Thr Leu Leu Ser Lys Lys Glu Lys Gly Gly Glu Asn Ala Ser
                245                 250                 255

Ile Lys Lys Pro Arg Val Arg Gly Ser Phe Ser Phe Gln Gly Gly Met
            260                 265                 270

Gln Thr Leu Val Asp Thr Met Cys Lys Gln Leu Gly Glu Asp Glu Leu
        275                 280                 285

Lys Leu Gln Cys Glu Val Leu Ser Leu Ser Tyr Asn Gln Lys Gly Ile
    290                 295                 300

Pro Ser Leu Gly Asn Trp Ser Val Ser Ser Met Ser Asn Asn Thr Ser
305                 310                 315                 320

Glu Asp Gln Ser Tyr Asp Ala Val Val Val Thr Ala Pro Ile Arg Asn
                325                 330                 335

Val Lys Glu Met Lys Ile Met Lys Phe Gly Asn Pro Phe Ser Leu Asp
            340                 345                 350

Phe Ile Pro Glu Val Thr Tyr Val Pro Leu Ser Val Met Ile Thr Ala
        355                 360                 365

Phe Lys Lys Asp Lys Val Lys Arg Pro Leu Glu Gly Phe Gly Val Leu
    370                 375                 380

Ile Pro Ser Lys Glu Gln His Asn Gly Leu Lys Thr Leu Gly Thr Leu
385                 390                 395                 400

Phe Ser Ser Met Met Phe Pro Asp Arg Ala Pro Ser Asp Met Cys Leu
                405                 410                 415

Phe Thr Thr Phe Val Gly Gly Ser Arg Asn Arg Lys Leu Ala Asn Ala
            420                 425                 430

Ser Thr Asp Glu Leu Lys Gln Ile Val Ser Ser Asp Leu Gln Gln Leu
        435                 440                 445

Leu Gly Thr Glu Asp Glu Pro Ser Phe Val Asn His Leu Phe Trp Ser
    450                 455                 460

Asn Ala Phe Pro Leu Tyr Gly His Asn Tyr Asp Ser Val Leu Arg Ala
465                 470                 475                 480
```

```
Ile Asp Lys Met Glu Lys Asp Leu Pro Gly Phe Phe Tyr Ala Gly Asn
            485                 490                 495

His Lys Gly Gly Leu Ser Val Gly Lys Ala Met Ala Ser Gly Cys Lys
        500                 505                 510

Ala Ala Glu Leu Val Ile Ser Tyr Leu Asp Ser His Ile Tyr Val Lys
        515                 520                 525

Met Asp Glu Lys Thr Ala
    530

<210> SEQ ID NO 49
<211> LENGTH: 30
<212> TYPE: DNA
<213> ORGANISM: Artificial
<220> FEATURE:
<223> OTHER INFORMATION: Synthetic:  oligonucleotide useful as primer

<400> SEQUENCE: 49
ttgctcttcc atggtaattc aatccattac                                    30

<210> SEQ ID NO 50
<211> LENGTH: 32
<212> TYPE: DNA
<213> ORGANISM: Artificial
<220> FEATURE:
<223> OTHER INFORMATION: Synthetic:  oligonucleotide useful as primer

<400> SEQUENCE: 50
ttgctcttcg ttacgcggtc ttctcatcca tc                                 32

<210> SEQ ID NO 51
<211> LENGTH: 34
<212> TYPE: DNA
<213> ORGANISM: Artificial
<220> FEATURE:
<223> OTHER INFORMATION: Synthetic:  oligonucleotide useful as primer

<400> SEQUENCE: 51
catcgatcaa actcgagacc tctgcctcac tttc                               34

<210> SEQ ID NO 52
<211> LENGTH: 34
<212> TYPE: DNA
<213> ORGANISM: Artificial
<220> FEATURE:
<223> OTHER INFORMATION: Synthetic:  oligonucleotide useful as primer

<400> SEQUENCE: 52
gaggcagagg tctcgagttt gatcgatgat cttg                               34

<210> SEQ ID NO 53
<211> LENGTH: 38
<212> TYPE: DNA
<213> ORGANISM: Artificial
<220> FEATURE:
<223> OTHER INFORMATION: Synthetic:  oligonucleotide useful as primer

<400> SEQUENCE: 53
ttcaccaagc tgtttgcaca ttgtgtcaac aagtgtct                           38

<210> SEQ ID NO 54
<211> LENGTH: 38
<212> TYPE: DNA
<213> ORGANISM: Artificial
<220> FEATURE:
<223> OTHER INFORMATION: Synthetic:  oligonucleotide useful as primer
```

<400> SEQUENCE: 54
agacacttgt tgacacaatg tgcaaacagc ttggtgaa                    38

<210> SEQ ID NO 55
<211> LENGTH: 504
<212> TYPE: PRT
<213> ORGANISM: Nicotiana tabacum

<400> SEQUENCE: 55

```
Met Ala Pro Ser Ala Gly Glu Asp Lys His Ser Ala Lys Arg Val
1               5                   10                  15

Ala Val Ile Gly Ala Gly Val Ser Gly Leu Ala Ala Tyr Lys Leu
            20                  25                  30

Lys Ile His Gly Leu Asn Val Thr Val Phe Glu Ala Glu Gly Lys Ala
        35                  40                  45

Gly Gly Lys Leu Arg Ser Val Ser Gln Asp Gly Leu Ile Trp Asp Glu
    50                  55                  60

Gly Ala Asn Thr Met Thr Glu Ser Glu Gly Asp Val Thr Phe Leu Ile
65                  70                  75                  80

Asp Ser Leu Gly Leu Arg Glu Lys Gln Gln Phe Pro Leu Ser Gln Asn
                85                  90                  95

Lys Arg Tyr Ile Ala Arg Asn Gly Thr Pro Val Leu Leu Pro Ser Asn
            100                 105                 110

Pro Ile Asp Leu Ile Lys Ser Asn Phe Leu Ser Thr Gly Ser Lys Leu
        115                 120                 125

Gln Met Leu Leu Glu Pro Ile Leu Trp Lys Asn Lys Lys Leu Ser Gln
    130                 135                 140

Val Ser Asp Ser His Glu Ser Val Ser Gly Phe Gln Arg His Phe
145                 150                 155                 160

Gly Lys Glu Val Val Asp Tyr Leu Ile Asp Pro Phe Val Ala Gly Thr
                165                 170                 175

Cys Gly Gly Asp Pro Asp Ser Leu Ser Met His His Ser Phe Pro Glu
            180                 185                 190

Leu Trp Asn Leu Glu Lys Arg Phe Gly Ser Val Ile Leu Gly Ala Ile
        195                 200                 205

Arg Ser Lys Leu Ser Pro Lys Asn Glu Lys Gln Gly Pro Pro Lys
    210                 215                 220

Thr Ser Ala Asn Lys Lys Arg Gln Arg Gly Ser Phe Ser Phe Leu Gly
225                 230                 235                 240

Gly Met Gln Thr Leu Thr Asp Ala Ile Cys Lys Asp Leu Arg Glu Asp
                245                 250                 255

Glu Leu Arg Leu Asn Ser Arg Val Leu Glu Leu Ser Cys Ser Cys Thr
            260                 265                 270

Glu Asp Ser Ala Ile Asp Ser Trp Ser Ile Ile Ser Ala Ser Pro His
        275                 280                 285

Lys Arg Gln Ser Glu Glu Glu Ser Phe Asp Ala Val Ile Met Thr Ala
    290                 295                 300

Pro Leu Cys Asp Val Lys Ser Met Lys Ile Ala Lys Arg Gly Asn Pro
305                 310                 315                 320

Phe Leu Leu Asn Phe Ile Pro Glu Val Asp Tyr Val Pro Leu Ser Val
                325                 330                 335

Val Ile Thr Thr Phe Lys Arg Glu Asn Val Lys Tyr Pro Leu Glu Gly
            340                 345                 350
```

```
Phe Gly Val Leu Val Pro Ser Lys Glu Gln Gln His Gly Leu Lys Thr
        355                 360                 365
Leu Gly Thr Leu Phe Ser Ser Met Met Phe Pro Asp Arg Ala Pro Asn
    370                 375                 380
Asn Val Tyr Leu Tyr Thr Thr Phe Val Gly Gly Ser Arg Asn Arg Glu
385                 390                 395                 400
Leu Ala Lys Ala Ser Arg Thr Glu Leu Lys Glu Ile Val Thr Ser Asp
                405                 410                 415
Leu Lys Gln Leu Leu Gly Ala Glu Gly Glu Pro Thr Tyr Val Asn His
            420                 425                 430
Leu Tyr Trp Ser Lys Ala Phe Pro Leu Tyr Gly His Asn Tyr Asp Ser
        435                 440                 445
Val Leu Asp Ala Ile Asp Lys Met Glu Lys Asn Leu Pro Gly Leu Phe
    450                 455                 460
Tyr Ala Gly Asn His Arg Gly Gly Leu Ser Val Gly Lys Ala Leu Ser
465                 470                 475                 480
Ser Gly Cys Asn Ala Ala Asp Leu Val Ile Ser Tyr Leu Glu Ser Val
                485                 490                 495
Ser Thr Asp Ser Lys Arg His Cys
            500

<210> SEQ ID NO 56
<211> LENGTH: 502
<212> TYPE: PRT
<213> ORGANISM: Glycine max

<400> SEQUENCE: 56

Met Ala Ser Ser Ala Thr Asp Asp Asn Pro Arg Ser Val Lys Arg Val
1               5                   10                  15
Ala Val Val Gly Ala Gly Val Ser Gly Leu Ala Ala Ala Tyr Lys Leu
            20                  25                  30
Lys Ser His Gly Leu Asp Val Thr Val Phe Glu Ala Glu Gly Arg Ala
        35                  40                  45
Gly Gly Arg Leu Arg Ser Val Ser Gln Asp Gly Leu Ile Trp Asp Glu
    50                  55                  60
Gly Ala Asn Thr Met Thr Glu Ser Glu Ile Glu Val Lys Gly Leu Ile
65                  70                  75                  80
Asp Ala Leu Gly Leu Gln Glu Lys Gln Gln Phe Pro Ile Ser Gln His
                85                  90                  95
Lys Arg Tyr Ile Val Lys Asn Gly Ala Pro Leu Leu Val Pro Thr Asn
            100                 105                 110
Pro Ala Ala Leu Leu Lys Ser Lys Leu Leu Ser Ala Gln Ser Lys Ile
        115                 120                 125
His Leu Ile Phe Glu Pro Phe Met Trp Lys Arg Ser Asp Pro Ser Asn
    130                 135                 140
Val Cys Asp Glu Asn Ser Val Glu Ser Val Gly Arg Phe Phe Glu Arg
145                 150                 155                 160
His Phe Gly Lys Glu Val Val Asp Tyr Leu Ile Asp Pro Phe Val Gly
                165                 170                 175
Gly Thr Ser Ala Ala Asp Pro Glu Ser Leu Ser Met Arg His Ser Phe
            180                 185                 190
Pro Glu Leu Trp Asn Leu Glu Lys Arg Phe Gly Ser Ile Ile Ala Gly
        195                 200                 205
Ala Leu Gln Ser Lys Leu Phe Ala Lys Arg Glu Lys Thr Gly Glu Asn
    210                 215                 220
```

```
Arg Thr Ala Leu Arg Lys Asn Lys His Lys Arg Gly Ser Phe Ser Phe
225                 230                 235                 240

Gln Gly Gly Met Gln Thr Leu Thr Asp Thr Leu Cys Lys Glu Leu Gly
            245                 250                 255

Lys Asp Asp Leu Lys Leu Asn Glu Lys Val Leu Thr Leu Ala Tyr Gly
            260                 265                 270

His Asp Gly Ser Ser Ser Gln Asn Trp Ser Ile Thr Ser Ala Ser
            275                 280                 285

Asn Gln Ser Thr Gln Asp Val Asp Ala Val Ile Met Thr Ala Pro Leu
    290                 295                 300

Tyr Asn Val Lys Asp Ile Lys Ile Thr Lys Arg Gly Thr Pro Phe Pro
305                 310                 315                 320

Leu Asn Phe Leu Pro Glu Val Ser Tyr Val Pro Ile Ser Val Met Ile
                325                 330                 335

Thr Thr Phe Lys Lys Glu Asn Val Lys Arg Pro Leu Glu Gly Phe Gly
            340                 345                 350

Val Leu Val Pro Ser Lys Glu Gln Lys Asn Gly Leu Lys Thr Leu Gly
            355                 360                 365

Thr Leu Phe Ser Ser Met Met Phe Pro Asp Arg Ala Pro Ser Asp Leu
    370                 375                 380

Tyr Leu Tyr Thr Thr Phe Ile Gly Gly Thr Gln Asn Arg Glu Leu Ala
385                 390                 395                 400

Gln Ala Ser Thr Asp Glu Leu Arg Lys Ile Val Thr Ser Asp Leu Arg
            405                 410                 415

Lys Leu Leu Gly Ala Glu Gly Glu Pro Thr Phe Val Asn His Phe Tyr
            420                 425                 430

Trp Ser Lys Gly Phe Pro Leu Tyr Gly Arg Asn Tyr Gly Ser Val Leu
            435                 440                 445

Gln Ala Ile Asp Lys Ile Glu Lys Asp Leu Pro Gly Phe Phe Phe Ala
    450                 455                 460

Gly Asn Tyr Lys Gly Gly Leu Ser Val Gly Lys Ala Ile Ala Ser Gly
465                 470                 475                 480

Cys Lys Ala Ala Asp Leu Val Ile Ser Tyr Leu Asn Ser Ala Ser Asp
            485                 490                 495

Asn Thr Val Pro Asp Lys
            500

<210> SEQ ID NO 57
<211> LENGTH: 547
<212> TYPE: PRT
<213> ORGANISM: Arabidopsis thaliana

<400> SEQUENCE: 57

Met Gly Leu Ile Lys Asn Gly Thr Leu Tyr Cys Arg Phe Gly Ile Ser
1               5                   10                  15

Trp Asn Phe Ala Ala Val Phe Phe Ser Thr Tyr Phe Arg His Cys Phe
            20                  25                  30

Arg Leu Val Arg Asp Phe Asp Ser Glu Leu Leu Gln Ile Ala Met Ala
        35                  40                  45

Ser Gly Ala Val Ala Asp His Gln Ile Glu Ala Val Ser Gly Lys Arg
    50                  55                  60

Val Ala Val Val Gly Ala Gly Val Ser Gly Leu Ala Ala Ala Tyr Lys
65                  70                  75                  80

Leu Lys Ser Arg Gly Leu Asn Val Thr Val Phe Glu Ala Asp Gly Arg
```

-continued

```
                85                  90                  95
Val Gly Gly Lys Leu Arg Ser Val Met Gln Asn Gly Leu Ile Trp Asp
            100                 105                 110

Glu Gly Ala Asn Thr Met Thr Glu Ala Glu Pro Glu Val Gly Ser Leu
        115                 120                 125

Leu Asp Asp Leu Gly Leu Arg Glu Lys Gln Gln Phe Pro Ile Ser Gln
    130                 135                 140

Lys Lys Arg Tyr Ile Val Arg Asn Gly Val Pro Val Met Leu Pro Thr
145                 150                 155                 160

Asn Pro Ile Glu Leu Val Thr Ser Val Leu Ser Thr Gln Ser Lys
            165                 170                 175

Phe Gln Ile Leu Leu Glu Pro Phe Leu Trp Lys Lys Ser Ser Lys
        180                 185                 190

Val Ser Asp Ala Ser Ala Glu Glu Ser Val Ser Glu Phe Gln Arg
    195                 200                 205

His Phe Gly Gln Glu Val Val Asp Tyr Leu Ile Asp Pro Phe Val Gly
    210                 215                 220

Gly Thr Ser Ala Ala Asp Pro Asp Ser Leu Ser Met Lys His Ser Phe
225                 230                 235                 240

Pro Asp Leu Trp Asn Ser Phe Gly Ser Ile Ile Val Gly Ala Ile Arg
            245                 250                 255

Thr Lys Phe Ala Ala Lys Gly Gly Lys Ser Arg Asp Thr Lys Ser Ser
            260                 265                 270

Pro Gly Thr Lys Lys Gly Ser Arg Gly Ser Phe Ser Phe Lys Gly Gly
        275                 280                 285

Met Gln Ile Leu Pro Asp Thr Leu Cys Lys Ser Leu Ser His Asp Glu
    290                 295                 300

Ile Asn Leu Asp Ser Lys Val Leu Ser Leu Ser Tyr Asn Ser Gly Ser
305                 310                 315                 320

Arg Gln Glu Asn Trp Ser Leu Ser Cys Val Ser His Asn Glu Thr Gln
            325                 330                 335

Arg Gln Asn Pro His Tyr Asp Ala Ala Pro Leu Cys Asn Val Lys Glu
        340                 345                 350

Met Lys Val Met Lys Gly Gly Gln Pro Phe Gln Leu Asn Phe Leu Pro
    355                 360                 365

Glu Ile Asn Tyr Met Pro Leu Ser Val Leu Ile Thr Thr Phe Thr Lys
    370                 375                 380

Glu Lys Val Lys Arg Pro Leu Glu Gly Phe Gly Val Leu Ile Pro Ser
385                 390                 395                 400

Lys Glu Gln Lys His Gly Phe Lys Thr Leu Gly Thr Leu Phe Ser Ser
            405                 410                 415

Met Met Phe Pro Asp Arg Ser Pro Ser Asp Val His Leu Tyr Thr Thr
            420                 425                 430

Phe Ile Gly Gly Ser Arg Asn Gln Glu Leu Ala Lys Ala Ser Thr Asp
        435                 440                 445

Glu Leu Lys Gln Val Val Thr Ser Asp Leu Gln Arg Leu Leu Gly Val
    450                 455                 460

Glu Gly Glu Pro Val Ser Val Asn His Tyr Tyr Trp Arg Lys Ala Phe
465                 470                 475                 480

Pro Leu Tyr Asp Ser Ser Tyr Asp Ser Val Met Glu Ala Ile Asp Lys
            485                 490                 495

Met Glu Asn Asp Leu Pro Gly Phe Phe Tyr Ala Gly Asn His Arg Gly
            500                 505                 510
```

```
Gly Leu Ser Val Gly Lys Ser Ile Ala Ser Gly Cys Lys Ala Ala Asp
        515                 520                 525

Leu Val Ile Ser Tyr Leu Glu Ser Cys Ser Asn Asp Lys Lys Pro Asn
        530                 535                 540

Asp Ser Leu
545

<210> SEQ ID NO 58
<211> LENGTH: 548
<212> TYPE: PRT
<213> ORGANISM: Nicotiana tabacum

<400> SEQUENCE: 58

Met Thr Thr Thr Pro Ile Ala Asn His Pro Asn Ile Phe Thr His Gln
1               5                   10                  15

Ser Ser Ser Ser Pro Leu Ala Phe Leu Asn Arg Thr Ser Phe Ile Pro
            20                  25                  30

Phe Ser Ser Ile Ser Lys Arg Asn Ser Val Asn Cys Asn Gly Trp Arg
        35                  40                  45

Thr Arg Cys Ser Val Ala Lys Asp Tyr Thr Val Pro Ser Ser Ala Val
    50                  55                  60

Asp Gly Gly Pro Ala Ala Glu Leu Asp Cys Val Ile Val Gly Ala Gly
65                  70                  75                  80

Ile Ser Gly Leu Cys Ile Ala Gln Val Met Ser Ala Asn Tyr Pro Asn
                85                  90                  95

Leu Met Val Thr Glu Ala Arg Asp Arg Ala Gly Gly Asn Ile Thr Thr
            100                 105                 110

Val Glu Arg Asp Gly Tyr Leu Trp Glu Glu Gly Pro Asn Ser Phe Gln
        115                 120                 125

Pro Ser Asp Pro Met Leu Thr Met Ala Val Asp Cys Gly Leu Lys Asp
    130                 135                 140

Asp Leu Val Leu Gly Asp Pro Asn Ala Pro Arg Phe Val Leu Trp Lys
145                 150                 155                 160

Gly Lys Leu Arg Pro Val Pro Ser Lys Leu Thr Asp Leu Ala Phe Phe
                165                 170                 175

Asp Leu Met Ser Ile Pro Gly Lys Leu Arg Ala Gly Phe Gly Ala Ile
            180                 185                 190

Gly Leu Arg Pro Ser Pro Pro Gly His Glu Glu Ser Val Glu Gln Phe
        195                 200                 205

Val Arg Arg Asn Leu Gly Gly Glu Val Phe Glu Arg Leu Ile Glu Pro
    210                 215                 220

Phe Cys Ser Gly Val Tyr Ala Gly Asp Pro Ser Lys Leu Ser Met Lys
225                 230                 235                 240

Ala Ala Phe Gly Lys Val Trp Lys Leu Glu Glu Thr Gly Gly Ser Ile
                245                 250                 255

Ile Gly Gly Thr Phe Lys Ala Ile Lys Glu Arg Ser Ser Thr Pro Lys
            260                 265                 270

Ala Pro Arg Asp Pro Arg Leu Pro Lys Pro Lys Gly Gln Thr Val Gly
        275                 280                 285

Ser Phe Arg Lys Gly Leu Arg Met Leu Pro Asp Ala Ile Ser Ala Arg
    290                 295                 300

Leu Gly Ser Lys Leu Lys Leu Ser Trp Lys Leu Ser Ser Ile Thr Lys
305                 310                 315                 320

Ser Glu Lys Gly Gly Tyr His Leu Thr Tyr Glu Thr Pro Glu Gly Val
```

```
                325                 330                 335
Val Ser Leu Gln Ser Arg Ser Ile Val Met Thr Val Pro Ser Tyr Val
            340                 345                 350

Ala Ser Asn Ile Leu Arg Pro Leu Ser Val Ala Ala Asp Ala Leu
            355                 360                 365

Ser Asn Phe Tyr Tyr Pro Pro Val Gly Ala Val Thr Ile Thr Tyr Pro
    370                 375                 380

Gln Glu Ala Ile Arg Asp Glu Arg Leu Val Asp Gly Glu Leu Lys Gly
385                 390                 395                 400

Phe Gly Gln Leu His Pro Arg Thr Gln Gly Val Glu Thr Leu Gly Thr
            405                 410                 415

Ile Tyr Ser Ser Leu Phe Pro Asn Arg Ala Pro Lys Gly Arg Val
            420                 425                 430

Leu Leu Leu Asn Tyr Ile Gly Gly Ala Lys Asn Pro Glu Ile Leu Ser
            435                 440                 445

Lys Thr Glu Ser Gln Leu Val Glu Val Val Asp Arg Asp Leu Arg Lys
    450                 455                 460

Met Leu Ile Lys Pro Lys Ala Gln Asp Pro Leu Val Val Gly Val Arg
465                 470                 475                 480

Val Trp Pro Gln Ala Ile Pro Gln Phe Leu Val Gly His Leu Asp Thr
            485                 490                 495

Leu Ser Thr Ala Lys Ala Ala Met Asn Asp Asn Gly Leu Glu Gly Leu
            500                 505                 510

Phe Leu Gly Gly Asn Tyr Val Ser Gly Val Ala Leu Gly Arg Cys Val
            515                 520                 525

Glu Gly Ala Tyr Glu Val Ala Ser Glu Val Thr Gly Phe Leu Ser Arg
    530                 535                 540

Tyr Ala Tyr Lys
545

<210> SEQ ID NO 59
<211> LENGTH: 537
<212> TYPE: PRT
<213> ORGANISM: Arabidopsis thaliana

<400> SEQUENCE: 59

Met Glu Leu Ser Leu Leu Arg Pro Thr Thr Gln Ser Leu Leu Pro Ser
1               5                   10                  15

Phe Ser Lys Pro Asn Leu Arg Leu Asn Val Tyr Lys Pro Leu Arg Leu
            20                  25                  30

Arg Cys Ser Val Ala Gly Gly Pro Thr Val Gly Ser Ser Lys Ile Glu
        35                  40                  45

Gly Gly Gly Gly Thr Thr Ile Thr Thr Asp Cys Val Ile Val Gly Gly
    50                  55                  60

Gly Ile Ser Gly Leu Cys Ile Ala Gln Ala Leu Ala Thr Lys His Pro
65                  70                  75                  80

Asp Ala Ala Pro Asn Leu Ile Val Thr Glu Ala Lys Asp Arg Val Gly
            85                  90                  95

Gly Asn Ile Ile Thr Arg Glu Glu Asn Gly Phe Leu Trp Glu Glu Gly
            100                 105                 110

Pro Asn Ser Phe Gln Pro Ser Asp Pro Met Leu Thr Met Val Val Asp
            115                 120                 125

Ser Gly Leu Lys Asp Asp Leu Val Leu Gly Asp Pro Thr Ala Pro Arg
    130                 135                 140
```

Phe Val Leu Trp Asn Gly Lys Leu Arg Pro Val Pro Ser Lys Leu Thr
145                 150                 155                 160

Asp Leu Pro Phe Phe Asp Leu Met Ser Ile Gly Gly Lys Ile Arg Ala
            165                 170                 175

Gly Phe Gly Ala Leu Gly Ile Arg Pro Ser Pro Gly Arg Glu Glu
        180                 185                 190

Ser Val Glu Glu Phe Val Arg Arg Asn Leu Gly Asp Glu Val Phe Glu
        195                 200                 205

Arg Leu Ile Glu Pro Phe Cys Ser Gly Val Tyr Ala Gly Asp Pro Ser
        210                 215                 220

Lys Leu Ser Met Lys Ala Ala Phe Gly Lys Val Trp Lys Leu Glu Gln
225                 230                 235                 240

Asn Gly Gly Ser Ile Ile Gly Gly Thr Phe Lys Ala Ile Gln Glu Arg
                245                 250                 255

Lys Asn Ala Pro Lys Ala Glu Arg Asp Pro Arg Leu Pro Lys Pro Gln
                260                 265                 270

Gly Gln Thr Val Gly Ser Phe Arg Lys Gly Leu Arg Met Leu Pro Glu
            275                 280                 285

Ala Ile Ser Ala Arg Leu Gly Ser Lys Val Lys Leu Ser Trp Lys Leu
        290                 295                 300

Ser Gly Ile Thr Lys Leu Glu Ser Gly Gly Tyr Asn Leu Thr Tyr Glu
305                 310                 315                 320

Thr Pro Asp Gly Leu Val Ser Val Gln Ser Lys Ser Val Val Met Thr
                325                 330                 335

Val Pro Ser His Val Ala Ser Gly Leu Leu Arg Pro Leu Ser Glu Ser
                340                 345                 350

Ala Ala Asn Ala Leu Ser Lys Leu Tyr Tyr Pro Pro Val Ala Ala Val
            355                 360                 365

Ser Ile Ser Tyr Pro Lys Glu Ala Ile Arg Thr Glu Cys Leu Ile Asp
        370                 375                 380

Gly Glu Leu Lys Gly Phe Gly Gln Leu His Pro Arg Thr Gln Gly Val
385                 390                 395                 400

Glu Thr Leu Gly Thr Ile Tyr Ser Ser Ser Leu Phe Pro Asn Arg Ala
                405                 410                 415

Pro Pro Gly Arg Ile Leu Leu Leu Asn Tyr Ile Gly Gly Ser Thr Asn
            420                 425                 430

Thr Gly Ile Leu Ser Lys Ser Glu Gly Glu Leu Val Glu Ala Val Asp
        435                 440                 445

Arg Asp Leu Arg Lys Met Leu Ile Lys Pro Asn Ser Thr Asp Pro Leu
        450                 455                 460

Lys Leu Gly Val Arg Val Trp Pro Gln Ala Ile Pro Gln Phe Leu Val
465                 470                 475                 480

Gly His Phe Asp Ile Leu Asp Thr Ala Lys Ser Ser Leu Thr Ser Ser
                485                 490                 495

Gly Tyr Glu Gly Leu Phe Leu Gly Gly Asn Tyr Val Ala Gly Val Ala
            500                 505                 510

Leu Gly Arg Cys Val Glu Gly Ala Tyr Glu Thr Ala Ile Glu Val Asn
        515                 520                 525

Asn Phe Met Ser Arg Tyr Ala Tyr Lys
            530                 535

<210> SEQ ID NO 60
<211> LENGTH: 555
<212> TYPE: PRT

<213> ORGANISM: Cichorium intybus

<400> SEQUENCE: 60

```
Met Thr Ser Leu Thr Asp Val Cys Ser Leu Asn Cys Cys Arg Ser Trp
1               5                   10                  15

Ser Ser Leu Pro Pro Val Ser Gly Gly Ser Leu Thr Ser Lys Asn
            20                  25                  30

Pro Arg Tyr Leu Ile Thr Tyr Ser Pro Ala His Arg Lys Cys Asn Arg
                35                  40                  45

Trp Arg Phe Arg Cys Ser Ile Ala Lys Asp Ser Pro Ile Thr Pro Pro
            50                  55                  60

Ile Ser Asn Glu Phe Asn Ser Gln Pro Leu Leu Asp Cys Val Ile Val
65                  70                  75                  80

Gly Ala Gly Ile Ser Gly Leu Cys Ile Ala Gln Ala Leu Ala Thr Lys
                85                  90                  95

His Ala Ser Val Ser Pro Asp Val Ile Val Thr Glu Ala Arg Asp Arg
                100                 105                 110

Val Gly Gly Asn Ile Ser Thr Val Glu Arg Asp Gly Tyr Leu Trp Glu
            115                 120                 125

Glu Gly Pro Asn Ser Phe Gln Pro Ser Asp Ala Met Leu Thr Met Val
    130                 135                 140

Val Asp Ser Gly Leu Lys Asp Leu Val Leu Gly Asp Pro Thr Ala
145                 150                 155                 160

Pro Arg Phe Val Leu Trp Gly Gly Asp Leu Lys Pro Val Pro Ser Lys
                165                 170                 175

Pro Ala Asp Leu Pro Phe Phe Asp Leu Met Ser Phe Pro Gly Lys Leu
                180                 185                 190

Arg Ala Gly Phe Gly Ala Leu Gly Phe Arg Pro Ser Pro Pro Asp Arg
            195                 200                 205

Glu Glu Ser Val Glu Glu Phe Val Arg Arg Asn Leu Gly Asp Glu Val
    210                 215                 220

Phe Glu Arg Leu Ile Glu Pro Phe Cys Ser Gly Val Tyr Ala Gly Asp
225                 230                 235                 240

Pro Ser Lys Leu Ser Met Lys Ala Ala Phe Gly Lys Val Trp Asn Leu
                245                 250                 255

Glu Gln Asn Gly Gly Ser Ile Val Gly Gly Ala Phe Lys Ala Ile Gln
            260                 265                 270

Asp Arg Lys Asn Ser Gln Lys Pro Pro Arg Asp Pro Arg Leu Pro Lys
        275                 280                 285

Pro Lys Gly Gln Thr Val Gly Ser Phe Arg Lys Gly Gln Ala Met Leu
    290                 295                 300

Pro Asn Ala Ile Ser Thr Arg Leu Gly Ser Arg Val Lys Leu Cys Trp
305                 310                 315                 320

Lys Leu Thr Ser Ile Ser Lys Leu Glu Asn Arg Gly Tyr Asn Leu Thr
                325                 330                 335

Tyr Glu Thr Pro Gln Gly Phe Glu Ser Leu Gln Thr Lys Thr Ile Val
            340                 345                 350

Met Thr Val Pro Ser Tyr Val Ala Ser Asp Leu Leu Arg Pro Leu Ser
        355                 360                 365

Leu Gly Ala Ala Asp Ala Leu Ser Lys Phe Tyr Tyr Pro Pro Val Ala
    370                 375                 380

Ala Val Ser Ile Ser Tyr Pro Lys Asp Ala Ile Arg Ala Asp Arg Leu
385                 390                 395                 400
```

-continued

```
Ile Asp Gly Gln Leu Lys Gly Phe Gly Gln Leu His Pro Arg Ser Gln
                405                 410                 415
Gly Val Glu Thr Leu Gly Thr Ile Tyr Ser Ser Leu Phe Pro Asn
            420                 425                 430
Arg Ala Pro Pro Gly Arg Val Leu Leu Asn Tyr Ile Gly Ala
            435                 440                 445
Thr Asn Pro Glu Ile Leu Ser Lys Thr Glu Gly Glu Ile Val Asp Ala
    450                 455                 460
Val Asp Arg Asp Leu Arg Thr Met Leu Ile Arg Arg Asp Ala Glu Asp
465                 470                 475                 480
Pro Leu Thr Leu Gly Val Arg Val Trp Pro Arg Ala Ile Pro Gln Phe
                485                 490                 495
Leu Ile Gly His Tyr Asp Ile Leu Asp Ser Ala Lys Ala Ala Leu Ser
                500                 505                 510
Ser Gly Gly Phe Gln Gly Met Phe Leu Gly Gly Asn Tyr Val Ser Gly
            515                 520                 525
Val Ala Leu Gly Lys Cys Val Glu Ala Ala Tyr Asp Val Ala Ala Glu
530                 535                 540
Val Met Asn Phe Leu Ser Gln Gly Val Tyr Lys
545                 550                 555

<210> SEQ ID NO 61
<211> LENGTH: 18
<212> TYPE: PRT
<213> ORGANISM: Artificial Sequence
<220> FEATURE:
<223> OTHER INFORMATION: Synthetic construct --partial sequence

<400> SEQUENCE: 61

Ile Asp Pro Phe Val Ala Gly Thr Cys Gly Gly Asp Pro Gln Ser Leu
1               5                   10                  15
Ser Val

<210> SEQ ID NO 62
<211> LENGTH: 18
<212> TYPE: PRT
<213> ORGANISM: Artificial Sequence
<220> FEATURE:
<223> OTHER INFORMATION: Synthetic construct:  partial sequence

<400> SEQUENCE: 62

Ile Asp Pro Phe Val Ala Gly Thr Cys Gly Gly Asp Pro Asp Ser Leu
1               5                   10                  15
Ser Met

<210> SEQ ID NO 63
<211> LENGTH: 18
<212> TYPE: PRT
<213> ORGANISM: Artificial Sequence
<220> FEATURE:
<223> OTHER INFORMATION: Synthetic construct:  partial sequence

<400> SEQUENCE: 63

Ile Asp Pro Phe Val Ala Gly Thr Cys Gly Gly Asp Pro Asp Ser Leu
1               5                   10                  15
Ser Met

<210> SEQ ID NO 64
<211> LENGTH: 18
<212> TYPE: PRT
```

```
<213> ORGANISM: Artificial Sequence
<220> FEATURE:
<223> OTHER INFORMATION: Synthetic construct: partial sequence

<400> SEQUENCE: 64

Ile Asp Pro Phe Val Ala Gly Thr Cys Gly Gly Asp Pro Asp Ser Leu
1               5                   10                  15

Ser Met

<210> SEQ ID NO 65
<211> LENGTH: 18
<212> TYPE: PRT
<213> ORGANISM: Artificial Sequence
<220> FEATURE:
<223> OTHER INFORMATION: Synthetic construct: partial sequence

<400> SEQUENCE: 65

Ile Asp Pro Phe Val Ala Gly Thr Cys Gly Gly Asp Pro Asp Ser Leu
1               5                   10                  15

Ser Met

<210> SEQ ID NO 66
<211> LENGTH: 18
<212> TYPE: PRT
<213> ORGANISM: Artificial Sequence
<220> FEATURE:
<223> OTHER INFORMATION: Synthetic construct: partial sequence

<400> SEQUENCE: 66

Ile Asp Pro Phe Val Ala Gly Thr Ser Gly Gly Asp Pro Gln Ser Leu
1               5                   10                  15

Ser Met

<210> SEQ ID NO 67
<211> LENGTH: 18
<212> TYPE: PRT
<213> ORGANISM: Artificial Sequence
<220> FEATURE:
<223> OTHER INFORMATION: Synthetic construct: partial sequence

<400> SEQUENCE: 67

Ile Asp Pro Phe Val Ala Gly Thr Ser Gly Gly Asp Pro Glu Ser Leu
1               5                   10                  15

Ser Met

<210> SEQ ID NO 68
<211> LENGTH: 18
<212> TYPE: PRT
<213> ORGANISM: Artificial Sequence
<220> FEATURE:
<223> OTHER INFORMATION: Synthetic construct: partial sequence

<400> SEQUENCE: 68

Ile Asp Pro Phe Val Ala Gly Thr Ser Gly Gly Asp Pro Glu Ser Leu
1               5                   10                  15

Ser Ile

<210> SEQ ID NO 69
<211> LENGTH: 18
<212> TYPE: PRT
<213> ORGANISM: Artificial Sequence
<220> FEATURE:
<223> OTHER INFORMATION: Synthetic construct: partial sequence
```

-continued

```
<400> SEQUENCE: 69

Ile Asp Pro Phe Val Ala Gly Thr Ser Gly Gly Asp Pro Glu Ser Leu
1               5                   10                  15

Ser Ile

<210> SEQ ID NO 70
<211> LENGTH: 18
<212> TYPE: PRT
<213> ORGANISM: Artificial Sequence
<220> FEATURE:
<223> OTHER INFORMATION: Synthetic construct: partial sequence

<400> SEQUENCE: 70

Val Asp Pro Phe Val Ala Gly Thr Ser Ala Gly Asp Pro Glu Ser Leu
1               5                   10                  15

Ser Ile

<210> SEQ ID NO 71
<211> LENGTH: 18
<212> TYPE: PRT
<213> ORGANISM: Artificial Sequence
<220> FEATURE:
<223> OTHER INFORMATION: Synthetic construct: partial sequence

<400> SEQUENCE: 71

Val Asp Pro Phe Val Ala Gly Thr Ser Ala Gly Asp Pro Glu Ser Leu
1               5                   10                  15

Ser Ile

<210> SEQ ID NO 72
<211> LENGTH: 18
<212> TYPE: PRT
<213> ORGANISM: Artificial Sequence
<220> FEATURE:
<223> OTHER INFORMATION: Synthetic construct: partial sequence

<400> SEQUENCE: 72

Ile Asp Pro Phe Val Gly Gly Thr Ser Ala Ala Asp Pro Glu Ser Leu
1               5                   10                  15

Ser Met

<210> SEQ ID NO 73
<211> LENGTH: 18
<212> TYPE: PRT
<213> ORGANISM: Artificial Sequence
<220> FEATURE:
<223> OTHER INFORMATION: Synthetic construct: partial sequence

<400> SEQUENCE: 73

Ile Asp Pro Phe Val Gly Gly Thr Ser Ala Ala Asp Pro Asp Ser Leu
1               5                   10                  15

Ser Met

<210> SEQ ID NO 74
<211> LENGTH: 18
<212> TYPE: PRT
<213> ORGANISM: Artificial Sequence
<220> FEATURE:
<223> OTHER INFORMATION: Synthetic construct: partial sequence

<400> SEQUENCE: 74

Ile Asp Pro Phe Val Gly Gly Thr Ser Ala Ala Asp Pro Asp Ser Leu
1               5                   10                  15
```

Ser Met

<210> SEQ ID NO 75
<211> LENGTH: 18
<212> TYPE: PRT
<213> ORGANISM: Artificial Sequence
<220> FEATURE:
<223> OTHER INFORMATION: Synthetic construct: partial sequence

<400> SEQUENCE: 75

Ile Asp Pro Phe Val Gly Gly Thr Ser Ala Ala Asp Pro Asp Ser Leu
1               5                   10                  15

Ser Met

<210> SEQ ID NO 76
<211> LENGTH: 18
<212> TYPE: PRT
<213> ORGANISM: Artificial Sequence
<220> FEATURE:
<223> OTHER INFORMATION: Synthetic construct: partial sequence

<400> SEQUENCE: 76

Ile Asp Pro Phe Val Gly Gly Thr Ser Ala Ala Asp Pro Asp Ser Leu
1               5                   10                  15

Ser Met

<210> SEQ ID NO 77
<211> LENGTH: 18
<212> TYPE: PRT
<213> ORGANISM: Artificial Sequence
<220> FEATURE:
<223> OTHER INFORMATION: Synthetic construct: partial sequence

<400> SEQUENCE: 77

Ile Asp Pro Phe Val Gly Gly Thr Ser Ala Ala Asp Pro Asp Ser Leu
1               5                   10                  15

Ser Met

<210> SEQ ID NO 78
<211> LENGTH: 18
<212> TYPE: PRT
<213> ORGANISM: Artificial Sequence
<220> FEATURE:
<223> OTHER INFORMATION: Synthetic construct: partial sequence

<400> SEQUENCE: 78

Ile Asp Pro Phe Val Gly Gly Thr Ser Ala Ala Asp Pro Asp Ser Leu
1               5                   10                  15

Ser Met

<210> SEQ ID NO 79
<211> LENGTH: 21
<212> TYPE: DNA
<213> ORGANISM: Artificial Sequence
<220> FEATURE:
<223> OTHER INFORMATION: Synthetic construct: oligonucleotide useful as
      a primer

<400> SEQUENCE: 79
atgggcaaca tttctgagcg g                                         21

<210> SEQ ID NO 80
<211> LENGTH: 24

```
<212> TYPE: DNA
<213> ORGANISM: Artificial Sequence
<220> FEATURE:
<223> OTHER INFORMATION: Synthetic construct: oligonucleotide useful as
      a primer

<400> SEQUENCE: 80
tgcctccagc tctagaatca gctt                                             24

<210> SEQ ID NO 81
<211> LENGTH: 20
<212> TYPE: DNA
<213> ORGANISM: Artificial Sequence
<220> FEATURE:
<223> OTHER INFORMATION: Synthetic construct: oligonucleotide useful as
      a primer

<400> SEQUENCE: 81
cacgttttgc acccaaacta                                                  20

<210> SEQ ID NO 82
<211> LENGTH: 19
<212> TYPE: DNA
<213> ORGANISM: Artificial Sequence
<220> FEATURE:
<223> OTHER INFORMATION: Synthetic construct: oligonucleotide useful as
      a primer

<400> SEQUENCE: 82
tgttgcgggt acatgtgga                                                   19

<210> SEQ ID NO 83
<211> LENGTH: 19
<212> TYPE: DNA
<213> ORGANISM: Artificial Sequence
<220> FEATURE:
<223> OTHER INFORMATION: Synthetic construct: oligonucleotide useful as
      a primer

<400> SEQUENCE: 83
tacttctgga aatgtatgg                                                   19
```

HERBICIDE RESISTANCE GENE, COMPOSITIONS AND METHODS

CROSS-REFERENCE TO RELATED APPLICATIONS

This application is a Continuation-in-Part of U.S. application Ser. No. 11/466,662, filed Aug. 23, 2006, which application claims benefit of U.S. Provisional Application 60/807,780 filed Jul. 19, 2006 and of U.S. Provisional Application 60/711,204 filed Aug. 25, 2005; all of said applications are incorporated by reference herein to the extent there is no inconsistency with the present disclosure.

ACKNOWLEDGEMENT OF FEDERAL RESEARCH SUPPORT

Not applicable

BACKGROUND OF THE INVENTION

The field of the present invention is plant molecular biology, especially as related to genetically modified plants with resistance to herbicide. Specifically, the present invention relates to transgenic plants in which herbicide resistance is achieved by introducing a coding sequence which determines an herbicide resistance protoporphyrinogen oxidase (PPO) which is expressed in chloroplasts and mitochondria. Such transgenic crop plants are useful in fields where it is desired to spray herbicide to improve crop yield.

A major concern with the use of herbicides for weed control is the selection of resistant populations. To date, over 300 different herbicide-resistant weed biotypes have been identified worldwide (see weedscience.com on the internet). Numerous factors influence the likelihood of herbicide-resistance evolution in a weed population, and certain herbicides are more prone to resistance evolution than are others. For example, populations of 95 weed species have been reported with resistance to herbicides that inhibit acetolactate synthase (ALS), whereas evolved resistance to herbicides that inhibit protoporphyrinogen oxidase (PPO) has been reported for only three weeds (weedscience.com website), even though these herbicides were first commercialized in the 1960s (1). The first weed to evolve resistance to PPO inhibitors was *Amaranthus tuberculatus* (waterhemp), an increasingly problematic weed of agronomic production systems throughout the Midwestern United States.

The biosynthetic pathways which lead to the production of chlorophyll and heme share a number of common steps. Chlorophyll is a light harvesting pigment present in all green photosynthetic organisms. Heme is a cofactor of hemoglobin, cytochromes, P450 mixed-function oxygenases, peroxidases, and catalases (see, e.g. Lehninger, 1975, Biochemistry. Worth Publishers, New York), and is therefore a necessary component for all aerobic organisms. The last common step in chlorophyll and heme biosynthesis is the oxidation of protoporphyrinogen IX to protoporphyrin IX. Protoporphyrinogen oxidase (referred to herein as PPO or protox) is the enzyme which catalyzes this last oxidation step (Matringe et al. 1989. Biochem. J. 260: 231).

An approach that has been used to isolate biosynthetic genes in metabolic pathways from organisms including the higher eukaryotes is the complementation of microbial (auxotrophic) mutants deficient in the activity of interest. For this approach, a library of cDNAs from the higher eukaryote is cloned in a vector that can direct expression of the cDNA in the microbial host. The vector is then transformed or otherwise introduced into the mutant, and colonies are selected that no longer require the nutritional supplementation of interest. Microbial mutants believed defective in PPO activity have been described (e.g. *E. coli* (Sasarman et al. 1979. J. Gen. Microbiol. 113: 297), *Salmonella typhimurium* (Xu et al. 1992. J. Bacteriol. 174: 3953), and *Saccharomyces cerevisiae* (Camadro et al. 1982. Biochem. Biophys. Res. Comm. 106: 724.

The use of herbicides to control undesirable vegetation such as weeds or plants in crops has become common, with the relevant market exceeding a billion dollars a year. Despite extensive herbicide use, weed control remains a significant and costly problem for farmers. Since various weed species are resistant to herbicides, the production of effective herbicides becomes increasingly important, as is the development of agronomically important plants which are resistant to one or more herbicides.

The PPO enzyme is the target of a variety of herbicides. PPO-inhibiting herbicides include many different structural classes of molecules (Duke et al. 1991. Weed Sci. 39: 465; Nandihalli et al. 1992. Pesticide Biochem. Physiol. 43: 193; Matringe et al. 1989. FEBS Lett. 245: 35; Yanase and Andoh. 1989. Pesticide Biochem. Physiol. 35: 70). These herbicidal compounds include the diphenylethers {e.g. lactofen, (±)-2-ethoxy-1-methyl-2-oxoethyl 5-{2-chloro-4-(trifluoromethyl)phenoxy}-2-nitrobenzoate; acifluorfen, 5-{2-chloro-4-(trifluoromethyl)phenoxy}-2-nitrobezoic acid; its methyl ester; or oxyfluorfen, 2-chloro-1-(3-ethoxy-4-nitrophenoxy)-4-(trifluorobenzene)}, oxidiazoles, (e.g. oxidiazon, 3-{2,4-dichloro-5-(1-methylethoxy)phenyl}-5-(1,1-dimethylethyl)-1,3,4-oxadiazol-2-(3H)-one), cyclic imides (e.g. S-23142, N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-{1-(2,3,4-trichlorophenyl)-4-nitropyrazolyl-5-oxy}propionate; M&B 39279), pyridine derivatives (e.g. LS 82-556), and phenopylate and its O-phenylpyrrolidino- and piperidinocarbamate analogs. Many of these compounds competitively inhibit the normal reaction catalyzed by the enzyme, apparently acting as substrate analogs.

Additional herbicides of interest include 3-Phenyluracils of formula I

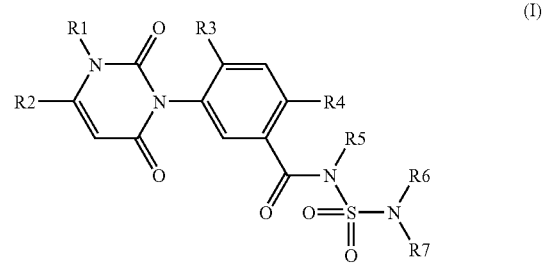

(I)

wherein $R^1$ is methyl or $NH_2$; $R^2$ is $C_1$-$C_2$-haloalkyl; $R^3$ is hydrogen or halogen; $R^4$ is halogen or cyano; $R^5$ is hydrogen, cyano, $C_1$-$C_6$-alkyl, $C_1$-$C_6$-alkoxy, $C_1$-$C_4$-alkoxy-$C_1$-$C_4$-alkyl, $C_3$-$C_7$-cycloalkyl, $C_3$-$C_6$-alkenyl, $C_3$-$C_6$-alkynyl or benzyl which is unsubstituted or substituted by halogen or alkyl; and $R^6$, $R^7$ independently of one another are hydrogen, $C_1$-$C_6$-alkyl, $C_1$-$C_6$-alkoxy, $C_3$-$C_6$-alkenyl, $C_3$-$C_6$-alkynyl, $C_3$-$C_7$-cycloalkyl, $C_3$-$C_7$-cycloalkenyl, phenyl or benzyl, where each of the 8 abovementioned substituents is unsubstituted or may be substituted by 1 to 6 halogen atoms and/or by one, two or three groups selected from: OH, $NH_2$, CN, CONH$_2$, C$_1$-C$_4$-alkoxy, C$_1$-C$_4$-haloalkoxy, C$_1$-C$_4$-alkylthio, C$_1$-C$_4$-haloalkylthio, C$_1$-C$_4$-alkylsulfonyl, C$_1$-C$_4$-haloalkylsulfonyl, C$_1$-C$_4$-alkylamino, di(C$_1$-C$_4$-alkyl)amino, formyl, C$_1$-C$_4$-alkylcarbonyl, C$_1$-C$_4$-alkoxycarbonyl, C$_1$-C$_4$-alkylaminocarbonyl, di(C$_1$-C$_4$-alkyl)aminocarbonyl, C$_3$-C$_7$-cycloalkyl, phenyl and benzyl; or R$^6$, R$^7$ together with the nitrogen atom form a 3-, 4-, 5-, 6- or 7-membered saturated or unsaturated nitrogen heterocycle which may be substituted by 1 to 6 methyl groups and which may contain 1 or 2 further heteroatoms selected from the group consisting of nitrogen, oxygen and sulfur as ring members, and their agriculturally acceptable salts (as described in the patent application PCT/EP 01/04850.

Application of PPO-inhibiting herbicides results in the accumulation of protoporphyrinogen IX in the chloroplast and mitochondria, which is believed to leak into the cytosol where it is oxidized by a peroxidase. When exposed to light, protoporphyrin IX causes formation of singlet oxygen in the cytosol and the formation of other reactive oxygen species, which can cause lipid peroxidation and membrane disruption leading to rapid cell death (Lee et al. 1993. Plant Physiol. 102: 881).

Not all PPO enzymes are sensitive to herbicides which inhibit plant PPO enzymes. Both the *Escherichia coli* and *Bacillus subtilis* PPO enzymes (Sasarmen et al. 1993. Can. J. Microbiol. 39: 1155; Dailey et al. 1994. J. Biol. Chem. 269: 813) are resistant to these herbicidal inhibitors. Mutants of the unicellular alga *Chlamydomonas reinhardtii* resistant to the phenylimide herbicide S-23142 have been reported (Kataoka et al. 1990. J. Pesticide Sci. 15: 449; Shibata et al. 1992. In Research in Photosynthesis, Vol. III, N. Murata, ed. Kluwer: Netherlands. pp. 567-70). At least one of these mutants appears to have an altered PPO activity that is resistant not only to the herbicidal inhibitor on which the mutant was selected, but also to other classes of protox inhibitors (Oshio et al. 1993. Z. Naturforsch. 48c: 339; Sato et al. 1994. In ACS Symposium on Porphyric Pesticides, S. Duke, ed. ACS Press: Washington, D.C.). A mutant tobacco cell line has also been reported that is resistant to the inhibitor S-21432 (Che et al. 1993. Z. Naturforsch. 48c: 350). Auxotrophic *E. coli* mutants have been used to confirm the herbicide resistance of cloned plant PPOs.

There is a need in the art for effective and efficient herbicide resistance genes in plants, especially crop plants, so that application of herbicide to cultivated fields results in good growth of the desired crop plants and eradication (or significant reduction) in pest plants, as well as for selectable markers for transgenic plants, plant cells and plant tissue.

SUMMARY OF THE INVENTION

The present invention provides a DNA construct comprising coding sequence for an herbicide resistant protoporphyrinogen oxidase (PPO) enzyme operably linked to a transcription regulatory sequence, especially one from a plant, and advantageously, a strong constitutive transcription regulatory sequence from a plant. A consensus sequence of an herbicide resistant PPO coding sequence is derived from *Amaranthus tuberculatus* and is presented in SEQ ID NO:13, and the consensus amino acid sequence is given in SEQ ID NO:14. Specifically exemplified sequences isolated from herbicide resistant *A. tuberculatus* are disclosed herein; see also SEQ ID NOs:13 and 14, 25 and 26, 29 and 30, and 45 and 46. The wild type (herbicide sensitive) *A. tuberculatus* coding and protein sequences are shown in SEQ ID NO:15 and SEQ ID NO:16; other herbicide-sensitive PPXL2 sequences are given in SEQ ID NOs: 21-22 and 27-28. Also within the scope of this invention are isolated nucleic acid molecules and vectors (plasmid or virus) comprising the herbicide resistant PPO coding sequences of the present invention, advantageously operably linked to transcription regulatory sequences. The critical feature of an herbicide resistant PPO enzyme of the present invention is a deletion of a glycine residue at amino acid 210 or 211, with reference to SEQ ID NO:16. See also FIG. 10B for various amino acid sequence polymorphisms that can be present in the Glycine210 deleted PPO, without loss of either enzymatic function or herbicide resistance. It is understood that there can be limited sequence variation from the specifically exemplified herbicide resistant sequences or consensus sequences, provided that the glycine deletion at a position corresponding to or aligned with position 210 or 211 of SEQ ID NO:16 is maintained, especially where there are from one to five amino acid substitutions, deletions or insertions and where the enzymatic activity and herbicide resistance of the enzyme is not eliminated.

Plants expressing the herbicide resistant PPX2L proteins or an equivalent herbicide resistant protein having the noted glycine (or functionally equivalent amino acid) deletion of the present invention are believed to be significantly improved in resistance over certain prior art herbicide resistant PPX2L proteins. In contrast to the corresponding wild type PPO, the resistant PPO of the present invention exhibits reduced sensitivity to PPO-inhibiting herbicides including lactofen, acifluorfen, flumiclorac, fomesafen, flumioxazin, and sulfentrazone. All synonymous sequences encoding the resistant PPO described herein are encompassed by the present invention.

Provided herein are recombinant plant cells, recombinant plant tissue, transgenic plants (including transgenic progeny plants) and transgenic plant seed which contain the DNA constructs of the present invention. Transgenic plants which contain the DNA construct are resistant to killing and/or growth inhibition by protoporphyrinogen-IX oxidase-inhibiting herbicides including, but not limited to, lactofen, acifluorfen, flumiclorac, fomesafen, flumioxazin, sulfentrazone, bifenox, chlomethoxyfen, chlornitrofen, ethoxyfen, fluorodifen, fluoroglycofen, fluoronitrofen, furyloxyfen, halosafen, nitrofen, nitrofluorfen, oxyfluorfen, fluazolate, pyraflufen, cinidon-ethyl, flumipropyn, fluthiacet, thidiazimin, oxadiazon, oxadiargyl, azafenidin, carfentrazone, pentoxazone, benzfendizone, butafenacil, pyraclonil, profluazol, flufenpyr, flupropacil, nipyraclofen and etnipromid, as well as other herbicides discussed herein, including 3-phenyluracils of Formula I given herein above. Recombinant plants, recombinant plant cells, recombinant plant tissue and recombinant herbicide resistant plants include those which have been engineered to delete a glycine (or functionally equivalent) residue from the PPO protein at a position homologous to Gly210 or Gly211 of SEQ ID NO:16, but which do not contain heterologous DNA sequences (thus being nontransgenic in that sense).

Also provided by the present disclosure are methods for rendering a plant of interest resistant to PPO-inhibiting herbicides. A method of the present invention comprises the steps of introducing a vector comprising a DNA construct containing a constitutive transcriptional regulatory sequence (active in a plant) operably linked to a coding sequence for an herbicide resistant PPO of the present invention into a plant cell or tissue to produce a transgenic plant cell or transgenic plant tissue which is resistant to PPO-inhibiting herbicides including, but not limited to, lactofen, acifluorfen, flumiclorac, fomesafen, flumioxazin, bifenox, chlomethoxyfen, chlornitrofen, ethoxyfen, fluorodifen, sulfentrazone, fluoroglycofen, fluoronitrofen, furyloxyfen, halosafen, lactofen, nitrofen, nitrofluorfen, oxyfluorfen, fluazolate, pyraflufen, cinidon-ethyl, flumipropyn, fluthiacet, thidiazimin, oxadiazon, oxadiargyl, azafenidin, carfentrazone, sulfentrazone, pentoxazone, benzfendizone, butafenacil, pyraclonil, profluazol, flufenpyr, flupropacil, nipyraclofen and etnipromid and to the herbicidal 3-phenyluracils disclosed herein above.

In addition to introducing a coding sequence of an herbicide resistant PPO, the present invention provides for genetically modifying a plant cell or plant tissue so to delete one codon of a glycine-glycine codon pair in the coding sequence of an herbicide sensitive PPO or of one of an alanine pair or of one residue of an alanine-glycine or glycine-alanine pair in the region homologous to the glycine pair at amino acids 210-211 of SEQ ID NO:16, the waterhemp wildtype sequence, which is converted to a single glycine or functionally equivalent amino acid residue in the specifically exemplified mutant PPO of the present invention), thereby converting that coding sequence to one of an herbicide resistant PPO, as taught herein, and then regenerating a plant from that genetically modified cell or tissue. This strategy has the advantage that the genetically modified plant does not retain any exogenous nucleic acid sequences and thus, poses no danger with respect to dissemination of drug resistance traits or carrying any known allergenic proteins derived from a heterologous plant. This is advantageously accomplished using a recombinagenic oligonucleotide lacking the noted codon.

Also, the present disclosure provides methods for selecting or screening for a genetic modification event, for example transformation, via the expression of the PPO-inhibiting herbicide resistant coding sequence of the present invention after introduction into a cell or tissue of interest the coding sequence operably linked to transcription control sequences functional in that cell or tissue. Similarly, one can select for a genetically engineered herbicide resistance mutation as taught herein or one can select for the presence of a gene comprising an introduced mutation (introduced via a recombinagenic, mutagenic oligonucleotide, for example).

The present invention further encompasses transgenic and engineered plants expressing an herbicide resistant PPX2L coding sequence as disclosed herein. For the specifically exemplified coding sequences, see SEQ ID NOs 13, 25, 29 and 45. Specifically exemplified herbicide-resistant PPO enzymes of the present invention include those of SEQ ID NOs: 14, 26 and 30. Alternatively, a PPO coding sequence of a plant of interest can be modified so as to delete a glycine (or alanine or functionally equivalent) residue at a position homologous to that encoding Gly210 or Gly 211 of SEQ ID NO:16 so that the PPO protein corresponds to the specifically exemplified herbicide resistant PPO, i.e., having the PPO enzyme activity but insensitive to the aforementioned herbicides. Such a plant can be engineered by art known techniques to alter the native sequence so as to delete the codon for a glycine residue as taught herein.

Also within the scope of the present disclosure are cultivated *Amaranthus* species (including, but not limited to, *A. hypochondriacus, A. cruentus, A. caudatus, A. dubius*, and *A. tricolor*) into which the herbicide resistant PPO gene from the weed *A. tuberculatus* has been introduced by conventional plant breeding and selection techniques. Other crops of interest into which a herbicide resistant PPO gene of the present invention can be introduced or engineered (without the incorporation of heterologous DNA sequence information as discussed herein) include, without limitation, cotton, corn, wheat, rice, oats, barley, vegetables including crucifers (cabbage, Brussels sprouts, kale, kohl rabi, broccoli and the like), tomatoes, potatoes, sunflowers, peppers, eggplants, stone fruits, berries, grapes, apples, pears, tobacco, petunias and ornamental plants including roses, shrubs, turf and grasses.

Additional embodiments relate to transformed seeds and transgenic progeny plants of the parent transgenic or otherwise genetically modified plant of the invention and the use of said plants, seeds, and plant parts in the agro-industry and/or in the production of food, feed, industrial products, oil, nutrients, and other valuable products. Preferably, these other embodiment of the invention relates to transformed seed of such a plant, method for breeding other plants using said plant, use of said plant in breeding or agriculture, and use of said plant to produce chemicals, food or feed products. Similarly, seeds, plants and progeny plants into which the glycine (or a functionally equivalent) deletion which confers the relevant herbicide resistance phenotype has been engineered are also embodiments of the present invention.

The present invention further provides a method for identifying a target site for introducing a deletion mutation to create an herbicide resistance gene in a plant of interest. First, a search against a plant protein database for PPO sequences is carried out using a sequence such as (but not limited to) amino acids 201-218 of SEQ ID NO:16, 18, 20, 22 or 28, as the query sequence and requiring at least a match of about 75%, in this case 14 out of 18 amino acids. Alternatively, amino acids 195-220 of SEQ ID NO:16, 18, 20, 22 or 28 could be used as the query sequence, with 75% match. Inspection of the subject related sequence allows identification of a glycine or an alanine (or other functionally equivalent amino acid) residue within said subject sequence, and then a recombinagenic oligonucleotide is designed using the coding sequence for the subject sequence, with the sequence of the recombinagenic oligonucleotide lacking an alanine or glycine or other codon of interest. Reference is made to Table 20, in which a number of subject sequences are set forth and the underlined alanine and glycine residues represent those for which deletion of one such residue results in the herbicide resistance phenotype. Then, a recombinagenic oligonucleotide lacking the relevant codon is introduced into cells of the cognate plant cell, the phenotype selected and a plant regenerated. Appropriate selection and breeding procedures produce a plant which is homozygous for the herbicide resistance trait. Progeny plants and seeds as well as plant cells and plant tissue with the resistance deletion mutation are also within the scope of this invention.

Also provided by the present disclosure are methods for controlling the growth of unwanted plants amongst crop or other plants containing and expressing a PPO-inhibiting herbicide resistant PPX2L coding sequence of the present invention or a functionally equivalent engineered herbicide resistant PPO, where the crop or other plants are cultivated and sprayed with a PPO-inhibiting herbicide, with the result that the unwanted plants, which are naturally sensitive to a PPO-inhibiting herbicide, are killed or retarded in growth. Thus, the crop or other plants of interest grow with greater efficiency and with less competition for nutrients, sunlight and water from unwanted species.

A further aspect of the present invention is an assay to determine the presence of the waterhemp Gly210 deletion mutation, using the PCR assay and primers described herein below. Ascertaining the prevalence of this mutation in a weed population allows the agriculturist or horticulturist to formulate an efficient and economical weed control strategy. Where this deletion mutation is prevalent, then an herbicide other than a PPO-inhibiting herbicide is advantageously chosen for weed control.

BRIEF DESCRIPTION OF THE DRAWINGS

FIG. 7 provides translated PPX2L amino acid sequences from *A. tuberculatus*. Amino acid differences are indicated by "*". Amino acid position 210 (black boxes) is the only difference that correlates with R or S responses to lactofen (GenBank accessions DQ386114, DQ386117, DQ386116, and DQ386118 and SEQ ID NO:22, 28, 26 and 30, respectively).

FIGS. 10A-10B provide a summary of positions within the *A. tuberculatus* PPX2L coding sequence which can be varied without either loss of function and without affecting herbicide resistance. In FIG. 10A the reference sequence is SEQ ID NO:15 (herbicide sensitive PPX2L), and in FIG. 10B, SEQ ID NO:13 (herbicide resistant PPX2L) Such varied sequences represent polymorphisms.

DETAILED DESCRIPTION OF THE INVENTION

Despite being used to control weeds in agricultural crops for the past 30 years, the mode-of-action of herbicides inhibiting protoporphyrinogen oxidase (PPO) was mostly unknown for the first 20 years of their use. Multiple chemical structures inhibit PPO, with the diphenylethers, triazolinones, and N-phenyl-phthalimides being the major families used in crop production.

PPO is the last common enzyme in the tetrapyrrole biosynthetic pathway that produces heme and chlorophyll (Beale and Weinstein 1990). In plants, chlorophyll biosynthesis takes place exclusively in chloroplasts, while heme is produced in both plastids and mitochondria (Smith et al. 1993; Chow et al. 1997). The tetrapyrrole biosynthetic pathway in plants begins with the formation of 5-aminolevulinic acid (ALA) from the C5-skeleton of glutamate. Eight molecules of ALA are combined to form protoporphyrinogen IX (protogen IX) (Papenbrock and Grimm 2001). Protogen IX is converted to protoporphyrin IX (proto IX) in both chloroplasts and mitochondria by the activity of PPO (Jacobs and Jacobs 1984). Studies conducted by Matringe et al. (1992) provided evidence that two constitutive PPO activities are found in chloroplasts: one associated with envelope membranes and another with thylakoid membranes. In mitochondria, PPO is associated exclusively with the envelope membranes (Deybach et al. 1985).

The genes that encode either plastid PPO (PPX1) or mitochondrial PPO (PPX2) have recently been cloned and sequenced from several plant species (Lermontova et al. 1997; Watanabe et al. 2001). Both PPX1 and PPX2 are nuclear encoded genes whose translation products must be imported into plastids or mitochondria, respectively. Interestingly, the translated product of PPX2 from spinach has been identified in two isoforms of different length due to the existence of dual in-frame initiation codons (Watanabe et al. 2001). The longer version of PPX2 includes a sequence encoding a chloroplast transit peptide, while the shorter version encodes a targeting sequence for import into the mitochondria.

When susceptible plants are treated with PPO inhibitors, the substrate of PPO, protogen IX, accumulates and is exported from the plastid to the cytoplasm (Kojima et al. 1991; Jacobs and Jacobs 1993) where herbicidally insensitive peroxidase-like enzymes in the plasma membrane convert it to proto IX (Lee et al. 1993; Lee and Duke 1994; Retzlaff and Böger 1996). Proto IX accumulates in the cytoplasm, and in the presence of light, induces the formation of singlet oxygen (Cox and Whitten 1983) that is damaging to cell membranes. Symptomatology following PPO inhibitor treatment occurs rapidly in the presence of light, with water soaked lesions and tissue necrosis appearing within hours after treatment (Dayan and Duke 1997).

Plants or plant cells resistant to PPO inhibitors have been generated by tissue culture selection (Horikoshi and Hirooka 1999; Pornprom et al. 1994; Wantanabe et al. 1998) and genetic engineering (Choi et al. 1998; Lee et al. 2000; Lermontova and Grimm 2000). Acifluorfen-resistant mutants of *Arabidopsis thaliana* have also been reported (Duke et al. 1997); however, no characterization related to resistance has been reported. Considerable effort has been devoted to the development of PPO inhibitor-resistant crops (Reviewed by Li and Nicholl 2005), but none are believed to have been commercialized.

Figure 1:
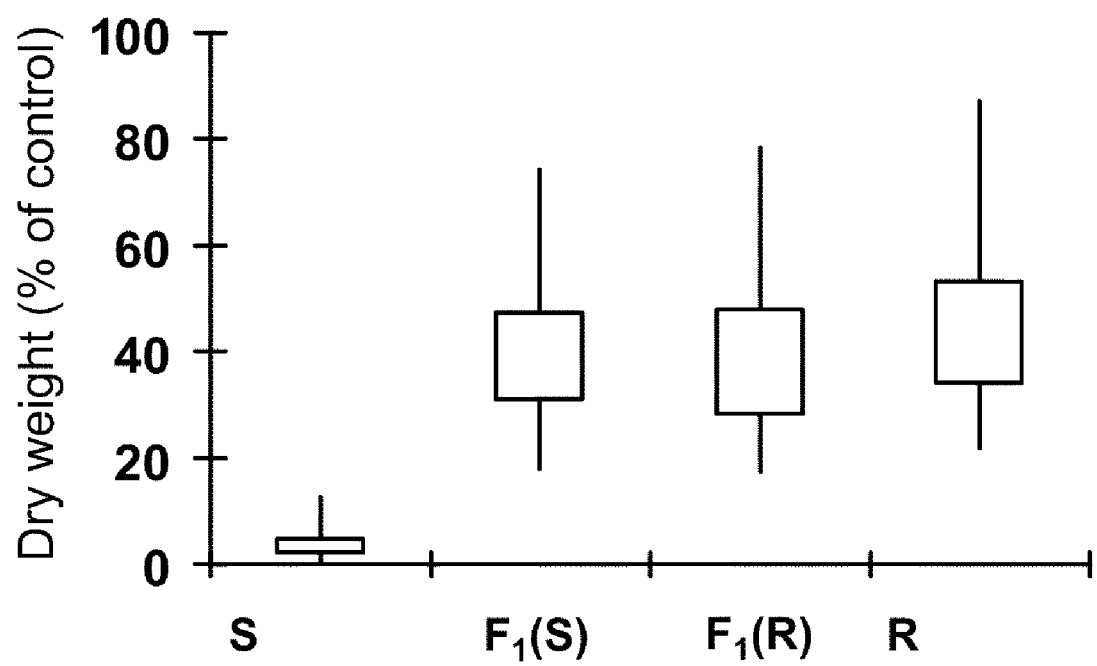
FIG. 1 shows Lactofen responses of the protoporphyrinogen oxidase inhibitor-susceptible parent (S), -resistant parent (R), hybrid where the maternal parent was R {$F_1(R)$}, or hybrid where the maternal parent was S {$F_1(S)$}. Waterhemp plants were harvested 15 days after treatment with lactofen at 110 g ai ha$^{-1}$ plus 1% (by vol) Crop Oil Concentrate (COC). Boxes represent the 25$^{th}$ to 75$^{th}$ percentile of responses, while whiskers include the remaining quartiles (n=100).

PPO inhibitor resistance in waterhemp was first documented in Kansas during the summer of 2000 (Shoup et al. 2003). In Illinois, a waterhemp biotype resistant to PPO inhibitors was first identified during the summer of 2001 (Patzoldt et al. 2005). According to Dayan and Duke (1997), resistance to PPO-inhibiting herbicides can be achieved by one of six predicted methods: 1) reduced herbicide uptake, 2) enhanced herbicide metabolism before reaching its site of action, 3) altered herbicide site of action, 4) removal or degradation of protogen 1x from the cytoplasm before it can be converted to proto IX, 5) inactivated extraplastidic PPO-like enzymes, and 6) sequestration of singlet oxygen and other toxic species. Other mechanisms of PPO inhibitor resistance might also be: 7) over-expression of the plastid form of PPO (Lermontova and Grimm 2000) and 8) over-expression of the mitochondrial form of PPO (Watanabe et al. 1998). Numerous structurally diverse compounds inhibit PPO, indicating that this herbicide target site is highly variable, similar to the target sites of herbicides that inhibit ALS or acetyl-CoA carboxylase (ACCase) (Duke et al. 1997). Currently, at least 18 amino acid substitutions have been identified within PPO that confer resistance to PPO-inhibiting herbicides (Volrath et al. 1999).

Waterhemp is the first weed species to have been selected for resistance to PPO inhibitors; thus it provides a unique opportunity for characterization of herbicide resistance mechanisms in plants. Therefore, the objectives of this study related to PPO inhibitor resistance were determine the inheritance, calculate the degree of dominance, and determine the mechanism of resistance in waterhemp.

As used herein, an herbicide resistant plant is one which germinates from a seed and/or grows in the concentration of pesticide where the comparison wild-type plant does not grow and/or does not germinate. The germination and growth of the resistant plant is similar in the presence or absence of the relevant PPO-inhibiting herbicide.

For recombinant production of the enzyme in a host organism, the PPO coding sequence is inserted into an expression cassette designed for the chosen host and introduced into the host where it is recombinantly produced. The choice of specific regulatory sequences such as promoter, signal sequence, 5' and 3' untranslated sequences, and enhancer, is within the level of skill of the one ordinarily skilled in the art. The resultant molecule, containing the individual elements linked in proper orientation and reading frame, may be inserted into a vector capable of being transformed into the host cell. Suitable expression vectors and methods for recombinant production of proteins are well known for host organisms such as *E. coli* (see, e.g. Studier and Moffatt. 1986. J. Mol. Biol. 189: 113; Brosius. 1989. DNA 8: 759), yeast (see, e.g., Schneider and Guarente. 1991. Meth. Enzymol. 194: 373) and insect cells (see, e.g. Luckow and Summers. 1988. Bio/Technol. 6: 47). Specific examples include plasmids such as pBluescript (Stratagene, La Jolla, Calif.), pFLAG (International Biotechnologies, Inc., New Haven, Conn.), pTrcHis (Invitrogen, Carlsbad, Calif.), and baculovirus expression vectors, e.g., those derived from the genome of *Autographica california* nuclear polyhedrosis virus (AcNPV). A preferred baculovirus/insect system is pV111392/Sf21 cells (Invitrogen, Carlsbad, Calif.).

A recombinantly produced herbicide resistant PPO of the present invention is useful for a variety of purposes, including, but not limited to, in an in vitro assay to screen known herbicidal compounds to determine if they inhibit this PPO, in an in vitro general screening assay to identify chemicals which do or do not inhibit the mutant PPO, or to characterize its association with known inhibitors in order to rationally design new inhibitory herbicides as well as herbicide tolerant forms of the enzyme.

The inhibitory effect on PPO can be determined by measuring fluorescence at about 622 to 635 nm, after excitation at about 395 to 410 nM (see, e.g. Jacobs and Jacobs. 1982. Enzyme 28: 206; Sherman et al. 1991. Plant Physiol. 97, 280). Protoporphyrin IX is a fluorescent pigment; protoporphyrinogen IX is not fluorescent. Protein extracts are prepared from selected subcellular fractions, e.g. etioplasts, mitochondria, microsomes, or plasma membrane, by differential centrifugation (see, e.g. Lee et al. 1993. Plant Physiol. 102:881; Prado et al. 1979. Plant Physiol. 65: 956; Jackson and Moore, in Plant Organelles, Reid, ed., pp. 1-12; Jacobs and Jacobs. 1993. Plant Physiol. 101: 1181). Protoporphyrinogen is prepared by reduction of protoporphyrin with a sodium amalgam as described by Jacobs and Jacobs (1982). Reactions mixtures typically consist of 100 mM Hepes (pH 7.5), 5 mM EDTA, 2 mM DTT, about 2 µM protoporphyrinogen IX, and about 1 mg/mL protein extract. Inhibitor solutions in various concentrations, e.g. 1 mM, 100 µM, 10 µM, 1 µM, 100 nM, 10 nM, 1 nM, 100 pM, are added to the enzyme extract prior to the initiation of the enzyme reaction. Once the protein extract is added, fluorescence is monitored for several minutes, and the slope of the slope (reaction rate) is calculated from a region of linearity. $IC_{50}$ is determined by comparing the slope of the inhibited reaction to a control reaction, and $IC_{50}$ is the concentration of herbicide at which the reaction rate of the wild type enzyme is reduced by 50%.

Herbicides that inhibit wild type PPO enzymes include many different structural classes of molecules (Duke et al. 9119. Weed Sci. 39: 465; Nandihalli et al. 1992. Pesticide Biochem. Physiol. 43: 193; Matringe et al. 1989. FEBS Lett. 245: 35; Yanase and Andoh. 1989. Pesticide Biochem. Physiol. 35: 70), including the diphenylethers (e.g. acifluorifen, 5-{2-chloro-4-(trifluoromethyl)phenoxy}-2-nitrobezoic acid; its methyl ester; or oxyfluorfen, 2-chloro-1-(3-ethoxy-4-nitrophenoxy)-4-(trifluorobenzene)), oxidiazoles (e.g. oxidiazon, 3-{2,4-dichloro-5-(1-methylethoxy)phenyl}-5-(1,1-dimethylethyl)-1,3,4-oxadiazol-2-(3H)-one), cyclic imides (e.g. S-23142, N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-{1-(2,3,4-trichlorophenyl)-4-nitropyrazolyl-5-oxy}propionate; M&B 39279), pyridine derivatives (e.g. LS 82-556), and phenopylate and its O-phenylpyrrolidino- and piperidinocarbamate analogs. The herbicidal activity of the above compounds is described in the Proceedings of the 1991 Brighton Crop Protection Conference, Weeds (British Crop Protection Council), Proceedings of the 1993 Brighton Crop Protection Conference, Weeds (British Crop Protection Council), U.S. Pat. Nos. 4,746,352 and 1993 Abstracts of the Weed Science Society of America vol. 33, pg. 9.

The imide herbicides include those classified as aryluracils and having the general formula wherein R signifies the group $(C_{2-6}$-alkenyloxy)carbonyl-$C_{1-4}$-alkyl, as disclosed in U.S. Pat. No. 5,183,492. See also WO 94/08999, WO 93/10100, and U.S. Pat. No. 5,405,829 assigned to Schering; N-phenylpyrazoles, 3-substituted-2-aryl-4,5,6,7-tetrahydroindazoles (Lyga et al. 1994. Pesticide Sci. 42:29-36).

Additional herbicides for which resistant crops and resistant ornamental plants are needed include those listed previously pertaining to the 3-phenyl uracils, such as those of Formula I as defined herein above.

Effective application rates of herbicide which normally are inhibitory to the activity of PPO are known in the art, for example, 0.0001 to 10 kg/ha, preferably from 0.005 to 2 kg/ha. Rates depend, at least in part, on external factors such as environment, time and method of application. This dosage rate or concentration of herbicide depends on the desired action and particular compound used, and can be determined by methods known in the art.

The present invention is further directed to transgenic plants, transgenic progeny plants, transgenic seeds, transgenic cells and transgenic plant tissue resistant to herbicides that inhibit the naturally occurring PPO activity in these plants, wherein the tolerance is conferred by an herbicide resistant PPO enzyme of the present invention. Plants, progeny plants, seeds, cells and tissue which are genetically engineered to delete a particular alanine or glycine (or functionally equivalent) codon of a PPO gene as taught herein with the result of herbicide resistance, are also within the scope of the present invention. Representative plants include any plants to which these herbicides are applied for their normally intended purpose, especially agronomically important angiosperms and gymnosperms, including but not limited to, cotton, soya, rape, sugar beet, maize, rice, wheat, barley, oats, rye, sorghum, millet, forage, turf grasses, berries, vegetables, stone fruits, grapevines, apples, pears, ornamental plants, tree species and the like.

The present invention also encompasses plants, progeny plants, seeds, plant tissue and plant cells which contain (and express) a genetically engineered PPO coding sequence for an herbicide resistant protein, with the coding sequence being characterized by the deletion of a glycine or alanine (or functionally equivalent) codon and where the herbicide resistance is dependent on the deletion of the glycine or alanine (or functionally equivalent) residue in the protein. The alanine or glycine residue (or functionally equivalent) which is targeted for deletion is identified in a sequence alignment of a PPO amino acid sequence of interest using amino acids 201-218 of one of SEQ ID NOs:16, 18, 20, 22 or 28, as specifically exemplified, with the alanine or glycine aligning with either amino acid 210 or 211 of one of SEQ ID NOs:16, 18, 20, 22 or 28. The relevant portion of the coding sequence for the targeted protein is found, especially in a sequence databank, and a recombinagenic oligonucleotide is designed and synthesized with deletion of the codon for the amino acid to be deleted in the resulting protein. Advantageously, the glycine or alanine (or functionally equivalent) codon of interest is deleted by homologous recombination of a mutagenic oligonucleotide, in which there is identity to the sequences flanking the codon in the genomic coding sequence, which is introduced into a plant cell of interest, for example by biolistic transformation or other means of introducing nucleic acid known to the art. The plant cell is incubated so as to allow recombination and expression of the mutated coding sequence, and then recombination events can be selected by placing the plant cell in contact with an herbicide-containing culture medium, thus selecting of those cells which contain and express the mutated sequence encoding the herbicide resistant PPO. Then the plant cells are regenerated to product herbicide resistant genetically engineered plants. Recombinagenic oligonucleotides and mutagenesis techniques using same are known to the art; see, e.g., U.S. Pat. Nos. 6,879,075; 5,565,350; US Patent Publications 2005/0044597; 2007/0028318; 2007/0033670; Beetham et al. (1999) Proc. Natl. Acad. Sci. US 96:8774-8778; Zhu et al. (1999) Proc. Natl. Acad. Sci. US 96:8768-8773; Zhu et al. (2000) Nature Biotech. 18:555-558; Kochevenko and Willmitzer (2003) Plant Physiol. 132:174-184; Okazuki and Toriyama (2004) Plant Cell Rep. 22:509-412; Dong et al. (2006) Plant Cell Rep. 25:457-465, for example. Recombinogenic oligonucleotide technology is described in U.S. Pat. No. 5,565,350, for example.

In the context of the present invention, an "herbicide resistant PPO" is a PPO activity different from that which occurs in a wild-type (herbicide-sensitive). Such a resistant PPO is one which is not inhibited significantly (more than 90%) by a "PPO-inhibiting" herbicide set forth herein.

Plants expressing the herbicide resistant PPO can be obtained by stably transforming an herbicide resistant PPO coding sequence of the present invention into a plant cell such that it is expressed in the above-ground plant tissues, and preferably in all plant tissues, and it stably maintained in the plant. Herbicide resistant PPO coding sequences can be obtained or identified by complementing a bacterial or yeast auxotrophic mutant with a cDNA expression library from the target plant. Alternatively, an herbicide sensitive PPX2L coding sequence can be converted to encode the resistant phenotype by site-directed mutagenesis to delete one of the two contiguous glycine codons for amino acid residues 210-211 of SEQ ID NO:16, 18, 20, 22 or 28 or a functional equivalent thereof.

The herbicide resistant PPO sequence of the present invention was obtained by cloning a PPO gene from a plant that was naturally resistant to PPO-inhibiting herbicides including lactofen, acifluorfen, flumiclorac, fomesafen, flumioxazin, and sulfentrazone. Specifically, a population of waterhemp was identified that was no longer effectively controlled by PPO-inhibiting herbicides.

An alternative strategy for producing an herbicide resistant plant cell, herbicide resistant plant tissue or an herbicide resistant plant is the introduction of a DNA molecule with a nucleotide sequence engineered to be identical with the native PPO coding sequence except that one of two glycine codons, two alanine codons or an alanine or Glycine codon of an alanine-glycine or a glycine-alanine (or functionally equivalent) pair corresponding to positions 210-211 of the specifically exemplified PPO coding sequence of A. tuberculatus as set forth in SEQ ID NOs:15, 17, 19, 21 or 27 is deleted. See Table 19 for alignments to show how the corresponding positions are identified (underlined in subject sequences). Alternatively, one of an alanine pair or one of an alanine-glycine or one of a glycine-alanine (or functionally equivalent) pair aligning with amino acids 210-211 of SEQ ID NO:16, 18, 20, 22 or 28 can be deleted to produce an herbicide resistant PPO. Selection for the resistance phenotype recovers those plant cells in which homologous recombination has resulted in deletion of one of the two contiguous glycine or functionally equivalent residues in the native gene. Regeneration of a plant results in an engineered plant which does not contain any heterologous genetic information but which does express an herbicide resistant PPO protein; thus allowing growth of the plant in the presence of herbicide. The absence of heterologous genetic information can facilitate regulatory approval of the plant, reduce the likelihood of deleterious health effects in consumers and provide for greater acceptance of the use of the plants in agriculture or the environment that occurs with those transgenic plants into which foreign nucleic acid sequences have been introduced. The technology for this type of genetic engineering is well known to the art. See, e.g., U.S. Pat. Nos. 5,565,350, 6,870,075; US Published Applications 2007/0033670, 2007/0028318, 2005/0044597, 2005/0177899; Beetham et al. Proc. NAtl. Acad, Sci. USA 96:8774-8778, Kochevenko and Lillmitzer (2003) Plant Physiol. 132:174-184, Zhu et al. Proc. NAtl. Acad, Sci. USA 96:8768-8773, Zhu et al. (2000) Nature Biotechnol. 18:555-558, Okazaki and Toriyama (2000) Plant Cell Rep. 22:509-512, Dong et al. (2006) Plant Cell Rep. 25:457-465, among others.

Recombinagenic oligonucleobases (also termed recombinagenic oligonucleotides herein) and their use to effect genetic changes in eukaryotic cells are described in U.S. Pat. No. 5,565,350 to Kmiec. The '350 patent teaches a method for introducing specific genetic alterations into a target gene. It discloses recombinagenic oligonucleobases having two strands, in which a first strand contains two segments of at least 8 RNA-like nucleotides that are separated by a third segment of from 4 to about 50 DNA-like nucleotides, termed an "interposed DNA segment." The nucleotides of the first strand are base paired to DNA-like nucleotides of a second strand. The first and second strands are additionally linked by a segment of single stranded nucleotides so that the first and second strands are parts of a single oligonucleotide chain. The '350 patent further teaches a method for introducing specific genetic alterations into a target gene. According to the '350 patent, the sequences of the RNA segments are selected to be homologous, i.e., identical, to the sequence of a first and a second fragment of the target gene. The sequence of the interposed DNA segment is homologous with the sequence of the target gene between the first and second fragment except for a region of difference, termed the "heterologous region." The heterologous region can effect an insertion or deletion, or can contain one or more bases that are mismatched with the sequence of target gene so as to effect a substitution. According to the '350 patent, the sequence of the target gene is altered as directed by the heterologous region, such that the target gene becomes homologous with the sequence of the recombinagenic oligonucleotide. The '350 patent specifically teaches that ribose and 2'-O-methylribose, i.e., 2'-methoxyribose, containing nucleotides can be used in recombinagenic oligonucleotides and that naturally-occurring deoxyribose-containing nucleotides can be used as DNA-like nucleotides.

U.S. Pat. No. 5,731,181 to Kmiec specifically disclose the use of recombinagenic oligonucleobases to effect genetic changes in plant cells and discloses further examples of analogs and derivatives of RNA-like and DNA-like nucleotides that can be used to effect genetic changes in specific target genes. Other patents discussing the use of recombinagenic oligonucleobases include: U.S. Pat. Nos. 5,756,325; 5,871,984; 5,760,012; 5,888,983; 5,795,972; 5,780,296; 5,945,339; 6,004,804; and 6,010,907 and in International Patent No. PCT/US00/23457; and in International Patent Publications WO 98/49350; WO 99/07865; WO 99/58723; WO 99/58702; and WO 99/40789.

Recombinagenic oligonucleotides include mixed duplex oligonucleotides, non-nucleotide containing molecules taught in U.S. Pat. No. 5,731,181 and other molecules taught in the above-noted patents and patent publications.

The recombinagenic oligonucleotide can be introduced into a plant cell using any method commonly used in the art, including but not limited to, microcarriers (biolistic delivery), microfibers, electroporation, and microinjection. An oligonucleobase is a polymer of nucleobases, which polymer can hybridize by Watson-Crick base pairing to a DNA having the complementary sequence, i.e., the target sequence into which the mutation is to be introduced.

Nucleobases comprise a base, which is a purine, pyrimidine, or a derivative or analog thereof (i.e., they may be modified nucleotides or nucleotides). Nucleobases include peptide nucleobases, the subunits of peptide nucleic acids, and morpholine nucleobases as well as nucleosides and nucleotides. Nucleosides are nucleobases that contain a pentosefuranosyl moiety, e.g., an optionally substituted riboside or 2'-deoxyriboside. Nucleosides can be linked by one of several linkage moieties, which may or may not contain phosphorus. Nucleosides that are linked by unsubstituted phosphodiester linkages are termed nucleotides. Alternative linkages may provide at least some resistance to degradation by the nucleases in the cells into which the oligonucleotides or oligonucleobases are introduced.

An oligonucleobase chain has a single 5' and 3' terminus, which are the ultimate nucleobases of the polymer. A particular oligonucleobase chain can contain nucleobases of all types. An oligonucleobase compound is a compound comprising one or more oligonucleobase chains that are complementary and hybridized by Watson-Crick base pairing. Nucleobases are either deoxyribo-type or ribo-type. Ribo-type nucleobases are pentosefuranosyl containing nucleobases wherein the 2' carbon is a methylene substituted with a hydroxyl, alkyloxy or halogen. Deoxyribo-type nucleobases are nucleobases other than ribo-type nucleobases and include all nucleobases that do not contain a pentosefuranosyl moiety.

An oligonucleobase strand generically includes both oligonucleobase chains and segments or regions of oligonucleobase chains. An oligonucleobase strand has a 3' end and a 5' end. When an oligonucleobase strand is coextensive with a chain, the 3' and 5' ends of the strand are also 3' and 5' termini of the chain.

The invention is also directed to the culture and regeneration of cells mutated according to the methods of the present invention in order to obtain a plant that produces seeds, henceforth a "fertile plant", and the production of seeds and additional plants from such a fertile plant, with those plants exhibiting the herbicide resistance phenotype as described herein.

Examples of constitutive promoters which function in plant cells include the cauliflower mosaic virus (CaMV) 19S or 35S promoters, CaMV 35S double or enhanced promoters, the 35S promoter and an enhanced or double 35S promoter such as that described in Kay et al., Science 236: 1299-1302 (1987); nopaline synthase promoter; pathogenesis-related (PR) protein promoters, the rice actin promoter (McElroy et al. 1991. Mol. Gen. Genet. 231: 150), maize ubiquitin promoter (EP 0 342 926; Taylor et al. 1993. Plant Cell Rep. 12: 491), and the Pr-1 promoter from tobacco, *Arabidopsis*, or maize (see U.S. Pat. No. 5,614,395), the peanut chlorotic streak caulimovirus (PCISV) promoter (U.S. Pat. No. 5,850,019), the 35S promoter from cauliflower mosaic virus (CaMV) (Odell et al. 1985. Nature 313:810-812), promoters of *Chlorella* virus methyltransferase genes (U.S. Pat. No. 5,563,328), the full-length transcript promoter from figwort mosaic virus (FMV) (U.S. Pat. No. 5,378,619); the promoters from such genes as rice actin (McElroy et al. 1990. Plant Cell 2:163-171), ubiquitin (Christensen et al. 1989. Plant Mol. Biol. 12:619-632) and Christensen et al. 1992. Plant Mol. Biol. 18:675-689), pEMU (Last et al. 1991. Theor. Appl. Genet. 81:581-588), MAS (Velten et al. 1984. EMBO J. 3:2723-2730), maize H3 histone (Lepetit et al. 1992. Mol. Gen. Genet. 231:276-285 and Atanassova et al. 1992. Plant Journal 2(3):291-300), *Brassica napus* ALS3 (WO 97/41228); and promoters of various *Agrobacterium* genes (see, e.g., U.S. Pat. Nos. 4,771,002, 5,102,796, 5,182,200 and 5,428,147). Light-regulated promoters suitable for expression in above-ground tissues include the small subunit of ribulose bisphosphate carboxylase (ssuRUBISCO) promoter and the like. The promoters themselves may be modified to manipulate promoter strength to increase herbicide resistant PPO expression, in accordance with art-recognized procedures.

Guidance for the design of promoters is provided by studies of promoter structure, such as that of Harley and Reynolds. 1987. Nucleic Acids Res. 15:2343-2361). Also, the location of the promoter relative to the transcription start may be optimized. See, e.g., Roberts, et al. 1979. Proc. Natl. Acad. Sci. USA 76:760-4. Many suitable promoters for use in plants are well known in the art.

Suitable inducible promoters for use in plants include: the promoter from the ACE1 system which responds to copper (Mett et al. 1993. PNAS 90:4567-4571); the promoter of the maize ln2 gene which responds to benzenesulfonamide herbicide safeners (Hershey et al. 1991. Mol. Gen. Genetics 227:229-237) and Gatz et al. 1994. Mol. Gen. Genetics 243: 32-38), and the promoter of the Tet repressor gene from Tn10 (Gatz et al. 1991. Mol. Gen. Genet. 227:229-237). A particularly preferred inducible promoter for use in plants is one that responds to an inducing agent to which plants do not normally respond. An exemplary inducible promoter of this type is the inducible promoter from a steroid hormone gene, the transcriptional activity of which is induced by a glucocorticosteroid hormone (Schena et al. 1991. Proc. Natl. Acad. Sci. USA 88:10421) or the recent application of a chimeric transcription activator, XVE, for use in an estrogen receptor-based inducible plant expression system activated by estradiol (Zuo et al. 2000. The Plant Journal 24:265-273). Other inducible promoters for use in plants are described in, e.g., EP 332104, WO 93/21334 and WO 97/06269. Plant promoters composed of portions of other promoters and partially or totally synthetic promoters can also be used; see, e.g., Ni et al. 1995. Plant J. 7:661-676; WO 95/14098.

The promoter may include or be modified to include one or more enhancer elements. Promoters with enhancer elements provide for higher levels of transcription as compared to promoters without them. Suitable enhancer elements for use in plants include the PCISV enhancer element (U.S. Pat. No. 5,850,019), the CaMV 35S enhancer element (U.S. Pat. Nos. 5,106,739 and 5,164,316) and the FMV enhancer element (Maiti et al. 1997. Transgenic Res. 6:143-156). See also WO 96/23898 and Enhancers and Eukaryotic Expression (Cold Spring Harbor Press, Cold Spring Harbor, N.Y., 1983).

A 5' untranslated sequence is also employed. The 5' untranslated sequence is the portion of an mRNA which extends from the 5' CAP site to the translation initiation codon. This region of the mRNA is necessary for translation initiation in plants and plays a role in the regulation of gene expression. Suitable 5' untranslated regions for use in plants include those of alfalfa mosaic virus, cucumber mosaic virus coat protein gene, and tobacco mosaic virus.

For efficient expression, the coding sequences are preferably also operatively linked to a 3' untranslated sequence. The 3' untranslated sequence will include a transcription termination sequence and a polyadenylation sequence. The 3' untranslated region can be obtained from the flanking regions of genes from *Agrobacterium*, plant viruses, plants or other eukaryotes. Suitable 3' untranslated sequences for use in plants include those of the cauliflower mosaic virus 35S gene, the phaseolin seed storage protein gene, the pea ribulose biphosphate carboxylase small subunit E9 gene, the soybean 7S storage protein genes, the octopine synthase gene, and the nopaline synthase gene.

The PPO gene of the present invention advantageously contains both chloroplast and mitochondrial transit peptides. Others known to the art can be substituted, if deemed advantageous.

The chimeric DNA construct(s) (non-naturally occurring nucleic acid molecules) of the invention may contain multiple copies of a promoter or multiple copies of the herbicide resistant PPO coding sequence of the present invention. In addition, the construct(s) may include coding sequences for selectable or detectable markers, each in proper reading frame with the other functional elements in the DNA molecule. The preparation of such constructs is within the ordinary level of skill in the art.

The DNA construct may be a vector. The vector may contain one or more replication systems which allow it to replicate in host cells. Self-replicating vectors include plasmids, cosmids and viral vectors. Alternatively, the vector may be an integrating vector which allows the integration into the host cell's chromosome of the DNA sequence encoding the herbicide resistant PPO. The vector desirably also has unique restriction sites for the insertion of DNA sequences. If a vector does not have unique restriction sites, it may be modified to introduce or eliminate restriction sites to make it more suitable for further manipulations.

The DNA constructs of the invention can be used to transform any type of plant cells (see below). A genetic marker must be used for selecting transformed plant cells (a selection marker). Selection markers typically allow transformed cells to be recovered by negative selection (i.e., inhibiting growth of cells that do not contain the selection marker) or by screening for a product encoded by the selection marker.

The most commonly used selectable marker gene for plant transformation is the neomycin phosphotransferase II (nptII) gene, isolated from Tn5, which, when placed under the control of plant expression control signals, confers resistance to kanamycin (Fraley et al. 1983. Proc. Natl. Acad. Sci. USA 80:4803). Another commonly used selectable marker gene is the hygromycin phosphotransferase gene which confers resistance to the antibiotic hygromycin. Vanden Elzen et al. 1995. Plant Mol. Biol. 5:299). Additional selectable marker genes of bacterial origin that confer resistance to antibiotics include gentamicin acetyl transferase, streptomycin phosphotransferase, aminoglycoside-3'-adenyl transferase, and the bleomycin resistance determinant (Hayford et al. 1988. Plant Physiol. 86:1216; Jones et al. 1987. Mol. Gen. Genet. 210:86; Svab et al. 1990. Plant Mol. Biol. 14:197; Hille et al. 1986. Plant Mol. Biol. 7:171). Other selectable marker genes confer resistance to herbicides such as glyphosate, glufosinate or bromoxynil (Comai et al. 1985. Nature 317:741-744; Stalker et al. 1988. Science 242:419-423; Hinchee et al. 1988. Bio/Technology 6:915-922; Stalker et al. 1988. J. Biol. Chem. 263:6310-6314; Gordon-Kamm et al. 1990. Plant Cell 2:603-618).

Other selectable markers useful for plant transformation include, without limitation, mouse dihydrofolate reductase, plant 5-enolpyruvylshikimate-3-phosphate synthase, and plant acetolactate synthase (Eichholtz et al. 1987. Somatic Cell Mol. Genet. 13:67; Shah et al. 1986. Science 233:478; Charest et al. 1990. Plant Cell Rep. 8:643; EP 154,204), and herbicide resistance markers including, or other than, the PPO derivatives of the present invention.

Commonly used genes for screening presumptively transformed cells include but are not limited to β-glucuronidase (GUS), β-galactosidase, luciferase, and chloramphenicol acetyltransferase (Jefferson, R. A. 1987. Plant Mol. Biol. Rep. 5:387; Teeri et al. 1989. EMBO J. 8:343; Koncz et al. 1987. Proc. Natl. Acad. Sci. USA 84:131; De Block et al.

1984. EMBO J. 3:1681), green fluorescent protein (GFP) (Chalfie et al. 1994. Science 263:802; Haseloff et al. 1995. TIG 11:328-329 and PCT application WO 97/41228). Another approach to the identification of relatively rare transformation events has been use of a gene that encodes a dominant constitutive regulator of the Zea mays anthocyanin pigmentation pathway (Ludwig et al. 1990. Science 247:449).

The level of resistance of a particular resistant PPO can be tested using transgenic plant cells, transgenic plant tissue (such as callus, for example) or transgenic plant. Resistance can also be confirmed using direct selection in plants. For example, the effect of an herbicide such those as described above, on the growth inhibition of plants such as wild-type Arabidopsis, soybean, or maize may be determined by plating seeds sterilized by art-recognized methods on plates on a simple minimal salts medium containing increasing concentrations of the inhibitor. Such concentrations are in the range of 0.001, 0.003, 0.01, 0.03, 0.1, 0.3, 1, 3, 10, 30, 110, 300, 1000 and 3000 parts per million (ppm). The lowest dose at which significant growth inhibition can be reproducibly detected is used for subsequent experiments with transgenic plants, cells, etc. Alternatively, heme auxotrophic E. coli expressing the PPO can be used in testing.

Two approaches can be taken to confirm that the genetic basis of the resistance of a transgenic plant is a PPO of the present invention. First, alleles of the PPO gene from plants exhibiting resistance to the inhibitor can be isolated using PCR with primers based either upon the mutant region(s) in the resistant cDNA sequence shown in SEQ ID NO:13, or a functionally equivalent sequence. The herbicide resistant enzyme of the present invention can be expressed in a plant of interest after incorporation into a pCambia vector under the transcriptional control of the CaMV 35S promoter, the Arabidopsis actin-2 promoter or the native waterhemp PPO promoter, among others well known in the art). Many gene expression systems for plants are well known and readily accessible to the art.

Figure 2:
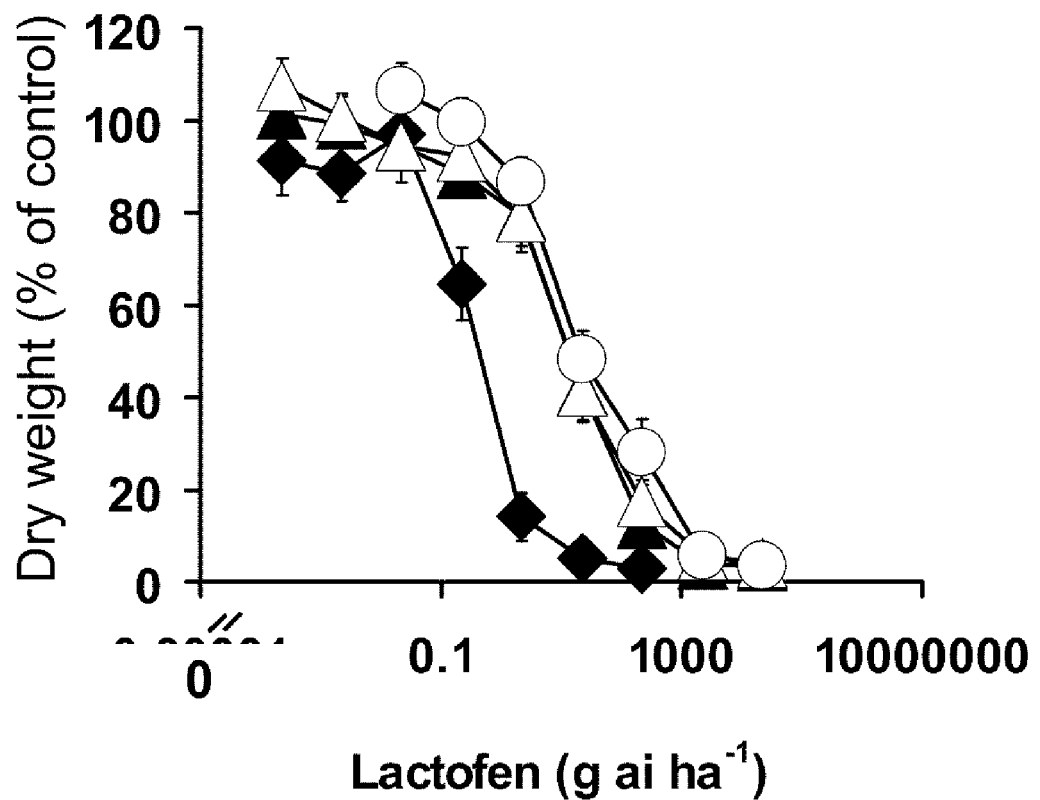
FIG. 2 provides the Lactofen dose-response curves of the protoporphyrinogen oxidase inhibitor-susceptible parent (S=♦), -resistant parent (R=○), hybrid where the maternal parent was R {$F_1(R)$=Δ}, or hybrid where the maternal parent was S {$F_1(S)$=▲}. Waterhemp plants were harvest 15 days after treatment. Vertical bars represent +/− the standard error of the mean (n=12).

To characterize the resistance mechanism in wild waterhemp, plants from a PPO inhibitor-resistant (R) A. tuberculatus biotype were reciprocally crossed with wild type (herbicide-susceptible, S) plants to create $F_1$ lines, followed by subsequent crossing to generate $F_2$ and backcross (BC) lines. In response to the PPO inhibitor, lactofen, the resultant A. tuberculatus lines segregated for resistance in ratios similar to those expected for a single genetic unit of inheritance (Table 1). Furthermore, plants from lines that were homozygous or heterozygous for resistance survived 53-fold or 31-fold higher doses of lactofen, respectively, when compared with S plants (FIG. 2; Table 2). Thus, resistance to lactofen was inherited as a single, incompletely dominant gene.

$F_2$ lines derived from the same male (half-sib lines) were not significantly different; therefore, the data from lines were combined. Results of $F_2$ progenies treated with lactofen segregated as expected if resistance were inherited as a single gene, with a segregation of 3:1 (R:S) (Table 1). Similarly, $BC_S$ or $BC_R$ lines responded as expected, with a 1:1 or 1:0 segregation for R:S lactofen responses, respectively (Table 1). Because there was no difference in lactofen resistance when it was inherited from the maternal or paternal parent, resistance to lactofen is assumed to be nuclear encoded. The results of these experiments suggest that PPO inhibitor resistance in the R waterhemp biotype is inherited as a single, nuclear encoded gene.

Figure 3A:
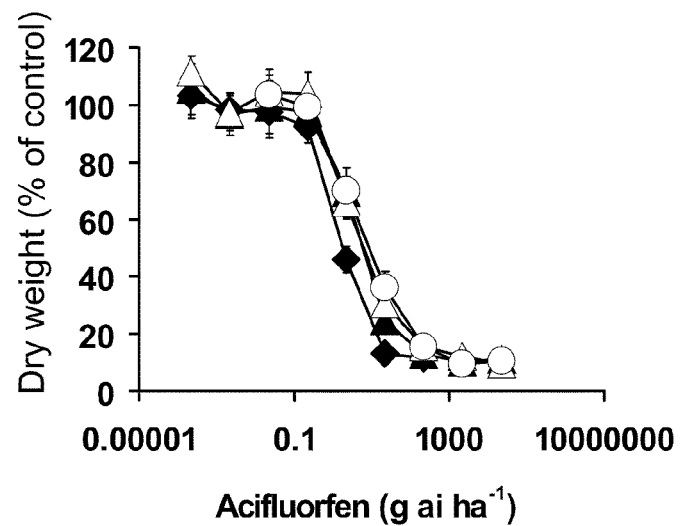
FIGS. 3A-3B show protoporphyrinogen oxidase inhibitor dose-response curves of the susceptible parent (S=♦), resistant parent (R=○), hybrid where the maternal parent was R {$F_1(R)$=Δ}, or hybrid where the maternal parent was S {$F_1(S)$=▲} with two PPO-inhibiting herbicides. Waterhemp plants were harvested 10 days after treatment. Vertical bars represent +/− the standard error of the mean (n=12).
Figure 3B:
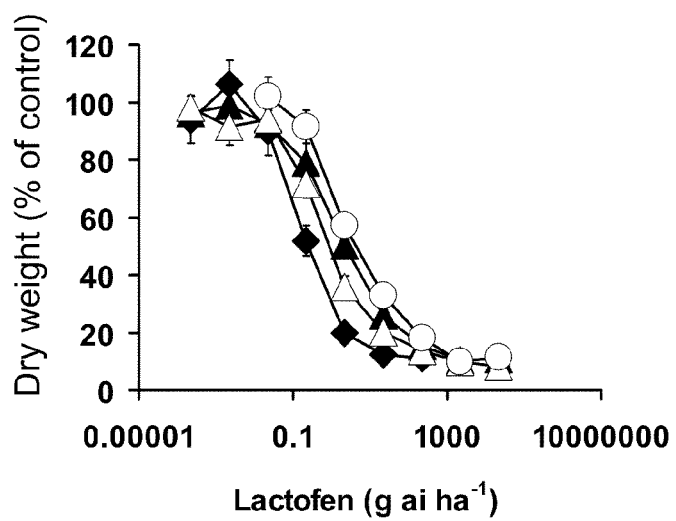

Herbicide dose-response experiments were conducted on the S parent, R parent, or $F_1$ lines to determine the dominance of PPO inhibitor resistance using the methods of Stone (1968) based on the calculation of $GR_{50}$ values. When waterhemp plants were harvested 15 days after lactofen treatment, dominance values of 0.72 or 0.76 were estimated using $F_1(R)$ or $F_1(S)$ lines, respectively (where 0 to 1=dominant, 0=partially dominant, or 0 to −1=recessive) (Table 2, FIG. 2). However, a potential problem with these results was that waterhemp plants might have been past their linear phase of growth, thus leading to an overestimate of dominance. Therefore, waterhemp plants used in subsequent dose-response experiments were harvested 10 DAT, and were challenged with lactofen or acifluorfen. Dominance values of −0.06 or 0.56 were estimated using $F_1(R)$ or $F_1(S)$ lines, respectively, in response to lactofen 10 DAT (Table 2, FIG. 3). In response to acifluorfen calculated 10 DAT, dominance values of 0.34 or 0.46 were estimated using $F_1(R)$ or $F_1(S)$ lines, respectively (Table 2, FIGS. 3A-3B). Results from all dominance experiments suggest that PPO inhibitor resistance in the R biotype is incompletely dominant because nearly all estimated dominance values ranged between 0 and 1.

Figure 9:
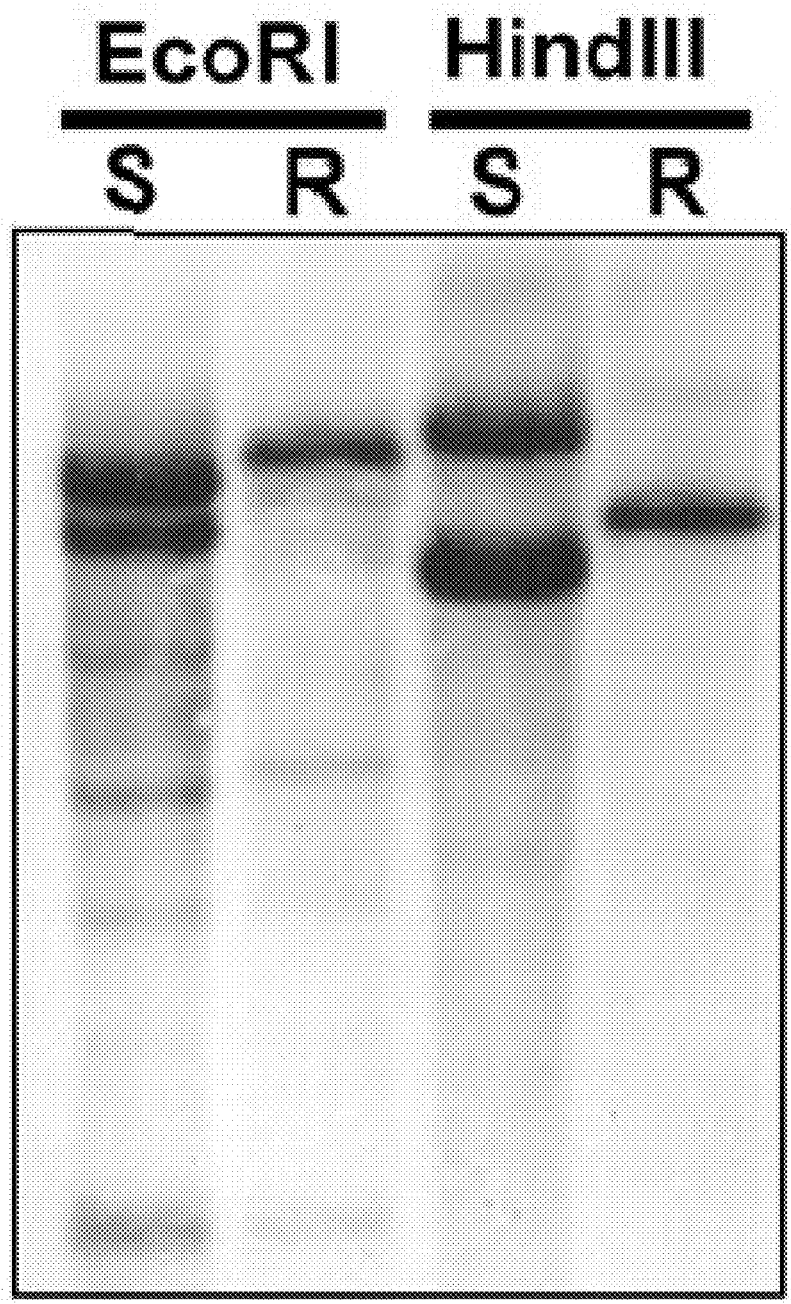
FIG. 9 shows the results of Southern blot analysis of *A. tuberculatus* genomic DNA probed with a fragment of PPX2L. DNA was isolated from plants that were derived from the R or S biotype and digested with EcoRI or HindIII.

To carry out molecular characterization of PPX genes from waterhemp, complementary DNA (cDNA) sequences that encode PPO isozymes were obtained from R and S A. tuberculatus plants, but with unexpected results. From S plants, cDNA sequences for PPX1, PPX2, and a longer version of PPX2, PPX2L, were identified and amino acid sequences encoded were deduced; See SEQ ID NOs: 17-18, 19-20 and 21-22; GenBank Accession Nos. DQ386112, DQ386113, and DQ386114. It is noted that PPO1, PPO2 and PPO2L refer to the proteins encoded by the genes PPX1, PPX2 (shorter sequence also termed PPX2S) and PPX2L, respectively. In this application where PPO is recited, it is synonymous with PPX2L unless otherwise obvious from context. Comparison of translated sequences of PPX2 and PPX2L indicated that they shared 98% amino acid identity, with the exception of a 30 amino acid extension in the 5' end that was unique to PPX2L. This extension is predicted to encode a signaling sequence for plastid import (Emmanuelson, 2000). Thus, it was thought that the PPX2L gene isolated from A. tuberculatus likely encodes both plastid- and mitochondria-targeted PPO isoforms due to the presence of alternate in-frame initiation codons, a phenomenon that was reported previously for Spinacia oleracea (spinach) PPX2 (Watanabe, 2001). In comparison, PPX1 shared 26% and 25% amino acid identity with PPX2 and PPX2L, respectively, and thus is an evolutionarily distinct isozyme. From R plants, only PPX1 and PPX2L genes (See SEQ ID NOs:23-24 and 25-26; GenBank Accession Nos. DQ386115 and DQ386116, respectively) were identified based on cDNA sequencing. To confirm the lack of PPX2 identification in R plants, Southern blot analysis was performed using genomic DNA probed with a fragment of PPX2L. Probing with the fragment of PPX2L identified two major bands (presumably PPX2 and PPX2L loci) from S plants, but only a single major band (presumably the PPX2L locus) from R plants, thus confirming the results obtained from sequencing efforts (FIG. 9). Without wishing to be bound by theory, it is believed that the PPX1 from the lactofen resistant waterhemp does not contribute to the resistant phenotype, and that the two different lengths of PPX2 resulted from two alleles of the PPX2 locus.

Figure 4:
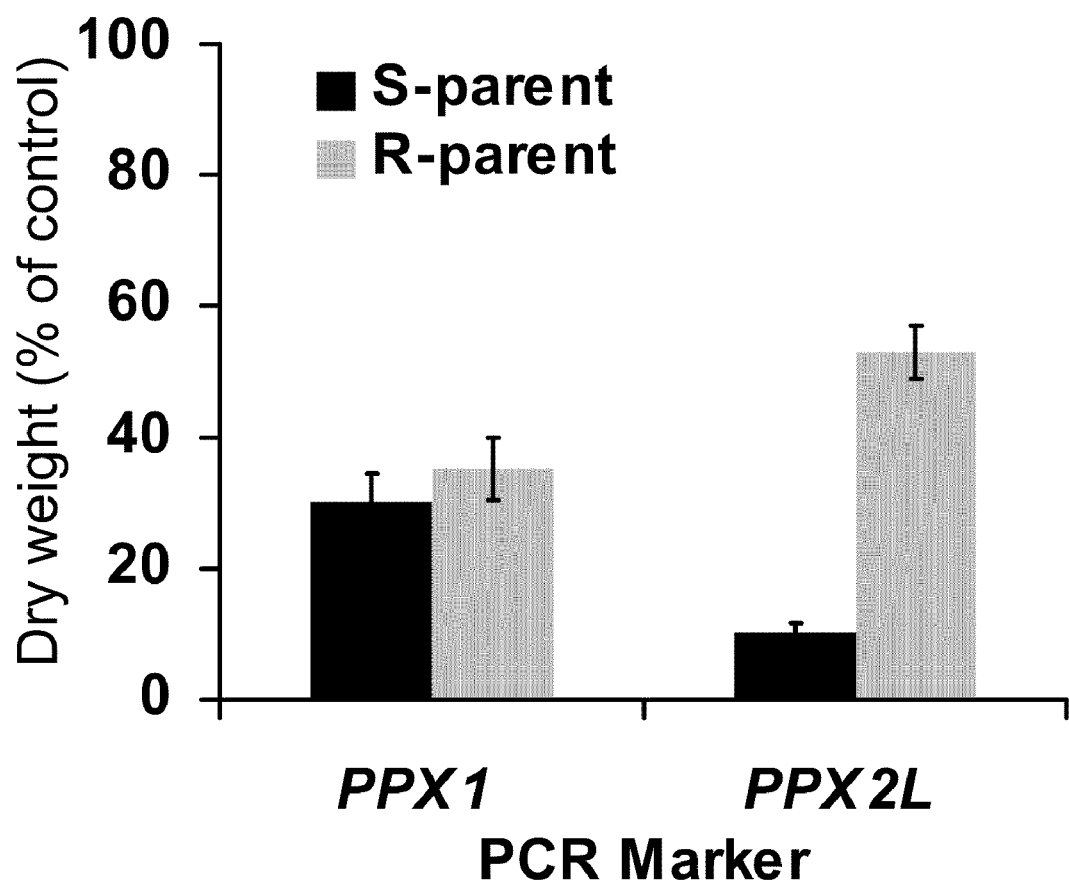
FIG. 4 shows the results of PCR-based molecular marker analysis of PPX1 or PPX2L alleles. *A. tuberculatus* plants used in the study were derived from $F_1$ hybrids backcrossed to the S parent ($BC_S$). Markers were used to determine if the $F_1$-derived pollen carried the S or R parental allele. $BC_S$ plants were treated with lactofen at 110 g ai ha$^{-1}$ plus 1% (by vol) COC and harvested 15 days after treatment. Vertical bars represent +/− the standard error of the mean (PPX1, n=42 or 40 for S or R parental alleles, respectively; PPX2L, n=39 or 49 for S or R parental alleles, respectively)

To determine whether PPX1 or PPX2L mediated PPO inhibitor resistance, polymerase chain reaction (PCR)-based molecular markers were used to follow the inheritance of alleles of these two genes in A. tuberculatus lines segregating 1:1 for R or S responses to lactofen. The molecular marker for PPX2L was significantly correlated with lactofen responses (P<0.0001), while the marker for PPX1 was not (P=0.4278) (FIG. 4). In other words, plants were resistant to lactofen only if they inherited the PPX2L allele from the R parent. Results of molecular markers studies focused further efforts toward differences among PPX2L alleles.

Figure 8:
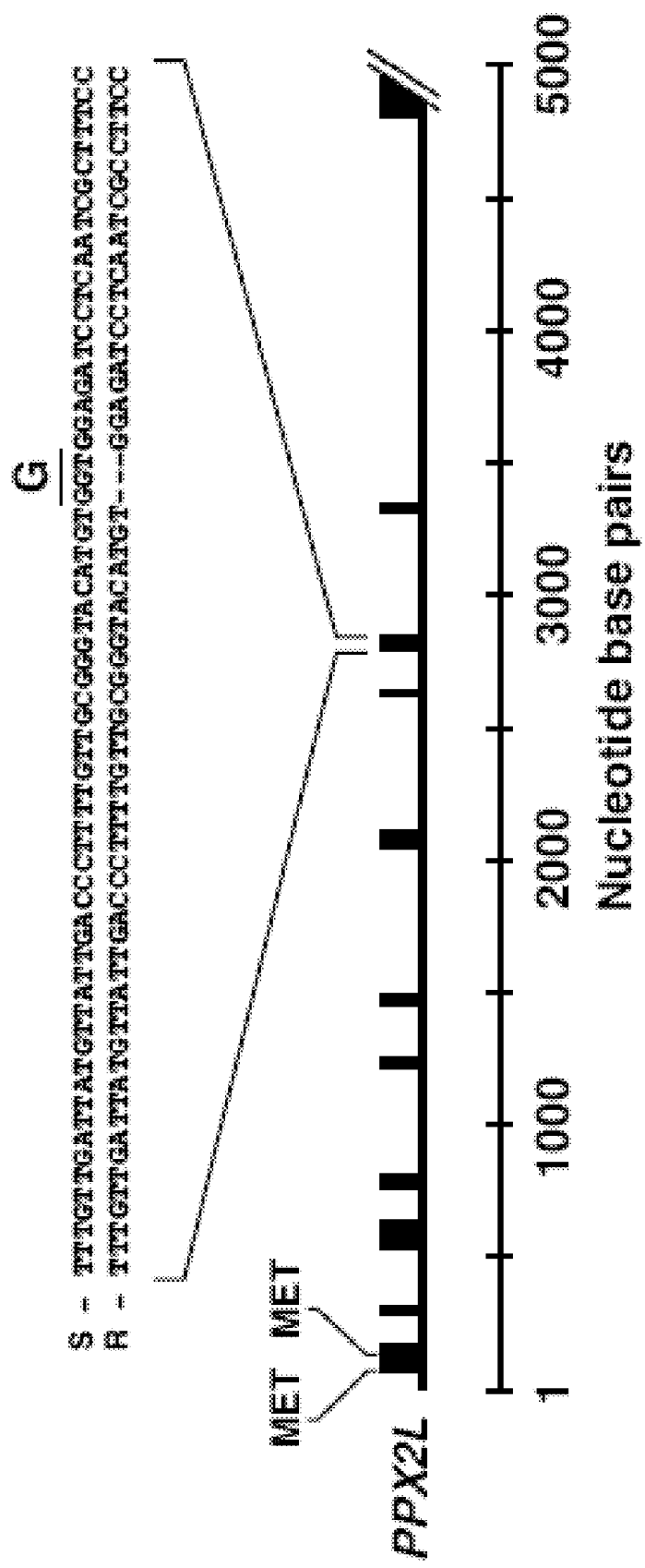
FIG. 8 shows partial coding regions of the 5' end of PPX2L from *A. tuberculatus*. The three-bp deletion leading to a G210 deletion in PPX2L from R plants was identified within the ninth exon starting from the 5' end (see also SEQ ID NO:43 and 44 for the sequences from the sensitive and resistant genes, respectively).

Inspection of the amino acid sequences of PPX2L among S and R plants revealed two amino acid polymorphisms that were correlated with resistance. In an attempt to identify only a single amino acid polymorphism, additional R and S plants were sequenced from independently identified *A. tuberculatus* biotypes (See SEQ ID NOs:27-28 and 29-30; GenBank accessions DQ386117 and DQ386118). Sequencing results and subsequent comparisons identified three additional amino acid polymorphisms (five total); however, only one, a glycine deletion at position 210 (ΔG210), was consistently polymorphic between all R and S plants analyzed (FIG. 7). PPX2L also was sequenced using genomic DNA (gDNA) as a template (See SEQ ID NOs:31-32 and 33-34; GenBank Accession Nos. DQ394875 and DQ394876 for S and R plants, respectively) to further confirm the existence of the three-bp deletion corresponding to the G210 codon. Alignment of gDNA and cDNA sequences of PPX2L identified the codon corresponding to the G210 residue in the ninth exon when starting from the 5' end (FIG. 8). The three-bp deletion was also identified in PPX2L gDNA sequences of R plants, therefore indicating that the ΔG210 mutation in PPO2L was not the result of an error introduced during mRNA processing.

The relationship of PPX2S and PPX2L has been studied to determine whether they represented two genetic loci or alleles of a single locus. Segregation analysis was used to examine the relationship between PPX2S and PPX2L. A cleaved amplified polymorphic sequence (CAPS) marker was designed based on an SNP previously identified (Genbank Accession Nos. DQ386114, DQ386113) between these genes (Patzoldt et al. 2006). WCS (herbicide sensitive waterhemp population, Wayne County, IL) individuals were screened to identify plants containing both PPX2S and PPX2L markers. A single male and several females with this genotype were allowed to cross and seed was collected from individual females. Two of the resultant F1 populations were tested for segregation of the SNP marker with the following expectations: if PPX2S and PPX2L are distinct loci, every individual in the F1 population would be expected to have markers for both genes. Alternatively, if PPX2S and PPX2L represent alleles of the same locus, the alleles should segregate in the F1 population in a 1:2:1 ratio. The results of two crosses were consistent with the independent segregation of two alleles defining a single genetic locus.

Sequence analysis was used to further examine the alleles at the PPX2 locus. Using sequence from grain amaranth genomic DNA (gDNA), primers were designed to amplify a fragment containing the 5' end of the PPX2 gene, including the transit peptide sequence. The sequence of this fragment from two WCS (Wayne County, IL, herbicide sensitive waterhemp population) individuals, one individual from the ACR (Adams County, IL, herbicide resistant waterhemp population), and one F1 individual from the cross that was previously determined to be homozygous for the PPX2S marker, were compared. In every case, two in-frame start codons were identified in this fragment. These data are consistent with a single PPX2 locus in waterhemp containing two translation initiation codons and thus encoding proteins that are predicted to be targeted to two different subcellular locations.

Previous studies suggested the presence of a short form of PPX2, PPX2S, which encoded a protein with only a mitochondrial targeting sequence similar to the PPX2 proteins described in mouse-ear cress (*Arabidopsis thaliana* L. Heynh.), soybean (*Glycine max* (L.) Merr.), and potato (*Solanum tuberosum* L.). This PPX2S sequence was only found in sensitive biotypes of waterhemp. This conclusion was based on both Southern blot and sequence data. However, the experiments described herein above led to the conclusion instead that waterhemp contains a single PPX2 locus. In light of these experiments and without wishing to be bound by any particular theory, the present inventors believe that the Southern blot data were most likely misleading due to heterozygosity at the PPX2L locus in the sensitive biotype while the resistant biotype was homozygous at this locus. With this in mind, a close examination of 5'-RACE sequence data from previous experiments revealed that the PPX2S sequence in fact included nearly the entire 5' end of the PPX2L gene. Therefore, again without wishing to be bound by theory, the inventors believe that PPX2L most likely represents the only PPX2 gene in waterhemp; i.e., waterhemp does not contain a "PPX2S". This is a phenomenon that previously has been seen in both spinach (Spinach oleracea) and corn (*Zea mays*) (Watanabe et al. 2001). With regards to herbicide-resistance evolution, it remains to be determined if a herbicide-resistant PPX2 gene must contain dual-targeting sequences to provide resistance at the whole plant level. If this characteristic promotes resistance, it is believed that weeds containing a PPX2L gene would evolve resistance to PPO-inhibitors faster than those lacking a dual-targeted PPX2.

The ΔG210 allele of PPX2L is unique; it is the first instance for which a deletion mutation has been shown to be the mechanism of resistance to any herbicide. To examine the prevalence of this mutation in waterhemp populations resistant to PPO-inhibitors, an allele-specific PCR marker was designed to amplify the ΔG210 allele of PPX2L. First, to test the accuracy of this assay, the marker was used to follow the inheritance of the ΔG210 allele of PPX2L in an F2 population from an ACR×WCS cross where the deletion mutation was previously shown to be sufficient to confer herbicide resistance. Individuals from this population were scored for the presence of the PCR marker then treated with lactofen to identify herbicide-resistant individuals. As expected, the presence of the marker was highly correlated with herbicide resistance (P<1e-12). Next, to test the prevalence of the deletion mutation in other known resistant populations, six plants each from four populations were tested with the PCR marker then treated with a single application of lactofen. The marker was highly correlated with herbicide resistance in all of these populations as well.

While the selection of such a unique sequence would be expected to be rare, these data suggest this allele is the predominant mechanism of resistance and, in fact, the only mechanism of resistance thus far identified among waterhemp populations in Illinois. The contribution of gene flow to the dispersal of this sequence was not considered in this study. However, there are polymorphisms between the resistant allele of PPX2L from ACR and that of a resistant biotype from Clinton County (CCR) (Genbank Accession Nos. DQ386118, DQ386116) suggesting that the ΔG210 allele of PPX2L was independently selected as the resistance mechanism in multiple waterhemp populations. This could indicate that the ΔG210 allele represents the mutation that confers the highest level of resistance while maintaining the lowest fitness penalty for single mutation in the gene. Alternatively, perhaps waterhemp is more prone to insertion/deletion polymorphisms than SNPs and, thus, there is a better chance that resistance mechanisms are based on indel polymorphisms. As described by Patzoldt et al. (2006) and Gressel and Levy (2006), the repeat nature of the nucleotide sequence within and proximal to the G210 codon in waterhemp PPX2L may foster indel mutations.

Figure 5:
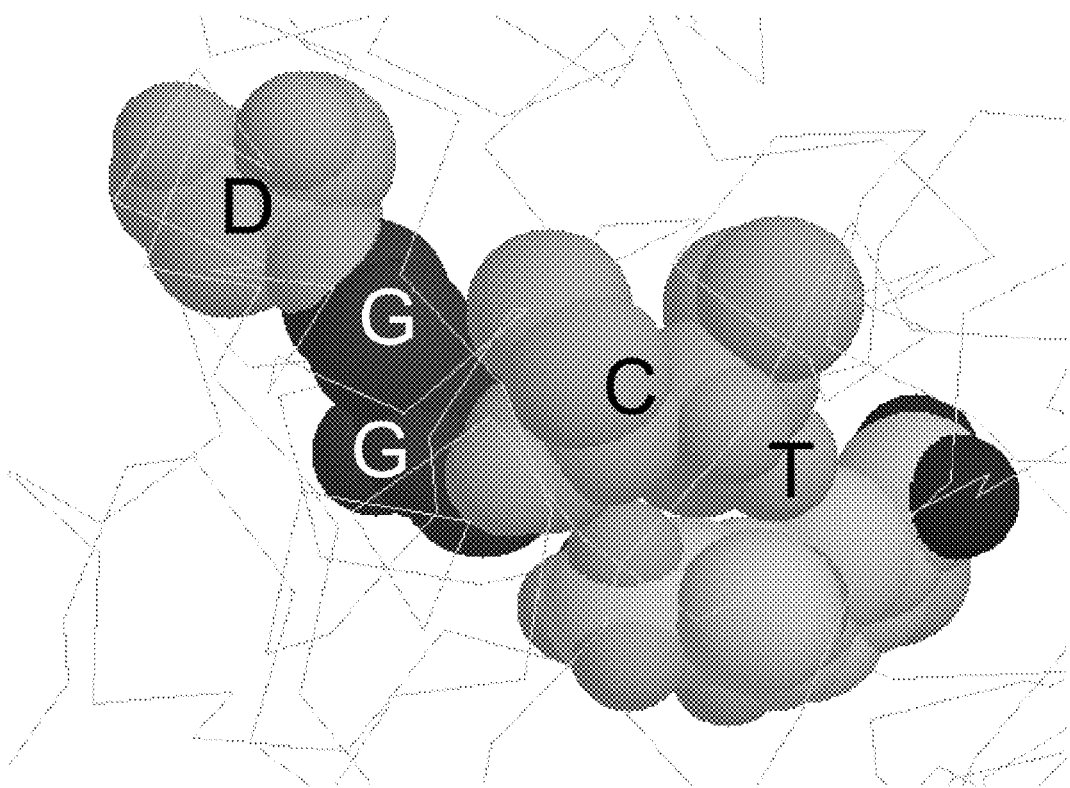
FIG. 5 shows selected amino acid residues of *N. tabacum* PPO2 in proximity to the herbicide-binding site. *A. tuberculatus* plants resistant to PPO inhibitors are missing a glycine residue equivalent to G178 of *N. tabacum*. This amino acid deletion is predicted to hinder PPO inhibitor binding. Letter abbreviations are: amino acid residues, D=aspartic acid, G=glycine, C=cysteine, T=threonine; PPO-inhibiting herbicide, Flz=fluazolate.

The ΔG210 mutation was also assessed using the resolved protein structure of PPO2 from *Nicotiana tabacum* (tobacco) as a reference (Koch, 2004; Martz, 2002). The equivalent amino acid to G210 of *A. tuberculatus* PPO2L (G178 of *N. tabacum* PPO) was located near the herbicide-binding site, thus supporting the prediction that the G210 deletion was responsible for herbicide resistance (FIG. 5). It is understood that a G211 deletion is equivalent in function to the G210 deletion mutant enzymes described herein, and either a G210 or a G211 deletion can be combined with any of the polymorphisms set forth in FIGS. 10A-10B.

The ΔG210 mutation appears to be the predominant resistance mechanism in waterhemp. This is significant because it is both economically and environmentally beneficial to be able to identify herbicide-resistant weeds before the application of a herbicide. Oftentimes such identification requires lengthy and/or labor-intensive bioassays because, in the case of many herbicides, multiple mechanisms exist by which plants can exhibit resistance. Herein we have described a PCR-based assay that accurately predicts resistance to the PPO-inhibiting herbicides in all six resistant populations tested. This simple yet robust assay is a valuable tool for weed management decisions. In an effort to characterize the sensitivity of this assay for field use, leaf samples of resistant and sensitive waterhemp were pooled to simulate sampling a field. Pools were created by progressively diluting the resistant leaf sample with sensitive leaf samples. Genomic DNA was isolated from these pools and then used as template in PCR. The presence of ΔG210 was reliably detected in pools where the resistant leaf sample represented 25% of the total sample. With additional modifications well understood and readily accessible to the art (e.g., quantitative real-time PCR), this assay could be made more sensitive and quantitative. From a practical standpoint, however, the use of a PPO-inhibiting herbicide could be recommended, at least as a rescue treatment, if less than 25% of the weed population (and all or most of the crop or ornamental plant population) were resistant.

The exemplary sequences of the waterhemp sensitive and resistant PPO proteins are given in SEQ ID NOs:16, 18, 20, 22 and 28 and NOs:14, 24, 26 and 30, respectively. CAA73866 (*Nicotiana tabacum*, SEQ ID NO:55), BAA76348 (*Glycine max*, SEQ ID NO:56), BAB08301 (*A. thaliana*, SEQ ID NO:57), CAA73865 (tobacco, SEQ ID NO:58), AAV97809 (*A. thaliana*, SEQ ID NO:59), AAF00194 (chickory, SEQ ID NO:60) and the consensus sequence are in aligned in Table 19, together with representative of the aforementioned waterhemp sequences. Table 20 shows the aligned with the relevant *A. tuberculatus* sequence encompassing amino acids 201-218 of SEQ ID NO:16.

A search of certain protein databases was undertaken, using amino acids 201 to 218 of SEQ ID NO:16 (herbicide sensitive PPO waterhemp) as the query sequence against the 780,949 sequences available on the internet on available sequence databases, including genbankpln0.aa; gbrefplant0.aa protein databases, and the BLAST 2.2.12 program. Searching and alignment was carried out essentially as described in Altschul et al. (1997), "Gapped BLAST and PSI-BLAST: a new generation of protein database search programs", Nucleic Acids Res. 25:3389-3402. Perfect match and alignments were found for wildtype waterhemp sequences, which are disclosed herein and for which the details are not shown below. Additional sequences from database PPO proteins were found, with the corresponding sequences being shown below. Those 18 amino acid sequences from sensitive and resistant PPO proteins which were disclosed in the present application have not been included in the detailed information given below.

TABLE 19

Alignment of PPO Sequences

```
waterhemp_sensi --------------------------------
MVIQSITHLSPNLALPSPLSVSTKNYP
waterhemp_resis --------------------------------
MVIQSITHLSPNLALPSPLSVSTKNYP
CAA73866  ------------------------------------------------------------
BAA76348  ------------------------------------------------------------
BAB08301  --------------MGLIKNGTLYCRFGISWNFAAVFFSTYFRHCFRLVRDFDSELLQIA
CAA73865  -MTTTPIANHPNIFTHQSSSSPLAFLNRTSFIPFSSISKRNS-VNCNG-WRTRCSVAKDY
AAV97809  -------------------MELSLLRPTTQSLLPSFSKPNLRLNVYKPLRLRCSVAGGP
AAF00194  MTSLTDVCSLNCCRSWSSLPPPVSGGSLTSKNPRYLITYSPAHRKCNR-WRFRCSIAKDS
consensus ---------------------l------s-----i-s-t----n---------sl---- waterhemp_sensi VAVMGNISEREEPTSAKRVAVVGAGVSGLAAAYKLKSHG----
LSVTLFEADSRAGGKLK
waterhemp_resis VAVMGNISEREEPTSAKRVAVVGAGVSGLAAAYKLKSHG----
LSVTLFEADSRAGGKLK
CAA73866  ---MAPSAGEDKHSSAKRVAVIGAGVSGLAAAYKLKIHG----LNVTVFEAEGKAGGKLR
BAA76348  ---MASSATDDNPRSVKRVAVVGAGVSGLAAAYKLKSHG----LDVTVFEAEGRAGGRLR
BAB08301  MASGAVADHQIEAVSGKRVAVVGAGVSGLAAAYKLKSRG----LNVTVFEADGRVGGKLR
CAA73865  TVPSSAVDGG--PAAELDCVIVGAGISGLCIAQVMSANYP----NLMVTEARDRAGGNIT
AAV97809  TVGSSKIEGGGGTTITTDCVIVGGGISGLCIAQALATKHPDAAPNLIVTEAKDRVGGNII
AAF00194  PITPP-ISNEFNSQPLLDCVIVGAGISGLCIAQALATKHASVSPDVIVTEARDRVGGNIS
consensus ---mg-i---e-ptsakrvavvGaGvSGLaaAyklkshg----lnvtvfEAd-raGGklk waterhemp_sensi TVKKDGFIWDEGANTMTESEAEVSSLIDDLGLREKQQLPISQNKRYIARDGLPVLLPSNP
waterhemp_resis TVKKDGFIWDEGANTMTESEAEVSSLIDDLGLREKQQLPISQNKRYIARDGLPVLLPSNP
CAA73866  SVSQDGLIWDEGANTMTESEGDVTFLIDSLGLREKQQFPLSQNKRYIARNGTPVLLPSNP
BAA76348  SVSQDGLIWDEGANTMTESEIEVKGLIDALGLQEKQQFPISQHKRYIVKNGAPLLVPTNP
BAB08301  SVMQNGLIWDEGANTMTEAEPEVGSLLDDLGLREKQQFPISQKKRYIVRNGVPVMLPTNP
CAA73865  TVERDGYLWEEGPNSFQPSDP-MLTMAVDCGLKDDLVLGDPNAPRFVLWKGKLRPVPSKL
AAV97809  TREENGFLWEEGPNSFQPSDP-MLTMVVDSGLKDDLVLGDPTAPRFVLWNGKLRPVPSKL
AAF00194  TVERDGYLWEEGPNSFQPSDA-MLTMVVDSGLKDDLVLGDPTAPRFVLWGGDLKPVPSKP
consensus tv-kdGfiWdEGaNtmteseaev-sliddlGLrekqqlpisq-kRyivrnG-pvllPsnp
```

TABLE 19-continued

Alignment of PPO Sequences

```
waterhemp_sensi AALLTSNILSAKSKLQIMLEPFLWRKHNATELSDEHVQESVGEFFERHFGKEFVDYVIDP
waterhemp_resis AALLTSNILSAKSKLQIMLEPFLWRKHNATELSDEHVQESVGEFFERHFGKEFVDYVIDP
CAA73866        IDLIKSNFLSTGSKLQMLLEPILWKNKKLSQVSDSH--ESVSGFFQRHFGKEVVDYLIDP
BAA76348        AALLKSKLLSAQSKIHLIFEPFMWKRSDPSNVCDENSVESVGRFFERHFGKEVVDYLIDP
BAB08301        IELVTSSVLSTQSKFQILLEPFLWKKKS-SKVSDASAEESVSEFFQRHFGQEVVDYLIDP
CAA73865        TDLAFFDLMSIPGKLRAGFGAIGLRP------SPPGHEESVEQFVRRNLGGEVFERLIEP
AAV97809        TDLPFFDLMSIGGKIRAGFGALGIRP------SPPGREESVEEFVRRNLGDEVFERLIEP
AAF00194        ADLPFFDLMSFPGKLRAGFGALGFRP------SPPDREESVEEFVRRNLGDEVFERLIEP
consensus       adLl-s-llS--sKlqim-epflwrk---t-lsd---eESV-eFf-RhfGkEvvdylIdP waterhemp_sensi FVAGTCGGDPQSLSMHHTFPEVWNIEKRFGSVFAGLIQSTLLSKKEK--
GGENASIKKPR
waterhemp_resis FVAGTCG-DPQSLSMHHTFPEVWNIEKRFGSVFAGLIQSTLLSKKEK--
GGENASIKKPR
CAA73866        FVAGTCGGDPDSLSMHHSFPELWNLEKRFGSVILGAIRSKLSPKNEKKQGPPKTSANKKR
BAA76348        FVGGTSAADPESLSMRHSFPELWNLEKRFGSIIAGALQSKLFAKREKTGENRTALRKNKH
BAB08301        FVGGTSAADPDSLSMKHSFPDLWN---SFGSIIVGAIRTKFAAKGGKSRDTKSSPGTKKG
CAA73865        FCSGVYAGDPSKLSMKAAFGKVWKLEETGGSIIGGTFKAIK-ERSSTPKAPRDPRLPKPK
AAV97809        FCSGVYAGDPSKLSMKAAFGKVWKLEQNGGSIIGGTFKAIQ-ERKNAPKAERDPRLPKPQ
AAF00194        FCSGVYAGDPSKLSMKAAFGKVWNLEQNGGSIVGGAFKAIQ-DRKNSQKPPRDPRLPKPK
consensus       FvaGt-agDP-sLSMkhtFpevWnlekrfGSiiaGairs-l--kkek-rg-r---i-kpr waterhemp_sensi VRGSFSFQGGMQTLVDTMCKQLGEDELKLQCEVLSLSYNQKGIPSLGNWSVSSMSNN--T
waterhemp_resis VRGSFSFQGGMQTLVDTMCKQLGEDELKLQCEVLSLSYNQKGIPSLGNWSVSSMSNN--T
CAA73866        QRGSFSFLGGMQTLTDAICKDLREDELRLNSRVLELSCSCTEDSAIDSWSIISASPHKRQ
BAA76348        KRGSFSFQGGMQTLTDTLCKELGKDDLKLNEKVLTLAYGHDGSSSSQNWSITSASNQ---
BAB08301        SRGSFSFKGGMQILPDTLCKSLSHDEINLDSKVLSLSYNSG--SRQENWSLSCVSHN---
CAA73865        GQTVGSFRKGLRMLPDAISARLG-SKLKLSWKLSSITK-----SEKGGYHLTYETPEG--
AAV97809        GQTVGSFRKGLRMLPEAISARLG-SKVKLSWKLSGITK-----LESGGYNLTYETPDG--
AAF00194        GQTVGSFRKGQAMLPNAISTRLG-SRVKLCWKLTSISK-----LENRGYNLTYETPQG--
consensus       -rgsfSFkgGmqtLpd-ick-Lg-delkLq-kvlslsy-----s--gnwslts-spn--- waterhemp_sensi SEDQSYDAVVVTAPIRNVKEMKIMKFGNPFSLDFIPEVTYVPLSVMITAFKKDKVKRP--
waterhemp_resis SEDQSYDAVVVTAPIRNVKEMKIMKFGNPFSLDFIPEVTYVPLSVMITAFKKDKVKRP--
CAA73866        SEEESFDAVIMTAPLCDVKSMKIAKRGNPFLLNFIPEVDYVPLSVVITTFKRENVKYP--
BAA76348        -STQDVDAVIMTAPLYNVKDIKITKRGTPFPLNFLPEVSYVPISVMITTFKKENVKRP--
BAB08301        -ETQRQNPHYDAAPLCNVKEMVMKGGQPFQLNFLPEINYMPLSVLITTFTKEKVKRP--
CAA73865        --VVSLQSRSIVMTVPSYVASNILRPLSVAAADALSNFYYPPVGAVTITYPQEAIRDERL
AAV97809        --LVSVQSKSVVMTVPSHVASGLLRPLSESAANALSKLYYPPVAAVSISYPKEAIRTECL
AAF00194        --FESLQTKTIVMTVPSYVASDLLRPLSLGAADALSKFYYPPVAAVSISYPKDAIRADRL
consensus       -e-qsvdavvvtapi-nvkemkimk-g-pf-l-flpev-YvPlsvvittfkke-vkrp-- waterhemp_sensi --------------------------------
MVIQSITHLSPNLALPSPLSVSTKNYP
waterhemp_resis --------------------------------
MVIQSITHLSPNLALPSPLSVSTKNYP
CAA73866        ------------------------------------------------------------
BAA76348        ------------------------------------------------------------
BAB08301        --------------MGLIKNGTLYCRFGISWNFAAVFFSTYFRHCFRLVRDFDSELLQIA
CAA73865        -MTTTPIANHPNIFTHQSSSSPLAFLNRTSFIPFSSISKRNS-VNCNG-WRTRCSVAKDY
AAV97809        -------------------MELSLLRPTTQSLLPSFSKPNLRLNVYKPLRLRCSVAGGP
AAF00194        MTSLTDVCSLNCCRSWSSLPPPVSGGSLTSKNPRYLITYSPAHRKCNR-WRFRCSIAKDS
consensus       ----------------------l------s-----i-s-t----n---------sl---- waterhemp_sensi VAVMGNISEREEPTSAKRVAVVGAGVSGLAAAYKLKSHG----
LSVTLFEADSRAGGKLK
waterhemp_resis VAVMGNISEREEPTSAKRVAVVGAGVSGLAAAYKLKSHG----
LSVTLFEADSRAGGKLK
CAA73866        ---MAPSAGEDKHSSAKRVAVIGAGVSGLAAAYKLKIHG----LNVTVFEAEGKAGGKLR
BAA76348        ---MASSATDDNPRSVKRVAVVGAGVSGLAAAYKLKSHG----LDVTVFEAEGRAGGRLR
BAB08301        MASGAVADHQIEAVSGKRVAVVGAGVSGLAAAYKLKSRG----LNVTVFEADGRVGGKLR
CAA73865        TVPSSAVDGG--PAAELDCVIVGAGISGLCIAQVMSANYP----NLMVTEARDRAGGNIT
AAV97809        TVGSSKIEGGGGTTITTDCVIVGGGISGLCIAQALATKHPDAAPNLVTEAKDRVGGNII
AAF00194        PITPP-ISNEFNSQPLLDCVIVGAGISGLCIAQALATKHASVPDVIVTEARDRVGGNIS
consensus       ---mg-i---e-ptsakrvavvGaGvSGLaaAyklkshg----lnvtvfEAd-raGGklk waterhemp_sensi TVKKDGFIWDEGANTMTESEAEVSSLIDDLGLREKQQLPISQNKRYIARDGLPVLLPSNP
waterhemp_resis TVKKDGFIWDEGANTMTESEAEVSSLIDDLGLREKQQLPISQNKRYIARDGLPVLLPSNP
CAA73866        SVSQDGLIWDEGANTMTESEGDVTFLIDSLGLREKQQFPLSQNKRYIARNGTPVLLPSNP
BAA76348        SVSQDGLIWDEGANTMTESEIEVKGLIDALGLQEKQQFPISQHKRYIVKNGAPLLVPTNP
BAB08301        SVMQNGLIWDEGANTMTEAEPEVGSLLDDLGLRPQQFPISQKKRYIVRNGVPVMLPTNP
CAA73865        TVERDGYLWEEGPNSFQPSDP-MLTMAVDCGLKDDLVLGDPNAPRFVLWGKLRPVPSKL
AAV97809        TREENGFLWEEGPNSFQPSDP-MLTMVVDSGLKDDLVLGDPTAPRFVLWNGKLRPVPSKL
AAF00194        TVERDGYLWEEGPNSFQPSDA-MLTMVVDSGLKDDLVLGDPTAPRFVLWGGDLKPVPSKP
consensus       tv-kdGfiWdEGaNtmteseaev-sliddlGLrekqqlpisq-kRyivrnG-pvllPsnp
```

TABLE 19-continued

Alignment of PPO Sequences

```
waterhemp_sensi AALLTSNILSAKSKLQIMLEPFLWRKHNATELSDEHVQESVGEFFERHFGKEFVDYVIDP
waterhemp_resis AALLTSNILSAKSKLQIMLEPFLWRKHNATELSDEHVQESVGEFFERHFGKEFVDYVIDP
CAA73866        IDLIKSNFLSTGSKLQMLLEPILWKNKKLSQVSDSH--ESVSGFFQRHFGKEVVDYLIDP
BAA76348        AALLKSKLLSAQKIHLIFEPFMWKRSDPSNVCDENSVESVGRFFERHFGKEVVDYLIDP
BAB08301        IELVTSSVLSTQSKFQILLEPFLWKKKS-SKVSDASAEESVSEFFQRHFGQEVVDYLIDP
CAA73865        TDLAFFDLMSIPGKLRAGFGAIGLRP------SPPGHEESVEQFVRRNLGGEVFERLIEP
AAV97809        TDLPFFDLMSIGGKIRAGFGALGIRP------SPPGREESVEEFVRRNLGDEVFERLIEP
AAF00194        ADLPFFDLMSFPGKLRAGFGALGFRP------SPPDREESVEEFVRRNLGDEVFERLIEP
consensus       adLl-s-llS--sKlqim-epflwrk---t-lsd---eESV-eFf-RhfGkEvvdyLIdP waterhemp_sensi FVAGTCGGDPQSLSMHHTFPEVWNIEKRFGSVFAGLIQSTLLSKKEK--
                GGENASIKKPR
waterhemp_resis FVAGTCG-DPQSLSMHHTFPEVWNIEKRFGSVFAGLIQSTLLSKKEK--
                GGENASIKKPR
CAA73866        FVAGTCGGDPDSLSMHHSFPELWNLEKRFGSVILGAIRSKLSPKNEKKQGPPKTSANKKR
BAA76348        FVGGTSAADPESLSMRHSFPELWNLEKRFGSIIAGALQSKLFAKREKTGENRTALRKNKH
BAB08301        FVGGTSAADPDSLSMKHSFPDLWN---SFGSIIVGAIRTKFAAKGGKSRDTKSSPGTKKG
CAA73865        FCSGVYAGDPSKLSMKAAFGKVWKLEETGSIIGGTFKAIK-ERSSTPKAPRDPRLPKPK
AAV97809        FCSGVYAGDPSKLSMKAAFGKVWKLEQNGGSIIGGTFKAIQ-ERKNAPKAERDPRLPKPQ
AAF00194        FCSGVYAGDPSKLSMKAAFGKVWNLEQNGGSIVGGAFKAIQ-DRKNSQKPPRDPRLPKPK
consensus       FvaGt-agDP-sLSMkhtFpevWnlekrfGSiiaGairs-l--kkek-rg-r---i-kpr waterhemp_sensi VRGSFSFQGGMQTLVDTMCKQLGEDELKLQCEVLSLSYNQKGIPSLGNWSVSSMSNN--T
waterhemp_resis VRGSFSFQGGMQTLVDTMCKQLGEDELKLQCEVLSLSYNQKGIPSLGNWSVSSMSNN--T
CAA73866        QRGSFSFLGGMQTLTDAICKDLREDELRLNSRVLELSCSCTEDSAIDSWSIISASPHKRQ
BAA76348        KRGSFSFQGGMQTLTDTLCKELGKDDLKLNEKVLTLAYGHDGSSSSQNWSITSASNQ---
BAB08301        SRGSFSFKGGMQILPDTLCKSLSHDEINLDSKVLSLSYNSG--SRQENWSLSCVSHN---
CAA73865        GQTVGSFRKGLRMLPDAISARLG-SKLKLSWKLSSITK-----SEKGGYHLTYETPEG--
AAV97809        GQTVGSFRKGLRMLPEAISARLG-SKVKLSWKLSGITK-----LESGGYNLTYETPDG--
AAF00194        GQTVGSFRKGQAMLPNAISTRLG-SRVKLCWKLTSISK-----LENRGYNLTYETPQG--
consensus       -rgsfSFkgGmqtLpd-ick-Lg-delkLq-kvlslsy-----s--gnwslts-spn--- waterhemp_sensi SEDQSYDAVVVTAPIRNVKEMKIMKFGNPFSLDFIPEVTYVPLSVMITAFKKDKVKRP--
waterhemp_resis SEDQSYDAVVVTAPIRNVKEMKIMKFGNPFSLDFIPEVTYVPLSVMITAFKKDKVKRP--
CAA73866        SEEESFDAVIMTAPLCDVKSMKIAKRGNPFLLNFIPEVDYVPLSVVITTFKRENVKYP--
BAA76348        -STQDVDAVIMTAPLYNVKDIKITKRGTPFPLNFLPEVSYVPISVMITTFKKENVKRP--
BAB08301        -ETQRQNPHYDAAPLCNVKEMKVMKGGQPFQLNFLPEINYMPLSVLITTFTKEKVKRP--
CAA73865        --VVSLQSRSIVMTVPSYVASNILRPLSVAAADALSNFYYPPVGAVTITYPQEAIRDERL
AAV97809        --LVSVQSKSVVMTVPSHVASGLLRPLSESAANALSKLYYPPVAAVSISYPKEAIRTECL
AAF00194        --FESLQTKTIVMTVPSYVASDLLRPLSLGAADALSKFYYPPVAAVSISYPKDAIRADRL
consensus       -e-qsvdavvvtapi-nvkemkimk-g-pf-l-flpev-YvPlsvvittfkke-vkrp--
```

TABLE 20

Sequences producing significant alignments included the following

| | (bits) | Value |
|---|---|---|
| GBPLN: 88862005_88862006 mitochondrial PPO . . . | 42 | 9e-04 |
| GBPLN: 88809984_88809985 waterhemp mitochondrial PPO | 42 | 9e-04 |
| GBPLN: 88809978_88809979 waterhemp mitochondrial PPO | 42 | 9e-04 |
| GBPLN: 88809976_88809977 waterhemp | 42 | 9e-04 |
| GBPLN: 154269385_154269386 mitochondrial PPO | 41 | 0.003 |
| GBPLN: 2370334_2370335 PPO *Nicotiana tabacum* | 40 | 0.003 |
| GBPLN: 7544063_3093412 PPO *Solanum tuberosum* | 40 | 0.003 |
| GBPLN: 4105187_4105188 PPO PX-2 [*Nicotiana* . . . | 40 | 0.003 |
| GBPLN: 3929919_3929920 mitochondrial PPO | 40 | 0.003 |
| GBPLN: 14349152_14349153 PPO *Spinacia* | 39 | 0.013 |
| GBPLN: 147788410_147788412 protein *Vitis vinifera* | 37 | 0.028 |
| GBPLN: 32483304_38347440 *Oryza sativa* genomic DNA, chromosome 4, . . . | 36 | 0.083 |
| GBPLN: 32480009_38345232 *Oryza sativa* genomic DNA, chromosome 4, . . . | 36 | 0.083 |

TABLE 20-continued

Sequences producing significant alignments included the following

| | | |
|---|---|---|
| GBPLN: 88862007_88862008 mitochondrial PPO | 35 | 0.11 |
| GBPLN: 88809986_88809987 mitochondrial PPO | | 0.11 |
| GBPLN: 88809982_88809983 mitochondrialPPO | 35 | 0.11 |
| GBREFPLANT: 162462665_162462666 PPO | 33 | 0.54 |
| GBPLN: 9857978_9857979 PPO (*Zea mays*) | 33 | 0.54 |
| GBPLN: 4586307_4586308 PPO *Glycine max* . . . | 31 | 2.0 |
| GBREFPLANT: 145358007_22326801 HEMG2/MEE61 (maternal effect embry . . . | 30 | 3.5 |
| GBREFPLANT: 30698605_22326801 HEMG2/MEE61 (maternal effect embryo . . . | 30 | 3.5 |
| GBPLN: 20856026_20856027 AT5g14220/MUA22_22 *Arabidopsis thaliana* | 30 | 3.5 |
| GBPLN: 18700120_18700121 AT5g14220/MUA22_22 *Arabidopsis thaliana* | 30 | 3.5 |
| GBPLN: 7573446_7573447 protoporphyrinogen oxidase-like protein A . . . | 30 | 3.5 |
| GBPLN: 2564050_9757803 protoporphyrinogen IX oxidase *Arabidopsis* . . . | 30 | 3.5 |

```
In all cases in this table, the Query sequence was amino acids 201-218
of SEQ ID NO: 16.
>GBPLN: 154269385_154269386 mitochondrial protoporphyrinogen oxidase
(Amaranthus hypochondriacus) ABS72165.1 (EU024569)
Length = 535
Score = 40.8 bits (94), Expect = 0.003
Identities = 17/18 (94%), Positives = 18/18 (100%)
Query:    1 IDPFVAGTCGGDPQSLSM 18
            IDPFVAGTCGGDPQSLS+
Sbjct:  201 IDPFVAGTCGGDPQSLSV 218 (SEQ ID NO: 61)

>GBPLN: 2370334_2370335 protoporphyrinogen oxidase (Nicotiana
tabacum) CAA73866.1 (Y13466)
Length = 504
Score = 40.4 bits (93), Expect = 0.003
Identities = 17/18 (94%), Positives = 17/18 (94%)
Query:    1 IDPFVAGTCGGDPQSLSM 18
            IDPFVAGTCGGDP SLSM
Sbjct:  169 IDPFVAGTCGGDPDSLSM 186 (SEQ ID NO: 62)

>GBPLN: 7544063_3093412 protoporphyrinogen oxidase (Solanum
tuberosum) CAA12401.1 (AJ225108)
Length = 404
Score = 40.4 bits (93), Expect = 0.003
Identities = 17/18 (94%), Positives = 17/18 (94%)
Query:    1 IDPFVAGTCGGDPQSLSM 18
            IDPFVAGTCGGDP SLSM
Sbjct:  169 IDPFVAGTCGGDPDSLSM 186 (SEQ ID NO: 63)

>GBPLN: 4105187_4105188 protoporphyrinogen oxidase PX-2 (Nicotiana
tabacum) AAD02291.1 (AF044129)
Length = 504
Score = 40.4 bits (93), Expect = 0.003
Identities = 17/18 (94%), Positives = 17/18 (94%)
Query:    1 IDPFVAGTCGGDPQSLSM 18
            IDPFVAGTCGGDP SLSM
Sbjct:  169 IDPFVAGTCGGDPDSLSM 186 (SEQ ID NO: 64)

>GBPLN: 3929919_3929920 mitochondrial protoporphyrinogen oxidase
(Nicotiana tabacum) BAA34712.1 (AB020500)
Length = 504
Score = 40.4 bits (93), Expect = 0.003
Identities = 17/18 (94%), Positives = 17/18 (94%)
Query:    1 IDPFVAGTCGGDPQSLSM 18
            IDPFVAGTCGGDP SLSM
Sbjct:  169 IDPFVAGTCGGDPDSLSM 186 (SEQ ID NO: 65)

>GBPLN: 14349152_14349153 protoporphyrinogen oxidase-II (Spinacia
Oleracea) BAB60710.1 (AB046993)
Length = 531
Score = 38.5 bits (88), Expect = 0.013
Identities = 17/18 (94%), Positives = 17/18 (94%)
Query:    1 IDPFVAGTCGGDPQSLSM 18
```

TABLE 20-continued

Sequences producing significant alignments included the following

```
          IDPFVAGT GGDPQSLSM
Sbjct: 200 IDPFVAGTSGGDPQSLSM 217 (SEQ ID NO: 66)

>GBPLN: 147788410_147788412 hypothetical protein (Vitis vinifera)
CAN69962.1 (AM453176)
Length = 809
Score = 37.4 bits (85), Expect = 0.028
Identities = 16/18 (88%), Positives = 17/18 (94%)
Query:    1 IDPFVAGTCGGDPQSLSM 18
            IDPFVAGT GGDP+SLSM
Sbjct: 185 IDPFVAGTSGGDPESLSM 202 (SEQ ID NO: 67)

>GBPLN: 32483304_38347440 Oryza sativa genomic DNA,
chromosome 4, BAC clone: OSJNBa0076N16, complete sequence. CAE02483.2
(AL731617)
Length = 506
Score = 35.8 bits (81), Expect = 0.083
Identities = 15/18 (83%), Positives = 17/18 (94%)
Query:    1 IDPFVAGTCGGDPQSLSM 18
            IDPFVAGT GGDP+SLS+
Sbjct: 170 IDPFVAGTSGGDPESLSI 187 (SEQ ID NO: 68)

>GBPLN: 32480009_38345232 Oryza sativa genomic DNA, chromosome
4, BAC clone: OSJNBa0084K20, complete sequence. CAE01661.2
(AL606613)
Length = 506
Score = 35.8 bits (81), Expect = 0.083
Identities = 15/18 (83%), Positives = 17/18 (94%)
Query:    1 IDPFVAGTCGGDPQSLSM 18
            IDPFVAGT GGDP+SLS+
Sbjct: 170 IDPFVAGTSGGDPESLSI 187 (SEQ ID NO: 69)

>GBREFPLANT: 162462665_162462666 protoporphyrinogen IX
oxidase (Zea mays) NP_001105004.1 (NM_001111534)
Length = 544
Score = 33.1 bits (74), Expect = 0.54
Identities = 13/18 (72%), Positives = 16/18 (88%)
Query:    1 IDPFVAGTCGGDPQSLSM 18
            +DPFVAGT  GDP+SLS+
Sbjct: 206 VDPFVAGTSAGDPESLSI 223 (SEQ ID NO: 70)

>GBPLN: 9857978_9857979 protoporphyrinogen IX oxidase (Zea mays)
AAG00946.1 (AF273767)
Length = 544
Score = 33.1 bits (74), Expect = 0.54
Identities = 13/18 (72%), Positives = 16/18 (88%)
Query:    1 IDPFVAGTCGGDPQSLSM 18
            +DPFVAGT  GDP+SLS+
Sbjct: 206 VDPFVAGTSAGDPESLSI 223 (SEQ ID NO: 71)

>GBPLN: 4586307_4586308 protoporphyrinogen IX oxidase (Glycine max)
BAA76348.1 (AB025102)
Length = 502
Score = 31.2 bits (69), Expect = 2.0
Identities = 13/18 (72%), Positives = 14/18 (77%)
Query:    1 IDPFVAGTCGGDPQSLSM 18
            IDPFV GT   DP+SLSM
Sbjct: 171 IDPFVGGTSAADPESLSM 188 (SEQ ID NO: 72)

>GBREFPLANT: 145358007_22326801 HEMG2/MEE61 (maternal effect embryo
arrest 61); (Arabidopsis thaliana) NP_196926.2
(NM_121426)
Length = 508
Score = 30.4 bits (67), Expect = 3.5
Identities = 13/18 (72%), Positives = 13/18 (72%)
Query:    1 IDPFVAGTCGGDPQSLSM 18
            IDPFV GT    DP SLSM
Sbjct: 173 IDPFVGGTSAADPDSLSM 190 (SEQ ID NO: 73)

>GBREFPLANT: 30698605_22326801 HEMG2/MEE61 (maternal effect embryo
arrest 61); (Arabidopsis thaliana) NP_196926.2
(NC_003076)
Length = 508
Score = 30.4 bits (67), Expect = 3.5
Identities = 13/18 (72%), Positives = 13/18 (72%)
Query:    1 IDPFVAGTCGGDPQSLSM 18
            IDPFV GT    DP SLSM
```

TABLE 20-continued

Sequences producing significant alignments included the following

```
Sbjct: 173 IDPFVGGTSAADPDSLSM 190 (SEQ ID NO: 74)

>GBPLN: 20856026_20856027 AT5g14220/MUA22_22
(Arabidopsis thaliana)
AAM26644.1 (AY101523)
Length = 508
Score = 30.4 bits (67), Expect = 3.5
Identities = 13/18 (72%), Positives = 13/18 (72%)
Query:    1 IDPFVAGTCGGDPQSLSM 18
            IDPFV GT   DP SLSM
Sbjct: 173 IDPFVGGTSAADPDSLSM 190 (SEQ ID NO: 75)

>GBPLN: 18700120_18700121 AT5g14220/MUA22_22 (Arabidopsis thaliana)
AAL77672.1 (AY075665)
Length = 508
Score = 30.4 bits (67), Expect = 3.5
Identities = 13/18 (72%), Positives = 13/18 (72%)
Query:    1 IDPFVAGTCGGDPQSLSM 18
            IDPFV GT   DP SLSM
Sbjct: 173 IDPFVGGTSAADPDSLSM 190 (SEQ ID NO: 76)

>GBPLN: 7573446_7573447 protoporphyrinogen oxidase-like protein
(Arabidopsis thaliana) CAB87761.1 (AL163817)
Length = 501
Score = 30.4 bits (67), Expect = 3.5
Identities = 13/18 (72%), Positives = 13/18 (72%)
Query:    1 IDPFVAGTCGGDPQSLSM 18
            IDPFV GT   DP SLSM
Sbjct: 173 IDPFVGGTSAADPDSLSM 190 (SEQ ID NO: 77)

>GBPLN: 2564050_9757803 protoporphyrinogen IX oxidase (Arabidopsis
thaliana BAB08301.1 (AB007650)
Length = 547
Score = 30.4 bits (67), Expect = 3.5
Identities = 13/18 (72%), Positives = 13/18 (72%)
Query:    1 IDPFVAGTCGGDPQSLSM 18
            IDPFV GT   DP SLSM
Sbjct: 219 IDPFVGGTSAADPDSLSM 236 (SEQ ID NO: 78)

Database: genbankpln0.aa
Number of sequences in database:   607,682
Database: gbrefplant0.aa
Number of sequences in database:   173,267

Lambda K       H
0.319  0.141  0.455

Gapped
Lambda K       H
0.267  0.0410 0.140
```

---

```
Matrix: BLOSUM62
Gap Penalties: Existence: 11, Extension: 1
Number of Hits to DB: 11,789,412
Number of Sequences: 780949
Number of extensions: 95485
Number of successful extensions: 181
Number of sequences better than 10.0: 25
Number of HSP's better than 10.0 without gapping: 22
Number of HSP's successfully gapped in prelim test: 3
Number of HSP's that attempted gapping in prelim test: 156
Number of HSP's gapped (non-prelim): 25
length of query: 18
length of database: 277,085,727
effective HSP length: 0
effective length of query: 18
X1: 16 (7.4 bits)
X2: 38 (14.6 bits)
X3: 64 (24.7 bits)
S1: 41 (21.7 bits)
S2: 64 (29.3 bits)
```

Figure 6:
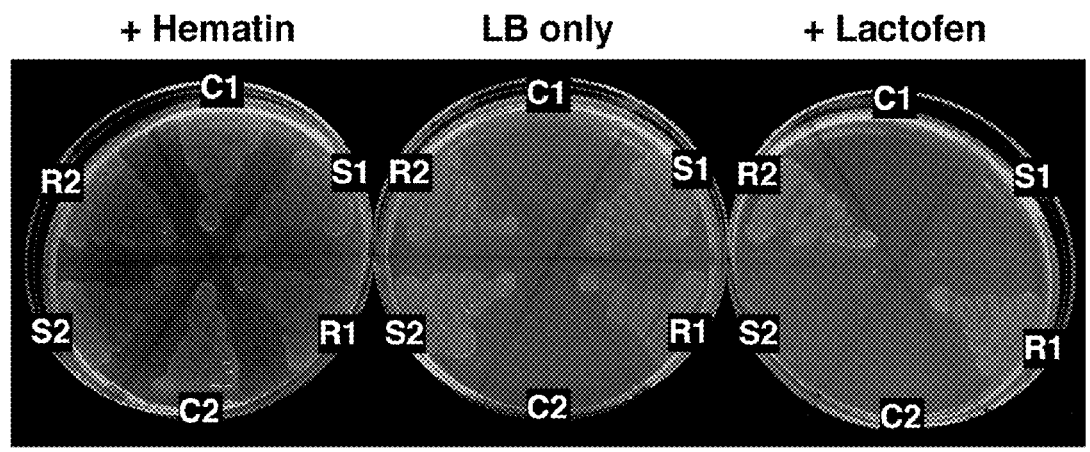
FIG. 6 illustrates PPO expression in a hemG mutant strain of *E. coli*. *E. coli* cells were grown on LB medium alone or supplemented with hematin (20 µg ml$^{-1}$) or lactofen (100 nM). *E. coli* isolates were: C1 and C2, non-transformed controls; S1 and S2, transformed with vector encoding *A. tuberculatus*-derived PPO2L with glycine at position 210; R1 and R2, transformed with vector encoding identical PPO2L with the exception of a deletion of glycine at position 210.

Complementation assays utilized a hemG (PPO) mutant strain of *E. coli*, SASX38 (Sasarman, 1979), to access the effect of the G210 deletion toward herbicide responses. The SASX38 strain grows very slowly unless supplied with exogenous heme or rescued with an alternative source of PPO. Furthermore, since wild type *E. coli* is naturally tolerant to PPO inhibitors, use of the SASX38 strain enabled a relatively direct assay for herbicide sensitivity of the S and R PPO2Ls from *A. tuberculatus* (Li, 2003; Sasarman, 1993). The SASX38 *E. coli* strain was transformed with plasmid constructs encoding PPO2L proteins differing only in the presence/absence of G210. Both constructs were able to rescue growth of the SASX38 *E. coli* strain, thus indicating both PPX2L genes encoded functional proteins (FIG. 6). However, supplementation of the growth medium with lactofen dramatically inhibited growth of *E. coli* transformed with the wild type PPX2L, but not *E. coli* transformed with the ΔG210 PPX2L (FIG. 6). Thus, the three-bp deletion in PPX2L resulting in deletion of a glycine at position 210 of PPO2L was sufficient to confer resistance to lactofen.

TABLE 1

Inheritance of resistance to the PPO inhibitor, lactofen, in *A. tuberculatus*. $F_1$ plants were obtained from reciprocal crosses between a resistant (R) and sensitive (S) biotype ($F_1(R)$: female parent was R; $F_1(S)$: female parent was S). Plants from $F_2$ and backcross lines were treated with lactofen at 110 g ai ha$^{-1}$ plus 1% (by vol) COC, and scored as R or S 15 days after treatment. The expected segregation ratio of R to S responses assumes a single genetic unit of inheritance.

| Male parent | Female parent | N | Observed numbers R | S | Expected ratio (R:S) | $\chi^2$ | P-value |
|---|---|---|---|---|---|---|---|
| $F_1$ (R) | $F_1$ (R) | 400 | 297 | 103 | 3:1 | 0.120 | 0.7290 |
|  | S | 200 | 98 | 102 | 1:1 | 0.080 | 0.7772 |
|  | R | 200 | 200 | 0 | 1:0 | 0 | 1 |
| $F_1$ (S) | $F_1$ (S) | 400 | 304 | 96 | 3:1 | 0.213 | 0.6441 |
|  | S | 200 | 109 | 91 | 1:1 | 1.620 | 0.2030 |
|  | R | 200 | 200 | 0 | 1:0 | 0 | 1 |

TABLE 2

$GR_{50}$ (growth reduction by 50%) and degree of dominance[b] estimates for PPO inhibitor-resistance in *A. tuberculatus*. Plants from R, S, $F_1(R)$, or $F_1(S)$ lines were treated with lactofen or acifluorfen, and data collected either 10 or 15 days after treatment (DAT). Dominance estimates are interpreted as: 0 to 1 = dominant; 0 = partially dominant; 0 to −1 = recessive.

| | | | $GR_{50}$ | | | Dominance | |
|---|---|---|---|---|---|---|---|
| DAT | Herbicide | R | $F_1(R)$ | $F_1(S)$ | S | $F_1(R)$ | $F_1(S)$ |
| | | (g ai ha$^{-1}$) | | | | | |
| 15 | Lactofen | 21 | 12 | 13 | 0.4 | 0.72 | 0.76 |
| 10 | Acifluorfen | 5.8 | 3.8 | 4.1 | 1.6 | 0.34 | 0.46 |
| | Lactofen | 2.9 | 0.7 | 1.6 | 0.2 | −0.06 | 0.56 |

[a]$GR_{50}$ estimates were calculated using PROC NLIN in SAS as described by Seefeldt et al. (1995).
[b]The degree of dominance (D) = $(2W_3 - W_2 - W_1)/(W_2 - W_1)$, where $W_1$ = log($GR_{50}$) of the S-parent, $W_2$ = log($GR_{50}$) or the R-parent, and $W_3$ = log($GR_{50}$) of the $F_1$ lines (0 to 1 = dominant; 0 = partially dominant; 0 to −1 = recessive) (Stone 1968).

Numerous transformation vectors are available for plant transformation, and the genes of this invention can be used in conjunction with any such vectors. The selection of vector for use will depend upon the preferred transformation technique and the target species for transformation. For certain target species, different antibiotic or herbicide selection markers may be preferred. Selectable markers used routinely in transformation include the nptII gene which confers resistance to kanamycin and related antibiotics (Messing and Vierra. 1982. Gene 19: 259-268; Bevan et al. 1983. Nature 304:184-187), the bar gene which confers resistance to the herbicide phosphinothricin (White et al. 1990. Nucl Acids Res 18: 1062; Spencer et al. 1990. Theor Appl Genet 79: 625-631), the hph gene which confers resistance to the antibiotic hygromycin (Blochinger and Diggelmann. 1984. Mol Cell Biol 4: 2929-2931), and the dhfr gene, which confers resistance to methotrexate (Bourouis et al. 1983. EMBO J. 2(7): 1099-1104).

Many vectors are available for transformation using *A. tumefaciens*. These typically carry at least one T-DNA border sequence and include vectors such as pBIN19 (Bevan. 1984. Nucl. Acids Res.). Below the construction of two typical vectors is described. pCAMBIA vectors are well known to the art as well.

The exemplary binary vector pCIB10 contains a gene encoding kanamycin resistance for selection in plants, T-DNA right and left border sequences and incorporates sequences from the wide host-range plasmid pRK252 allowing it to replicate in both *E. coli* and *Agrobacterium*. Its construction is described by Rothstein et al. 1987. Gene 53: 153-161. Various derivatives of pCIB10 have been constructed which incorporate the gene for hygromycin B phosphotransferase described by Gritz et al. 1983. Gene 25: 179-188. These derivatives enable selection of transgenic plant cells on hygromycin only (pCIB743), or hygromycin and kanamycin (pCIB715, pCIB717). See, e.g., Rogers et al., Methods for Plant Molecular Biology, Weissbach and Weissbach, eds, Academic Press, San Diego, Calif., 1988, for a description of a kanamycin resistance marker. Other selective agents for use in plants include bleomycin, gentamicin and certain herbicide resistance markers (not via the PPX2L of the present invention).

Transformation without the use of *A. tumefaciens* circumvents the requirement for T-DNA sequences in the chosen transformation vector and consequently vectors lacking these sequences can be utilized in addition to vectors such as the ones described above which contain T-DNA sequences. Transformation techniques which do not rely on *Agrobacterium* include transformation via particle bombardment, protoplast uptake (e.g. PEG and electroporation) and microinjection. The choice of vector depends largely on the preferred selection for the species being transformed.

Gene sequences intended for expression in transgenic plants are first assembled in expression cassettes behind a suitable promoter and upstream of a suitable transcription terminator. These expression cassettes can then be easily transferred to the plant transformation vectors of choice.

The selection of a promoter used in expression cassettes determines the spatial and temporal expression pattern of the transgene in the transgenic plant. Selected promoters express transgenes in specific cell types (such as leaf epidermal cells, mesophyll cells, root cortex cells) or in specific tissues or organs (roots, leaves or flowers, for example), and this selection reflects the desired location of expression of the transgene. Alternatively, the selected promoter may drive expression of the gene under a light-induced or other temporally regulated promoter.

A variety of transcriptional terminators are available for use in expression cassettes. These are responsible for the termination of transcription beyond the transgene and its correct polyadenylation. Appropriate transcriptional terminators and those which are known to function in plants and include the CaMV 35S terminator, the tml terminator, the nopaline synthase (nos) terminator, the pea rbcS E9 terminator. These can be used in both monocotyledonous and dicotyledonous plants.

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene significantly enhance the expression of the wild-type gene under its cognate promoter when introduced into maize cells. Intron 1 enhances expression in fusion constructs with the chloramphenicol acetyltransferase gene (Callis et al. 1987. Genes Develop. 1: 1183-1200). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses also enhance expression, especially in dicotyledonous cells. Leader sequences from Tobacco Mosaic Virus (TMV, the "W-sequence"), Maize Chlorotic Mottle Virus (MCMV), and Alfalfa Mosaic Virus (AMV) have been shown to enhance expression (e.g. Gallie et al. 1987. Nucl. Acids Res. 15: 8693-8711; Skuzeski et al. 1990. Plant Molec. Biol. 15:65-79).

While the herbicide resistant PPO of the present invention contains targeting sequences for chloroplast and mitochondria, various mechanisms for targeting gene products are known in plants; the sequences controlling the functioning of these mechanisms have been studied. Targeting of gene products to the chloroplast is controlled by a signal sequence at the N-terminus a protein; it is cleaved during chloroplast import to yield the mature protein (e.g. Comai et al. 1988. J. Biol. Chem. 263: 15104-15109). These signal sequences can be fused to heterologous gene products (lacking such sequences) to effect the import of heterologous products into the chloroplast (van den Broeck et al. 1985. Nature 313: 358-363). DNA encoding for appropriate signal sequences can be isolated from the 5' end of the cDNAs encoding the RUBISCO protein, the CAB protein, the EPSP synthase enzyme, the GS2 protein and many other chloroplast-localized proteins.

Other gene products are localized to other organelles such as the mitochondrion and the peroxisome (e.g. Unger et al. 1989. Plant Molec. Biol. 13: 411-418). Sequences encoding these products can also be manipulated to effect the targeting of heterologous gene products to these organelles. Examples of such sequences are the nuclear-encoded ATPases and specific aspartate amino transferase isoforms for mitochondria. Targeting to cellular protein bodies has been described by Rogers et al. 1985. Proc. Natl. Acad. Sci. USA 82: 6512-6516).

In addition, sequences are known which target gene products to other cell compartments. N-terminal sequences are responsible for targeting to the ER, the apoplast, and extracellular secretion from aleurone cells (Koehler and Ho. 1990. Plant Cell 2: 769-783). Additionally, N-terminal sequences, in conjunction with C-terminal sequences, are responsible for vacuolar targeting (Shinshi et al. 1990. Plant Molec. Biol. 14: 357-368).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site and the fusion constructed should take into account any amino acids after the cleavage site which are required for cleavage. In some cases this requirement may be fulfilled by the addition of a small number of amino acids between the cleavage site and the transgene ATG or alternatively replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by (Bartlett et al. In: Edelmann et al. (Eds.) Methods in Chloroplast Molecular Biology, Elsevier, pp 1081-1091, 1982; Wasmann et al. 1986. Mol. Gen. Genet. 205: 446-453). These construction techniques are well known in the art and are equally applicable to mitochondria and peroxisomes. The choice of targeting which may be required for expression of the transgenes will depend on the cellular localization of the precursor required as the starting point for a given pathway. This will usually be cytosolic or chloroplastic, although it may is some cases be mitochondrial or peroxisomal. The products of transgene expression will not normally require targeting to the ER, the apoplast or the vacuole.

The above described mechanisms for cellular targeting can be utilized not only in conjunction with their cognate promoters, but also in conjunction with heterologous promoters so as to effect a specific targeting goal (where the heterologous promoter has an expression pattern different to that of the promoter from which the targeting signal is derived).

*Agrobacterium*-mediated transformation is a preferred technique for transformation of dicots because of the high efficiency of transformation and success with many different species. The many crop species which are routinely transformable by *Agrobacterium* include tobacco, tomato, sunflower, cotton, oilseed rape, potato, soybean, alfalfa and poplar (EP 317 511, cotton; EP 0 249 432, tomato, to Calgene; WO 87/07299, *Brassica*, to Calgene; U.S. Pat. No. 4,795,855, poplar). *Agrobacterium* transformation typically involves the transfer of the binary vector carrying the foreign DNA of interest to an appropriate *Agrobacterium* strain which may depend of the complement of vir genes carried by the host *Agrobacterium* strain either on a co-resident Ti plasmid or chromosomally (e.g. strain CIB542 for pCIB200 and pCIB2001 (Uknes et al. 1993. Plant Cell 5: 159-169). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Hofgen and Willmitzer. 1988. Nucl. Acids Res. 16: 9877).

Once an expression construct or expression vector of the invention has been established, it can be transformed into a plant cell. A variety of methods for introducing nucleic acid sequences (e.g., vectors) into the genome of plants and for the regeneration of plants from plant tissues or plant cells are known (Plant Molecular Biology and Biotechnology (CRC Press, Boca Raton, Fla., pp. 71-119 (1993); White F F. 1993. Vectors for Gene Transfer in Higher Plants; in: Transgenic Plants, vol. 1, Engineering and Utilization, Ed.: Kung and Wu R, Academic Press, 15-38; Jenes et al. 1993. Techniques for Gene Transfer, in: Transgenic Plants, vol. 1, Engineering and Utilization, Ed.: Kung and R. Wu, Academic Press, pp. 128-143; Potrykus et al. 1991. Annu. Rev. Plant Physiol. Plant Molec. Biol. 42:205-225; Halford and Shewry. 2000. Br. Med. Bull. 56:62-73).

Transformation methods may include direct and indirect methods of transformation. Suitable direct methods include polyethylene glycol induced DNA uptake, liposome-mediated transformation (U.S. Pat. No. 4,536,475), biolistic methods using the gene gun (particle bombardment; Fromm et al. 1990. Bio/Technology. 8:833-9; Gordon-Kamm et al. 1990. Plant Cell 2:603), electroporation, incubation of dry embryos in DNA-comprising solution, and microinjection. In the case of these direct transformation methods, the plasmid used need not meet any particular requirements. Simple plasmids, such as those of the pUC series, pBR322, M13 mp series, pACYC184 and the like can be used. If intact plants are to be regenerated from the transformed cells, an additional selectable marker gene is preferably located on the plasmid. The direct transformation techniques are equally suitable for dicotyledonous and monocotyledonous plants.

Transformation can also be carried out by bacterial infection by means of *Agrobacterium* (for example EP 116,718), viral infection by means of viral vectors (EP 067,553; U.S. Pat. No. 4,407,956; WO 95/34668; WO 93/03161) or by means of pollen (EP 270,356; WO 85/01856; U.S. Pat. No. 4,684,611). *Agrobacterium* based transformation techniques (especially for dicotyledonous plants) are well known in the art. The *Agrobacterium* strain (e.g., *Agrobacterium tumefaciens* or *Agrobacterium rhizogenes*) comprises a plasmid (Ti or Ri plasmid) and a T-DNA element which is transferred to the plant following infection with *Agrobacterium*. The T-DNA (transferred DNA) is integrated into the genome of the plant cell. The T-DNA may be localized on the Ri- or Ti-plasmid or is separately comprised in a so-called binary vector. Methods for the *Agrobacterium*-mediated transformation are described, for example, in Horsch R B et al. 1985. Science 225:1229f. The *Agrobacterium*-mediated transformation is best suited to dicotyledonous plants but has also been adapted to monocotyledonous plants. The transformation of plants by *Agrobacteria* is described, for example, in White F F, Vectors for Gene Transfer in Higher Plants; in Transgenic Plants, Vol. 1, Engineering and Utilization, edited by S. D. Kung and R. Wu, Academic Press, 1993, pp. 15-38; Jenes B et al. 1993. Techniques for Gene Transfer, in: Transgenic Plants, Vol. 1, Engineering and Utilization, edited by S. D. Kung and R. Wu, Academic Press, pp. 128-143; Potrykus 1991. Annu Rev Plant Physiol Plant Molec Biol 42:205-225).

Transformation may result in transient or stable transformation and expression; stable transformation is preferred in the practice of the present invention. Although a nucleotide sequence of the present invention can be inserted into any plant and plant cell, it is particularly useful in crop plant cells. Alternatively, the herbicide resistance deletion mutation can be introduced into plant cells and the mutation paced in the genome via homologous recombination of a recombinagenic oligonucleotide carrying the deletion of appropriate codon, with about 10 to about 70 flanking nucleotides on either side of the deletion, with the flanking nucleotides matched to the genomic sequence on either side of the codon to be deleted.

Various tissues are suitable as starting material (explant) for the *Agrobacterium*-mediated transformation process including but not limited to callus (U.S. Pat. No. 5,591,616; EP 604 662), immature embryos (EP 672 752), pollen (U.S. Pat. No. 5,929,300), shoot apex (U.S. Pat. No. 5,164,310), or in planta transformation (U.S. Pat. No. 5,994,624). The method and material described herein can be combined with virtually all *Agrobacterium* mediated transformation methods known in the art. Preferred combinations include, but are not limited, to the following starting materials and methods:

| Variety | Material/Citation |
| --- | --- |
| Monocotyledonous plants: | Immature embryos (EP-A1 672 752)<br>Callus (EP-A1 604 662)<br>Embryogenic callus (U.S. Pat. No. 6,074,877)<br>Inflorescence (U.S. Pat. No. 6,037,522)<br>Flower (in planta) (WO 01/12828) |

-continued

| Variety | Material/Citation |
| --- | --- |
| Banana | U.S. Pat. No. 5,792,935; EP 731 632;<br>U.S. Pat. No. 6,133,035 |
| Barley | WO 99/04618 |
| Maize | U.S. Pat. No. 5,177,010; U.S. Pat. No. 5,987,840 |
| Pineapple | U.S. Pat. No. 5,952,543; WO 01/33943 |
| Rice | EP 897 013; U.S. Pat. No. 6,215,051; WO 01/12828 |
| Wheat | AU 738 153; EP 856 060 |
| Beans | U.S. Pat. No. 5,169,770; EP 397 687 |
| *Brassica* | U.S. Pat. No. 5,188,958; EP 270 615;<br>EP-A1 1,009,845 |
| Cacao | U.S. Pat. No. 6,150,587 |
| Citrus | U.S. Pat. No. 6,103,955 |
| Coffee | AU 729 635 |
| Cotton | U.S. Pat. No. 5,004,863; EP-A1 270<br>355; U.S. Pat. No. 5,846,797; EP-A1<br>1,183,377; EP-A1 1,050,334; EP-A1 1,197,579;<br>EP-A1 1,159,436<br>Pollen transformation (U.S. Pat. No. 5,929,300)<br>In planta transformation (U.S. Pat. No. 5,994,624) |
| Pea | U.S. Pat. No. 5,286,635 |
| Pepper | U.S. Pat. No. 5,262,316 |
| Poplar | U.S. Pat. No. 4,795,855 |
| Soybean | cotyledonary node of germinated soybean seedlings<br>shoot apex (U.S. Pat. No. 5,164,310)<br>axillary meristematic tissue of primary, or higher<br>leaf node of about 7 days germinated soybean<br>seedlings organogenic callus cultures<br>dehydrated embryo axes<br>U.S. Pat. No. 5,376,543; EP 397 687;<br>U.S. Pat. No. 5,416,011;<br>U.S. Pat. No. 5,968,830; U.S. Pat. No.<br>5,563,055; U.S. Pat. No. 5,959,179; EP 652 965;<br>EP 1,141,346 |
| Sugarbeet | EP 517 833; WO 01/42480 |
| Tomato | U.S. Pat. No. 5,565,347 |

In another embodiment, a nucleotide sequence of the present invention is directly transformed into the plastid genome. Plastid expression, in which genes are inserted by homologous recombination into the several thousand copies of the circular plastid genome present in each plant cell, takes advantage of the enormous copy number advantage over nuclear-expressed genes to permit high expression levels. In a preferred embodiment, the nucleotide sequence is inserted into a plastid targeting vector and transformed into the plastid genome of a desired plant host. Plants homoplasmic for plastid genomes containing the nucleotide sequence are obtained, and are preferentially capable of high expression of the nucleotide sequence.

Plastid transformation technology is, for example, extensively described in U.S. Pat. Nos. 5,451,513; 5,545,817; 5,545,818; and 5,877,462; in WO 95/16783 and WO 97/32977; and in McBride et al. 1994. Proc. Natl. Acad. Sci. USA 91: 7301-7305, all incorporated herein by reference in their entireties. The basic technique for plastid transformation involves introducing regions of cloned plastid DNA flanking a selectable marker together with the nucleotide sequence into a suitable target tissue, e.g., using biolistic or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al. 1990 Proc. Natl. Acad. Sci. USA 87: 8526-8530; Staub et al. (1992) Plant Cell 4, 39-45). The presence of cloning sites between these markers allowed creation of a plastid targeting vector for introduction of foreign genes (Staub et al. 1993. EMBO J. 12: 601-606). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyl-transferase (Svab et al. 1993. Proc. Natl. Acad. Sc. USA 90: 913-917). Other selectable markers useful for plastid transformation are known in the art and encompassed within the scope of the invention. However, in the context of the present invention, the use of nuclear herbicide resistance gene is preferred, especially when expression is achieved in plastids as well as cytoplasm, and if a marker is used which confers herbicide resistance, there should be no cross resistance between that marker and the herbicide resistant PPO of the present invention.

For using the methods according to the invention, the skilled worker has available well-known tools, such as expression vectors with promoters which are suitable for plants, and methods for the transformation and regeneration of plants.

To select cells which have successfully undergone transformation, it is preferred to introduce a selectable marker which confers, to the cells which have successfully undergone transformation, a resistance to a biocide (for example a herbicide), a metabolism inhibitor such as 2-deoxyglucose-6-phosphate (WO 98/45456) or an antibiotic. The selection marker permits the transformed cells to be selected from untransformed cells (McCormick et al. 1986. Plant Cell Reports 5:81-84). Suitable selection markers are described above and includes antibiotic resistance markers, among others.

Transgenic plants can be regenerated in the known manner from the transformed cells. The resulting plantlets can be planted and grown in the customary manner. Preferably, two or more generations should be cultured to ensure that the genomic integration is stable and hereditary. Suitable methods are described (Fennell et al. 1992. Plant Cell Rep. 11: 567-570; Stoeger et al. 1995. Plant Cell Rep. 14:273-278; Jahne et al. 1994. Theor Appl Genet 89:525-533).

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e., co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. 1986. Biotechnology 4: 1093-1096). EP 0 292 435, EP 0 392 225 and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. 1990. Plant Cell 2: 603-618 and Fromm et al. 1990. Biotechnology 8: 833-839 have published techniques for transformation of A188-derived maize line using particle bombardment. Furthermore, WO 93/07278 and Koziel et al. 1993. Biotechnology 11: 194-200 describe techniques for the transformation of elite inbred lines of maize by particle bombardment. This technique utilizes immature maize embryos of 1.5-2.5 mm length excised from a maize ear 14-15 days after pollination and a biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. 1988. Plant Cell Rep 7: 379-384; Shimamoto et al. 1989. Nature 338: 274-277; Datta et al. 1990. Biotechnology 8: 736-740). Both types are also routinely transformable using particle bombardment (Christou et al. 1991. Biotechnology 9: 957-962).

EP 332 581 describes techniques for the generation, transformation and regeneration of Pooideae protoplasts. These techniques allow the transformation of *Dactylis* and wheat. Furthermore, wheat transformation was been described by Vasil et al. 1992. Biotechnology 10: 667-674) using particle bombardment into cells of type C long-term regenerable callus, and also by Vasil et al. 1993. Biotechnology 11: 1553-1558 and Weeks et al. 1993. Plant Physiol. 102: 1077-1084 using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashige and Skoog. 1962. Physiologia Plantarum 15: 473-497) and 3 mg/l 2,4-D for induction of somatic embryos which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2-3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics, helium device using a burst pressure of .about.1000 psi using a standard 80 mesh screen. After bombardment, the embryos are placed back into the dark to recover for about 24 h (still on osmoticum). After 24 hrs, the embryos are removed from the osmoticum and placed back onto induction. medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contained half-strength MS, 2% sucrose, and the same concentration of selection agent. U.S. patent application Ser. No. 08/147,161 describes methods for wheat transformation.

Resistant mutant plasmids, selected for resistance against a single herbicide, are tested against a spectrum of other protox-inhibiting compounds. A strain containing the wild-type plasmid is plated on a range of concentrations of each compound to determine the lethal concentration for each one. Resistant mutant plasmids in the same genetic background are plated and scored for the ability to survive on a concentration of each compound which is at least 10 fold higher than the concentration that is lethal to the strain containing the wild-type plasmid.

The herbicide resistant PPO isolated from waterhemp confers the resistant phenotype to transformed *E. coli*, and it likewise confers the resistant phenotype to transgenic plants into which it has been introduced. Table 4 gives the consensus amino acid sequence derived from at least three specific examples of a PPX2L sequence. Unlike various herbicide resistant mutants previously described (see, e.g., U.S. Pat. Nos. 6,282,837; 5,939,602; and 6,808,904), the present resistant mutants have undergone a spontaneous deletion mutation such that where there was Gly-Gly, there is now only one Gly residue (wild type Gly-Gly at amino acids 210-211 of SEQ ID NO:16). The PPO mutant coding sequence in Table 4 only varies from the wild type in the deletion of a Gly codon; the PPO amino acid sequence depicted in Table 4 et seq. further contain an amino acid substitution at residue Gln for Arg at position 182 and Cys for Ser at position 448. See also FIGS. 10A-10B for additional polymorphisms. Without wishing to be bound by any particular theory, the present inventors believe that the Gly deletion alone is sufficient to confer the herbicide resistant phenotype. Thus the wild type sequence can be modified only to effect the Gly-Gly to Gly mutation, or it can include one or the other of the substitutions in addition to the Gly deletion, with the result of conferring resistant to herbicides, as described herein. Expression of any of these Gly-deleted enzymes in a transgenic plant results in a plant with robust resistance to herbicides.

As an alternative to genetic modification of a crop of interest, the herbicide resistant PPO gene of the present invention can be introduced into cultivated amaranth species by conventional plant breeding (crossing the resistant weed with the crop, selecting for herbicide resistant progeny with the desired crop characteristics, and then backcrossing for three to ten cycles progeny plants to the crop species, selecting for herbicide resistance and crop characteristics) to produce the resistant crop. *Amaranthus* species which are cultivated as crops include, but are not limited to, *A. hypochondriacus, A. cruentus, A. caudatus, A. dubius*, and *A. tricolor*.

The amino acids which occur in the various amino acid sequences referred to in the specification have their usual three- and one-letter abbreviations routinely used in the art: A, Ala, Alanine; C, Cys, Cysteine; D, Asp, Aspartic Acid; E, Glu, Glutamic Acid; F, Phe, Phenylalanine; G, Gly, Glycine; H, His, Histidine; I, Ile, Isoleucine; K, Lys, Lysine; L, Leu, Leucine; M, Met, Methionine; N, Asn, Asparagine; P, Pro, Proline; Q, Gln, Glutamine; R, Arg, Arginine; S, Ser, Serine; T, Thr, Threonine; V, Val, Valine; W, Try, Tryptophan; Y, Tyr, Tyrosine.

A protein is considered an isolated protein if it is a protein isolated from or produced in a host cell in which it is recombinantly produced. It can be purified or it can simply be free of other proteins and biological materials with which it is associated in nature.

A transgenic plant is one which contains and expresses a gene (or transgene) which it does not contain and express in nature. The transgene can be a gene found in the particular plant but altered in the laboratory to be covalently attached to sequences which it does not occur in nature, the gene can have been altered in the laboratory to have a particular sequence of interest or to have a particular function that it did not previously, or the gene can have been isolated from a mutant plant of the same species and introduced into the genome of a plant of that species, which plant had not had that particular gene or sequence. Progeny transgenic plants are offspring (and succeeding generations of offspring which contain and express a copy of the transgene of interest. Transgenic seed are those produced by a transgenic plant or progeny transgenic plant which contain the transgene of interest.

Expression directed by a particular sequence means there is transcription and translation of an associated downstream sequence. With reference to tissue-specific regulation of expression of a PPO sequence of interest operably linked to the plant-expressible transcription regulatory sequence, expression may be advantageously determined by a strong constitutive promoter such as the Cauliflower Mosaic Virus 19S or 35 S promoter, a tandem repeat 35S promoter, the actin 2 promoter from *Arabidopsis thaliana*, among others.

A transcription regulatory sequence includes a promoter sequence and the cis-active sequences necessary for regulated expression of the operably linked sequence in the desired plant tissues. A promoter includes sequences sufficient to cause transcription of an associated (downstream, operably linked) sequence. The promoter is desirably constitutive, or it may be regulated, e.g., inducible, the transcription regulatory sequences cause expression of the operably linked coding sequence in response to an environmental signal (light, chemical, cold, heat, etc).

One DNA portion or sequence is downstream of second DNA portion or sequence when it is located 3' of the second sequence. One DNA portion or sequence is upstream of a second DNA portion or sequence when it is located 5' of that sequence.

One DNA molecule or sequence and another are heterologous to another if the two are not derived from the same ultimate natural source. The sequences may be natural sequences, or at least one sequence can be designed by man, as in the case of a multiple cloning site region. The two sequences can be derived from two different species or one sequence can be produced by chemical synthesis provided that the nucleotide sequence of the synthesized portion was not derived from the same organism as the other sequence.

An isolated or substantially pure nucleic acid molecule or polynucleotide is a polynucleotide which is substantially separated from other polynucleotide sequences which naturally accompany a native herbicide resistant PPO coding sequence. This coding sequence may be operably linked to its native transcription regulatory sequences or another native transcription regulatory sequence functional in a plant cell. The term embraces a polynucleotide sequence which has been removed from its naturally occurring environment, and includes recombinant or cloned DNA isolates, chemically synthesized analogues and analogues biologically synthesized by heterologous systems.

A polynucleotide is said to encode a polypeptide if, in its native state or when manipulated by methods known to those skilled in the art, it can be transcribed and/or translated to produce the polypeptide or a fragment thereof. The anti-sense strand of such a polynucleotide is also said to encode the sequence.

A nucleotide sequence is operably linked when it is placed into a functional relationship with another nucleotide sequence. For instance, a promoter is operably linked to a coding sequence if the promoter effects its transcription or expression. Generally, operably linked means that the sequences being linked are contiguous and, where necessary to join two protein coding regions, contiguous and in the same reading frame. However, it is well known that certain genetic elements, such as enhancers, may be operably linked even at a distance, i.e., even if not contiguous.

The term recombinant polynucleotide refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Polynucleotide probes include an isolated polynucleotide attached to a label or reporter molecule and may be used to identify and isolate other PPO coding sequences or other transcriptional regulatory sequences. Probes comprising synthetic oligonucleotides or other polynucleotides may be derived from naturally occurring or recombinant single or double stranded nucleic acids or be chemically synthesized. Polynucleotide probes may be labeled by any of the methods known in the art, e.g., random hexamer labeling, nick translation, or the Klenow fill-in reaction.

Large amounts of the polynucleotides may be produced by replication in a suitable host cell. Natural or synthetic DNA fragments coding for a protein of interest are incorporated into recombinant polynucleotide constructs, typically DNA constructs, capable of introduction into and replication in a prokaryotic or eukaryotic cell, especially *Escherichia coli*, wherein protein expression is desired or in a PPO-deficient strain of *Escherichia coli* when testing of PPO activity and/or herbicide resistance is desired. Commonly used prokaryotic hosts include strains of *Escherichia coli*, although other prokaryotes, such as *Bacillus subtilis* or a pseudomonad, may also be used. Eukaryotic host cells can include various plant species such as *Arabidopsis thaliana, Nicotiana tabacum, Glycine max, Zea mays, Medicago*, yeast, filamentous fungi, plant, insect, amphibian and avian species.

The polynucleotides of interest may also be produced by chemical synthesis, e.g., by the phosphoramidite method described by Beaucage and Caruthers (1981) Tetra. Letts. 22: 1859-1862 or the triester method according to Matteuci et al. (1981) J. Am. Chem. Soc. 103: 3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

DNA constructs prepared for introduction into a prokaryotic or eukaryotic host will typically comprise a replication system (i.e. vector) recognized by the host, including the intended DNA fragment encoding the desired polypeptide, and will preferably also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

An appropriate promoter and other necessary vector sequences will be selected so as to be functional in the host. Examples of workable combinations of cell lines and expression vectors are described in Sambrook et al. (1989) vide infra; Ausubel et al. (Eds.) (1999) Short Protocols in Molecular Biology, fourth edition, Wiley and Sons, New York; and Metzger et al. (1988) Nature, 334: 31-36. Many useful vectors for expression in bacteria, yeast, fungal, mammalian, insect, plant or other cells are well known in the art and may be obtained such vendors as Clontech, Invitrogen, Stratagene, New England Biolabs, Promega and others. In addition, the construct may be joined to an amplifiable gene (e.g., DHFR) so that multiple copies of the gene may be made. For appropriate enhancer and other expression control sequences, see also Enhancers and Eukaryotic Gene Expression, Cold Spring Harbor Press, N.Y. (1983). While such expression vectors may replicate autonomously, they may less preferably replicate by being inserted into the genome of the host cell.

Expression and cloning vectors likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning or expression vector. Only those host cells into which the marker gene has been introduced will survive and/or grow under selective conditions. Typical selection genes encode proteins that confer resistance to antibiotics or other toxic substances, e.g., ampicillin, neomycin, methotrexate, etc.; complement auxotrophic deficiencies; or supply critical nutrients not available from complex media. The choice of the proper selectable marker depends on the host cell; appropriate markers for different hosts are known in the art.

Recombinant host cells, in the present context, are those which have been genetically modified to contain and express an isolated DNA molecule of the instant invention. The DNA can be introduced by any means known to the art which is appropriate for the particular type of cell, including without limitation, transformation, lipofection, microinjection, Agro-infection, electroporation or particle bombardment.

It is recognized by those skilled in the art that the DNA sequences may vary due to the degeneracy of the genetic code and codon usage. All DNA sequences which code for the specifically exemplified herbicide resistant PPO having the particular glycine deletion taught herein are included in this invention, including the DNA sequence as given in Table 3, as well as functional equivalents thereto including or lacking substitution mutations as further taught herein.

Additionally, it is recognized by those skilled in the art that allelic variations occur in the DNA sequences which do not significantly change activities of the proteins they encode. All synonymous and functionally equivalent DNA sequences are included within the scope of this invention. The skilled artisan understands that the sequence of the exemplified herbicide resistant PPO sequences can be used to identify and isolate additional, nonexemplified nucleotide sequences which are functionally equivalent to the sequences given in SEQ ID NO:13, 25, 29 and 45, including naturally occurring variations in PPX2L sequences.

Hybridization and/or polymerase chain reaction procedures are useful for identifying polynucleotides with sufficient homology to the subject regulatory sequences to be useful as taught herein. The particular hybridization technique is not essential to the subject invention. As improvements are made in hybridization techniques, they can be readily applied by one of ordinary skill in the art.

A probe and sample are combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. As is well known in the art, if the probe molecule and nucleic acid sample hybridize by forming a strong non-covalent bond between the two molecules, it can be reasonably assumed that the probe and sample are essentially identical, or completely complementary, if the annealing and washing steps are carried out under conditions of high stringency. The probe's detectable label provides a means for determining whether hybridization has occurred.

In the use of the oligonucleotides or polynucleotides as probes, the particular probe is labeled with any suitable label known to those skilled in the art, including radioactive and non-radioactive labels. Typical radioactive labels include $^{32}P$, $^{35}S$, or the like. Non-radioactive labels include, for example, ligands such as biotin or thyroxine, as well as enzymes such as hydrolases or peroxidases, or a chemiluminescer such as luciferin, or fluorescent compounds like fluorescein and its derivatives. Alternatively, the probes can be made inherently fluorescent as described in WO 93/16094.

Various degrees of stringency of hybridization can be employed. The more stringent the conditions, the greater the complementarity required for duplex formation. Stringency can be controlled by temperature, probe concentration, probe length, ionic strength, time, and the like. Preferably, hybridization is conducted under moderate to high stringency conditions by techniques well know in the art, as described, for example in Keller, G. H., M. M. Manak (1987) DNA Probes, Stockton Press, New York, N.Y., pp. 169-170.

As used herein, moderate to high stringency conditions for hybridization are conditions which achieve the same, or about the same, degree of specificity of hybridization as the conditions employed by the current inventors. An example of high stringency conditions are hybridizing at 68° C. in 5×SSC/5× Denhardt's solution/0.1% SDS, and washing in 0.2×SSC/0.1% SDS at room temperature. An example of conditions of moderate stringency are hybridizing at 68° C. in 5×SSC/5× Denhardt's solution/0.1% SDS and washing at 42° C. in 3×SSC. The parameters of temperature and salt concentration can be varied to achieve the desired level of sequence identity between probe and target nucleic acid. See, e.g., Sambrook et al. (1989) vide infra or Ausubel et al. (1995) Current Protocols in Molecular Biology, John Wiley & Sons, NY, N.Y., for further guidance on hybridization conditions.

Specifically, hybridization of immobilized DNA in Southern blots with $^{32}P$-labeled gene specific probes was performed by standard methods (Maniatis et al.) In general, hybridization and subsequent washes were carried out under moderate to high stringency conditions that allowed for detection of target sequences with homology to the exemplified PPO sequences. For double-stranded DNA gene probes, hybridization can be carried out overnight at 20-25° C. below the melting temperature (Tm) of the DNA hybrid in 6×SSPE 5×Denhardt's solution, 0.1% SDS, 0.1 mg/ml denatured DNA. The melting temperature is described by the following formula (Beltz, G. A et al. (1983) Meth. Enzymol. R. Wu, et al. (eds.) Academic Press, New York 100:266-285).

Tm=81.5° C.+16.6 Log(Na+)+0.41(+G+C)−0.61(% formamide)-600/length of duplex in base pairs.

Washes are typically carried out as follows: twice at room temperature for 15 minutes in 1×SSPE, 0.1% SDS (low stringency wash), and once at TM-20° C. for 15 minutes in 0.2× SSPE, 0.1% SDS (moderate stringency wash).

For oligonucleotide probes, hybridization was carried out overnight at 10-20° C. below the melting temperature (Tm) of the hybrid 6×SSPE, 5×Denhardt's solution, 0.1% SDS, 0.1 mg/ml denatured DNA. Tm for oligonucleotide probes was determined by the following formula: TM(° C.)=2(number T/A base pairs+4(number G/C base pairs) (Suggs, S. V. et al. (1981) ICB-UCLA Symp. Dev. Biol. Using Purified Genes, D. D. Brown (ed.), Academic Press, New York, 23:683-693).

Washes were typically carried out as follows: twice at room temperature for 15 minutes 1×SSPE, 0.1% SDS (low stringency wash), and once at the hybridization temperature for 15 minutes in 1×SSPE, 0.1% SDS (moderate stringency wash).

In general, salt and/or temperature can be altered to change stringency. With a labeled DNA fragment>70 or so bases in length, the following conditions can be used: Low, 1 or 2×SSPE, room temperature; Low, 1 or 2×SSPE, 42° C.; Moderate, 0.2× or 1×SSPE, 65° C.; and High, 0.1×SSPE, 65° C.

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and those methods are known to an ordinarily skilled artisan.

Polymerase Chain Reaction (PCR) is a repetitive, enzymatic, primed synthesis and amplification of a nucleic acid sequence. This procedure is well known and commonly used by those skilled in this art (see, e.g., Mullis, U.S. Pat. Nos. 4,683,195, 4,683,202, and 4,800,159; Saiki et al. 1985. Science 230:1350-1354). Kits and reagents are readily available from commercial sources. The skilled artisan can routinely produce deletion-, insertion-, or substitution-type mutations and identify those resulting mutants which contain the desired characteristics of the specifically exemplified sequences, i.e., those which retain herbicide resistance and PPX2L activity, although other means for making mutations in a particular sequence are known to the art. Methods for confirming herbicide resistance and PPO activity are known in the art.

DNA sequences having at least 85, 90, 95%, and all integers from 85 to 99%, identity to the recited DNA sequences of Tables 3 and 5 and functioning to encode an herbicide resistant PPO are considered the most preferred equivalents to these sequences. Such functional equivalents are included in the definition of an herbicide resistant PPO coding sequence. Following the teachings herein and using knowledge and techniques well known in the art, the skilled worker will be able to make a large number of operative embodiments having equivalent DNA sequences to those listed herein without the expense of undue experimentation.

As used herein percent sequence identity of two nucleic acids is determined using the algorithm of Karlin and Altschul. 1990. Proc. Natl. Acad. Sci. USA 87:2264-2268, modified as in Karlin and Altschul. 1993. Proc. Natl. Acad. Sci. USA 90:5873-5877. Such an algorithm is incorporated into the NBLAST and XBLAST programs of Altschul et al. 1990. J. Mol. Biol. 215:402-410. BLAST nucleotide searches are performed with the NBLAST program, score=100, wordlength=12, to obtain nucleotide sequences with the desired percent sequence identity. To obtain gapped alignments for comparison purposes, Gapped BLAST is used as described in Altschul et al. 1997. Nucl. Acids. Res. 25:3389-3402. When utilizing BLAST and Gapped BLAST programs, the default parameters of the respective programs (NBLAST and XBLAST) are used. See the National Center for Biotechnology Information website.

The choice of vector in which the DNA of interest is inserted depends, as is well known in the art, on the functional properties desired, e.g., replication, protein expression, and the host cell to be transformed. The vector desirably includes a prokaryotic replicon, i.e., a DNA sequence having the ability to direct autonomous replication and maintenance of the recombinant DNA molecule extra-chromosomally when introduced into a prokaryotic host cell, such as a bacterial host cell. Such replicons are well known in the art. In addition, preferred embodiments that include a prokaryotic replicon also include a gene whose expression confers a selective advantage, such as a drug resistance, to the bacterial host cell when introduced into those transformed cells. Typical bacterial drug resistance genes are those that confer resistance to ampicillin or tetracycline, among other selective agents. The neomycin phosphotransferase gene has the advantage that it is expressed in eukaryotic as well as prokaryotic cells; others are well known.

Those vectors that include a prokaryotic replicon also typically include convenient restriction sites for insertion of a recombinant DNA molecule of the present invention; such vectors include pUC8, pUC9, pBR322, and pBR329. Vectors are available from BioRad Laboratories (Richmond, Calif.), Pharmacia (Piscataway, N.J.), Stratagene (La Jolla, Calif.), Promega Corporation, Madison, Wis., and many other commercial sources. The vector may also be a Lambda phage vector; see. e.g. *Molecular Cloning: A Laboratory Manual, Second Edition*, Maniatis et al., eds., Cold Spring Harbor Press (1989) and commercial sources. Other exemplary vectors include pCMU (Nilsson et al. (1989) Cell 58:707) and derivatives.

Typical expression vectors capable of expressing a recombinant nucleic acid sequence in plant cells and capable of directing stable integration within the host plant cell include vectors derived from the tumor-inducing (Ti) plasmid of *A. tumefaciens* described by Rogers et al. 1987. Meth. Enzymol. 153:253-277, and several other expression vector systems known to function in plants. See for example, WO87/00551; Cocking and Davey. 1987. Science 236:1259-1262.

A transgenic plant can be produced by any means known to the art, including but not limited to *A. tumefaciens*-mediated DNA transfer, *Agrobacterium rhizogenes*-mediated DNA transfer, both preferably with a disarmed T-DNA vector, electroporation, direct DNA transfer, liposomes, diffusion, microinjection, virus vectors, calcium phosphate, and particle bombardment. Techniques are well-known to the art for the introduction of DNA into monocots as well as dicots, as are the techniques for culturing such plant tissues and regenerating those tissues.

Many of the procedures useful for practicing the present invention, whether or not described herein in detail, are well known to those skilled in the art of plant molecular biology. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) Molecular Cloning, Second Edition, Cold Spring Harbor Laboratory, Plainview, N.Y.; Maniatis et al. (1982) Molecular Cloning, Cold Spring Harbor Laboratory, Plainview, N.Y.; Wu (ed.) (1993) Meth. Enzymol. 218, Part I; Wu (ed.) (1979) Meth. Enzymol. 68; Wu et al. (eds.) (1983) Meth. Enzymol. 100 and 101; Grossman and Moldave (eds.) Meth. Enzymol. 65; Glover (ed.) (1985) DNA Cloning Vol. I and II, IRL Press, Oxford, UK; Hames and Higgins (eds.) (1985) Nucleic Acid Hybridization, IRL Press, Oxford, UK; Kaufman (1987) in Genetic Engineering Principles and Methods, J. K. Setlow, ed., Plenum Press, NY, pp. 155-198; Fitchen et al. 1993. Annu. Rev. Microbiol. 47:739-764; Tolstoshev et al. (1993) in Genomic Research in Molecular Medicine and Virology, Academic Press. Abbreviations and nomenclature are standard in the field and commonly used in professional journals as cited herein.

All references and patent documents cited herein reflect the level of skill in the relevant arts and are incorporated by reference in their entireties to the extent there is no inconsistency with the present disclosure.

Where features or aspects of the invention are described in terms of Markush groups or other groupings of alternatives, those skilled in the art recognize that the invention is intended to relate to any individual member or subgroup of members of the Markush group or other group.

TABLE 3

| DNA Sequence encoding Herbicide resistant Waterhemp PPX2L (SEQ ID NO: 13), derived from analysis of multiple cloning events |
|---|
| ATGGTAATTCAATCCATTACCCACCTTTCACCAAACCTTGCATTGCCATCGCCATTGTCAGTTTCAACCA |
| AGAACTACCCAGTAGCTGTAATGGGCAACATTTCTGAGCGGGAAGAACCCACTTCTGCTAAAAGGGTTGC |
| TGTTGTTGGTGCTGGAGTTAGTGGACTTGCTGCTGCATATAAGCTAAAATCCCATGGTTTGAGTGTGACA |
| TTGTTTGAAGCTGATTCTAGAGCTGGAGGCAAACTTAAAACTGTTAAAAAAGATGGTTTTATTTGGGATG |
| AGGGGGCAAATACTATGACAGAAAGTGAGGCAGAGGTCTCGAGTTTGATCGATGATCTTGGGCTTCGTGA |
| GAAGCAACAGTTGCCAATTTCACAAAATAAAAGATACATAGCTAGAGACGGTCTTCCTGTGCTACTACCT |
| TCAAATCCCGCTGCACTACTCACGAGCAATATCCTTTCAGCAAAATCAAAGCTGCAAATTATGTTGGAAC |
| CATTTCTCTGGAGAAAACACAATGCTACTGAACTTTCTGATGAGCATGTTCAGGAAAGCGTTGGTGAATT |
| TTTTGAGCGACATTTTGGGAAAGAGTTTGTTGATTATGTTATCGACCCTTTTGTTGCGGGTACATGTGGA |
| GATCCTCAATCGCTTTCCATGCACCATACATTTCCAGAAGTATGGAATATTGAAAAAAGGTTTGGCTCTG |
| TGTTTGCTGGACTAATTCAATCAACATTGTTATCTAAGAAGGAAAAGGGTGGAGAAAATGCTTCTATTAA |
| GAAGCCTCGTGTACGTGGTTCATTTTCATTTCAAGGTGGAATGCAGACACTTGTTGACACAATGTGCAAA |
| CAGCTTGGTGAAGATGAACTCAAACTCCAGTGTGAGGTGCTGTCCTTGTCATATAACCAGAAGGGGATCC |
| CCTCATTAGGGAATTGGTCAGTCTCTTCTATGTCAAATAATACCAGTGAAGATCAATCTTATGATGCTGT |

TABLE 3-continued

DNA Sequence encoding Herbicide resistant Waterhemp PPX2L (SEQ ID NO: 13), derived from analysis of multiple cloning events

GGTTGTCACTGCTCCAATTCGCAATGTCAAAGAAATGAAGATTATGAAATTTGGAAATCCATTTTCACTT

GACTTTATTCCAGAGGTGACGTACGTACCCCTTTCCGTTATGATTACTGCATTCAAAAAGGATAAAGTGA

AGAGACCTCTTGAGGGCTTCGGAGTTCTTATCCCCTCTAAAGAGCAACATAATGGACTGAAGACTCTTGG

TACTTTATTTTCCTCCATGATGTTTCCTGATCGTGCTCCATCTGACATGTGTCTCTTTACTACATTTGTC

GGAGGAAGCAGAAATAGAAAACTTGCAAACGCTTCAACGGATGAATTGAAGCAAATAGTTTCTTCTGACC

TTCAGCAGCTGTTGGGCACTGAGGACGAACCTTCATTTGTCAATCATCTCTTTTGGAGCAACGCATTCCC

ATTGTATGGACACAATTACGATTCTGTTTTGAGAGCCATAGACAAGATGGAAAAGGATCTTCCTGGATTT

TTTTATGCAGGTAACCATAAGGGTGGACTTTCAGTGGGAAAAGCGATGGCCTCCGGATGCAAGGCTGCGG

AACTTGTAATATCCTATCTGGACTCTCATATATATGTGAAGATGGATGAGAAGACCGCGTAA

TABLE 4

Herbicide-resistant PPO2 Protein Sequence (SEQ ID NO: 14), derived from analysis of multiple cloning events. Bolded G corresponds to single glycine residue where sensitive protein has double glycine residue.

MVIQSITHLSPNLALPSPLSVSTKNYPVAVMGNISEREEPTSAKRVAVVGAGVSGLAA

AYKLKSHGLSVTLFEADSRAGGKLKTVKKDGFIWDEGANTMTESEAEVSSLIDDLGLR

EKQQLPISQNKRYIARDGLPVLLPSNPAALLTSNILSAKSKLQIMLEPFLWRKHNATE

LSDEHVQESVGEFFERHFGKEFVDYVIDPFVAGTCGDPQSLSMHHTFPEVWNIEKRFG

SVFAGLIQSTLLSKKEKGGENASIKKPRVRGSFSFQGGMQTLVDTMCKQLGEDELKLQ

CEVLSLSYNQKGIPSLGNWSVSSMSNNTSEDQSYDAVVVTAPIRNVKEMKIMKFGNPF

SLDFIPEVTYVPLSVMITAFKKDKVKRPLEGFGVLIPSKEQHNGLKTLGTLFSSMMFP

DRAPSDMCLFTTFVGGSRNRKLANASTDELKQIVSSDLQQLLGTEDEPSFVNHLFWSN

AFPLYGHNYDSVLRAIDKMEKDLPGFFYAGNHKGGLSVGKAMASGCKAAELVISYLDS

HIYVKMDEKTA

TABLE 5

DNA Sequence Encoding Wild type (Herbicide-sensitive) Waterhemp PPO (SEQ ID NO: 15), derived from analysis of multiple cloning events

ATGGTAATTCAATCCATTACCCACCTTTCACCAAACCTTGCATTGCCATCGCCATTGTCAGTTTCAACCA

AGAACTACCCAGTAGCTGTAATGGGCAACATTTCTGAGCGGGAAGAACCCACTTCTGCTAAAAGGGTTGC

TGTTGTTGGTGCTGGAGTTAGTGGACTTGCTGCTGCATATAAGCTAAAATCCCATGGTTTGAGTGTGACA

TTGTTTGAAGCTGATTCTAGAGCTGGAGGCAAACTTAAAACTGTTAAAAAAGATGGTTTTATTTGGGATG

AGGGGGCAAATACTATGACAGAAAGTGAGGCAGAGGTCTCGAGTTTGATCGATGATCTTGGGCTTCGTGA

GAAGCAACAGTTGCCAATTTCACAAAATAAAAGATACATAGCTAGAGACGGTCTTCCTGTGCTACTACCT

TCAAATCCCGCTGCACTACTCACGAGCAATATCCTTTCAGCAAATCAAAGCTGCAAATTATGTTGGAAC

CATTTCTCTGGAGAAAACACAATGCTACTGAACTTTCTGATGAGCATGTTCAGGAAAGCGTTGGTGAATT

TTTTGAGCGACATTTTGGGAAAGAGTTTGTTGATTATGTTATCGACCCTTTTGTTGCGGGTACATGTGGT

TABLE 5-continued

DNA Sequence Encoding Wild type (Herbicide-sensitive) Waterhemp
PPO (SEQ ID NO: 15), derived from analysis of multiple
cloning events

GGAGATCCTCAATCGCTTTCCATGCACCATACATTTCCAGAAGTATGGAATATTGAAAAAAGGTTTGGCT

CTGTGTTTGCTGGACTAATTCAATCAACATTGTTATCTAAGAAGGAAAAGGGTGGAGAAAATGCTTCTAT

TAAGAAGCCTCGTGTACGTGGTTCATTTTCATTTCAAGGTGGAATGCAGACACTTGTTGACACAATGTGC

AAACAGCTTGGTGAAGATGAACTCAAACTCCAGTGTGAGGTGCTGTCCTTGTCATATAACCAGAAGGGGA

TCCCCTCATTAGGGAATTGGTCAGTCTCTTCTATGTCAAATAATACCAGTGAAGATCAATCTTATGATGC

TGTGGTTGTCACTGCTCCAATTCGCAATGTCAAAGAAATGAAGATTATGAAATTTGGAAATCCATTTTCA

CTTGACTTTATTCCAGAGGTGACGTACGTACCCCTTTCCGTTATGATTACTGCATTCAAAAAGGATAAAG

TGAAGAGACCTCTTGAGGGCTTCGGAGTTCTTATCCCCTCTAAAGAGCAACATAATGGACTGAAGACTCT

TGGTACTTTATTTTCCTCCATGATGTTTCCTGATCGTGCTCCATCTGACATGTGTCTCTTTACTACATTT

GTCGGAGGAAGCAGAAATAGAAAACTTGCAAACGCTTCAACGGATGAATTGAAGCAAATAGTTTCTTCTG

ACCTTCAGCAGCTGTTGGGCACTGAGGACGAACCTTCATTTGTCAATCATCTCTTTTGGAGCAACGCATT

CCCATTGTATGGACACAATTACGATTCTGTTTTGAGAGCCATAGACAAGATGGAAAAGGATCTTCCTGGA

TTTTTTTATGCAGGTAACCATAAGGGTGGACTTTCAGTGGGAAAAGCGATGGCCTCCGGATGCAAGGCTG

CGGAACTTGTAATATCCTATCTGGACTCTCATATATATGTGAAGATGGATGAGAAGACCGCGTAA

TABLE 6

Wild type Waterhemp PPO Amino Acid Sequence (SEQ ID NO: 16),
derived from analysis of multiple cloning events

MVIQSITHLSPNLALPSPLSVSTKNYPVAVMGNISEREEPTSAKRVAVVGAGVSGLAAAYKLKSHGLSVTLFEAD

SRAGGKLKTVKKDGFIWDEGANTMTESEAEVSSLIDDLGLREKQQLPISQNKRYIARDGLPVLLPSNPAALLTSN

ILSAKSKLQIMLEPFLWRKHNATELSDEHVQESVGEFFERHFGKEFVDYVIDPFVAGTCGGDPQSLSMHHTFPEV

WNIEKRFGSVFAGLIQSTLLSKKEKGGENASIKKPRVRGSFSFQGGMQTLVDTMCKQLGEDELKLQCEVLSLSYN

QKGIPSLGNWSVSSMSNNTSEDQSYDAVVVTAPIRNVKEMKIMKFGNPFSLDFIPEVTYVPLSVMITAFKKDKVK

RPLEGFGVLIPSKEQHNGLKTLGTLFSSMMFPDPAPSDMCLFTTFVGGSRNRKLANASTDELKQIVSSDLQQLLG

TEDEPSFVNHLFWSNAFPLYGHNYDSVLRAIDKMEKDLPGFFYAGNHKGGLSVGKAMASGCKAAELVISYLDSHI

YVKMDEKTA

TABLE 7

Amino acid and cDNA sequences of herbicide-susceptible
*Amaranthus tuberculatus* biotype WC plastid protoporphyrinogen oxidase
(PPX1) mRNA, complete cds; nuclear gene for plastid product,
corresponding to NCBI ACCESSION DQ386112; SEQ ID NO: 17
(cDNA) and NO: 18 (amino acid)

MSAMALSSSILQCPPHSDISFRFFAHTRTQPPIFFGRPRKLSYI

HCSTSSSSTANYQNTITSQGEGDKVLDCVIVGAGISGLCIAQALSTKHIQSNLNFIVT

EAKHRVGGNITTMESDGYIWEEGPNSFQPSDPVLTMAVDSGLKDDLVLGDPNAPRFVL

WNGKLRPVPSKPTDLPFFDLMSFPGKIRAGLGALGLRPPPPSYEESVEEFVRRNLGDE

VFERLIEPFCSGVYAGDPAKLSMKAAFGKVWTLEQKGGSIIAGTLKTIQERKNNPPPP

RDPRLPKPKGQTVGSFRKGLIMLPTAIAARLGSKVKLSWTLSNIDKSLNGEYNLTYQT

PDGPVSVRTKAVVMTVPSYIASSLLRPLSDVAADSLSKFYYPPVAAVSLSYPKEAIRP

TABLE 7-continued

Amino acid and cDNA sequences of herbicide-susceptible
*Amaranthus tuberculatus* biotype WC plastid protoporphyrinogen oxidase
(PPX1) mRNA, complete cds; nuclear gene for plastid product,
corresponding to NCBI ACCESSION DQ386112; SEQ ID NO: 17
(cDNA) and NO: 18 (amino acid)

ECLIDGELKGFGQLHPRSQGVETLGTIYSSSLFPGRAPPGRTLILSYIGGATNLGILQ

KSEDELAETVDKDLRKILINPNAKGSRVLGVRVWPKAIPQFLVGHFDVLDAAKAGLAN

AGQKGLFLGGNYVSGVALGRCIEGAYDSASEVVDFLSQYKDK

```
   1 atgagtgcga tggcgttatc gagcagcatt ctacaatgtc cgccgcactc cgacatctcg
  61 ttccgctttt ttgctcatac acgaacccaa cccccatct tcttcggaag accacgaaaa
 121 ttatcatata tccattgttc cacaagctca agctcaactg ccaattacca gaacaccatt
 181 acgagccaag gagaaggaga taaagtatta gattgtgtaa ttgttggagc tggtatcagt
 241 ggactttgca ttgctcaggc tctttctacc aaacacattc aatccaatct caatttcatt
 301 gtcactgaag ctaaacatcg tgttggaggt aatatcacta ccatggagtc cgatggctat
 361 atctgggaag agggtcctaa tagtttccaa ccctccgatc ctgtgcttac tatggcggtt
 421 gacagtggat tgaaagacga tttggtcttg ggagatccta atgccctcg tttcgtgctc
 481 tggaatggta aattaaggcc tgttccttcc aaacctacgg accttccctt ttttgatctc
 541 atgagctttc ctggtaagat tagggctggt cttggtgcac ttggtcttcg tcctcctcct
 601 ccttcttatg aggaatctgt tgaagaattt gtgcgccgta atctcggcga tgaggtcttc
 661 gaacgcttga tcgaaccctt tgttctggt gtctatgctg gtgatcctgc aaagttgagt
 721 atgaaagctg catttggaaa ggtctggacc ttagagcaaa agggtggtag tatcatagcc
 781 ggtacactca aaactattca ggaaaggaaa aataatcctc caccccctcg agaccccgc
 841 cttcctaaac ctaagggcca gactgttgga tcctttagga aagggctcat tatgttacct
 901 accgccattg ctgctaggct tggcagtaaa gtcaaactat cgtggacact ttctaatatt
 961 gataagtcgc tcaatggaga atacaatctc acttatcaaa cacccgatgg accggtttct
1021 gttaggacca agcggttgt catgaccgtc ccttcgtaca ttgcaagtag cttgcttcgt
1081 ccgctctcag atgttgctgc agattctctt tctaaatttt actatccacc agtcgcagca
1141 gtgtcccttt cttatcccaa gaagcaatt agaccagaat gcttgatcga tggtgaacta
1201 aaaggattcg ggcaattgca tccccgcagc cagggtgtgg aaaccttggg aacaatttat
1261 agttcatctc ttttccctgg tcgagcaccc cccggtagga ccttgatctt gagctacatt
1321 ggaggtgcta caaatcttgg catattacaa aagagtgaag atgaacttgc ggagacagtt
1381 gataaggatc tcagaaaaat tctgataaat ccaaatgcga aaggcagccg tgttctggga
1441 gtgagagtat ggccaaaagc aatcccccaa tttttagttg gtcactttga tgtgctagat
1501 gctgcaaaag ctggtttggc aaatgctggg caaaagggt tgtttcttgg tggtaattat
1561 gtatcaggtg ttgccttggg gaggtgtata gagggtgcta tgactctgc ttctgaggta
1621 gtggatttcc tctcacagta caaagataag tag
```

TABLE 8

Coding and amino acid sequences of *Amaranthus tuberculatus* biotype herbicide-susceptible WC mitochondrial protoporphyrinogen oxidase (PPX2) mRNA, nuclear gene for mitochondrial product, corresponding to NCBI Accession DQ386113 and SEQ ID NO: 19 (cDNA) and NO: 20 (amino acid)

MGNISERDEPTSAKRVAVVGAGVSGLAAAYKLKSHGLNVTLFEA

DSRAGGKLKTVKKDGFIWDEGANTMTESEAEVSSLIDDLGLREK

QQLPISQNKRYIARDGLPVLLPSNPAALLTSNILSAKSKLQIMLEPF

FWRKHNATELSDEHVQESVGEFFERHFGKEFVDYVIDPFVAGTC

GGDPQSLSMHHTFPEVWNIEKRFGSVFAGLIQSTLLSKKEKGGGG

NASIKKPRVRGSFSFHGGMQTLVDTICKQLGEDELKLQCEVLSLS

YNQKGIPSLGNWSVSSMSNNTSEDQSYDAVVVTAPIRNVKEMKIM

KFGNPFSLDFIPEVSYVPLSVMITAFKKDKVKRPLEGFGVLIPSKEQ

HNGLKTLGTLFSSMMFPDRAPSDMCLFTTFVGGSRNRKLANASTD

ELKQIVSSDLQQLLGTEDEPSFVNHLFWSNAFPLYGHNYDSVLRAI

DKMEKDLPGFFYAGNHKGGLSVGKAMASGCKAAELVISYLDSHIY

VKMDEKTA

```
   1 atgggcaaca tttctgagcg ggatgaaccc acttctgcta aaagggttgc tgttgttggt
  61 gctggagtta gtggacttgc tgctgcatat aagctaaaat cccatggttt gaatgtgaca
 121 ttgtttgaag ctgattctag agctggaggc aaacttaaaa ctgttaaaaa agatggtttt
 181 atttgggatg aggggcaaa tactatgaca gaaagtgagg cagaagtctc gagtttgatc
 241 gatgatcttg gcttcgtga gaagcaacag ttgccaattt cacaaaataa agatacata
 301 gctagagatg gtcttcctgt gctactacct tcaaatcccg ctgcactgct cacgagcaat
 361 atcctttcag caaaatcaaa gctgcaaatt atgttggaac cattttttctg agaaaaacac
 421 aatgctactg agctttctga tgagcatgtt caggaaagcg ttggtgaatt ttttgagcga
 481 cattttggga aagagtttgt tgattatgtt attgaccctt tgttgcggg tacatgtggt
 541 ggagatcctc aatcgctttc tatgcaccat acatttccag aagtatggaa tattgaaaaa
 601 aggtttggct ctgtgtttgc tggactaatt caatcaacat tgttatctaa gaaggaaaag
 661 ggtggaggag gaaatgcttc tatcaagaag cctcgtgtac gtggttcatt ttcattccat
 721 ggtggaatgc agacacttgt tgacacaata tgcaaacagc ttggtgaaga tgaactcaaa
 781 ctccagtgtg aggtgctgtc cttgtcatac aaccagaagg ggatcccttc attagggaat
 841 tggtcagtct cttctatgtc aaataatacc agtgaagatc aatcttatga tgctgtggtt
 901 gtcactgctc caattcgcaa tgtcaaagaa atgaagatta tgaaattcgg aaatccattt
 961 tcacttgact ttattccaga ggtgagttac gtaccccctct ctgttatgat tactgcattc
1021 aagaaggata aagtgaagag accactcgag ggctttggag ttcttatccc ctctaaagag
1081 caacataatg gactgaagac tcttggtact ttattttcct ccatgatgtt tcccgatcgt
1141 gctccatctg acatgtgtct ctttactaca tttgtcggag gaagcagaaa tagaaaactt
1201 gcaaacgctt caacggatga attgaagcaa atagtttctt ctgaccttca gcagctgttg
1261 ggcactgagg acgaaccttc atttgtcaat catctcttt ggagcaacgc attccgttg
1321 tatggacaca attacgattc tgttttgaga gccatagaca gatggaaaa ggatcttcct
1381 ggatttttt atgcaggtaa ccataagggt ggactttcag tgggaaaagc gatggcctcc
```

TABLE 8-continued

Coding and amino acid sequences of *Amaranthus tuberculatus*
biotype herbicide-susceptible WC mitochondrial protoporphyrinogen
oxidase (PPX2) mRNA, nuclear gene for mitochondrial product,
corresponding to NCBI Accession DQ386113 and SEQ ID NO:
19 (cDNA) and NO: 20 (amino acid)

1441 ggatgcaagg ctgcggaact tgtaatatcc tatctggact ctcatatata tgtgaagatg 1501 gatgagaaga ccgcgtaa

TABLE 9

Coding and amino acid sequence of *Amaranthus tuberculatus* biotype
herbicide-susceptible WC mitochondrial protoporphyrinogen oxidase
(PPX2L) mRNA, nuclear gene for mitochondrial product,
corresponding to NCBI Accession DQ386114 and SEQ ID NO: 21
(cDNA) and NO: 22 (amino acid)

MVIQSITHLSPNLALPSPLSVSTKNYPVAVMGNISEREEPTSAK

RVAVVGAGVSGLAAAYKLKSHGLSVTLFEADSRAGGKLKTVKKD

GFIWDEGANTMTESEAEVSSLIDDLGLREKQQLPISQNKRYIARDG

LPVLLPSNPAALLTSNILSAKSKLQIMLEPFLWRKHNATELSDEHV

QESVGEFFERHFGKEFVDYVIDPFVAGTCGGDPQSLSMHHTFPEV

WNIEKRFGSVFAGLIQSTLLSKKEKGGENASIKKPRVRGSFSFQGG

MQTLVDTMCKQLGEDELKLQCEVLSLSYNQKGIPSLGNWSVSSM

SNNTSEDQSYDAVVVTAPIRNVKEMKIMKFGNPFSLDFIPEVTYVPL

SVMITAFKKDKVKRPLEGFGVLIPSKEQHNGLKTLGTLFSSMMFPD

RAPSDMCLFTTFVGGSRNRKLANASTDELKQIVSSDLQQLLGTEDE

PSFVNHLFWSNAFPLYGHNYDSVLRAIDKMEKDLPGFFYAGNHKG

GLSVGKAMASGCKAAELVISYLDSHIYVKMDEKTA 1 atggtaattc aatccattac ccacctttca ccaaaccttg cattgccatc gccattgtca 61 gtttcaacca agaactaccc agtagctgta atgggcaaca tttctgagcg ggaagaaccc 121 acttctgcta aaagggttgc tgttgttggt gctggagtta gtggacttgc tgctgcatat 181 aagctaaaat cccatggttt gagtgtgaca ttgtttgaag ctgattctag agctggaggc 241 aaacttaaaa ctgttaaaaa agatggtttt atttgggatg aggggcaaa tactatgaca 301 gaaagtgagg cagaggtctc gagtttgatc gatgatcttg gcttcgtga aagcaacag 361 ttgccaattt cacaaaataa aagatacata gctagagacg tcttcctgt gctactacct 421 tcaaatcccg ctgcactact cacgagcaat atcctttcag caaaatcaaa gctgcaaatt 481 atgttggaac catttctctg gagaaaacac aatgctactg aactttctga tgagcatgtt 541 caggaaagcg ttggtgaatt ttttgagcga cattttggga aagagtttgt tgattatgtt 601 atcgacccctt tgttgcggg tacatgtggt ggagatcctc aatcgctttc catgcaccat 661 acatttccag aagtatggaa tattgaaaaa aggtttggct ctgtgtttgc tggactaatt 721 caatcaacat tgttatctaa gaaggaaaag ggtggagaaa atgcttctat taagaagcct 781 cgtgtacgtg gttcattttc atttcaaggt ggaatgcaga cacttgttga cacaatgtgc 841 aaacagcttg gtgaagatga actcaaactc cagtgtgagg tgctgtcctt gtcatataac 901 cagaagggga tccctcatt agggaattgg tcagtctctt ctatgtcaaa taataccagt 961 gaagatcaat cttatgatgc tgtggttgtc actgctccaa ttcgcaatgt caagaaaatg

TABLE 9-continued

Coding and amino acid sequence of *Amaranthus tuberculatus* biotype herbicide-susceptible WC mitochondrial protoporphyrinogen oxidase (PPX2L) mRNA, nuclear gene for mitochondrial product, corresponding to NCBI Accession DQ386114 and SEQ ID NO: 21 (cDNA) and NO: 22 (amino acid)

```
1021 aagattatga aatttggaaa tccattttca cttgacttta ttccagaggt gacgtacgta
1081 cccctttccg ttatgattac tgcattcaaa aaggataaag tgaagagacc tcttgagggc
1141 ttcggagttc ttatcccctc taaagagcaa cataatggac tgaagactct tggtacttta
1201 ttttcctcca tgatgtttcc tgatcgtgct ccatctgaca tgtgtctctt tactacattt
1261 gtcggaggaa gcagaaatag aaaacttgca aacgcttcaa cggatgaatt gaagcaaata
1321 gtttcttctg accttcagca gctgttgggc actgaggacg aaccttcatt tgtcaatcat
1381 ctcttttgga gcaacgcatt cccattgtat ggacacaatt acgattctgt tttgagagcc
1441 atagacaaga tggaaaagga tcttcctgga ttttttatg caggtaacca taagggtgga
1501 ctttcagtgg gaaaagcgat ggcctccgga tgcaaggctg cggaacttgt aatatcctat
1561 ctggactctc atatatacgt gaagatggat gagaagaccg cgtaa //
```

TABLE 10

*Amaranthus tuberculatus* biotype herbicide-resistant AC plastid protoporphyrinogen oxidase (PPX1) mRNA, nuclear gene for plastid product, corresponding to NCBI Accession DQ386115 and SEQ ID NO: 23 (cDNA) and NO: 24 (amino acid)

MSAMALSSSILQCPPHSDISFRFFAHTRTPSPIFFGRTRKLSYI

HCSTSSSSTANYQNTITSQGEGDKVLDCVIVGAGISGLCIAQALS

TKHIQSNLNFIVTEAKHRVGGNITTMESDGYIWEEGPNSFQPSDP

VLTMAVDSGLKDDLVLGDPNAPRFVLWNGKLRPVPSKPTDLPF

FDLMSFPGKIRAGLGALGLRPPPPPPSYEESVEEFVRRNLGDEV

FERLIEPFCSGVYAGDPAKLSMKAAFGKVWTLEQKGGSIIAGTL

KTIQERKNNPPPPRDPRLPKPKGQTVGSFRKGLIMLPTAIAARLG

SKVKLSWTLSNIDKSLNGEYNLTYQTPDGPVSVRTKAVVMTVPSY

IASSLLRPLSDVAADSLSKFYYPPVAAVSLSYPKEAIRPECLIDGEL

KGFGQLHPRSQGVETLGTIYSSSLFPGRAPPGRTLILSYIGGATNLGI

LQKSEDELAETVDKDLRKILINPNAKGSRVLGVRVWPKAIPQFLVG

HFDVLDAAKAGLANAGLKGLFLGGNYVSGVALGRCIEGAYDSASE

VVDFLSQYKDK

```
   1 atgagtgcga tggcgttatc gagcagcatt ctacaatgtc cgccgcactc cgacatctcg
  61 ttccgctttt ttgctcatac acgaaccca tcccccatct tcttcggaag aacacgaaaa
 121 ttatcatata tccattgttc cacaagctca agctcaactg ccaattacca gaacacgatt
 181 acgagccaag gagaaggaga taagtatta gattgtgtaa ttgttggagc tggtatcagt
 241 ggactttgca ttgctcaggc tctttctacc aaacacattc aatccaatct caatttcatt
 301 gtcactgaag ctaaacatcg tgttggaggt aatatcacta ccatggagtc cgatggctat
 361 atctgggaag agggtcctaa tagtttccaa ccctccgatc ctgtgcttac tatggcggtt
 421 gacagtggat tgaaagacga tttagtcttg ggagatccta tgcccctcg tttcgtgctc
```

TABLE 10-continued

*Amaranthus tuberculatus* biotype herbicide-resistant AC plastid protoporphyrinogen oxidase (PPX1) mRNA, nuclear gene for plastid product, corresponding to NCBI Accession DQ386115 and SEQ ID NO: 23 (cDNA) and NO: 24 (amino acid)

```
 481 tggaatggta aattaaggcc tgttccttcc aaacctacgg accttccctt ttttgatctc
 541 atgagctttc ctggtaagat tagggctggt cttggtgcac ttggtcttcg tcctcctcct
 601 cctcctcctt cttatgagga atctgttgaa gaatttgtgc gccgtaatct cggcgatgag
 661 gtcttcgaac gcttgatcga accctttgt tctggtgtct atgctggtga tcctgcaaag
 721 ttgagtatga aagctgcatt tggaaaggtc tggaccttag agcaaaaggg tggtagtatc
 781 atagccggta cactcaaaac tattcaggaa aggaaaaata atcctccacc ccctcgagac
 841 ccccgccttc ctaaacctaa gggccagact gttggatcct ttaggaaagg gctcattatg
 901 ttacctaccg ccattgctgc taggcttggc agtaaagtca aactatcgtg gacactttct
 961 aatattgata gtcgctcaa tggagaatac aatctcactt atcaaacacc cgatggaccg
1021 gtttctgtta ggaccaaagc ggttgtcatg accgtccctt cgtacattgc aagtagcttg
1081 cttcgtccgc tctcagatgt tgctgcagat tctctttcta aattttacta tccaccagtc
1141 gcagcagtgt cccttcttta tcccaaagaa gcaattagac cagaatgctt gattgatgga
1201 gaactaaaag gattcgggca attgcatccc cgcagccagg gtgtggaaac cttgggaaca
1261 atttatagtt catctctttt ccctggtcga gcaccacccg gtaggacctt gatcttgagc
1321 tacattggag gtgctacaaa tcttggcata ttacaaaaga gtgaagatga actcgcggag
1381 acagttgata aggatctcag aaaaattctg ataaatccaa atgcgaaagg cagccgtgtt
1441 ctgggagtga gagtatggcc aaaggcaatc ccccaatttt tagttggtca ctttgatgtg
1501 ctagatgctg caaaagctgg tttggcaaat gctgggctaa aggggttgtt tcttggtggt
1561 aattatgtat caggtgttgc cttggggagg tgtatagagg gtgcttatga ctctgcttct
1621 gaggtagtgg atttcctctc acagtacaaa gataagtag //
```

TABLE 11

*Amaranthus tuberculatus* biotype herbicide-resistant AC mitochondrial protoporphyrinogen oxidase (PPX2L) mRNA, complete cds; nuclear gene for mitochondrial product, corresponding to NCBI Accession DQ386116 and to SEQ ID NO: 25 (cDNA) and NO: 26 (amino acid)

MVIQSITHLSPNLALPSPLSVSTKNYPVAVMGNISEREEPTSAK

RVAVVGAGVSGLAAAYKLKSHGLSVTLFEADSRAGGKLKTVKK

DGFIWDEGANTMTESEAEVSSLIDDLGLREKQQLPISQNKRYIAR

DGLPVLLPSNPAALLTSNILSAKSKLQIMLEPFLWRKHNATELSDE

HVQESVGEFFERHFGKEFVDYVIDPFVAGTCGDPQSLSMHHTF

PEVWNIEKRFGSVFAGLIQSTLLSKKEKGGENASIKKPRVRGSFS

FQGGMQTLVDTMCKQLGEDELKLQCEVLSLSYNQKGIPSLGNWS

VSSMSNNTSEDQSYDAVVVTAPIRNVKEMKIMKFGNPFSLDFIPEV

TYVPLSVMITAFKKDKVKRPLEGFGVLIPSKEQHNGLKTLGTLFSS

MMFPDRAPSDMCLFTTFVGGSRNRKLANASTDELKQIVSSDLQQLL

GTEDEPSFVNHLFWSNAFPLYGHNYDCVLRAIDKMEKDLPGFFYA

GNHKGGLSVGKAMASGCKAAELVISYLDSHIYVKMDEKTA

TABLE 11-continued

*Amaranthus tuberculatus* biotype herbicide-resistant AC mitochondrial protoporphyrinogen oxidase (PPX2L) mRNA, complete cds; nuclear gene for mitochondrial product, corresponding to NCBI Accession DQ386116 and to SEQ ID NO: 25 (cDNA) and NO: 26 (amino acid)

```
   1 atggtaattc aatccattac ccacctttca ccaaacttg cattgccatc gccattgtca
  61 gtttccacca agaactaccc agtagctgta atgggcaaca tttctgagcg agaagaaccc
 121 acttctgcta aaagggttgc tgttgttggt gctggagtta gtggacttgc tgctgcatat
 181 aagctaaaat cccatggttt gagtgtgaca ttgtttgaag ctgattctag agctggaggc
 241 aaacttaaaa ctgttaaaaa agatggtttt atttgggatg aggggggcaaa tactatgaca
 301 gaaagtgagg cagaggtctc gagtttgatc gatgatcttg gcttcgtga gaagcaacag
 361 ttgccaattt cacaaaataa aagatacata gctagagacg tcttcctgt gctactacct
 421 tcaaatcccg ctgcactact cacgagcaat atcctttcag caaaatcaaa gctgcaaatt
 481 atgttggaac catttctctg gagaaaacac aatgctactg aacttctga tgagcatgtt
 541 caggaaagcg ttggtgaatt ttttgagcga cattttggga aagagtttgt tgattatgtt
 601 attgacccctt ttgttgcggg tacatgtgga gatcctcaat cgctttccat gcaccataca
 661 tttccagaag tatggaatat tgaaaaaagg tttggctctg tgtttgctgg actaattcaa
 721 tcaacattgt tatctaagaa ggaaaagggt ggagaaaatg cttctattaa gaagcctcgt
 781 gtacgtggtt cattttcatt tcaaggtgga atgcagacat tgttgacac aatgtgcaaa
 841 cagcttggtg aagatgaact caaactccag tgtgaggtgc tgtccttgtc atataaccag
 901 aaggggatcc cctcattagg gaattggtca gtctcttcta tgtcaaataa taccagtgaa
 961 gatcaatctt atgatgctgt ggttgtcact gctccaattc gcaatgtcaa gaaatgaag
1021 attatgaaat ttgaaaatcc attttcactt gactttattc cagaggtgac gtacgtaccc
1081 ctttccgtta tgattactgc attcaaaaag gataaagtga agagacctct tgagggcttc
1141 ggagttctta tcccctctaa agagcaacat aatggactga agactcttgg tactttattt
1201 tcctccatga tgtttcctga tcgtgctcca tctgacatgt gtctcttac tacatttgtc
1261 ggaggaagca gaaatagaaa acttgcaaac gcttcaacgg atgaattgaa gcaaatagtt
1321 tcttctgacc ttcagcagct gttgggcact gaggacgaac cttcatttgt caatcatctc
1381 ttttggagca acgcattccc attgtatgga cacaattacg attgtgtttt gagagccata
1441 gacaagatgg aaaaggatct tcctggattt ttttatgcag gtaaccataa gggtggactt
1501 tcagtgggaa aagcgatggc ctccgatgc aaggctgcgg aacttgtaat atcctatctg
1561 gactctcata tacgtgaa gatggatgag aagaccgcgt aa //
```

TABLE 12

*Amaranthus tuberculatus* biotype herbicide-susceptible AC mitochondrial protoporphyrinogen oxidase (PPX2L) mRNA, nuclear gene for mitochondrial product, corresponding to NCBI Accession DQ386117 and to SEQ ID NO: 27 and NO: 28

MVIQSITHLSPNLALPSPLSVSTKNYPVAVMGNISEREEPTSAK

RVAVVGAGVSGLAAAYKLKSHGLSVTLFEADSRAGGKLKTVKKDGFIWDEG

ANTMTESEAEVSSLIDDLGLREKQQLPISQNKRYIARAGLPVLLPSNPAALLTS

NILSAKSKLQIMLEPFLWRKHNATELSDEHVQESVGEFFERHFGKEFVDYVID

PFVAGTCGGDPQSLSMHHTFPEVWNIEKRFGSVFAGLIQSTLLSKKEKGG

TABLE 12-continued

*Amaranthus tuberculatus* biotype herbicide-susceptible AC
mitochondrial protoporphyrinogen oxidase (PPX2L) mRNA, nuclear gene
for mitochondrial product, corresponding to NCBI Accession DQ386117
and to SEQ ID NO: 27 and NO: 28

ENASIKKPRVRGSFSFQGGMQTLVDTMCKQLGEDELKLQCEVLSLSYNQKGIP

SLGNWSVSSMSNNTSEDQSYDAVVVTAPIRNVKEMKIMKFGNPFSLDFIPEV

TYVPLSVMITAFKKDKVKRPLEGFGVLIPSKEQHNGLKTLGTLFSSMMFPDR

APSDMCLFTTFVGGSRNRKLANASTDELKQIVSSDLQQLLGTEDEPSFVNH

LFWSNAFPLYGHNYDSVLRAIDKMEKDLPGFFYAGNHKGGLSVGKAMASGC

KAAELVISYLDSHIYVKMDEKTA

```
   1 atggtaattc aatccattac ccacctttca ccaaaccttg cattgccatc gccattgtca
  61 gtttcaacca agaactaccc agtagctgta atgggcaaca tttctgagcg ggaagaaccc
 121 acttctgcta aaagggttgc tgttgttggt gctggagtta gtggacttgc tgctgcatat
 181 aagctaaaat cccatggttt gagtgtgaca ttgtttgaag ctgattctag agctggaggc
 241 aaacttaaaa ctgttaaaaa agatggtttt atttgggatg agggggcaaa tactatgaca
 301 gaaagtgagg cagaggtctc gagtttgatc gatgatcttg gcttcgtga eagcaacag
 361 ttgccaattt cacaaaataa agatacata gctagagccg tcttcctgt gctactacct
 421 tcaaatcccg ctgcactact cacgagcaat atcctttcag caaaatcaaa gctgcaaatt
 481 atgttggaac catttctctg gagaaaacac aatgctactg aactttctga tgagcatgtt
 541 caggaaagcg ttggtgaatt ttttgagcga cattttggga aagagtttgt tgattatgtt
 601 attgacccctt tgttgcggg tacatgtggt ggagatcctc aatcgctttc catgcaccat
 661 acatttccag aagtatggaa tattgaaaaa aggtttggct ctgtgtttgc cggactaatt
 721 caatcaacat tgttatctaa gaaggaaaag ggtggagaaa atgcttctat taagaagcct
 781 cgtgtacgtg gttcattttc atttcaaggt ggaatgcaga cacttgttga cacaatgtgc
 841 aaacagcttg gtgaagatga actcaaactc cagtgtgagg tgctgtcctt gtcatataac
 901 cagaagggga tcccctcact agggaattgg tcagtctctt ctatgtcaaa taataccagt
 961 gaagatcaat cttatgatgc tgtggttgtc actgctccaa ttcgcaatgt caagaaatg
1021 aagattatga aattggaaa tccattttca cttgactta ttccagaggt gacgtacgta
1081 cccctttccg ttatgattac tgcattcaaa aaggataaag tgaagagacc tcttgagggc
1141 ttcggagttc ttatcccctc taaagagcaa cataatggac tgaagactct ggtacttta
1201 ttttcctcca tgatgtttcc tgatcgtgct ccatctgaca tgtgtctctt tactacattt
1261 gtcggaggaa gcagaaatag aaaacttgca aacgcttcaa cggatgaatt gaagcaaata
1321 gtttcttctg accttcagca gctgttgggc actgaggacg aaccttcatt tgtcaatcat
1381 ctctttttgga gcaacgcatt cccattgtat ggacacaatt acgattctgt tttgagagcc
1441 atagacaaga tggaaaagga tcttcctgga ttttttttatg caggtaacca taagggtgga
1501 ctttcagtgg gaaaagcgat ggcctccgga tgcaaggctg cggaacttgt aatatcctat
1561 ctggactctc atatatacgt gaagatggat gagaagaccg cgtaa //
```

TABLE 13

*Amaranthus tuberculatus* biotype herbicide-resistant CC mitochondrial protoporphyrinogen oxidase (PPX2L) mRNA, nuclear gene for mitochondrial product,
corresponding to Accession DQ386118 and SEQ ID NO: 29 and NO: 30.

MVIQSITHLSPNLALPSPLSVSTKNYPVAVMGNISEREEPTSAK

RVAVVGAGVSGLAAAYKLKSHGLSVTLFEANSRAGGKLKTVKKDGFIWDEGANTMTES

EAEVSSLIDDLGLREKQQLPISQNKRYIARDGLPVLLPSNPAALLTSNILSAKSKLQI

MLEPFLWRKHNATELSDEHVQESVGEFFERHFGKEFVDYVIDPFVAGTCGDPQSLSMY

HTFPEVWNIEKRFGSVFAGLIQSTLLSKKEKGGENASIKKPRVRGSFSFQGGMQTLVD

TMCKQLGEDELKLQCEVLSLSYNQKGIPSLGNWSVSSMSNNTSEDQSYDAVVVTAPIR

NVKEMKIMKFGNPFSLDFIPEVTYVPLSVMITAFKKDKVKRPLEGFGVLIPSKEQHNG

LKTLGTLFSSMMFPDRAPSDMCLFTTFVGGSRNRKLANASTDELKQIVSSDLQQLLGT

EDEPSFVNHLFWSNAFPLYGHNYDSVLRAIDKMEKDLPGFFYAGNHKGGLSVGKAMAS

GCKAAELVISYLDSHIYVKMDEKTA

```
   1 atggtaattc aatccattac ccacctttca ccaaaccttg cattgccatc gccattgtca
  61 gtttccacca agaactaccc agtagctgta atgggcaaca tttctgagcg ggaagaaccc
 121 acttctgcta aaagggttgc tgttgttggt gctggagtta gtggacttgc tgctgcatat
 181 aagctaaaat cccatggttt gagtgtgaca ttgtttgaag ctaattctag agctggaggc
 241 aaacttaaaa ctgttaaaaa agatggtttt atttgggatg aggggcaaa tactatgaca
 301 gaaagtgagg cagaggtctc gagtttgatc gatgatcttg gcttcgtga aagcaacag
 361 ttgccaattt cacaaaataa aagatacata gctagagcg tcttcctgt gctactacct
 421 tcaaatcccg ctgcactact cacgagcaat atcctttcag caaaatcaaa gctgcaaatt
 481 atgttgaac catttctctg gagaaaacac aatgctactg aactttctga tgagcatgtt
 541 caggaaagcg ttggtgaatt ttttgagcga cattttggga aagagtttgt tgattatgtt
 601 attgacccctt ttgttgcggg tacatgtgga gatcctcaat cgctttccat gtaccataca
 661 tttccagaag tatggaatat tgaaaaaagg tttggctctg tgtttgctgg actaattcaa
 721 tcaacattgt tatctaagaa ggaaaagggt ggagaaaatg cttctattaa gaagcctcgt
 781 gtacgtggtt cattttcatt tcaaggtgga atgcagacac ttgttgacac aatgtgcaaa
 841 cagcttggtg aagatgaact caaactccag tgtgaggtgc tgtccttgtc atataaccag
 901 aaggggatcc cctcattagg gaattggtca gtctcttcta tgtcaaataa taccagtgaa
 961 gatcaatctt atgatgctgt ggttgtcact gctccaattc gcaatgtcaa agaaatgaag
1021 attatgaaat ttggaaatcc atttcacctt gactttattc cagaggtgac gtacgtaccc
1081 ctttccgtta tgattactgc attcaaaaag gataaagtga agagacctct tgagggcttc
1141 ggagttctta tcccctctaa agagcaacat aatggactga agactcttgg tactttattt
1201 tcctccatga tgtttcctga tcgtgctcca tctgacatgt gtctcttac tacatttgtc
1261 ggaggaagca gaaatagaaa acttgcaaac gcttcaacgg atgaattgaa gcaaatagtt
1321 tcttctgacc ttcagcagct gttgggcact gaggacgaac cttcatttgt caatcatctc
1381 ttttggagca acgcattccc attgtatgga cacaattacg attctgtttt gagagccata
1441 gacaagatgg aaaaggatct tcctggattt ttttatgcag gtaaccataa gggtggactt
1501 tcagtgggaa aagcgatggc ctccggatgc aaggctgcgg aacttgtaat atcctatctg
1561 gactctcata tatacgtgaa gatggatgag aagaccgcgt aa //
```

TABLE 14

*Amaranthus tuberculatus* biotype WCS (herbicide sensitive) mitochondrial protoporphyrinogen oxidase long form (PPX2L) gene, partial cds from genomic DNA; nuclear gene for mitochondrial product, corresponding to Accesssion DQ394875 and to SEQ ID NO: 31 and NO: 32. The protein coding region begins at 65 and continues beyond 4797, with coding sequence splicing as follows: join(<65 . . . 185, 287 . . . 326, 516 . . . 651, 755 . . . 820, 1227 . . . 1277, 1399 . . . 1455, 2081 . . . 2157, 2646 . . . 2682, 2777 . . . 2842, 3374 . . . >3414)

MVIQSITHLSPNLALPSPLSVSTKNYPVAVMGNISEREEPTSAK

RVAVVGAGVSGLAAAYKLKSHGLSVTLFEADSRAGGKLKTVKKDGFIWDEGANTMTES

EAEVSSLIDDLGLREKQQLPISQNKRYIARDGLPVLLPSNPAALLTSNILSAKSKLQI

MLEPFLWRKHNATELSDEHVQESVGEFFERHFGKEFVDYVIDPFVAGTCGGDPQSLSM

HHTFPEVWNIEK

```
   1 aagaattgaa ttggcagatt gagacaaaat tggattcaga atttagcaaa tttaaaccga
  61 tcgtatggta attcaatcca ttacccacct ttcaccaaac cttgcattgc catcgccatt
 121 gtcagtttca accaagaact acccagtagc tgtaatgggc aacatttctg agcgggaaga
 181 acccagtaag tcaacctttc ttcacatatc ttaaagcaat cccttttcaa ctacactttc
 241 ttttgatgat ttcacattct gagttttttt tattggggat ttttagcttc tgctaaaagg
 301 gttgctgttg ttggtgctgg agttaggtaa attttatgtt tcttttccag aaagattgta
 361 aaattttgct ttgattgttc tgaattttga tgggttttttg cataatgatt tgtatttggg
 421 atgggcaaat ttttcagtag atcatactac ttttaacttc tattttctgt ataattttat
 481 tgatttccta aactgttttt gtggaattgt tctagtggac ttgctgctgc atataagcta
 541 aaatcccatg gtttaagtgt gacattgttt gaagctgatt ctagagctgg aggcaaactt
 601 aaaactgtta aaaagatgg ttttatttgg gatgaggggg caaatactat ggtaatgttt
 661 atcaacaatg ctggttttct gatttagaac caattacttg ctggattttg ggtcaattct
 721 gtggttaaca tgtcactttc tgatatgctt gtagacagaa agtgaggcag aggtctcgag
 781 tttgatcgat gatcttgggc ttcgtgagaa gcaacagttg gtaagtttttc tgtctaagcc
 841 cattcccttt gcttgctaga gtccgtagcg caaaaatacg gtaatagtca tgatcgtggt
 901 aatgacatgg tgatgcggtg acaggagtca tgtgatcgtt attccaacta taggtcaaaa
 961 acatgatatt ttccttgtga cgccccaaaa tgcagtattt ttacaccttt acattgcggg
1021 gaaaaatagg tttattatgt tgaaaacctt tacaaggcgg ctgatgcgat gcggccttgt
1081 ttttgcatta tgttcttgaa gcaacttatt atatctttga ttaatgtatc atcagcttaa
1141 aacagcctta ttgtacttct taatctagtt ttgacttttg aggttgcttt tacaagatct
1201 ttatatgatt ggttcttctg tcacagccaa tttcacaaaa taaaagatac atagctagag
1261 acggtcttcc tgtgctagta agtcctctgc atttactttt gacctctatg aacttctaac
1321 actggatact aagttgtatt cgaggcaaat tctgtatttt ccaatctgct tattgacagt
1381 tgcttgcaaa ctttgcagct accttcaaat cccgctgcac tactcacgag caatatcctt
1441 tcagcaaaat caaaggttat caatgctaaa atcatgtttg gtatttgatt acttagcttt
1501 tggtgtatgc aataatttgg tttctaaaac taagtgattg acggaaaagg agggacgaag
1561 gacatagaat tgcaattttg tgttcttcat gtatttttac ttttagagta ggtaagtcac
1621 tttcggtccg tttggttaat ggtactagtt ggtggtaata ggaatgattt gtagtgtaaa
1681 ttttcaagat atatatcatg tcattcccat ggtaatgaaa gtttgatcat aaaaaggttt
1741 tttgttcaca attttccatt accacctaat accacatgtt taaatggtaa tgcattggaa
```

TABLE 14-continued

*Amaranthus tuberculatus* biotype WCS (herbicide sensitive) mitochondrial protoporphyrinogen oxidase long form (PPX2L) gene, partial cds from genomic DNA; nuclear gene for mitochondrial product, corresponding to Accesssion DQ394875 and to SEQ ID NO: 31 and NO: 32. The protein coding region begins at 65 and continues beyond 4797, with coding sequence splicing as follows: join(<65 . . . 185, 287 . . . 326, 516 . . . 651, 755 . . . 820, 1227 . . . 1277, 1399 . . . 1455, 2081 . . . 2157, 2646 . . . 2682, 2777 . . . 2842, 3374 . . . >3414)

```
1801 tgagttttgt gaagaaaatg agtttgttga gaaagaataa gcatggtcat taaatttgtc
1861 aagagatatt cctatcaaaa ttacactagc tttccattat catttcacca tttagtaccg
1921 attaccaaat gggccgttta tagtttggga agagcatacg tttgtgtaaa acttttattt
1981 tgaagttgaa agaatttgtt gcaccttttg ttatgattag gttttgatgt ttttagctgc
2041 aataaatttg ttgatgaaaa agccactact tttttctcag ctgcaaatta tgttggaacc
2101 atttctctgg agaaaacaca atgctactga actttctgat gagcatgttc aggaaaggca
2161 agtgccacat actattaagt gttagttgct gagaatatat ttgaatctaa gatgcacgaa
2221 gaccactggt gcccttgctc tatcaattct gatggaaagg attatcgctg aatttacctt
2281 ctactaaaac atcgataaaa tacttcatta ttagcatcaa aagattccct ccatccttct
2341 ggttttgcta gacttgcctt atgaaggtgt tcaaggagta gtttgctacc cttcaagata
2401 gggtagtggt tgccgtctct cataatttca gtcactcgtt ttcctctcct aattcaagcc
2461 ataatttta tggttcctcc acacaacact tgctaaattt gaaaagtagc aaagaggaag
2521 tgagcaaaat cagcaggagt aggactgatg agtaagagct tgattaagtg tagaggattt
2581 tcttttgtgt tgaatatgaa tgcatcatgc atgactgtag aattgacata atgatttgtc
2641 tgcagcgttg gtgaattttt tgagcgacat tttgggaaag aggtattgtt gccaattgcc
2701 atgctctatt cattccggtg aattaacaaa tgttgtgctt ctgcttacta ttgcttataa
2761 ttattgtttg ttgcagtttg ttgattatgt tattgaccct tttgttgcgg gtacatgtgg
2821 tggagatcct caatcgcttt ccgtgagtta aatactgtgc ttgctttttt ttttcaacat
2881 tttctggagg ctgtaaataa attatactcc ttcctattct aatcaaatat cctatttccc
2941 cttttggcat attcaaattt agttaaatat tgtgtaaatt atttacacaa ttgccattaa
3001 attttcactt ttcccttact cactcttctc atgtgtccct tcccccttt cttaaaattg
3061 gtgcattatc aaataggaca tttgatttga ataggcggga gtttccaatt gtgcttccaa
3121 aggtagcttg tcacttttc ttttttcttta aattttgtac catgccatgc attttgaacc
3181 tcaactcatt tcgccataaa ggaatattat gtttgagaag aacgaggata ctattatctt
3241 atagataaca tataggtttc attatcaatg attgtttgat tttcaactct tcttttcctt
3301 tcatgctcat attgatgtta tttctatttg ttatgaatta tgtccattgt gttaatgtct
3361 ttctttattg tagatgcacc atacattcc agaagtatgg aatattgaaa aaaggtatga
3421 accttaaagc tttaattttc ttcgaactta atgtttctta attgattctt ttggatcaat
3481 ttccataaga atggaaattt aaaaaaaggt atgaaccta aagatttctt cgaacttata
3541 tgttttgtaa ttcatgcttt tagatgttgc accatttat ctatgtgtct taagtttgtt
3601 gtaatcattt gtagaccaaa agaatgaatg gtctggtttg aaatggttca tcgtgcaaaa
3661 atgcgatttt gcttgtgatt gaggtaacat tcaaggtgat gtgtttgtcg tactgtcaaa
3721 tgtcttccta taccatatga tatatatata agcctaaaat gatatattgt ataccttttag
3781 gatgtggata gcaggggttc agtacatatg aaaaatcctt gcaatttgat ctgtacgata
```

TABLE 14-continued

*Amaranthus tuberculatus* biotype WCS (herbicide sensitive)
mitochondrial protoporphyrinogen oxidase long form (PPX2L) gene,
partial cds from genomic DNA; nuclear gene for mitochondrial product,
corresponding to Accesssion DQ394875 and to SEQ ID NO: 31 and NO:
32. The protein coding region begins at 65 and continues beyond 4797,
with coding sequence splicing as follows: join(<65 . . . 185,
287 . . . 326, 516 . . . 651, 755 . . . 820, 1227 . . . 1277,
1399 . . . 1455, 2081 . . . 2157, 2646 . . . 2682,
2777 . . . 2842, 3374 . . . >3414)

```
3841 caatgtgatt ttgccttttg cctttgcct tttgttatat gatgatgatt ccatgtgaaa 3901 ttttgggatt tagaaaattc acttgtttaa gaacatttga atcaaacttt caccaatttc 3961 aaccacattt aattgcggca aagccgaact ttaaaagtca ctcccaatct ttgagatatc 4021 caaactccaa aacttctatt agctttcatg ttttcactaa gtaaagttgg tgcgactcct 4081 taccatttc tttattatgc atttcgttga tgtataatag tatagattgg tgctctcttc 4141 gctctccttc caacatgcat aacttctagt tcttgtcgtt ttcttttcct ccctattttt 4201 atttgacttg tagctatttt tgttcactct tctcgcccaa tccaaaactt gtagctaaag 4261 aaacttgatt tcattgattt tgtaactgat atgcaattca ttttgtttg cttttagttg 4321 ttgattcaaa aacaataatg ctaaagcccct aatcctaaca tgtcgggtta gctgttgaaa 4381 caatacttga aattgctata aaaagggatt tttttcgggt acttcagttg ttgagattga 4441 tatggtcaag tataatttgt tttaacacaa tttgtaatga tttaatggct tagtttcata 4501 gctgtttgta ttaataaagg aaggaggact atccgaaatt gcaataggaa agagatttta 4561 gttcggtatt tggttgttta aattgatatg gccaagtaat gttcatttta cacaattggt 4621 aatgttttat tggctcaata gtgtttgtaa gtatgcgact caaatttaat caagtataac 4681 ttattgaaac ataaataaat atccattagg tttggctctg tgtttgctgg actaattcaa 4741 tcaacattgt tatctaagaa ggaaaagggt ggagaaaatg cttcataaga agcctcg
```

TABLE 15

*Amaranthus tuberculatus* biotype ACR mitochondrial
protoporphyrinogen oxidase long form (PPX2L) gene with partial cds;
nuclear gene for mitochondrial product, corresponding to NCBI
Accession DQ394876 and SEQ ID NO: 33 (DNA) and NO: 34
(amino acid). Splicing is as follows for mRNA: join(<65 . . . 185,
287 . . . 326, 516 . . . 651, 755 . . . 820, 1227 . . . 1277,
1399 . . . 1455, 2080 . . . 2156, 2645 . . . 2681, 2776 . . . 2838,
3366 . . . >3406) CDS join(65 . . . 185, 287 . . . 326,
516 . . . 651, 755 . . . 820, 1227 . . . 1277, 1399 . . . 1455,
2080 . . . 2156, 2645 . . . 2681, 2776 . . . 2838,
3366 . . . >3406)

MVIQSITHLSPNLALPSPLSVSTKNYPVAVMGNISEREEPTSAK

RVAVVGAGVSGLAAAYKLKSHGLSVTLFEADSRAGGKLKTVKKDGFIWDEGANTMTES

EAEVSSLIDDLGLREKQQLPISQNKRYIARDGLPVLLPSNPAALLTSNILSAKSKLQI

MLEPFLWRKHNATELSDEHVQESVGEFFERHFGKEFVDYVIDPFVAGTCGDPQSLSMH

HTFPEVWNIEK

```
  1 aagaattgaa ttggcagatt gagacaaaat tggattcaga atttagcaaa tttaaaccga 61 tcgtatggta attcaatcca ttacccacct ttcaccaaac cttgcattgc catcgccatt 121 gtcagtttcc accaagaact acccagtagc tgtaatgggc aacatttctg agcgagaaga 181 acccagtaag tcaaccttc ttcacatatc ttaaagcaat ccctttcaa ctacactttc 241 ttttgatgat ttcacattct gagtttttt tattggggat tttagcttc tgctaaaagg
```

TABLE 15-continued

*Amaranthus tuberculatus* biotype ACR mitochondrial protoporphyrinogen oxidase long form (PPX2L) gene with partial cds; nuclear gene for mitochondrial product, corresponding to NCBI Accession DQ394876 and SEQ ID NO: 33 (DNA) and NO: 34 (amino acid). Splicing is as follows for mRNA: join(<65 . . . 185, 287 . . . 326, 516 . . . 651, 755 . . . 820, 1227 . . . 1277, 1399 . . . 1455, 2080 . . . 2156, 2645 . . . 2681, 2776 . . . 2838, 3366 . . . >3406) CDS join(65 . . . 185, 287 . . . 326, 516 . . . 651, 755 . . . 820, 1227 . . . 1277, 1399 . . . 1455, 2080 . . . 2156, 2645 . . . 2681, 2776 . . . 2838, 3366 . . . >3406)

```
 301 gttgctgttg ttggtgctgg agttaggtaa attttatgtt tcttttccag aaagattgta
 361 aaattttgct ttgattgttc tgaattttga tgggtttttg cataatgatt tgtatttggg
 421 atgggcaaat ttttcagtag atcatactac ttttaacttc tattttctgt ataattttat
 481 tgatttccta aattgttttt gtggaattgt tctagtggac ttgctgctgc atataagcta
 541 aaatcccatg gtttgagtgt gacattgttt gaagctgatt ctagagctgg aggcaaactt
 601 aaaactgtta aaaagatgg ttttatttgg atgaggggg caaatactat ggtaatgttt
 661 atcaacaatg ctggttttct gatttagaac caattacttg ctggattttg ggtcaattct
 721 gtggttaaca tgtcactttc tgatatgctt gtagacagaa agtgaggcag aggtctcgag
 781 tttgatcgat gatcttgggc ttcgtgagaa gcaacagttg gtaagttttc tgtctaagcc
 841 cattcccttt gcttgctaga gtccgtagcg caaaaatacg gtaatagtca tgatcgtggt
 901 aatgacatgg tgatgcggtg acaggagtca tgtgatcgtt attccaacta taggtcaaaa
 961 acatgatatt ttccttgtga cgccccaaaa tgcggtattt ttacaccttt acattgcggg
1021 gaaaaatagg tttattatgt tgaaaacctt tacaaggcgg ctgatgcgat gcggccttgt
1081 ttttgcatta tgttctagaa gcaacttatt atatctttga ttaatgtatc atcagcttaa
1141 aacagcctta ttgtacttct taatctagtt ttgacttttg aggttgcttt tacaagatct
1201 ttatatgatt ggttcttctg tcacagccaa tttcacaaaa taaagatac atagctagag
1261 acggtcttcc tgtgctagta agtcctctgc atttacttt gacctctatg aacttctaac
1321 actggatact aagttgtatt cgaggcaaat tctgtatttt ccaatctgct tattgacagt
1381 tgcttgcata ctttgcagct accttcaaat cccgctgcac tactcacgag caatatcctt
1441 tcagcaaaat caaggttat caatgctaaa atcatgtttg gtatttgatt acttagcttt
1501 tggtgtatgc aataatttgg tttctaaaac taagtgattg acggaaaagg agggacgaag
1561 gacatagaat tgcaattttg tgttcttcat gtatttttac ttttagagta ggtaagtcac
1621 tttcggtccg tttggttaat ggtactagtt ggtggtaata ggaatgattt gtagtgtaaa
1681 ttttcaagat atatcatg tcattcccat ggtaatgaaa gtttgatcat aaaaggttt
1741 tttgttcaca attttccatt accacctaat accacatgtt taaatggtaa tgcattggaa
1801 tgagttttgt gaagaaaatg agtttgttga gaaagaataa gcatggtcat taaatttgtc
1861 aagagatatt cctatcaaaa ttacactagc tttccattat catttcacca tttagtaccg
1921 attaccaaat gggccgttta tagtttggga agagcatacg tttgtgtaaa acttttattt
1981 tgaagttgaa agaatttgtt gcacctttg ttatgattaa gttttgatgt ttttagctgc
2041 aataatttgt tgatgaaaaa gccactactt ttttctcagc tgcaaattat gttggaacca
2101 tttctctgga gaaacacaa tgctactgaa ctttctgatg agcatgttca ggaaaggcaa
2161 gtgccacata ctattaagtg ttagttgctg agaatatatt tgaatctaag atgcacgaag
2221 accactggtg cccttgctct atcaattctg atggaaagga ttatcgctga atttaccttc
2281 tactaaaaca tcgataaaat acttcattat tagcatcaaa agattccctc catccttctg
```

TABLE 15-continued

*Amaranthus tuberculatus* biotype ACR mitochondrial protoporphyrinogen oxidase long form (PPX2L) gene with partial cds; nuclear gene for mitochondrial product, corresponding to NCBI Accession DQ394876 and SEQ ID NO: 33 (DNA) and NO: 34 (amino acid). Splicing is as follows for mRNA: join(<65 . . . 185, 287 . . . 326, 516 . . . 651, 755 . . . 820, 1227 . . . 1277, 1399 . . . 1455, 2080 . . . 2156, 2645 . . . 2681, 2776 . . . 2838, 3366 . . . >3406) CDS join(65 . . . 185, 287 . . . 326, 516 . . . 651, 755 . . . 820, 1227 . . . 1277, 1399 . . . 1455, 2080 . . . 2156, 2645 . . . 2681, 2776 . . . 2838, 3366 . . . >3406)

```
2341 gttttgctag acttgcctta tgaaggtgtt caaggagtag tttgctaccc ttcaagatag
2401 ggtagtggtt gccgtctctc ataatttcag tcactcgttt tcctctccta attcaagcca
2461 taatttttat ggttcctcca cacaacactt gctaaatttg aaaagtagca aagaggaagt
2521 gagcaaaatc agcaggagta ggactgatga gtaagagctt gattaagtgt agaggatttt
2581 cttttgtgtt gaatatgaat gcatcatgca tgactgtaga attgacataa tgatttgtct
2641 gcagcgttgg tgaatttttt gagcgacatt ttgggaaaga ggtattgttg ccaattgcca
2701 tgctctattc attccggtga attaacaaat gttgtgcttc tgcttactat tgcttataat
2761 tattgtttgt tgcagtttgt tgattatgtt attgaccctt ttgttgcggg tacatgtgga
2821 gatcctcaat cgcttccgt gagttaaata ctgtgcttgc tttttttttt caacattttc
2881 tggaggctgt aaataaatta tactccttcc tattctaatc aaatatccta tttccccttt
2941 tggcatattc aaatttagtt aaatattgtg taaattattt acacaattgc cattaaattt
3001 tcacttttcc cttactcttc tcatgtgtcc cttcccccctt ttcttaaaat tggtgcatta
3061 tcaaatagga catttgattt gaataggcgg gagtttccaa ttgtgcttcc aaaggtagct
3121 tgtcactttt tcttttttctt taaatttttgt accatgccat gcattttgaa cctcaactca
3181 tttcgccata aaggaatatt atgtttgaga agaacgagga tactattatc ttatagataa
3241 catataggtt tcattatcaa tgattgtttg attttcaact cttcttttcc tttcatgctc
3301 atattgatgt tatttctatt tgttatgaat tatgtccatt gtgttaatgt ctttctttat
3361 tgtagatgca ccatacattt ccagaagtat ggaatattga aaaaaggtat gaaccttaaa
3421 gctttaattt tcttcgaact taatgtttct taattgattc ttttggatca atttccataa
3481 gaatggaaat ttaaaaaagg gtatgaacct taaagatttc ttcgaactta tatgttttgt
3541 aattcatgct tttagatgct gcaccatttt atctatgtgt cttaagtttg ttgtaatcat
3601 ttgtagacca aaagaatgaa tggtctggtt tgaaatggtt catcgtgcaa aaatgcgatt
3661 ttgcttgtga ttgaggtaac attcaaggtg gtgtgtttgt cgtactgtca aatgtcttcc
3721 tataccatgt gatatatata agcctaaaat gatatattgt acacctttag gatgtggata
3781 gcaggggttc agtacatatg aaaaatcctt gcaatttgat ctgtacgatc aatgtgatt
3841 tgccttttgc cttttgcctt tgttatatg atgatgattc catgtgaaat tttgggatttt
3901 agaaaattca cttgtttaag aacatttgaa tcaaactttc accaatttca accacattta
3961 attgcggcaa agccgaactt taaaagtcac tcccaatctt tgagatatcc aaactccaaa
4021 acttctatta gctttcatgt tttcactaag taaagttggt gcgactcctt accattttct
4081 ttattatgca tttcgttgat gtataatagt atagattggc gctctcttcg ctctccttcc
4141 aacatgcata acttctagtt cttgtcgttt tcttttcctc cctatttttta tttgacttgt
4201 agctattttt gttcactctt ctcgcccaat ccatagctaa agaaacttga tttcattgat
4261 tttgtaactg atatgcaatt cattttgtt tgcttttagt tgttgattca aaacaataa
```

TABLE 15-continued

*Amaranthus tuberculatus* biotype ACR mitochondrial protoporphyrinogen oxidase long form (PPX2L) gene with partial cds; nuclear gene for mitochondrial product, corresponding to NCBI Accession DQ394876 and SEQ ID NO: 33 (DNA) and NO: 34 (amino acid). Splicing is as follows for mRNA: join(<65 . . . 185, 287 . . . 326, 516 . . . 651, 755 . . . 820, 1227 . . . 1277, 1399 . . . 1455, 2080 . . . 2156, 2645 . . . 2681, 2776 . . . 2838, 3366 . . . >3406) CDS join(65 . . . 185, 287 . . . 326, 516 . . . 651, 755 . . . 820, 1227 . . . 1277, 1399 . . . 1455, 2080 . . . 2156, 2645 . . . 2681, 2776 . . . 2838, 3366 . . . >3406)

```
4321 tgctaaagcc ctaatcctaa catgtcgggt tagctgttga aacaatactt gaaattgcta 4381 taaaaaggga ttttttttcgg gtacttcagt tgttgagatt gatatggtca agtataattt 4441 gtttttaacac aatttgtaat gatttaatgg cttagtttca tagctgtttg tattaataaa 4501 ggaaggagga ctatctgaaa ttgcaatagg aaagagattt tagttcggta tttggttgtt 4561 taaattgata tggccaagta atgttcattt tacacaattg gtaatgtttt attggctcaa 4621 tagtgtttgt aagtatgcga ctcaaattta atcaagtata acttattgaa acataaataa 4681 atatccatta ggtttggctc tgtgtttgct ggactaattc aatcaacatt gttatctaag 4741 aaggaaaagg gtggagaaaa tgcttcataa gaagcctcgg acgtc
```

TABLE 16

Coding Squence of Chimeric Herbicide resistant PPXL2 Used in *Arabidopsis* Transformation Experiments (MTX_SRS; SEQ ID NO: 45; encodes protein of SEQ ID NO: 14 which is identical to SEQ ID NO: 46)

```
ATGGTAATTCAATCCATTACCCACCTTTCACCAAACCTTGCATTGCCATCGCCATTGTCAGTTTCA

ACCAAGAACTACCCAGTAGCTGTAATGGGCAACATTTCTGAGCGGGAAGAACCCACTTCTGCTAA

AAGGGTTGCTGTTGTTGGTGCTGGAGTTAGTGGACTTGCTGCTGCATATAAGCTAAAATCCCATG

GTTTGAGTGTGACATTGTTTGAAGCTGATTCTAGAGCTGGAGGCAAACTTAAAACTGTTAAAAAG

ATGGTTTTATTTGGGATGAGGGGGCAAATACTATGACAGAAAGTGAGGCAGAGGTCTCGAGTTTG

ATCGATGATCTTGGGCTTCGTGAGAAGCAACAGTTGCCAATTTCACAAAATAAAGATACATAGCT

AGAGACGGTCTTCCTGTGCTACTACCTTCAAATCCCGCTGCACTACTCACGAGCAATATCCTTTCA

GCAAAATCAAAGCTGCAAATTATGTTGGAACCATTTCTCTGGAGAAAACACAATGCTACTGAACTT

TCTGATGAGCATGTTCAGGAAAGCGTTGGTGAATTTTTTGAGCGACATTTTGGGAAAGAGTTTGTT

GATTATGTTATTGACCCTTTTGTTGCGGGTACATGTGGAGATCCTCAATCGCTTTCCATGCACCAT

ACATTTCCAGAAGTATGGAATATTGAAAAAAGGTTTGGCTCTGTGTTTGCTGGACTAATTCAATCA

ACATTGTTATCTAAGAAGGAAAAGGGTGGAGAAAATGCTTCTATTAAGAAGCCTCGTGTACGTGG

TTCATTTTCATTTCAAGGTGGAATGCAGACACTTGTTGACACAATGTGCAAACAGCTTGGTGAAGA

TGAACTCAAACTCCAGTGTGAGGTGCTGTCCTTGTCATATAACCAGAAGGGGATCCCCTCATTAG

GGAATTGGTCAGTCTCTTCTATGTCAAATAATACCAGTGAAGATCAATCTTATGATGCTGTGGTTG

TCACTGCTCCAATTCGCAATGTCAAAGAAATGAAGATTATGAAATTTGGAAATCCATTTTCACTTGA

CTTTATTCCAGAGGTGACGTACGTACCCCTTTCCGTTATGATTACTGCATTCAAAAAGGATAAAGT

GAAGAGACCTCTTGAGGGCTTCGGAGTTCTTATCCCCTCTAAAGAGCAACATAATGGACTGAAGA

CTCTTGGTACTTTATTTTCCTCCATGATGTTTCCTGATCGTGCTCCATCTGACATGTGTCTCTTTAC

TACATTTGTCGGAGGAAGCAGAAATAGAAACTTGCAAACGCTTCAACGGATGAATTGAAGCAAA

TAGTTTCTTCTGACCTTCAGCAGCTGTTGGGCACTGAGGACGAACCTTCATTTGTCAATCATCTCT
```

TABLE 16-continued

Coding Squence of Chimeric Herbicide resistant PPXL2 Used in *Arabidopsis* Transformation Experiments (MTX_SRS; SEQ ID NO: 45; encodes protein of SEQ ID NO: 14 which is identical to SEQ ID NO: 46)

TTTGGAGCAACGCATTCCCATTGTATGGACACAATTACGATTCTGTTTTGAGAGCCATAGACAAGA

TGGAAAAGGATCTTCCTGGATTTTTTTATGCAGGTAACCATAAGGGTGGACTTTCAGTGGGAAAA

GCGATGGCCTCCGGATGCAAGGCTGCGGAACTTGTAATATCCTATCTGGACTCTCATATATACGT

GAAGATGGATGAGAAGACCGCGTAA

TABLE 17

Coding Sequence for herbicide sensitive PPX2L used in certain experiments (SEQ ID NO: 47; encodes protein of SEQ ID NO: 48)

ATGGTAATTCAATCCATTACCCACCTTTCACCAAACCTTGCATTGCCATCGCCATTGTCAGTTTCA

ACCAAGAACTACCCAGTAGCTGTAATGGGCAACATTTCTGAGCGGGAAGAACCCACTTCTGCTAA

AAGGGTTGCTGTTGTTGGTGCTGGAGTTAGTGGACTTGCTGCTGCATATAAGCTAAATCCCATG

GTTTGAGTGTGACATTGTTTGAAGCTGATTCTAGAGCTGGAGGCAAACTTAAAACTGTTAAAAAAG

ATGGTTTTATTTGGGATGAGGGGGCAAATACTATGACAGAAAGTGAGGCAGAGGTCTCGAGTTTG

ATCGATGATCTTGGGCTTCGTGAGAAGCAACAGTTGCCAATTTCACAAAATAAAAGATACATAGCT

AGAGACGGTCTTCCTGTGCTACTACCTTCAAATCCCGCTGCACTACTCACGAGCAATATCCTTTCA

GCAAAATCAAAGCTGCAAATTATGTTGGAACCATTTCTCTGGAGAAAACACAATGCTACTGAACTT

TCTGATGAGCATGTTCAGGAAAGCGTTGGTGAATTTTTTGAGCGACATTTTGGGAAAGAGTTTGTT

GATTATGTTATCGACCCTTTTGTTGCGGGTACATGTGGTGGAGATCCTCGATCGCTTTCCATGCA

CCATACATTTCCAGAAGTATGGAATATTGAAAAAAGGTTTGGCTCTGTGTTTGCTGGACTAATTCA

ATCAACATTGTTATCTAAGAAGGAAAAGGGTGGAGAAAATGCTTCTATTAAGAAGCCTCGTGTAC

GTGGTTCATTTTCATTTCAAGGTGGAATGCAGACACTTGTTGACACAATGTGCAAACAGCTTGGTG

AAGATGAACTCAAACTCCAGTGTGAGGTGCTGTCCTTGTCATATAACCAGAAGGGGATCCCCTCA

TTAGGGAATTGGTCAGTCTCTTCTATGTCAAATAATACCAGTGAAGATCAATCTTATGATGCTGTG

GTTGTCACTGCTCCAATTCGCAATGTCAAAGAAATGAAGATTATGAAATTTGGAAATCCATTTTCA

CTTGACTTTATTCCAGAGGTGACGTACGTACCCCTTTCCGTTATGATTACTGCATTCAAAAAGGAT

AAAGTGAAGAGACCTCTTGAGGGCTTCGGAGTTCTTATCCCCTCTAAAGAGCAACATAATGGACT

GAAGACTCTTGGTACTTTATTTTCCTCCATGATGTTTCCTGATCGTGCTCCATCTGACATGTGTCT

CTTTACTACATTTGTCGGAGGAAGCAGAAATAGAAAACTTGCAAACGCTTCAACGGATGAATTGAA

GCAAATAGTTTCTTCTGACCTTCAGCAGCTGTTGGGCACTGAGGACGAACCTTCATTTGTCAATCA

TCTCTTTTGGAGCAACGCATTCCCATTGTATGGACACAATTACGATTCTGTTTTGAGAGCCATAGA

CAAGATGGAAAAGGATCTTCCTGGATTTTTTTATGCAGGTAACCATAAGGGTGGACTTTCAGTGG

GAAAAGCGATGGCCTCCGGATGCAAGGCTGCGGAACTTGTAATATCCTATCTGGACTCTCATATA

TACGTGAAGATGGATGAGAAGACCGCGTAA

DISCUSSION

While PPO inhibitor-resistant plants have been generated through genetic engineering approaches (Choi, 1998; Lee, 2000; Lermontova. 2000; Ha, 2004; Jung, 2004; Lee, 2004; Li, 2005), *A. tuberculatus* populations have developed resistance from the repeated use of these herbicides in agronomic production systems. The consequence of *A. tuberculatus* evolving resistance to PPO inhibitors, combined with its already widespread resistance to ALS-inhibiting herbicides, is that the only remaining chemical option for its control following emergence in *Glycine max* (soybean) production systems is glyphosate, which requires the planting of glyphosate-resistant varieties (Patzoldt, 2005). Although the molecular mechanisms of evolved resistance to many herbicides have been identified, such has not yet been elucidated for resistance to PPO inhibitors.

Seven different mechanisms of PPO inhibitor resistance have been proposed for plants (Dayan, 1997). Two of these mechanisms include either enhanced metabolic degradation of the herbicide or an alteration of the herbicide target site, which together constitute the majority of mechanisms for herbicide resistance in weed species. Of these, an altered herbicide target enzyme (PPO) was investigated based on previous characterization of R *A. tuberculatus* plants (Patzoldt, 2004). It was later determined in an independently identified PPO inhibitor-resistant *A. tuberculatus* population that enhanced metabolism was not responsible for resistance (Shoup, 2005).

The mechanism of PPO inhibitor resistance that was selected within natural populations of *A. tuberculatus* populations was a codon deletion in a gene encoding PPO. While alterations of herbicide target proteins are common mechanisms for conferring resistance, several characteristics about this specific mechanism merit highlighting. First, PPO inhibitors have two herbicide target sites in plants; i.e., in plastids and mitochondria (Jacobs, 1984); therefore, in order for target-site resistance to occur, two altered genes would need to be selected. However, *A. tuberculatus* plants have overcome this obstacle via mutation in a single gene (PPX2L) that encodes both plastidic and mitochondrial PPO isoforms. Second, the specific alteration of PPO2L that confers resistance to PPO-inhibiting herbicides is an amino acid deletion resulting from a three-bp deletion in the genomic (coding) DNA. This is the first report of an amino acid deletion, rather than a substitution, in a herbicide target site being selected in a natural (field) population as a resistance mechanism. While intentional selection for resistance to PPO inhibitors identified amino acid substitutions that conferred resistance (Li, 2005; U.S. Pat. No. 5,939,602), the codon-deletion approach revealed by *A. tuberculatus* is instructive of an alternative approach to achieve resistance. Third, the R biotype was found to be resistant to multiple chemical families of PPO inhibitors, albeit at different levels (Patzoldt, 2005), indicating that the ΔG210 mutation confers resistance to all PPO inhibitors. Finally, that R *A. tuberculatus* plants lacked one of the PPO genes (PPX2) found in plants from the S biotype is curious and requires further research. However, the absence of PPX2 in the R biotype likely is not related to the resistance phenotype since resistance was (incompletely) dominant and exhibited single-locus inheritance, PPX2L co-segregated with resistance, and the ΔG210 mutation was sufficient to confer lactofen insensitivity.

While the origin of the G210 codon deletion of PPX2L identified in the R *A. tuberculatus* biotype is uncertain, nucleotide length polymorphisms are not uncommon in this plant species. Codon insertion/deletions (indels) among populations of *A. tuberculatus* were previously identified in other genes encoding herbicide target proteins, e.g., ALS, and EPSPS (5-enolpyruvylshikimate-3-phosphate synthase. Furthermore, other indels, in addition to the G210 indel, were found among PPX genes in this study. In PPX1 (see SEQ ID NOs:13 and 14 and SEQ ID NO19 and 20 and GenBank Accession Nos. DQ386112 and DQ386115), there were two additional, adjacent proline codons in the nucleotide sequence from R plants relative to S plants. An indel was also identified when PPX2 was compared with PPX2L from S plants (See SEQ ID NOs: 19-20 and 21-22; NCBI Accession Nos. DQ386113 and DQ386114). As observed for the G210 polymorphism between R and S PPX2Ls, this also resulted in a glycine amino acid indel, but was located at a different position (128 nucleotides downstream of the G210 codon). The codon indels observed in *A. tuberculatus* typically are associated with short, simple sequence repeats (SSRs). The G210 indel in PPX2L is part of a bi-GTG repeat (or a bi-TGG repeat), the PPX2/PPX2L indel is part of a tri-GGA repeat, and the PPX1 indel is part of a hexa-CCT repeat. SSRs are recognized as a means to provide adaptive genetic variation for evolutionary processes because of their high mutability (Kashi, 2006). Although the numbers of repeats associated with some of the PPX indels are fewer than typically recognized for SSRs that the indels are found within repeated nucleotides suggests a means for their evolutionary origin.

In regards to PPO inhibitor-resistant *A. tuberculatus* in agro-ecosystems, resistance can be transmitted maternally and paternally, and therefore is able to spread through seed dispersal or, more rapidly, via wind dispersal of pollen. Since *A. tuberculatus* is a dioecious plant, it is forced to outcross. This obligate outcrossing, combined with a significant level of resistance that is expressed in the heterozygous state (FIG. 2), will make pollen a very effective means for dissemination of the resistance. In addition to dissemination from a single "source" population, resistance to PPO inhibitors could become more widespread in *A. tuberculatus* populations by independent selection events. In fact, it seems likely that this already has occurred given the distinct locations where PPO inhibitor-resistant populations have been identified (Shoup, 2003; Li, 2004; Patzoldt, 2005), and the different PPX2L alleles containing the ΔG210 mutation identified in this study (FIG. 7).

*A. tuberculatus* is one of the most problematic weeds in agronomic fields throughout the Midwestern United States. In particular, the propensity of *A. tuberculatus* to rapidly evolve herbicide resistance makes its management difficult (Patzoldt, 2004). The herbicide resistance mechanism reported herein illustrates the sophisticated means by which it can adapt and evolve in response to weed control efforts. With the loss of PPO inhibitors as an effective *A. tuberculatus* management tool in soybean, farmers may become even more reliant on glyphosate.

In summary, an altered herbicide target site confers PPO inhibitor resistance in the R biotype. Several unique characteristics about this herbicide resistance mechanism deserve mention. First, PPO inhibitors have two herbicide target sites in plants (i.e. plastids and mitochondria (Jacobs and Jacobs, 1984); therefore, in order for target-site resistance to occur, two altered genes would need to be selected. Without wishing to be bound by theory, the inventors believe that plants from the R waterhemp biotype have overcome this obstacle with natural selection of a mutation in a single gene (PPX2L) that encodes two proteins that theoretically function in both plastids and mitochondria. Second, the specific alteration of PPO2 that confers resistance to PPO-inhibiting herbicides is an amino acid deletion rather than a substitution, unlike prior art mutations (see, e.g., U.S. Pat. Nos. 6,282,837; 5,939,602; and 6,808,904). Substitution mutations, in addition to the Gly deletion, have been observed in naturally resistant waterhemp.

The examples provided herein are for illustrative purposes and are not intended to limit the scope of the invention as claimed. Any variations in the exemplified compositions, plants and methods which occur to the skilled artisan are intended to fall within the scope of the present invention.

EXAMPLES

Detailed procedures for generation and analysis of *A. tuberculatus* lines, herbicide dose-response, and calculation of degree of dominance experiments and certain other procedures follow.

Example 1

*A. tuberculatus* Biotypes

The R biotype used in this study was derived from an *A. tuberculatus* (waterhemp) population originally collected in Adams County, Illinois, and confirmed resistant to PPO-, ALS-, and photosystem II-inhibiting herbicides (Patzoldt, 2005). The S biotype was collected in Wayne County, Illinois, and was identified in previous experiments to be susceptible to all herbicides tested (Patzoldt, 2002). *A. tuberculatus* plants derived from the original Adams County population that were PPO inhibitor-susceptible (S-BioAC), and those from a PPO inhibitor-resistant biotype collected in Clinton County, Illinois (R-BioCC), were utilized for sequencing of PPX2L alleles only.

Example 2

Plant Culture

*A. tuberculatus* seeds for each experiment were sown in flats (surface area of 930 cm$^2$) containing a 1:1:1 mixture of soil:peat:sand. Seedlings for each experiment were transplanted when needed into 12-cm square pots containing 800 ml of soil plus 0.2% (by vol) 14-14-14 Nutricote (Agrivert Inc., Glenpool, Okla.) when they were approximately 1-cm in height. Plants were grown in a greenhouse maintained at 28/22° C. day/night with supplemental light (minimum of 800 µmol m$^{-2}$ s$^{-1}$ photon flux at the plant canopy) provided by mercury halide and sodium vapor lamps programmed for a 16-hour photoperiod.

Example 3

Herbicide Applications

Herbicide treatments were applied using a compressed air, moving nozzle laboratory sprayer equipped with an 80° flat fan nozzle (Teejet, Spraying Systems Co, Wheaton, Ill.) delivering 187 L ha$^{-1}$ of water at 207 kPa. The nozzle was maintained approximately 45 cm above the plant canopy. Plants were returned to the greenhouse immediately after herbicide treatment. All foliar-applied herbicide treatments were made when *A. tuberculatus* plants were 10-12 cm in height.

Example 4

Generation of $F_1$, $F_2$, and BC Lines

To create $F_1$ lines, *A. tuberculatus* plants from the R biotype were crossed with plants from the S biotype. Plants from the R biotype were confirmed herbicide-resistant by treatment with a herbicide mixture containing lactofen at 175 g active ingredient (ai) ha$^{-1}$, imazamox at 44 g acid equivalent (ae) ha$^{-1}$, and atrazine at 1000 g ai ha$^{-1}$, a PPO, acetolactate synthase (ALS), and photosystems II (PSII) inhibitor, respectively, plus 1% (by vol) crop oil concentrate (COC; Herbimax, Loveland Industries) and 2.5% (by vol) ammonium sulfate (AMS; Agriliance, St. Paul, Minn.). $F_1$ lines were created where the maternal parent was either S $\{F_1(S)\}$ or R $\{F_1(R)\}$. Following maturity, seeds were harvested from each female individually as full-sib lines. $F_1$ male plants were crossed with female plants from the S biotype, R biotype, or $F_1$ full-sibs to create $BC_E$, $BC_R$, or $F_2$ lines, respectively. Separate crosses were conducted using males from $F_1(S)$ or $F_1(R)$ lines. All F1 plants used for crossing were confirmed herbicide-resistant by treating with a mixture of lactofen, imazamox and atrazine as described herein. Each genetic combination was conducted twice with new *A. tuberculatus* plants, thus constituting a complete replication of the experiment. Crosses were conducted in growth chambers maintained at 28/22° C. day/night with fluorescent and incandescent bulbs providing 400 µmol m$^{-2}$ s$^{-1}$ photon flux at the plant canopy programmed for a 16-hour photoperiod.

Example 5

Evaluation of $F_2$ and BC Lines

To confirm that $F_1$ lines were uniform in response, *A. tuberculatus* plants from $F_1(S)$, $F_1(R)$, R-parent, or S-parent lines were treated with lactofen at 110 g ai ha$^{-1}$ plus 1% (by vol) COC when they were 10-12 cm in height. Plants were qualitatively assessed 15 days after treatment as either R or S, followed by removal of above-ground tissue, drying at 65° C. for at least three days, and weighing to obtain dry mass measurements. *A. tuberculatus* lines were evaluated in a completely randomized design with 100 replications (plants) per line. Dry weight measurements of lactofen-treated plants were compared with control plants from the same line that received an application of 1% (by vol) COC only. Data from $F_1$ lines were compared to the parental biotypes and analyzed using PROC GLM in SAS (SAS Systems Inc.) using single degree of freedom contrast statements.

When analyzed, the R parent and both $F_1$ lines were significantly different from the S-parent in their response to lactofen at 110 g ai ha$^{-1}$ (P<0.0001). Furthermore, both $F_1(S)$ and $F_1(R)$ lines were significantly different from the R-parent (P=0.0009 or P=0.0008, respectively), but were not different from one another (P=0.9790). Even though $F_1$ lines were significantly different from the R-parent when comparing mean responses, individual heterozygous plants could not be distinguished from homozygous R plants due to their wide overlap of responses (FIG. A6). These results demonstrated that treatments with lactofen at 110 g ai ha$^{-1}$ plus 1% (by vol) COC were able to distinguish lactofen-susceptible plants based on dry weights, and were useful for determining the inheritance of PPO inhibitor resistance in $F_2$ and backcrossed (BC) lines.

Inheritance of PPO inhibitor resistance was determined by evaluating R or S responses of plants from $F_2$ and BC lines 15 days after treatment with lactofen at 110 g ai ha$^{-1}$ plus 1% (by vol) COC. From each $F_2$ or BC line, 50 plants from each cross (including replicated crosses) were assessed in a completely randomized design. The entire experiment was conducted twice, with a total of 100 plants assessed from each cross. Responses of each cross were subjected to Chi-square analysis to determine if responses were due to the inheritance of a single genetic unit of inheritance. No differences were observed among replications of the same cross; therefore, data obtained from similar crosses were combined.

Alternatively, waterhemp plants from $F_1(S)$, $F_1(R)$, R-parent, or S-parent lines were treated with lactofen at 110 g ai ha$^{-1}$ plus 1% (by vol) COC when they reached 10-12 cm in height. Plants were qualitatively assessed 15 days after treatment as either R or S, followed by removal of above-ground tissue, drying at 65° C. for at least three days, and weighing to obtain dry mass measurements. Waterhemp lines were evaluated in a completely randomized design with 100 replications (plants) per line. Dry weight measurements of lactofen-treated plants were compared with control plants from the same line that received an application of 1% (by vol) COC only. Data from $F_1$ lines were compared to the parental biotypes and analyzed using PROC GLM in SAS software (SAS Institute, Cary, N.C.) using single degree of freedom contrast statements.

Example 6

Calculation of Degree of Dominance

*A. tuberculatus* plants from the $F_1(S)$ or $F_1(R)$ lines, including plants from the S or R parental biotypes, were treated with various rates of lactofen or acifluorfen to calculate dominance of PPO inhibitor resistance. Herbicides were applied at rates incrementally spaced along a base 10 logarithmic scale. Herbicide rates for acifluorfen and lactofen for each *A. tuberculatus* line were: 0.00022 to 220 g ai ha$^{-1}$ for the S-parent; 0.00022 to 22000 g ai ha$^{-1}$ for $F_1$s; and 0.0022 to 22000 g ai ha$^{-1}$ for the R-parent.

Herbicide treatment dispersions with acifluorfen or lactofen included 1% (by vol) COC. Herbicide dose-response experiments were conducted using a completely randomized design with six replications per treatment. Both sets of $F_1$s (including reciprocals) were used in dose-response experiments, thus constituting a complete replication. Above-ground tissue from all herbicide dose-response experiments with acifluorfen was harvested 10 days after treatment (DAT), while tissue treated with lactofen was harvested either 10 or 15 DAT. Plant material was dried at 65° C. for at least three days, and dry weights recorded. SAS was used to analyze differences between experimental runs using PROC GLM, and GR$_{50}$ (growth reduction by 50%) estimates were calculated using PROC NLIN using percent dry weight values compared with control plants (Seefeldt et al. 1995). Control plants from each *A. tuberculatus* line received a treatment solution containing 1% (by vol) COC only. The degree of dominance (D) for PPO inhibitor resistance was calculated using the formula $D=(2W_3-W_2-W_1)/(W_2-W_1)$, where $W_1=\log(GR_{50})$ of the S-parent, $W_2=\log(GR_{50})$ of the R-parent, and $W_3=\log(GR_{50})$ of the $F_1(S)$ or $F_1(R)$ lines (0 to 1=dominant; 0=partially dominant; 0 to −1=recessive) (Stone, 1968).

Waterhemp plants from the $F_1(S)$ or $F_1(R)$ lines, plus plants from the S or R parents, were treated with lactofen or acifluorfen when they reached 10 to 12 cm in height. Herbicides were applied at rates incrementally spaced along a base 10 logarithmic scale. Herbicide rates for acifluorfen and lactofen for each waterhemp line were: 0.00022 to 220 g ai ha$^{-1}$ for the S-parent; 0.00022 to 22000 g ai ha$^{-1}$ for $F_1$s; and 0.0022 to 22000 g ai ha$^{-1}$ for the R-parent. Herbicide treatment dispersions with acifluorfen or lactofen included 1.0% (by vol) COC.

Herbicide dose-response experiments were conducted using a completely randomized design with six replications per treatment. Both sets of $F_1$s (including reciprocals) were used in dose-response experiments, thus constituting a complete replication. Above-ground tissue from all herbicide dose-response experiments with acifluorfen was harvested 10 days after treatment (DAT), while those treated with lactofen were harvested either 10 or 15 DAT. Plant material was dried at 65° C. for at least three days, and dry weights recorded. SAS (statistical software package, SAS Institute Inc., Cary, N.C.) was used to analyze differences between experimental runs using PROC GLM, and GR$_{50}$ (growth reduction by 50%) estimates were calculated using PROC NLIN as described by Seefeldt et al. (1995) using percent dry weight values compared with control plants. Control plants from each waterhemp line received a treatment solution containing 1% (by vol) COC only. The degree of dominance (D) for PPO inhibitor resistance was calculated using the formula $D=(2W_3-W_2-W_1)/(W_2-W_1)$, where $W_1=\log(GR_{50})$ of the S-parent, $W_2=\log(GR_{50})$ of the R-parent, and $W_3=\log(GR_{50})$ of the $F_1(S)$ or $F_1(R)$ lines (0 to 1=dominant; 0=partially dominant; 0 to −1=recessive) (Stone 1968).

Example 7 cDNA Sequencing

Total RNA was isolated using young leaf tissue from a single plant from each of the R and S biotype (McCarty, 1986), followed by purification of mRNA (Promega, Madison, Wis.). Upon sequencing PPX2 from the S biotype, two transcripts were identified of different length; these were designated as PPX2S or PPX2L for short or long forms, respectively.

Purified mRNA was used to obtain full-length sequences of PPX1 or PPX2 using 5' and 3' RACE (Rapid Amplification of cDNA Ends, Invitrogen, Carlsbad, Calif.). Primers were designed based on conserved regions of nucleotide sequences of PPX1 or PPX2 from numerous plant species (Che et al. 2000; Horikoshi et al. 1999; Johnston et al. 1998; Lermontova et al. 1997; Narita et al. 1996; Watanabe et al. 2001). Sequencing of the resultant fragments facilitated the design of gene-specific primers for *A. tuberculatus* PPX1 and PPX2 that were used to obtain their full-length sequences.

Total RNA was individually isolated from three *A. tuberculatus* plants each of the R or S biotypes, and used to create cDNA in reactions with reverse transcriptase (Invitrogen). PCR was used to amplify PPX1, PPX2, or PPX2L with the following primers: PPX1, forward 5'-gagagagtgcgagagagat-gag-3' (SEQ ID NO:1) and reverse 5'-caagatgctggagccctat-tgac-3' (SEQ ID NO:2); PPX2, forward 5'-gccatcgccattgt-cagtttac-3' (SEQ ID NO:3) and reverse 5'-gaattacgcggtcttctcatccat-3' (SEQ ID NO:4); PPX2L, forward 5'-gacaaaattggattcagaatttagc-3' (SEQ ID NO:5) and reverse 5'-gaattacgcggtcttctcatccat-3' (SEQ ID NO:6). PCRs contained 1 µl cDNA, 400 nM each of forward and reverse primers, 0.2 mM each of dATP, dCTP, dGTP, and dTTP, 1.5 mM MgCl$_2$, and 1.0 unit of High Fidelity Taq polymerase (Roche Molecular Biochemicals, Indianapolis, Ind.) with a 1× concentration of supplied buffer in a final volume of 25 µl. The reactions were subjected to a 3 min incubation at 95° C.; 35 cycles of 0.5 min at 95° C., 1 min at 58° C., and 1.5 min at 72° C.; then 5 min at 72° C. Resultant PCR products were isolated by gel electrophoresis, sequenced (Patzoldt, 2001), and compared using both Sequencher 4.1™ (Gene Codes Corporation, Ann Arbor, Mich.) and online software (described in Thompson et al. 1994. Nucl. Acids Res. 22:4673-4690). Sequences among plants from the same biotypes were similar: therefore, only a single sequence is presented for each gene/biotype combination.

Example 8

Southern Blot

Genomic DNA (gDNA) was isolated from young leaves of *A. tuberculatus* plants from the S or R biotypes (Ausubel, 1999). PPO inhibitor responses of each plant were confirmed by treatment with lactofen at 175 g ai ha$^{-1}$ plus 1% (by vol) COC. Samples were prepared by digesting 7.5 µg gDNA with 100 units of either EcoRI or HindIII to completion, followed by separation in a 1% (by wt) agarose gel, and then transferred to a nylon membrane (Roche Molecular Biochemicals, Indianapolis, Ind.). The membrane was probed with a DIG-labeled (Roche Molecular Biochemicals) PCR fragment of PPX2L amplified from gDNA isolated from a single S plant. Hybridization and probe detection were performed following the manufacturer's instructions.

Example 9

PCR-Based Molecular Markers

Inheritance of PPX1 and PPX2L alleles in $BC_s$ progeny was studied by treating plants with lactofen at 110 g ai ha$^{-1}$ plus 1% (by vol) COC when they were 10-12 cm in height. Prior to lactofen applications, tissue samples were obtained from each plant to isolate DNA (Doyle and Doyle, 1990). PCR-based molecular markers were used to identify the parental origin (R or S) of the PPX alleles contributed by the $F_1$ male to the $BC_s$ progeny.

To differentiate R or S PPX1 alleles, a fragment of genomic PPX1 was amplified via PCR using the forward primer, 5'-tgataagtcgctcaatggaga-3' (SEQ ID NO:7), and reverse primer 5'-agatttgtagcacctccaatg-3' (SEQ ID NO:8), followed by BspDI digestion to identify S alleles (i.e., S PPX1 alleles contain a recognition sequence for BspDI, while R alleles do not).

To identify parent-specific PPX2L alleles, a fragment of genomic PPX2L was amplified via PCR using the forward primer, 5'-aagagacctcttgagggcttc-3' (SEQ ID NO:9), and reverse primer 5'-gaattacgcggtcttctcatccat-3' (SEQ ID NO:10), followed by Tfil digestion to identify S alleles (i.e., S PPX2L alleles contain a recognition sequence for Tfil, while R alleles do not). PCRs contained 40 ng total DNA, 400 nM each of forward and reverse primers, 0.2 mM each of dATP, dCTP, dGTP, and dTTP, 2.0 mM $MgCl_2$, and 1 unit of Taq polymerase (Invitrogen) with a 1× concentration of supplied buffer in a final volume of 20 µl. The reactions were subjected to a 3 min incubation at 95° C.; 40 cycles of 0.5 min at 95° C., 1 min at 60° C. or 64° C. for reactions with PPX1 or PPX2L primers, respectively, and 1.5 min at 72° C.; then 5 min at 72° C. Following PCR amplification, a mixture containing 0.5 unit of the appropriate restriction enzyme with a 1× concentration of supplied buffer in a final volume of 10 µl was added to each reaction. Digests with BspDI were incubated at 37° C. for four hrs, while digests with Tfil were incubated at 65° C. for two hrs. PCR products were fractionated in a 1% (by wt) agarose gel containing 0.5 µg ml$^{-1}$ ethidium bromide and visualized with ultraviolet light.

Example 10

PPX2L Genomic DNA Sequencing gDNA was isolated from leaf tissue of S or R plants (37) to sequence a portion of genomic PPX2L. Primers were designed that flanked the G210 codon of PP02L, then subsequent sequencing of amplified fragments facilitated the design of new primers until the exon containing the G210 codon was identified. Primer sets (A-D), starting with the largest fragment, were (forward then reverse): A, 5'-gccatcgc-cattgtcagtttac-3' (SEQ ID NO:3) and 5'-ggagcagtgacaacca-cagcatca-3' (SEQ ID NO:36); B, 5'-atcgatgatcttgggcttcgtg-3' (SEQ ID NO:37) and 5'-aatggtaaggagtcgcaccaac-3' (SEQ ID NO:38); C, 5'-cttcaaatcccgctgcacta-3' (SEQ ID NO:39) and 5'-tacttctggaaatgtatgg-3' (SEQ ID NO:40) and D, 5'-gagaaaa-cacaatgctactgaa-3' (SEQ ID NO:41) and 5'-acagcctcca-gaaaatgttg-3' (SEQ ID NO:42). PCR amplification, sequencing, and analysis were similar to the method used for cDNA sequencing of PPX genes.

Example 11

Functional Complementation

A shortened version of PPX2L from the S *A. tuberculatus* biotype was cloned into a pBAD-TOPO expression vector (Invitrogen) so that translation began at the second ATG start codon (+91). PPX2L cDNA was PCR-amplified using the forward primer 5'-caggaataagtaatgggcaacatttctgag-3' (SEQ ID NO:11) containing both a ribosome binding site (AGGA) and ATG start codon, and reverse primer 5'-gaagaattacgcg-gtcttctcatc-3' (SEQ ID NO:12) containing a stop codon. In order to create PPO inhibitor R and S plasmids that would encode proteins differing only in the presence/absence of G210, PPX2L was PCR-amplified from multiple cDNA samples and a region of the gene encompassing an approximately 500-bp XhoI/DraIII fragment was sequenced. The 3-bp polymorphism corresponding to the ΔG210 mutation was within this XhoI/DraIII fragment. Two XhoI/DraIII fragments were identified that were identical except for the presence/absence of the G210 codon and a C/T nucleotide polymorphism that was in the third position of a serine codon (and therefore did not alter the encoded protein). These two fragments were each used to replace the corresponding fragment in the pBAD-TOPO PPX2L construct. The region encompassing the replaced fragment was sequenced from the two resulting constructs to confirm the existence of the 3-bp polymorphism, and that no other polymorphisms were created during the cloning process.

Susceptible and R PPO plasmids were used to transform a hemG mutant strain of *E. coli*, SASX38 (Sasarman, 1979). The SASX38 *E. coli* strain was maintained on LB media supplemented with 20 µg ml$^{-1}$ hematin. Transformation-competent *E. coli* were prepared using $CaCl_2$ (Sambrook, 1989). Transformed colonies of SASX38 and non-transformed controls were tested for their ability to grow on LB media alone or supplemented with 20 µg ml$^{-1}$ hematin or with the PPO inhibitor lactofen ranging from 0.01 to 100 µM, and incubated at 37° C. for 14 hrs.

Example 12

Herbicide-Tolerant Plants by Overexpression of Plant PPO Genes

To express the herbicide resistant PPO from waterhemp in transgenic plants, the appropriate full length cDNA is inserted into a plant expression vector, desirably under the regulatory control of a plant expressible, constitutive promoter and desirably a binary vector suitable for *Agrobacterium tumefaciens* mediated transformation of plant cells, plant tissue. The resulting plasmid is transformed into a suitable *A. tumefaciens* strain. See, e.g. Uknes et al. 1993. Plant Cell 5:159-169.

Leaf disks of *Nicotiana tabacum* cv. Xanthi-nc are infected with *A. tumefaciens* harboring the herbicide resistant PPO expression vector generally as described by Horsch et al. 1985. Science 227: 1229. Kanamycin-resistant shoots from 15 independent leaf disks are transferred to rooting medium, transplanted to soil and the resulting plants are grown to maturity in the greenhouse. Seeds from these plants are collected and germinated on MS agar medium containing kanamycin. Multiple individual kanamycin resistant seedlings from each independent primary transformant are grown to maturity in the greenhouse, and their seed collected. These seeds are germinated on MS agar medium containing kanamycin.

Plant lines that give rise to exclusively kanamycin resistant seedlings are homozygous for the inserted gene and are subjected to further analysis. Leaf disks of each of the 15 independent transgenic lines are excised with a paper punch and placed onto MS agar containing various increasing concentrations of a PPO inhibitory herbicide. After three weeks, two sets of 10 disks from each line are weighed, and the results recorded. Transgenic lines more resistant to the inhibitor than wild type (non-transformed) plants are selected for further analysis.

RNA is extracted from leaves of each of these lines. Total RNA from each independent homozygous line, and from non-transgenic control plants, is separated by agarose gel electrophoresis in the presence of formaldehyde (Ausubel et al. 1989. Current Protocols in Molecular Biology, Wiley & Sons, New York). The gel is blotted to nylon membrane (Ausubel et al., supra.) and hybridized with the radiolabeled *Arabidopsis* protox cDNA. Hybridization and washing conditions are as described by Church and Gilbert. 1984. Proc. Natl. Acad. Sci. USA 81:1991-1995. The filter is analyzed by autoradiography, and intense RNA bands corresponding to the protox transgene are detected in all herbicide-tolerant transgenic plant lines.

To further evaluate resistance of the protox-overexpressing line, plants are grown in the greenhouse and treated with various concentrations of a protox-inhibiting herbicide.

Example 13

Growth of Tobacco Cells in Suspension Culture Media

MX1 medium consists of Murashige and Skoog ("MS", T. Murashige et al. 1962. Physiol. Plant. 15:473-497) major salts, minor salts and Fe-EDTA (Gibco #500-1117; 4.3 g/l), 100 mg/l myo-inositol, 1 mg/l nicotinic acid, 1 mg/l pyridoxine-HCl, 10 mg/l thiamine—HCl, 2-3 g/l sucrose, 0.4 mg/l 2,4-dichlorophenoxyacetic acid, and 0.04 mg/l kinetin, pH 5.8. The medium is sterilized by autoclaving.

N6 medium comprises macroelements, microelements and Fe-EDTA as described by C-C. Chu et al. 1075. Scientia Sinica 18:659, and the following organic compounds: pyridoxine-HCl (0.5 mg/l), thiamine-HCl (0.1 mg/l), nicotinic acid (0.5 mg/l), glycine (2.0 mg/l), and sucrose (30.0 g/l). The solution is autoclaved. The final pH is 5.6.

Macroelements are made up as a 10× concentrated stock solution, and microelements as a 1000× concentrated stock solution. Vitamin stock solution is normally prepared 100× concentrated. Suspension cultured cells of *Nicotiana tabacum*, line S3, are grown in liquid culture medium MX1. 100 ml Erlenmeyer flasks containing 25 ml medium MX1 are inoculated with 10 ml of a cell culture previously grown for 7 days. Cells are incubated at 25° C. in the dark on an orbital shaker at 100 rpm (2 cm throw). Cells are subcultured at 7 day intervals by inoculating an aliquot sample into fresh medium, by decanting or pipetting off around 90% of the cell suspension followed by replenishing fresh medium to give the desired volume of suspension. 5-8 grams of fresh weight cell mass are produced within 10 days of growth from an inoculum of 250-350 mg cells.

Example 14

Production of Tobacco Cell Cultures Tolerant to Herbicidal PPO

Inhibitors by Plating Cells on Solidified Selection Medium

Cells are pregrown and harvested by allowing cells to sediment, or by brief centrifugation at 500×g, and the spent culture medium is removed. Cells are then diluted with fresh culture medium to give a cell density suitable for cell plating, about 10,000 colony forming units per ml. For plating, cells in a small volume of medium (approx. 1 ml) are evenly spread on top of solidified culture medium (MX1, 0.8% agar) containing the desired concentration of the inhibitor. About 20-30 ml of medium are used per 10 cm Petri plate. The suitable inhibitor concentration is determined from a dose-response curve, and is at least twofold higher than the $IC_{50}$ of sensitive wild-type cells. Transgenic plant cells carrying either the wild type waterhemp or the resistant waterhemp PPO are compared with respect to their properties.

Culture plates containing cells spread onto selection medium are incubated under normal growth conditions at 25-28° C. in the dark until colonies are formed. Emerging colonies are transferred to fresh medium containing the inhibitor in the desired concentration. In a modification of the described method, the pregrown suspension of cultured cells is first spread in a small volume of liquid medium on top of the solidified medium. An equal amount of warm liquid agar medium (1.2-1.6% agar) kept molten at around 40° C. is added and the plate gently but immediately swirled to spread the cells evenly over the medium surface and to mix cells and agar medium, before the medium solidifies.

Alternatively, the cells are mixed with the molten agar medium prior to spreading on top of the selection medium. This method has the advantage that the cells are embedded and immobilized in a thin layer of solidified medium on top of the selection medium. It allows for better aeration of the cells as compared to embedding cells in the whole volume of 20-30 ml.

Example 15

Production of Tobacco Cell Cultures Tolerant to an Herbicidal PPO Inhibitor by Growing Cells in Liquid Selection Medium Cells cultured as described above are inoculated at a suitable cell density into liquid medium MX1 containing the desired concentration of an herbicidal PPO inhibitor. Cells are incubated and grown as described above. Cells are subcultured, as appropriate depending on the rate of growth, using fresh medium containing the desired inhibitor concentration after a period of 7-10 days. Depending on the inhibitor concentration used, cell growth may be slower than in the absence of inhibitor.

Example 16

Production of Tobacco Cells with Enhanced Levels of PPO Enzyme

To obtain cell cultures or callus with enhanced levels of an herbicide resistant PPO of the present invention, transgenic suspension cultures or callus are transferred, in a step-wise manner, to increasingly higher concentrations of an herbicidal PPO inhibitor. In particular, the following steps are performed:

Colonies emerging from plated cells are transferred to liquid MX1 medium containing the same concentration of PPO inhibitor as used in the selection described above in order to form suspension cultures. Alternatively, selected cell suspension cultures are subcultured in liquid MX1 medium containing the same concentration of PPO inhibitor as used for selection as set forth above.

Cultures are subcultured 1-20 times at weekly intervals, and they are then subcultured into MX1 medium containing the next higher herbicide concentration. The cells are cultured for 1-10 subcultures in medium containing this higher concentration of herbicide. The cells are then transferred to MX1 medium containing the next higher concentration of herbicide.

Alternatively, pieces of selected transgenic callus are transferred to solidified MX1 medium supplemented with the desired herbicide concentration. Transfer to higher herbicide concentrations follows the procedure outlined in the preceding paragraph except that solidified medium is used.

Example 17

Herbicide Dose-Dependent Growth of Cells in Suspension Cultures

To establish a dose-response curve, the growth of cells in medium in the presence of different concentrations of herbicide is determined. Suspension culture cells of herbicidal PPO inhibitor sensitive wild-type tobacco cells S3 and herbicide tolerant transgenic cells are pregrown in liquid medium at high cell density for 2-4 days. The cells are washed free of spent medium; fresh medium without herbicide is added to give the desired cell density (about 150 mg fresh weight, FW) cells per ml of suspension). A 2.5 ml aliquot of cell suspension, containing approx. 250-300 mg fresh weight (FW) cells, is inoculated into about 30 ml of liquid medium with the desired herbicide concentration contained in a 100 ml Erlenmeyer flask. Care is taken to inoculate the same amount of cells into each flask. Each flask contains an equal volume of medium. 3-6 replicate flasks are inoculated per herbicide concentration. The herbicide concentrations are zero (=control), 0.1 ppb, 0.3 ppb, 1 ppb, 3 ppb, 10 ppb, 30 ppb, 100 ppb, 300 ppb, 1000 ppb, 3000 ppb, and 10,000 ppb. Samples of inoculum are also analyzed to determine the mass of cells inoculated per flask.

Cells are then incubated for growth under controlled conditions at 28° C. in the dark for 10 days. The cells are harvested by pouring the contents of each flask onto a filter paper disk attached to a vacuum suction device to remove all liquid and to obtain a mass of reasonably dry fresh cells. The fresh mass of cells is weighed. The dry weight of samples may be obtained after drying.

Cell growth is determined and expressed as relative cell gain within 10 days and expressed as a percentage relative to cells grown in the absence of herbicide according to the formula: (final mass of herbicide-grown cells minus inoculum mass.times.100 divided by final mass of cells grown without herbicide minus inoculum mass). $IC_{50}$ values are determined from graphs of plotted data (relative cell mass vs. herbicide concentration). $IC_{50}$ denotes the herbicide concentration at which cell growth is 50% of control growth (cells grown in the absence of herbicide).

In a modification of the method several pieces of transgenic callus derived from a herbicide resistant cell culture, obtained as described above, are transferred to solidified callus culture medium containing the different herbicide concentrations. Relative growth is determined after a culture period of 2-6 weeks by weighing callus pieces and comparing to a control culture grown in medium without herbicide. However, the suspension culture method has its greater accuracy.

Example 18

Determination of Cross Tolerance

To determine the extent at which cells show tolerance to analogous or other herbicides, cells are grown in increasing concentrations of chosen herbicides. The relative growth of the cells and their $IC_{50}$ value is determined for each herbicide for comparison.

Example 19

Determining the Stability of the Herbicide Tolerance Phenotype

To determine whether the herbicide resistant phenotype of a cell culture is maintained over time, cells are transferred from herbicide-containing medium to medium without herbicide. Cells are grown as described above in the absence of herbicide for a period of 3 months, employing regular subcultures at suitable intervals (7-10 days for suspension cultures; 3-6 weeks for callus cultures). A known quantity of cells is then transferred back to herbicide-containing medium and cultured for 10 days (suspension cultures) or 4 weeks (callus cultures). Relative growth is determined as described above.

Example 20

Production of Herbicide Resistant Corn

Ears are harvested from self pollinated corn plants of a line of corn susceptible to transformation and regeneration 12-14 days post pollination. Husks are removed, and the ears are sterilized for about 15 minutes by shaking in a 20% solution of commercial bleach (5% sodium hypochlorite) solution with detergent added for better wetting. Ears are then rinsed several times with sterile water. All further steps are performed aseptically in a sterile air flow hood. Embryos (1.5-2.5 mm in length) are removed from the kernels with a spatula and placed, embryo axis downward, onto solid MS culture medium containing 2 mg/l 2,4-dichlorophenoxyacetic acid (2,4-D), 3% sucrose, solidified with 0.24% gellan gum.

Embryogenic callus forms on the scutellum tissue of the embryos within 2-4 weeks of culture at about 28° C. in the dark. The callus is removed from the explant and transferred to fresh solidified MS medium containing 2 mg/l 2,4-D. The subculture of embryogenic callus is repeated at weekly intervals. Only callus portions having an embryogenic morphology are subcultured. The cultured callus tissue is transformed with the resistant PPO of the present invention.

Plants are regenerated from the selected embryogenic callus cultures by transferring to fresh regeneration medium. Regeneration media used are: ON6 medium consisting of N6 medium lacking 2, 4-3, or N61 consisting of N6 medium containing 0.25 mg/l 2,4-D and 10 mg/l kinetin (6-furfurylaminopurine), or N62 consisting of N6 medium containing 0.1 mg/l 2,4-D and 1 mg/l kinetin, all solidified with 0.24% gellan gum. Cultures are grown at 28° C. in the light (16 h per day of 10-100 µEinsteins/m$^2$ sec from white fluorescent lamps). The cultures are subcultured every two weeks onto fresh medium. Plantlets develop within 3 to 8 weeks. Plantlets at least 2 cm tall are removed from adhering callus and transferred to root promoting medium. Different root-promoting media are used. The media consist of N6 or MS medium lacking vitamins with either the usual amount of salts or with salts reduced to one half, sucrose reduced to 1 g/l, and further either lacking growth regulating compounds or containing 0.1 mg/l α-naphthaleneacetic acid. Once roots are sufficiently developed, plantlets are transplanted to a potting mixture consisting of vermiculite, peat moss and garden soil. At transplanting all remaining callus is trimmed away, all agar is rinsed off and the leaves are clipped about half. Plantlets are grown in the greenhouse initially covered for some days with an inverted clear plastic cup to retain humidity and grown with shading. After acclimatization plants are repotted and grown to maturity. Fertilizer Peters 20-20-20 is used to ensure healthy plant development. Upon flowering plants are pollinated, preferably self pollinated.

As an alternative, the following protocol is used to produce herbicide resistant corn using a resistance gene of the present invention. *Agrobacterium* cells harboring the waterhemp herbicide resistance sequence of the present invention on a plasmid are grown in YP medium supplemented with appropriate antibiotics for 1-3 days. A loop of *Agrobacterium* cells is collected and suspended in 2 ml M-LS-002 medium (LS-inf) and the tube containing *Agrobacterium* cells is kept on a shaker for 1-3 hrs at 1,200 rpm.

Corncobs of genotype J553x(HIIIAxA188) are harvested at 7-12 days after pollination. The cobs are sterilized in a 20% Clorox solution for 15 min followed by thorough rinsing with sterile water. Immature embryos with size 0.8-2.0 mm are dissected into the tube containing *Agrobacterium* cells in LS-inf solution.

Agro-infection is carried out by keeping the tube horizontally in the laminar hood at room temperature for 30 min. The *Agrobacterium* infection mixture is poured on to a plate containing the co-cultivation medium (M-LS-011). After the liquid agro-solution is removed (using a pipette, for example), the embryos are plated on the co-cultivation medium with scutellum side up and cultured in the dark at 22° C. for 2-4 days.

Embryos are transferred to M-MS-101 medium without selection. Seven to ten days later, embryos are transferred to M-LS-401 medium containing 0.75 uM imazethapyr (or lactofen) and grown for 4 weeks to select for transformed callus cells.

Plant regeneration is initiated by transferring resistant calli to M-LS-504 medium supplemented with 0.75 µM imazethapyr (or lactofen) and grown under light at 26° C. for two to three weeks. Regenerated shoots are then transferred to a rooting box with M-MS-607 medium (0.5 µM imazethapyr or lactofen).

Plantlets with roots are transferred to potting mixture and grown in a growth chamber for a week, then transplanted to larger pots and maintained in a greenhouse till maturity.

Example 21

Production of Herbicide Tolerant Plants by Overexpression of PPO Sequences

The wild-type and the resistant waterhemp PPO coding sequences are excised by restriction endonuclease digestion and cloned into a suitable plant vector, for example, the binary vector pCIB200. These binary plasmids are transformed by electroporation into *Agrobacterium* and then into *Arabidopsis thaliana* using the vacuum infiltration method (Bechtold et al., 1993). Transformants are selected on kanamycin, and T2 seed is generated from a number of independent lines. This seed is plated on GM media containing various concentrations of PPO-inhibiting herbicide and scored for germination and survival. Multiple transgenic lines overexpressing either the wild type or the resistant mutant PPO enzyme produce significant numbers of green seedlings on an herbicide concentration that is lethal to the empty vector control.

Example 22

Production of Transgenic Herbicide Resistant *Arabidopsis*

Reverse transcription PCR (RT-PCR) products from resistant and sensitive biotypes were used as template for cloning the resistant and sensitive genes through PCR amplifications. These amplifications were performed using the ligation independent cloning (LIC) adapted oligonucleotide primers specific to PPX2L, P1 and P2, and cloned into the LIC site of a plant transformation vector, using techniques known to those skilled in the art. These primers used in these experiments were as follows: P1, TTGCTCTTCCATGGTAATTCAATC-CATTAC, SEQ ID NO:49; P2, TTGCTCTTCGTTACGCG-GTCTTCTCATCCATC, SEQ ID NO:50; P3, CATCGAT-CAAACTCGAGACCTCTGCCTCACTTTC, SEQ ID NO:51; P4, GAGGCAGAGGTCTCGAGTTTGATCGAT-GATCTTG, SEQ ID NO:52; P5, TTCACCAAGCTGTTTG-CACATTGTGTCAACAAGTGTCT, SEQ ID NO:53; and P6, AGACACTTGTTGACACAATGTGCAAA-CAGCTTGGTGAA, SEQ ID NO:54. These plant transformation vectors contained an imidazolinone tolerant *Arabidopsis* AHAS large subunit gene under the control of the actin promoter and octopine synthase terminator, which allowed selection on Pursuit (imazethapyr) for all transformants, especially for selection of lactofen sensitive transformants. For expression of the resistant and sensitive genes in *Arabidopsis*, the coding sequences for each resistant or sensitive gene were inserted after the parsley ubiquitin promoter and before the nopaline synthase terminator. Several clones each of susceptible and resistant PPX2L were obtained from different biotype isolates and each was sequenced.

In addition, a chimeric "SRS" gene (see SEQ ID NO:45), which has the 5' end of the susceptible coding sequence up to the unique XhoI site, the internal XhoI to DraIII fragment of the resistant coding sequence containing the resistance mutation, and the 3' end of the susceptible from the unique DraIII site to the stop codon, was produced by amplifying sensitive RT-PCR template with P1 and P3 as well as with P6 and P2. Resistant template was also amplified with P4 and P5. These amplicons were digested with XhoI and DraIII and purified, then ligated. The ligation reaction was cloned into the LIC site of the plant transformation vector, as above.

Three vector plasmids were constructed: VC-MBW101-1, containing the susceptible version of the PPX2L gene (SEQ ID NO:47); VC-MBW102-1, containing the resistant version of the PPX2L gene (SEQ ID NO:25); and VC-MBW103-1, containing the SRS version of the PPX2L gene (SEQ ID NO:45); All three of these plasmids were transformed into *Agrobacterium tumefaciens*. as follows:

1-5 ng of the plasmid DNA isolated was transformed by electroporation into competent cells of *Agrobacterium tumefaciens*, of strain GV 3101 pMP90 (Koncz and Schell. 1986. Mol. Gen. Gent. 204:383-396). Thereafter, complete medium (YEP) was added and the mixture was transferred into a fresh reaction vessel for 3 hours at 28° C. Thereafter, all of the reaction mixture was plated onto YEP agar plates supplemented with the respective antibiotics, e.g. rifampicin (0.1 mg/ml), gentamicin (0.025 mg/ml and kanamycin (0.05 mg/ml) and incubated for 48 hours at 28° C. The agrobacterial cells containing the desired, relevant plasmid constructs were then used for the transformation of plants.

A colony was picked from the agar plate with the aid of a pipette tip and taken up in 3 ml of liquid TB medium, which also contained suitable antibiotics as described above. This preculture was grown for 48 hours at 28° C. and 120 rpm.

400 ml of LB medium containing the same antibiotics as above were used for the main culture. The preculture was transferred into the main culture. It was grown for 18 hours at 28° C. and 120 rpm. After centrifugation at 4 000 rpm, the pellet was resuspended in infiltration medium (MS medium, 10% sucrose).

In order to grow the plants for the transformation, dishes (Piki Saat 80, green, provided with a screen bottom, 30×20× 4.5 cm, from Wiesauplast, Kunststofftechnik, DE) were half-filled with a GS 90 substrate (standard soil, Werkverband E.V., Germany). The dishes were watered overnight with 0.05% Proplant solution (Chimac-Apriphar, BE). *Arabidopsis thaliana* C24 seeds (Nottingham *Arabidopsis* Stock Centre, UK; NASC Stock N906) were scattered over the dish, approximately 1 000 seeds per dish. The dishes were covered with a hood and placed in the stratification facility (8 h, 110 µmol/m2/s-1, 22° C.; 16 h, dark, 6° C.). After 5 days, the dishes were placed into the short-day controlled environment chamber (8 h 130 µmol/m2/s-1, 22° C.; 16 h, dark 20° C.), where they remained for approximately 10 days until the first true leaves had formed.

The seedlings were transferred into pots containing the same substrate (Teku pots, 7 cm, LC series, manufactured by Poppelmann GmbH & Co, DE). Five plants were picked out into each pot. The pots were then returned into the short-day controlled environment chamber for the plant to continue growing.

After 10 days, the plants were transferred into the greenhouse cabinet (supplementary illumination, 16 h, 340 µE, 22° C.; 8 h, dark, 20° C.), where they were allowed to grow for further 17 days.

For the transformation, 6-week-old *Arabidopsis* plants, which had just started flowering were immersed for 10 seconds into the above-described agrobacterial suspension which had previously been treated with 10 µl Silwett L77 (Crompton S. A., Osi Specialties, CH). The method is described in Clough and Bent. 1998. Plant J. 16:735-743.

The plants were subsequently placed for 18 hours into a humid chamber. Thereafter, the pots were returned to the greenhouse for the plants to continue growing. The plants remained in the greenhouse for another 10 weeks until the seeds were ready for harvesting. Seeds harvested from these plants are the T1 seed generation.

These T1 generation seeds, which represented a collection of a few transformed seeds in a population of untransformed seeds, were sterilized by liquid sterilization (rinsing in a solution of 400 mL of ddH2O+100 mL of bleach+250 uL of 20% SDS, followed by rinsing in sterile distilled water).

These T1 seeds were put into 0.8% agarose and plated onto MS media with 1% sucrose, Cefotaxmine (500 ug/mL) and benomyl (2 ug/mL). For selection of transformants, these contained either 100 nM Pursuit (imazethapyr), 70 nM Cobra (lactofen) or 125 nM Cobra. *Arabidopsis* ecotype Columbia-0 (Co10) was also plated as a control on all types of plates and the imidazolinone tolerant mutant csr1-2 was plated on Pursuit plates as a positive control. The seeds were stratified on the plates for three days at 4° C.

The plates were then incubated in a Percival Scientific (Perry, Iowa) growth chamber at 21-22° C. and 15 hours of light for six days and scored for viable seedlings on the selective plates. The results are given in Table 18.

TABLE 18

Results of Plant Transformation Experiment. Seeds able to germinate on the herbicide-containing medium are those which contain and express the herbicide resistant PPX2L coding sequence.

| T1 Seed Description | Number of Seeds plated on 70 nM Lactofen | Number of Germinated Seedlings on 70 nM lactofen | Number of Seeds plated on 125 nM Lactofen | Number of Germinated Seedlings on 125 nM Lactofen | Number of Germinated Seedlings on Imazethapyr | Calculated Number of Germinated Seedlings per 1000 Seeds for both rates of Lactofen |
|---|---|---|---|---|---|---|
| Columbia-0 (untransformed control) | 884 | 0 | 600 | 0 | 0 | 0 |

TABLE 18-continued

Results of Plant Transformation Experiment. Seeds able to germinate on the herbicide-containing medium are those which contain and express the herbicide resistant PPX2L coding sequence.

| T1 Seed Description | Number of Seeds plated on 70 nM Lactofen | Number of Germinated Seedlings on 70 nM lactofen | Number of Seeds plated on 125 nM Lactofen | Number of Germinated Seedlings on 125 nM Lactofen | Number of Germinated Seedlings on Imazethapyr | Calculated Number of Germinated Seedlings per 1000 Seeds for both rates of Lactofen |
|---|---|---|---|---|---|---|
| PPX2L Resistant plasmid, transformation set 1 | 640 | 4 | 560 | 4 | 9 | 7 |
| PPX2L Resistant plasmid, transformation set 2 | 1276 | 3 | 1152 | 4 | 9 | 3 |
| PPX2L Resistant plasmid, transformation set 3 | 980 | 3 | 1664 | 1 | 6 | 2 |
| PPX2L "SRS" plasmid, transformation set 4-390 | 1176 | 14 | 1160 | 6 | 10 | 9 |
| PPX2L "SRS" plasmid, transformation set 4-414 | 1036 | 7 | 880 | 2 | 11 | 5 |
| PPX2L Susceptible plasmid, transformation set 4-291 | 500 | 0 | 680 | 0 | 4 | 0 |
| PPX2L Susceptible plasmid, transformation set 5 | 460 | 1 | 764 | 0 | 12 | 1 |

The numbers of seeds were the raw counts of actual seeds on the selection plates. The numbers of seedlings were the number of green seedlings found on each plate, indicative of resistance to the selective agent (lactofen or imazethapyr). If there were no seedlings, there were no resistant plants. Only the "resistant" forms of PPX2L conferred lactofen tolerance, confirming that the isolated PPX2L coding sequence from the herbicide resistant waterhemp was sufficient to confer the PPO-inhibiting herbicide resistance phenotype on transgenic plants into which the plant expressible sequence was introduced. The seed number for imazethapyr was not shown; rather, the seedling number from approximately 1000 seeds is indicated in the table. Plants obtained from the imazethapyr selection indicated the presence of transformed seeds with the sensitive form of PPX2L. Without wishing to be bound by any particular theory, the single seedling on transformation set 5 is believed to have been a stray resistant transformant. These data demonstrate that the resistant form of PPX2L conferred resistance to a PPO inhibiting herbicide, lactofen, to the transgenic plants expressing the resistant PPX2L.

Example 23

Genetic Engineering of Herbicide Resistant Tobacco

*N. tabacum* plant cells in culture are collected and prepared for biolistic transformation. Reference is made to the second sequence comparison in Table 20 herein above. One Glycine codon determining the underline Glycine pair is deleted in the sequence encoding this portion of the PPO protein which is embodied in the recombinagenic oligonucleotide. Particles are coated with recombinagenic oligonucleotide designed to introduce the herbicide resistance deletion mutation of the present in the PPO coding sequence, and they are introduced into the cells by biolistic transformation. Herbicide resistant cells are selected and cultured, and then plants are regenerated from those selected cells. Conventional screening and breeding techniques are employed to produce plants that are homozygous for this genetic trait. These plants can be used in improved production, in that treating with a PPO-inhibiting herbicide will not damage these plants, but will curtail the growth of herbicide sensitive weeds.

Example 24

Relationship of PPX2S and PPX2L

Segregation analysis was used to examine the genetic relationship between PPX2S and PPX2L. Total DNA was extracted from young leaf tissue using a modified hexadecyl-trimethyl-ammonium bromide (CTAB) protocol as in Doyle and Doyle (1990). A fragment of PPX2 genomic DNA (gDNA) was amplified via polymerase chain reaction (PCR) using primers designed to amplify both PPX2S and PPX2L: PPX-CAPS-F, 5'-atgggcaacatttctgagcgg-3' (SEQ ID NO:79), and PPX-CAPS-R, 5'-tgcctccagctctagaatcagctt-3' (SEQ ID NO:80). PCRs contained about 100 ng total gDNA, 300 nM each of forward and reverse primers, 0.2 mM dNTPs, 2.5 mM $MgCl_2$, and 1 unit of Taq polymerase3 in 1×PCR buffer. The resulting product was digested with Fok14 to differentiate between PPX2S and PPX2L. The products were separated in 4% agarose gel containing 0.5 μg ml-1 ethidium bromide and visualized with ultraviolet light. A single nucleotide polymorphism (SNP) in PPX2S introduced an extra FokI site in this gene. Using this marker, individuals from a herbicide-sensitive population from Wayne County, IL (WCS) (Patzoldt et al.

2006) were screened to identify plants testing positive for both PPX2S and PPX2L markers. A single male and multiple female plants with this genotype were allowed to cross. Two of the resultant F1 populations were tested for segregation of the SNP marker. Results were subjected to Chi-square analysis to determine if the results fit a single gene model.

Example 25

Sequencing 5' End of PPX2

Sequence analysis of a gDNA fragment containing the 5' end of PPX2 alleles was used to identify two in-frame start codons indicative of PPX2L. PCR was used to amplify this fragment from two WCS individuals, an individual from a herbicide-resistant population from Adams County, IL (ACR) (Patzoldt et al. 2006), and an F1 individual from the cross used for the PPX2 allele test that was determined to be homozygous for the PPX2S marker. PCRs were performed utilizing a primer designed from the 5'-UTR sequence of grain amaranth cv. 'Plainsman' (*Amaranthus hypochondriacus* L.) gDNA (provided by Jeff Maughan, Brigham Young University), PPX-5'-F, 5'-cacgttttgcacccaaacta-3' (SEQ ID NO:81), in conjunction with PPX-CAPS-R (SEQ ID NO:80). PCR conditions were 2 minutes at 95 C followed by 37 cycles of 0.5 min at 95 C, 0.5 min at 55 C and 1.5 min at 72 C. The products were separated by gel electrophoresis then sequenced as described previously (Patzoldt et al. 2006).

Example 26

Testing Deletion-Specific PCR Marker

Inheritance of the ΔG210 PPX2L allele in F2 progeny from an ACR X WCS cross was studied by treating two replicates of 36 plants with 110 g ai ha-1 lactofen plus 1% COC. Fourteen DAT the plants were visually scored for herbicide damage. DNA was isolated from tissue samples taken prior to herbicide treatment. An allele-specific PCR marker was used to test for the presence of ΔG210. PCR with primers PPX2LR-F, 5'-tgttgcgggtacatgtgga-3' (SEQ ID NO:82), and PPX2LR-R, 5'-tacttctggaaatgtatgg-3' (SEQ ID NO:83), amplifies only the ΔG210 allele of PPX2L.

Products were fractionated in 2% agarose gel containing 0.5 μg ml-1 ethidium bromide and visualized with ultraviolet light. PCR assay data were compared to visual herbicide ratings. After this marker was tested on a segregating F2 population of known resistance mechanism, the assay was applied to other resistant populations where the resistance mechanism was unknown. Two replicates of six plants each from four suspected resistant populations and three sensitive populations were processed in the same manner as outlined for the F2 population.

REFERENCES CITED IN THE TEXT OF THE APPLICATION

*Arabidopsis* Genome Initiative. (2000). Analysis of the genome sequence of the flowering plant *Arabidopsis thaliana*. Nature 408:796-815.

Beale, S. I. and J. D. Weinstein. 1990. Tetrapyrrole metabolism in photosynthetic organisms in Biosynthesis of heme and chlorophylls (ed. by H. A. Dailey). McGraw-Hill, New York. pp. 287-391.

Bevan, M. W. (1984). Binary *Agrobacterium* vectors for plant transformation. *Nucl. Acids Res.* 12:8711-8721.

Chabregas, S. M., Luche, D. D., Farias, L. P., Ribeiro, A. F., van Sluys, M. A., Menck, C. F., and Silva-Filho, M. C. (2001). Plant Mol. Biol. 46:639-650.

Che, F. S., N. Wantanabe, M. Iwano, H. Inokuchi, S. Takayama, S. Yoshida, and A. Isogai. 2000. Plant Physiol. 124:59-70.

Choi K. W. et al. 1998. Biosci. Biotech. Biochem. 62:558-560.

Chow, K. S. et al. 1997. J. Biol. Chem. 272:27565-27571.

Cox, G. S. and D. G. Whitten. 1983. Excited state interactions of protoporphyrin 1× and related porphyrins with molecular oxygen in solutions and organized assemblies, in Porphyrin photosensitization (ed. by D. Kessel and T. J. Dougherty). Plenum Press, New York, N.Y.

Dayan, F. E. and S. O. Duke. 1997. Phytotoxicity of protoporphyrinogen oxidase inhibitors: phenomenology, mode of action and mechanisms of resistance, in Herbicide activity: toxicology, biochemistry and molecular biology (ed. by R. M. Roe, J. D. Burton and R. J. Kuhr) IOS Press, Amsterdam, Netherlands. pp 11-36.

Deybach, J. C. et al. 1985. Eur. J. Biochem. 149:431-435.

Doyle, J. J. and J. L. Doyle. 1990. Focus 12:13-15.

Duke, S. O. et al. 1997. Mechanisms of resistance to protoporphyrinogen oxidase-inhibiting herbicides in Weed and crop resistance to herbicides (ed. by R. De Prado, J. Jorrin, and L. Garcia-Torres). Kluwer Academic Publishers. Netherlands. pp. 155-160.

Duke, S. O., Lydon, J., Becerril, J. M., Sherman, T. D., Lehnen, L. P., & Matsumoto, H. 1991. Weed Sci. 39: 465-473.

Emanuelsson, O., H. et al. 2000. J. Mol. Biol. 300:1005-1016.

Ha, S. B., Lee, S. B., Lee, Y., Yang, K., Lee, N., Jang, S. M., Chung, J. S., Jung, S., Kim, Y. S., Wi, S. G., and Back, K. 2004. Plant Cell Environ. 27: 79-88.

Horikoshi, M. and T. Hirooka. 1999. Pestic. Sci. 24:13-16.

Horikoshi, M., K. et al. 1999. *Nicotiana tabacum* protoporphyrinogen oxidase PX-2 mRNA. GenBank Accession No. AF044129.

Jacobs, J. M. and N. J. Jacobs. 1984. Arch. Biochem. Biophys. 229:312-319.

Jacobs, J. M. and N. J. Jacobs. 1993. Plant Physiol. 101:1181-1187.

Johnson, D. J. et al. 1998. Plant Physiol. 118:330-330.

Jung, S., Lee, Y., Yang, K., Lee, S. B., Jang, S. M., Ha, S. B. and Back, K. 2004. Plant Cell Environ. 27, 1436-1446.

Kashi, Y. and King, D. G. 2006. Trends Genetics 22: 253-259.

Koch, M., C. et al. 2004. EMBO 23:1720-1728.

Kojima, S. et al. 1991. Weed Res. 36:318-323.

Lee, H. J. et al. 1993. Plant Physiol. 102:881-889.

Lee, H. J. and S. O. Duke. 1994. J. Agric. Food Chem. 42:2610-2618.

Lee, H. J. et al. 2000. Plant Cell Physiol. 41:743-749.

Lee, Y., Jung, S., & Back, K. (2004) Pestic. Biochem. Physiol. 80, 65-74.

Lermontova, I. and B. Grimm. 2000. Plant Physiol. 122:75-83.

Lermontova, I. et al. 1997. PNAS 94:8895-8900.

Li, X. and D. Nicholl. 2005. Pest Manag. Sci. 61:277-285.

Li, X. et al. 2003. Plant Physiol. 133:736-747.

Li, J., Smeda, R. J., Nelson, K. A., and Dayan, F. E. (2004) Weed Sci. 52: 333-338.

Martz, E. 2002. Trends Biochem. Sci. 27: 107-109.

Matringe, M. et al. 1992. J. Biol. Chem. 267:4646-4651.

Matsunaka, S. (1976) in Herbicides: chemistry, degradation, and mode of action, vol 2, eds. Kearney, P. C. and Kaufman D. D. (Marcel-Dekker, New York), pp. 709-739.

McCarty, D. R. 1986. Maize Genetics Coop. Newslett. 60:61.

Narita, S. et al. 1996. Gene 182:169-175.

Papenbrock, J. and B. Grimm. 2001. Planta 213:667-681.
Patzoldt, W. L. et al. 2005. Weed Sci. 53:30-36.
Patzoldt, W. L. et al. 2002. Crop Prot. 21:707-712.1.
Patzoldt, W. L., Tranel, P. J., Alexander, A. L., and Schmitzer, P. R. 2001. Weed Sci. 49: 485-490.
Patzoldt et al. 2006. Proc. Natl. Acad. Sci. USA 103:12329-12334.
Pornprom, T. et al. 1994. Pestic. Biochem. Physiol. 50:107-114.
Retzlaff, K. and P. Böger. 1996. Pest. Biochem. Physiol. 54:105-114.
Sasarman, A. et al. 1993. Can. J. Microbiol. 39:1155-1161.
Sasarman, A., Chartrand, P., Lavoie, M., Tardif, D., Proschek, R. and Lapointe, C. 1979. J. Gen. Microbiol. 113: 297-303.
Seefeldt, S. S. et al. 1995. Weed Technol. 9:218-227.
Shoup, D. E. et al. 2003. Weed Sci. 51:145-150.
Shoup, D. E. and Al-Khatib, K. 2005. Weed Sci. 53: 284-289
Smith, A. G. et al. 1993. Biochem J. 292:503-508.
Stone, B. F. 1968. A formula for determining degree of dominance in cases of monofactorial inheritance of resistance to chemicals Bull. W.H.O. 38:325-6. Thompson, J. D., Higgins, D. G., and Gibson, T. J. 1994. Nucleic Acids Res. 22: 4673-4690.
Volrath, S. L et al. 1999. U.S. Pat. No. 5,939,602.
Watanabe, N. et al. 1998. Plant Physiol. 118:751-758.
Watanabe, N. et al. 2001. J. Biol. Chem. 276:20474-204811.
Yang, H. et al. 1996. Proc. Natl. Acad. Sci. USA 93:2459-2463.

What is claimed is:

1. A method for producing a genetically engineered, non-transgenic, herbicide resistant or tolerant plant cell, said method comprising the steps of:
   (a) introducing into a plant cell a recombinagenic oligonucleotide with a targeted mutation in the protoporphyrin oxidase (PPO) gene to produce plant cells with a mutant PPO gene that expresses a mutant PPO protein that is deleted at an amino acid position corresponding to Gly210 or Gly 211 in the *Amaranthus tuberculatus* PPO protein or at an analogous amino acid residue in a PPO homolog; and
   (b) identifying a plant cell having a mutant PPO protein that has substantially the same catalytic activity as compared to a corresponding wild type PPO protein in the presence of herbicide except that said mutant PPO protein is not inhibited by the herbicide; and
   whereby a non-transgenic herbicide resistant plant cell is produced.

2. The method of claim 1, wherein said herbicide resistant PPO is resistant to inhibition by lactofen, (±)-2-ethoxy-1-methyl-2-oxoethyl 5-{2-chloro-4-(trifluoromethyl)phenoxy}-2-nitrobenzoate; acifluorfen, 5-{2-chloro-4-(trifluoromethyl)phenoxy}-2-nitrobezoic acid; its methyl ester; or oxyfluorfen, 2-chloro-1-(3-ethoxy-4-nitrophenoxy)-4-(trifluorobenzene)}, oxidiazoles, (e.g., oxidiazon, 3-{2,4-dichloro-5-(1-methylethoxy)phenyl}-5-(1,1-dimethylethyl)-1,3,4-oxadiazol-2-(3H)-one), cyclic imides (e.g., S-23142, N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-{1-(2,3,4-trichlorophenyl)-4-nitropyrazolyl-5-oxy}propionate; M&B 39279), pyridine derivatives (e.g. LS 82-556), phenopylate and O-phenylpyrrolidino- and piperidinocarbamate analogs thereof, and 3-phenyluracils of formula I

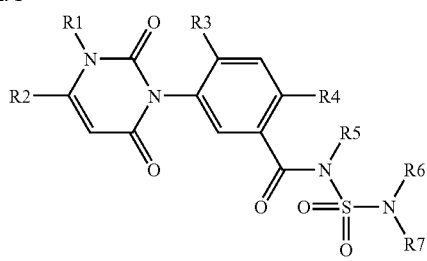

(I)

wherein R$^1$ is methyl or NH$_2$; R$^2$ is C$_1$-C$_2$-haloalkyl; R$^3$ is hydrogen or halogen; R$^4$ is halogen or cyano; R$^5$ is hydrogen, cyano, C$_1$-C$_6$-alkyl, C$_1$-C$_6$-alkoxy, C$_1$-C$_4$-alkoxy-C$_1$-C$_4$-alkyl, C$_3$-C$_7$-cycloalkyl, C$_3$-C$_6$-alkenyl, C$_3$-C$_6$-alkynyl or benzyl which is unsubstituted or substituted by halogen or alkyl; and R$^6$, R$^7$ independently of one another are hydrogen, C$_1$-C$_6$-alkyl, C$_1$-C$_6$-alkoxy, C$_3$-C$_6$-alkenyl, C$_3$-C$_6$-alkynyl, C$_3$-C$_7$-cycloalkyl, C$_3$-C$_7$-cycloalkenyl, phenyl or benzyl, where each of the 8 abovementioned substituents is unsubstituted or may be substituted by 1 to 6 halogen atoms and/or by one, two or three groups selected from: OH, NH$_2$, CN, CONH$_2$, C$_1$-C$_4$-alkoxy, C$_1$-C$_4$-haloalkoxy, C$_1$-C$_4$-alkylthio, C$_1$-C$_4$-haloalkylthio, C$_1$-C$_4$-alkylsulfonyl, C$_1$-C$_4$-haloalkylsulfonyl, C$_1$-C$_4$-alkylamino, di(C$_1$-C$_4$-alkyl)amino, formyl, C$_1$-C$_4$-alkylcarbonyl, C$_1$-C$_4$-alkoxycarbonyl, C$_1$-C$_4$-alkylaminocarbonyl, di(C$_1$-C$_4$-alkyl)aminocarbonyl, C$_3$-C$_7$-cycloalkyl, phenyl and benzyl; or R$^6$, R$^7$ together with the nitrogen atom form a 3-, 4-, 5-, 6- or 7-membered saturated or unsaturated nitrogen heterocycle which may be substituted by 1 to 6 methyl groups and which may contain 1 or 2 further heteroatoms selected from the group consisting of nitrogen, oxygen and sulfur as ring members.

3. The method according to claim 1 wherein the recombinagenic oligonucleotide is a mixed duplex nucleotide which contains a first homologous region which has a sequence identical to the sequence of at least 6 base pairs of the first fragment of the target PPO gene and a second homologous region which has a sequence identical to the sequence of at least 6 base pairs of a second fragment of the target PPO gene, and an intervening region which contains at least one nucleobase heterologous to the target PPO gene, which intervening region connects the first and second homologous region.

4. The method according to claim 1 in which the recombinagenic oligonucleotide is introduced by electroporation, biolistic transformation or polyethylene glycol precipitation.

5. The method of claim 1, further comprising after step (b), (c) regenerating a plant having a mutated PPO gene from said plant cell, whereby a non-transgenic herbicide resistant plant is produced.

6. The method according to claim 1 in which the amino acid deletion is in a corn, wheat, rice, barley, soybean, cotton, sugarbeet, oilseed rape, canola, flax, sunflower, potato, tobacco, tomato, alfalfa, poplar, pine, eucalyptus, apple, lettuce, pea, lentil, grape, turf grass, Brassica or *Arabidopsis thaliana* homolog of the PPO of *Amaranthus tuberculatus* as set forth in SEQ ID NO:16.

7. A plant, progeny plant, plant cell, plant tissue or seed of the plant produced by the method of claim 5, wherein said progeny plant, cell, tissue or seed contains within its genetic complement the mutant PPO gene that expresses a mutant PPO protein that is deleted at an amino acid position corresponding to Gly210 or Gly 211 in the *Amaranthus tuberculatus* PPO protein or at an analogous amino acid residue in a PPO homolog.

8. The plant, plant cell or plant tissue of claim 7, which is or is from a dicotyledonous plant.

9. The plant, plant cell or plant tissue of claim 8, which is or is from *Arabidopsis*, cotton, sunflower, cabbage, broccoli, cauliflower, Brussels sprout, canola, bean, pea, soybean, citrus, tomato, potato, sweet potato, plum, peach, apple, pear, cherry, grape, rose, tobacco, alfalfa, trefoil, sugar beet, blackberry, raspberry, blueberry, marionberry, loganberry, apricot, eggplant, pepper, pumpkin, squash, gourd, an ornamental plant, aspen, poplar, maple, oak, sunflower, rose or tobacco.

10. The plant, plant cell or plant tissue of claim 7, which is or is from a monocotyledonous plant.

11. The plant, plant cell or plant tissue of claim 10, which is or is from wheat, corn, rice, sorghum, oat, wild rice, barley, millet or turfgrass.

12. A method of controlling weeds comprising the step of planting a non-transgenic, genetically engineered, herbicide resistant plant, plant, progeny plant or seed containing within its genetic complement the mutant PPO gene that expresses a mutant PPO protein that is deleted at an amino acid position corresponding to Gly210 or Gly 211 in the *Amaranthus tuberculatus* PPO protein or at an analogous amino acid residue in a PPO homolog; and treating the plants with a herbicide to which resistance is conferred by said molecule, whereby growth of weeds is controlled.

13. A method of selecting a non-transgenic, genetically engineered, herbicide resistant plant cell or plant tissue containing within its genetic complement the mutant PPO gene that expresses a mutant PPO protein that is deleted at an amino acid position corresponding to Gly210 or Gly 211 in the *Amaranthus tuberculatus* PPO protein or at an analogous amino acid residue in a PPO homolog, said method comprising the steps of growing said plant cell or plant tissue on a medium comprising an amount of an inhibitor of protoporphoryinogen oxidase sufficient to prevent growth of a corresponding plant cell which does not contain and express said nucleic acid molecule.

* * * * *